(12) United States Patent
Anderson et al.

(10) Patent No.: US 8,163,769 B2
(45) Date of Patent: Apr. 24, 2012

(54) ANTIBACTERIAL COMPOUNDS

(75) Inventors: David Anderson, Kenosha, WI (US);
Bruce Beutel, Lake Forest, IL (US);
Todd D. Bosse, Chicago, IL (US);
Richard Clark, Gurnee, IL (US); Curt Cooper, Vernon Hills, IL (US); Peter Dandliker, Gurnee, IL (US); Caroline David, Green Oaks, IL (US); Yu-Gui Gu, Libertyville, IL (US); Todd Matthew Hansen, Gurnee, IL (US); Mira Hinman, Libertyville, IL (US); Douglas Kalvin, Buffalo Grove, IL (US); Daniel P. Larson, Highland Park, IL (US); Linda Lynch, Pleasant Prairie, WI (US); Zhenkun Ma, Dallas, TX (US); Christopher Motter, Oak Creek, WI (US); Fabio Palazzo, Waukegan, IL (US); Teresa Rosenberg, Gurnee, IL (US); Tamara Rehm, Lindenhurst, IL (US); William Sanders, Fox Lake, IL (US); Michael Tufano, Chicago, IL (US); Rolf Wagner, Gurnee, IL (US); Moshe Weitzberg, Highland Park, IL (US); Hong Yong, Grayslake, IL (US); Tianyuan Zhang, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 2251 days.

(21) Appl. No.: 10/387,318

(22) Filed: Mar. 12, 2003

(65) Prior Publication Data
US 2003/0232818 A1    Dec. 18, 2003

Related U.S. Application Data

(60) Provisional application No. 60/363,594, filed on Mar. 12, 2002.

(51) Int. Cl.
*A61K 31/04* (2006.01)
*C07D 215/38* (2006.01)
(52) U.S. Cl. .................. 514/300; 546/123
(58) Field of Classification Search .......... 546/123, 546/113, 84; 544/362, 310; 514/300, 292, 514/253.04, 269
See application file for complete search history.

(56) References Cited

U.S. PATENT DOCUMENTS

| | | | |
|---|---|---|---|
| 3,857,851 A | 12/1974 | Lesher et al. | |
| 4,497,816 A | 2/1985 | Matsumoto et al. | |
| 4,954,507 A | 9/1990 | Weber et al. | |
| 4,965,273 A * | 10/1990 | Weber et al. ................. | 514/300 |
| 5,137,892 A | 8/1992 | Chu et al. | |
| 5,412,098 A * | 5/1995 | Yasuhiro et al. ............. | 546/156 |
| 5,679,689 A | 10/1997 | Petersen et al. | |

FOREIGN PATENT DOCUMENTS

| | | |
|---|---|---|
| EP | 0343398 A2 | 11/1989 |
| EP | 387802 A2 * | 9/1990 |
| JP | 62-84085 A2 * | 4/1997 |
| WO | 90/06307 A | 6/1990 |
| WO | 01/32655 A | 5/2001 |
| WO | 01/36408 A | 5/2001 |
| WO | 02/085886 A | 10/2002 |

OTHER PUBLICATIONS

Mataumoto et al. J. Med. Chem. 1984, 27:292-301.*
Hansen, CA 143:133303, abstract only of Bioorg & Med Chem Lett, vol. 15(11), pp. 2716-2719, 2005.*
Remuzon, P., et al., "Fluoronaphthyridines as antibacterial agents, 6. synthesis and structure-activity relationships of new chiral 7-(1-,3-4-, and 6-methyl-2, 5-diazabiclou2.21heptan-2-yl) naphthyridine analogues of 7-U(1R,4R)-2,5- Diazabicyclou2.2.1 heptan-2-y1-1-(1.1-dimethylethyl)-6-fluoro-1,4-Dihydro-4-oxo- 1,8-NAP", Journal of Medicinal Chemistry, American Chemical Society, Washington, US, vol. 35, No. 15, 1992, pp. 2898-2909.
European Search Report from European Patent Application Publication No. EP1631570, dated Dec. 12, 2003.

* cited by examiner

*Primary Examiner* — D M Seaman
(74) *Attorney, Agent, or Firm* — Lisa V. Mueller; Michael Best & Friedrich LLP

(57) ABSTRACT

Antibacterials having formula (I)

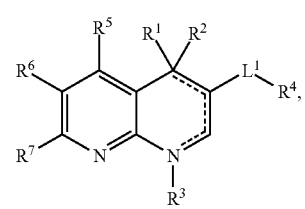

(I)

and salts, prodrugs, and salts of prodrugs thereof, processes for making the compounds and intermediates used in the processes, compositions containing the compounds, and methods of prophylaxis and treatment of bacterial infections using the compounds are disclosed.

19 Claims, No Drawings

ANTIBACTERIAL COMPOUNDS

This application claims benefit of co-pending U.S. Provisional Application Ser. No. 60/363,594, filed Mar. 12, 2002, the specification of which is hereby incorporated into this application by reference.

TECHNICAL FIELD

This invention is directed to compounds having antibacterial activity, processes for making the compounds and intermediates used in the processes, compositions containing the compounds, and methods for prophylaxis or treatment of bacterial infections using the compounds.

BACKGROUND OF THE INVENTION

Because the effectiveness of many drugs currently available for prophylaxis or treatment of bacterial infections is being compromised by the emergence of drug-resistant bacteria, the introduction of novel antibacterials would be beneficial for their therapeutic value and their contribution to the antibacterial arts.

SUMMARY OF THE INVENTION

Accordingly, a first embodiment of the invention is directed to compounds, and salts, prodrugs, and salts of prodrugs thereof, which are useful as antibacterials, the compounds having formula (I)

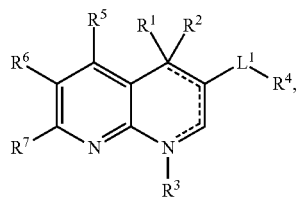

(I)

in which
--- is a single bond or a double bond;
one of $R^1$ and $R^2$ is absent or hydrogen and the other is hydrogen, —OH, —N(CH$_3$)$_2$, —NHR$^{12}$, or —NR$^{35}$R$^{12}$; or
$R^1$, and $R^2$ together are =O;
$R^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one R$^{3a}$ substituent;
$R^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C≡CH, —C≡CR$^{3B}$, —CH=C=CH$_2$, —C(O) (aryl), or —CH=C=CHR$^{3B}$;
$R^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O—(alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;
with the proviso that proper valencies are maintained for combinations of the forgoing variables;
$L^1$ is a covalent bond, —C(=O)—, or —(CH$_2$)$_m$—, in which m is 1, 2, 3, 4, or 5;
$R^4$ is hydrogen, aryl, —NH$_2$, —OH, —NH(R$^8$), —N(R$^9$)(R$^{10}$), —OR$^{11}$, —N(R$^{12}$)$_2$, or —NHR$^{37}$;
$R^5$ is hydrogen, alkyl, aryl, heteroaryl, halo, —OH, —CF$_3$, —CH$_2$CF$_3$, —CF$_2$CF$_3$, —NH$_2$, —NHR$^{11}$, NR$^{11}$R$^{12}$, NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;
$R^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or
$R^5$ and $R^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —O(O)OH, —O(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{6A}$;
$R^{6A}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;
$R^7$ is halo, aryl, heteroaryl, heterocyclyl, bicyclic heterocycloalkyl, —NH(R$^{12}$), or —N(R$^{13}$)(R$^{14}$);
$R^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

$R^9$ and $R^{10}$ are independently methyl, ethyl, propyl, or iso-propyl, each of which is unsubstituted or substituted with one substituent selected from the group consisting of —OH and —O(alkyl); or $R^9$ and $R^{10}$ together are alkylene or heteroalkylene;

$R^{11}$ is alkyl, —($C_1$-$C_4$-alkylene)-alkenyl, —($C_1$-$C_4$-alkylene)-alkynyl, or alkyl substituted with one aryl substituent;

$R^{12}$ is alkyl, —$NH_2$, —$NHR^{6a}$, or alkyl substituted with one substituent selected from the group consisting of cycloalkenyl, aryl, heteroaryl, heterocyclyl, —$NH_2$, —$N(R^{15})(R^{16})$, —NHC(=NH)$NH_2$, —OC(O)$CF_3$, —OH, —O-(alkyl), —S-(alkyl), and —C(O)$NH_2$;

$R^{13}$ and $R^{14}$ are independently alkyl or alkyl substituted with —$N(CH_3)_2$; or $R^{13}$ and $R^{14}$ together are alkylene;

$R^{15}$ and $R^{16}$ are independently alkyl or alkyl substituted with one substituent selected from the group consisting of —$NH_2$, —NH(alkyl), and —N(alkyl)$_2$;

$R^{30}$ is alkyl or alkyl substituted with one substituent selected from the group consisting of halo and —O(alkyl);

$R^{35}$, $R^{36}$, and $R^{37}$ are independently alkyl, alkenyl, alkyl substituted with four or five hydroxyl substituents, or alkyl substituted with one, two, or three substituents independently selected from the group consisting of —NH(=NH)$NH_2$, —OH, —$NH_2$, —NH(alkyl), —N(alkyl)$_2$, —NH($CH_2$(phenyl)), —S(alkyl), $R^{40}$, cycloalkyl, —$CO_2H$, =O, —NH(C=NH)NH$NO_2$, and cycloalkyl substituted with —$CH_2NH_2$;

$R^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)$NH_2$, —O— (alkyl)-$NR^{70}R^{71}$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2$NH(alkyl), —$SO_2$N(alkyl)$_2$, alkyl substituted with one phenyl substituent, and phenyl substituted with one, two, or three independently selected alkyl substituents;

$R^{70}$ and $R^{71}$ are independently hydrogen, alkyl, alkenyl, alkyl substituted with four or five hydroxyl substituents, or alkyl substituted with one, two, or three substituents independently selected from the group consisting of —NH(=NH)$NH_2$, —OH, —$NH_2$, —NH(alkyl), —N(alkyl)$_2$, —NH($CH_2$(phenyl)), —S(alkyl), $R^{80}$, cycloalkyl, —$CO_2H$, =O, —NH(C=NH)NH$NO_2$, and cycloalkyl substituted with —$CH_2NH_2$; and $R^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)-$NH_2$, —O— (alkyl)-$NH_2$, —O-(alkyl)-NH(alkyl), —O-(alkyl)-N(alkyl)$_2$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2$NH(alkyl), —$SO_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected $R^{5a}$ substituents, (b) alkyl substituted with one, two, three, four, or five independently selected $R^{20a}$ substituents, (c) —NH(alkyl), in which the alkyl part of the —NH(alkyl) is substituted with one, two, three, four, or five independently selected $R^{20a}$ substituents; and (d) —N($R^{35}$)-(alkyl), in which the alkyl part of the —N($R^{35}$)-(alkyl) is substituted with one, two, three, four or five independently selected $R^{20a}$ substituents;

in which $R^{5a}$ is alkyl, alkenyl, alkynyl, cycloalkyl, halo, —CN, —OH, —SH, —$NH_2$, —$NO_2$, =O, —$CF_3$, —$CH_2CF_3$, —$CF_2CF_3$, —$OCF_3$, —$OCH_2CF_3$, —$OCF_2CF_3$, —$OR^{30}$, —$SR^{30}$, —S(O)$R^{35}$, —$SO_2R^{35}$, —$B(OH)_2$, —C(O)H, —C(O)$R^{35}$, —C(O)OH, —C(O)$OR^{35}$, —NH($R^{35}$), —N($R^{35}$)($R^{36}$), —C(O)$NH_2$, —C(O)NH($R^{35}$), —C(O)N($R^{35}$)($R^{36}$), —OC(O)$R^{35}$, —OC(O)$OR^{35}$, —OC(O)$NH_2$, —OC(O)NH($R^{35}$), —OC(O)N($R^{35}$)($R^{36}$), —NHC(O)H, —NHC(O)$R^{35}$, —NHC(O)$OR^{35}$, —NHC(O)$NH_2$, —NHC(NH)$NH_2$, —NHC(O)NH($R^{35}$), —NHC(O)N($R^{35}$)($R^{36}$), —$SO_2NH_2$, —$SO_2$NH($R^{35}$), —$SO_2$N($R^{35}$)($R^{36}$), or $R^{81}$;

$R^{20A}$ is cycloalkyl, halo, —CN, —OH, —SH, =O, —$OR^{30}$, $SR^{30}$, —C(O)OH, —C(O)$OR^{35}$, —$NH_2$, —NH($R^{35}$), —N($R^{35}$)($R^{36}$), —C(O)$NH_2$, —C(O)NH($R^{35}$), —C(O)N($R^{35}$)($R^{36}$), —OC(O)$R^{35}$, —OC(O)$NH_2$, —NHC(NH)$NH_2$, —NHC(NH)NH$NO_2$, —OC(O)NH($R^{35}$), —OC(O)N($R^{35}$)($R^{36}$), —$SO_2NH_2$, —$SO_2$NH($R^{35}$), —$SO_2$N($R^{35}$)($R^{36}$), —CH=$CH_2$, or $R^{72}$; and $R^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)-$NH_2$, —O— (alkyl)-$NH_2$, —O-(alkyl)-NH(alkyl), —O-(alkyl)-N(alkyl)$_2$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, –OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

A second embodiment of this invention is directed to a process for making the compounds of the first embodiment.

A third embodiment of this invention is directed to intermediates which are useful in the second embodiment.

A fourth embodiment of this invention is directed to a composition for the prophylaxis or treatment of bacterial infections in a fish or a mammal, the composition comprising a therapeutically effective amount of a compound of the first embodiment.

A fifth embodiment of this invention is directed to a method of prophylaxis or treatment of bacterial infection in a fish or a mammal, the method comprising administering to the fish or the mammal a therapeutically effective amount of a compound of the first embodiment.

An sixth embodiment of this invention is directed to a composition for inhibiting bacterial protein synthesis, the composition comprising a therapeutically effective amount of a compound having formula (I)

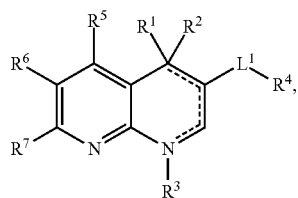

(I)

in which

--- is a single bond or a double bond;

one of R$^1$ and R$^2$ is absent or hydrogen and the other is hydrogen, —OH, —N(CH$_3$)$_2$, —NHR$^{12}$, or —NR$^{35}$R$^{12}$; or R$^1$ and R$^2$ together are =O;

R$^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one R$^{3a}$ substituent;

R$^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C≡CR$^{3B}$, —CH=C=CH$_2$, -C(O) (aryl), or —CH=C=CHR$^{3B}$;

R$^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

with the proviso that proper valencies are maintained for combinations of the forgoing variables;

L$^1$ is a covalent bond, —C(=O)—, or —(CH$_2$)$_m$—, in which m is 1, 2, 3, 4, or 5;

R$^4$ is hydrogen, aryl, —NH$_2$, —OH, —NH(R$^8$), —N(R$^9$)(R$^{10}$), —OR$^{11}$, —N(R$^{12}$)$_2$, or —NHR$^{37}$;

R$^5$ is hydrogen, alkyl, aryl, heteroaryl, halo, —OH, —CF$_3$, —CH$_2$CF$_3$, —CF$_2$CF$_3$, —NH$_2$, —NR$^{11}$R$^{12}$, NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;

R$^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or R$^5$ and R$^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, CF$_2$CF$_3$, —OCF$_3$, —OCH$_2$CF$_3$, —OCF$_2$CF$_3$—OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{6A}$;

R$^{6A}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O (alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

R$^7$ is halo, aryl, heteroaryl, heterocyclyl, bicyclic heterocycloalkyl, —NH(R$^{12}$), or —N(R$^{13}$)(R$^{14}$);

R$^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

R$^9$ and R$^{10}$ are independently methyl, ethyl, propyl, or iso-propyl, each of which is unsubstituted or substituted with one substituent selected from the group consisting of —OH and —O(alkyl); or R$^9$ and R$^{10}$ together are alkylene or heteroalkylene;

$R^{11}$ is alkyl, —($C_1$-$C_4$-alkylene)-alkenyl, —($C_1$-$C_4$-alkylene)-alkynyl, or alkyl substituted with one aryl substituent;

$R^{12}$ is alkyl, —$NH_2$, —$NHR^{6a}$, or alkyl substituted with one substituent selected from the group consisting of cycloalkenyl, aryl, heteroaryl, heterocyclyl, —$NH_2$, —$N(R^{15})(R^{16})$, —$NHC(=NH)NH_2$, —$OC(O)CF_3$, —OH, —O-(alkyl), —S-(alkyl), and —$C(O)NH_2$;

$R^{13}$ and $R^{14}$ are independently alkyl or alkyl substituted with —$N(CH_3)_2$; or $R^{13}$ and $R^{14}$ together are alkylene;

$R^{15}$ and $R^{16}$ are independently alkyl or alkyl substituted with one substituent selected from the group consisting of —$NH_2$, —NH(alkyl), and —N(alkyl)$_2$;

$R^{30}$ is alkyl or alkyl substituted with one substituent selected from the group consisting of halo and —O(alkyl);

$R^{35}$, $R^{36}$, and $R^{37}$ are independently alkyl, alkenyl, alkyl substituted with four or five hydroxyl substituents, or alkyl substituted with one, two, or three substituents independently selected from the group consisting of —NH(=NH)$NH_2$, —OH, —$NH_2$, —NH(alkyl), —N(alkyl)$_2$, —NH($CH_2$(phenyl)), —S(alkyl), $R^{40}$, cycloalkyl, —$CO_2H$, =O, —NH(C=NH)$NHNO_2$, and cycloalkyl substituted with —$CH_2NH_2$;

$R^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)$NH_2$, —O— (alkyl)-$NR^{70}R^{71}$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2NH$(alkyl), —$SO_2N$(alkyl)$_2$, alkyl substituted with one phenyl substituent, and phenyl substituted with one, two, or three independently selected alkyl substituents;

$R^{70}$ and $R^{71}$ are independently hydrogen, alkyl, alkenyl, alkyl substituted with four or five hydroxyl substituents, or alkyl substituted with one, two, or three substituents independently selected from the group consisting of —NH(=NH)$NH_2$, —OH, —$NH_2$, —NH (alkyl), —N(alkyl)$_2$, —NH($CH_2$(phenyl)), —S(alkyl), $R^{80}$, cycloalkyl, —$CO_2H$, =O, —NH(C=NH)$NHNO_2$, and cycloalkyl substituted with —$CH_2NH_2$; and $R^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)-$NH_2$, —O— (alkyl)-$NH_2$, —O-(alkyl)-NH(alkyl), —O-(alkyl)-N(alkyl)$_2$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2NH$(alkyl), —$SO_2N$(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected $R^{5a}$ substituents, (b) alkyl substituted with one, two, three, four, or five independently selected $R^{20a}$ substituents, (c) —NH (alkyl), in which the alkyl part of the —NH (alkyl) is substituted with one, two, three, four, or five independently selected $R^{20a}$ substituents; and (d) —N($R^{35}$)-(alkyl), in which the alkyl part of the —N($R^{35}$)-(alkyl) is substituted with one, two, three, four or five independently selected $R^{20a}$ substituents;

in which $R^{5a}$ is alkyl, alkenyl, alkynyl, cycloalkyl, halo, —CN, —OH, —SH, —$NH_2$, —$NO_2$, =O, —$CF_3$, —$CH_2CF_3$, —$CF_2CF_3$, —$OCF_3$, —$OCH_2CF_3$, —$OCF_2CF_3$, —$OR^{30}$, —$SR^{30}$, —S(O)$R^{35}$, —$SO_2R^{35}$, —B(OH)$_2$, —C(O)H, —C(O)$R^{35}$, —C(O)OH, —C(O)O$R^{35}$, —NH($R^{35}$), —N($R^{35}$)($R^{36}$), —C(O)$NH_2$, —C(O)NH($R^{35}$), —C(O)N($R^{35}$)($R^{36}$), —OC(O)$R^{35}$, —OC(O)O$R^{35}$, —OC(O)$NH_2$, —OC(O)NH($R^{35}$), —OC(O)N($R^{35}$)($R^{36}$), —NHC(O)H, —NHC(O)$R^{35}$, —NHC(O)O$R^{35}$, —NHC(O)$NH_2$, —NHC(NH)$NH_2$, —NHC(O)NH($R^{35}$), —NHC(O)N($R^{35}$)($R^{36}$), —$SO_2NH_2$, —$SO_2NH$($R^{35}$), —$SO_2N$($R^{35}$)($R^{36}$), or $R^{81}$;

$R^{20a}$ is cycloalkyl, halo, —CN, —OH, —SH, =O, —$OR^{30}$, —$SR^{30}$, —C(O)OH, —C(O)O$R^{35}$, —$NH_2$, —NH($R^{35}$), —N($R^{35}$)($R^{36}$), —C(O)$NH_2$, —C(O)NH($R^{35}$), —C(O)N($R^{35}$)($R^{36}$), —OC(O)$R^{35}$, —OC(O)$NH_2$, —NHC(NH)$NH_2$, —NHC(NH)$NHNO_2$, —OC(O)NH($R^{35}$), —OC(O)N($R^{35}$)($R^{36}$), —$SO_2NH_2$, —$SO_2NH$($R^{35}$), —$SO_2N$($R^{35}$)($R^{36}$), —CH=$CH_2$, or $R^{72}$; and $R^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)-$NH_2$, —O— (alkyl)-$NH_2$, —O-(alkyl)-NH(alkyl), —O-(alkyl)-N(alkyl)$_2$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2NH$(alkyl), —$SO_2N$(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

In a preferred sixth embodiment, the bacterial protein synthesis is antibacterial-resistant bacterial protein synthesis.

In another preferred sixth embodiment, the bacterial protein synthesis is bacterial protein synthesis in vitro.

In still another preferred sixth embodiment, the bacterial protein synthesis is cell-free bacterial protein synthesis in vitro.

In still yet another preferred sixth embodiment, the bacterial protein synthesis is bacterial protein synthesis in a fish or a mammal.

A seventh embodiment of this invention is directed to a composition for inhibiting bacterial growth, the composition comprising a therapeutically effective amount of a compound having formula (I)

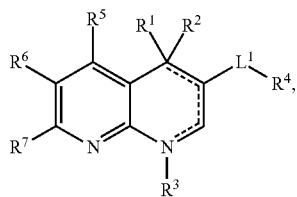

(I)

in which

--- is a single bond or a double bond;

one of R$^1$ and R$^2$ is absent or hydrogen and the other is hydrogen, —OH, —N(CH$_3$)$_2$, —NHR$^{12}$, or —NR$^{35}$R$^{12}$; or R$^1$ and R$^2$ together are =O;

R$^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one R$^{3a}$ substituent;

R$^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C≡CH, —C≡CH$^{3B}$, —CH=C=CH$_2$, —C(O)(aryl), or —CH=C=CHR$^{3B}$;

R$^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

with the proviso that proper valencies are maintained for combinations of the forgoing variables;

L$^1$ is a covalent bond, —C(=O)—, or —(CH$_2$)$_m$—, in which m is 1, 2, 3, 4, or 5;

R$^4$ is hydrogen, aryl, —NH$_2$, —OH, —NH(R$^8$), —N(R$^9$)(R$^{10}$), —OR$^{11}$, —N(R$^{12}$)$_2$, or —NHR$^{37}$;

R$^5$ is hydrogen, alkyl, aryl, heteroaryl, halo, —OH, —CF$_3$, —CH$_2$CF$_3$, —CF$_2$CF$_3$, —NH$_2$, —NHR$^{11}$, —NR$^{11}$R$^{12}$, —NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;

R$^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or R$^5$ and R$^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{6A}$;

R$^{6A}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

R$^7$ is halo, aryl, heteroaryl, heterocyclyl, bicyclic heterocycloalkyl, —NH(R$^{12}$), or —N(R$^{13}$)(R$^{14}$);

R$^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

R$^9$ and R$^{10}$ are independently methyl, ethyl, propyl, or iso-propyl, each of which is unsubstituted or substituted with one substituent selected from the group consisting of —OH and —O(alkyl); or R$^9$ and R$^{10}$ together are alkylene or heteroalkylene;

R$^{11}$ is alkyl, —(C$_1$-C$_4$-alkylene)-alkenyl, —(C$_1$-C$_4$-alkylene)-alkynyl, or alkyl substituted with one aryl substituent;

R$^{12}$ is alkyl, —NH$_2$, —NHR$^{6a}$, or alkyl substituted with one substituent selected from the group consisting of cycloalkenyl, aryl, heteroaryl, heterocyclyl, —NH$_2$, —N(R$^{15}$)(R$^{16}$), —NHC(=NH)NH$_2$, —OC(O)CF$_3$, —OH, —O-(alkyl), —S-(alkyl), and —C(O)NH$_2$;

R$^{13}$ and R$^{14}$ are independently alkyl or alkyl substituted with —N(CH$_3$)$_2$; or $R^{13}$ and $R^{14}$ together are alkylene;

$R^{15}$ and $R^{16}$ are independently alkyl or alkyl substituted with one substituent selected from the group consisting of —$NH_2$, —NH(alkyl), and —N(alkyl)$_2$;

$R^{30}$ is alkyl or alkyl substituted with one substituent selected from the group consisting of halo and —O(alkyl);

$R^{35}$, $R^{36}$, and $R^{37}$ are independently alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), $R^{40}$, cycloalkyl, —CO$_2$H, =O, —NH(C=NH)NHNO$_2$, and cycloalkyl substituted with —CH$_2$NH$_2$;

$R^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)NH$_2$, —O-(alkyl)-NR$^{70}$R$^{71}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

$R^{70}$ and $R^{71}$ are independently hydrogen, alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), $R^{80}$, cycloalkyl, —CO$_2$H, =O, —NH(C=NH)NHNO$_2$, and cycloalkyl substituted with —CH$_2$NH$_2$; and $R^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected $R^{5a}$ substituents, (b) alkyl substituted with one, two, three, four, or five independently selected $R^{20a}$ substituents, (c) —NH(alkyl), in which the alkyl part of the —NH(alkyl) is substituted with one, two, three, four, or five independently selected $R^{20a}$ substituents; and (d) —N($R^{35}$)-(alkyl), in which the alkyl part of the —N($R^{35}$)-(alkyl) is substituted with one, two, three, four or five independently selected $R^{20a}$ substituents;

in which $R^{5a}$ is alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), or $R^{81}$;

$R^{20a}$ is cycloalkyl, halo, —CN, —OH, —SH, =O, —OR$^{30}$, —SR$^{30}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —NHC(NH)NH$_2$, —NHC(NH)NHNO$_2$, —OC(O)NH(R$^{35}$), —OC(O)N(R$^{35}$)(R$^{36}$), —SO$_2$NH$_2$, —SO$_2$NH(R$^{35}$), —SO$_2$N(R$^{35}$)(R$^{36}$), —CH=CH$_2$, or $R^{72}$; and $R^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

In a preferred seventh embodiment, the bacterial growth is antibacterial-resistant bacterial growth.

In another preferred seventh embodiment, the bacterial growth is quinolone-resistant bacterial growth.

In still another preferred seventh embodiment, the bacterial growth is bacterial growth in vitro.

In still even yet another preferred seventh embodiment, the bacterial growth is bacterial growth in a fish or a mammal.

A eighth embodiment of this invention is directed to a composition for prophylaxis or treatment of antibacterial-resistant bacterial infection in a fish or a mammal, the composition comprising a therapeutically effective amount of compound having formula (I)

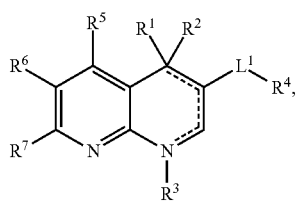

in which

--- is a single bond or a double bond;

one of $R^1$ and $R^2$ is absent or hydrogen and the other is hydrogen, —OH, —N(CH$_3$)$_2$, —NHR$^{12}$, or —NR$^{35}$R$^{12}$; or $R^1$ and $R^2$ together are =O;

$R^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one $R^{3a}$ substituent;

$R^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C≡CH, —C≡CR$^{3B}$, —CH=C=CH$_2$, —C(O)(aryl), or —CH=C=CHR$^{3B}$;

$R^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), —C(O)N(alkyl)$_2$, -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

with the proviso that proper valencies are maintained for combinations of the forgoing variables;

$L^1$ is a covalent bond, —C(=O)—, or —(CH$_2$)$_m$—, in which m is 1, 2, 3, 4, or 5;

$R^4$ is hydrogen, aryl, —NH$_2$, —OH, —NH(R$^8$), —N(R$^9$)(R$^{10}$), —OR$^{11}$, —N(R$^{12}$)$_2$, or —NHR$^{37}$;

$R^5$ is hydrogen, alkyl, aryl, heteroaryl, halo, —OH, —CF$_3$, —CH$_2$CF$_3$, —CF$_2$CF$_3$, —NH$_2$, —NHR$^{11}$, —NR$^{11}$R$^{12}$, —NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;

$R^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or $R^5$ and $R^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{6A}$;

$R^{6A}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

$R^7$ is halo, aryl, heteroaryl, heterocyclyl, bicyclic heterocycloalkyl, —NH(R$^{12}$), or —N(R$^{13}$)(R$^{14}$);

$R^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

$R^9$ and $R^{10}$ are independently methyl, ethyl, propyl, or iso-propyl, each of which is unsubstituted or substituted with one substituent selected from the group consisting of —OH and —O(alkyl); or $R^9$ and $R^{10}$ together are alkylene or heteroalkylene;

$R^{11}$ is alkyl, —(C$_1$-C$_4$-alkylene)-alkenyl, —(C$_1$-C$_4$-alkylene)-alkynyl, or alkyl substituted with one aryl substituent;

$R^{12}$ is alkyl, —NH$_2$, —NHR$^{6a}$, or alkyl substituted with one substituent selected from the group consisting of cycloalkenyl, aryl, heteroaryl, heterocyclyl, —NH$_2$, —N(R$^{15}$)(R$^{16}$), —NHC(=NH)NH$_2$, —OC(O)CF$_3$, —OH, —O-(alkyl), —S-(alkyl), and —C(O)NH$_2$;

$R^{13}$ and $R^{14}$ are independently alkyl or alkyl substituted with —N(CH$_3$)$_2$; or $R^{13}$ and $R^{14}$ together are alkylene;

$R^{15}$ and $R^{16}$ are independently alkyl or alkyl substituted with one substituent selected from the group consisting of —NH$_2$, —NH(alkyl), and —N(alkyl)$_2$;

$R^{30}$ is alkyl or alkyl substituted with one substituent selected from the group consisting of halo and —O(alkyl);

$R^{35}$, $R^{36}$, and $R^{37}$ are independently alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{40}$, cycloalkyl, —CO$_2$H, =O, —NH(C=NH)NHNO$_2$, and cycloalkyl substituted with —CH$_2$NH$_2$;

R$^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)NH$_2$, —O— (alkyl)-NR$^{70}$R$^{71}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

R$^{70}$ and R$^{71}$ are independently hydrogen, alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{80}$, cycloalkyl, —CO$_2$H, =O, —NH(C=NH)NHNO$_2$, and cycloalkyl substituted with —CH$_2$NH$_2$; and R$^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl), —NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH (alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH (alkyl), —OC(O)N (alkyl))$_2$, —NHC(O)H, —NHC(O)(alkyl), —NHC(O)O(alkyl), —NHC(O)NH$_2$, —NHC(O)NH (alkyl), —NHC(O)N (alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected R$^{5a}$ substituents, (b) alkyl substituted with one, two, three, four, or five independently selected R$^{20a}$ substituents, (c) —NH (alkyl), in which the alkyl part of the —NH (alkyl) is substituted with one, two, three, four, or five independently selected R$^{20a}$ substituents; and (d) —N(R$^{35}$)-(alkyl), in which the alkyl part of the —N(R$^{35}$)-(alkyl) is substituted with one, two, three, four or five independently selected R$^{20a}$ substituents;

in which R$^{5a}$ is alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$) —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), or R$^{81}$;

R$^{20A}$ is cycloalkyl, halo, —CN, —OH, —SH, =O, —OR$^{30}$, —SR$^{30}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —NHC(NH)NH$_2$, —NHC(NH)NHNO$_2$, —OC(O)NH(R$^{35}$), —OC(O)N(R$^{35}$)(R$^{36}$), —SO$_2$NH$_2$, —SO$_2$NH(R$^{35}$), —SO$_2$N(R$^{35}$)(R$^{36}$), —CH=CH$_2$, or R$^{72}$; and R$^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

In a preferred eighth embodiment, the antibacterial-resistant bacterial infection is quinolone-resistant bacterial infection.

An ninth embodiment of this invention is directed to a method for inhibiting bacterial protein synthesis in vitro or in a fish or a mammal, the method comprising administering to an administrant a therapeutically effective amount of a compound having formula (I)

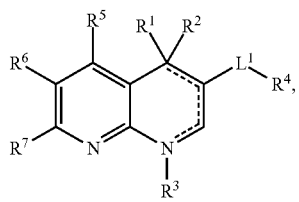

(I)

in which

--- is a single bond or a double bond;

one of $R^1$ and $R^2$ is absent or hydrogen and the other is hydrogen, —OH, —N(CH$_3$)$_2$, —NHR$^{12}$, or —NHR$^{35}$R$^{12}$; or $R^1$ and $R^2$ together are =O;

$R^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one R$^{3a}$ substituent;

$R^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C≡CH, —C≡CR$^{3B}$, —CH=C=CH$_2$, —C(O)(aryl), or —CH=C=CHR$^{3B}$;

$R^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O—(alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

with the proviso that proper valencies are maintained for combinations of the forgoing variables;

$L^1$ is a covalent bond, —C(=O)—, or —(CH$_2$)$_m$—, in which m is 1, 2, 3, 4, or 5;

$R^4$ is hydrogen, aryl, —NH$_2$, —OH, —NH(R$^8$), —N(R$^9$)(R$^{10}$), OR$^{11}$, —N(R$^{12}$)$_2$, or —NHR$^{37}$;

$R^5$ is hydrogen, alkyl, aryl, heteroaryl, halo, —OH, —CF$_3$, —CH$_2$CF$_3$, —CF$_2$CF$_3$, —NH$_2$, —NHR$^{11}$, —NR$^{11}$R$^{12}$, NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;

$R^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or $R^5$ and $R^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{64}$;

$R^{64}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_3$, —OCF$_3$, —OCH$_2$CF$_3$, —CF$_3$, -(alkyl)-NH$_2$, —O—(alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NR$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

$R^7$ is halo, aryl, heteroaryl, heterocyclyl, bicyclic heterocycloalkyl, —NH(R$^{12}$), or —N(R$^{13}$)(R$^{14}$);

$R^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

$R^9$ and $R^{10}$ are independently methyl, ethyl, propyl, or iso-propyl, each of which is unsubstituted or substituted with one substituent selected from the group consisting of —OH and —O(alkyl); or $R^9$ and $R^{10}$ together are alkylene or heteroalkylene;

$R^{11}$ is alkyl, —(C$_1$-C$_4$-alkylene)-alkenyl, —(C$_1$-C$_4$-alkylene)-alkynyl, or alkyl substituted with one aryl substituent;

$R^{12}$ is alkyl, —NH$_2$, —NHR$^{6a}$, or alkyl substituted with one substituent selected from the group consisting of cycloalkenyl, aryl, heteroaryl, heterocyclyl, —NH$_2$, —N(R$^{15}$)(R$^{16}$), —NHC(=NH)NH$_2$, —OC(O)CF$_3$, —OH, —O-(alkyl), —S-(alkyl), and —C(O)NH$_2$;

$R^{13}$ and $R^{14}$ are independently alkyl or alkyl substituted with —N(CH$_3$)$_2$; or $R^{13}$ and $R^{14}$ together are alkylene;

$R^{15}$ and $R^{16}$ are independently alkyl or alkyl substituted with one substituent selected from the group consisting of —NH$_2$, —NH(alkyl), and —N(alkyl)$_2$;

$R^{30}$ is alkyl or alkyl substituted with one substituent selected from the group consisting of halo and —O(alkyl);

$R^{35}$, $R^{36}$, and $R^{37}$ are independently alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{40}$, cycloalkyl, —CO$_2$H, =O, —NH(C=NH)NHNO$_2$, and cycloalkyl substituted with —CH$_2$NH$_2$;

$R^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)NH$_2$, —O— (alkyl)-NR$^{70}$R$^{71}$, —O(alkyl), —S(alkyl), —S(O)(alkyl), —SO$_2$(alkyl), —C(O)H, —C(O) (alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

R$^{70}$ and R$^{71}$ are independently hydrogen, alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{80}$, cycloalkyl, —CO$_2$H, =O, —NH(C=NH)NHNO$_2$, and cycloalkyl substituted with —CH$_2$NH$_2$; and R$^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected R$^{5a}$ substituents, (b) alkyl substituted with one, two, three, four, or five independently selected R$^{20a}$ substituents, (c) —NH(alkyl), in which the alkyl part of the —NH(alkyl) is substituted with one, two, three, four, or five independently selected R$^{20a}$ substituents; and (d) —N(R$^{35}$)-(alkyl), in which the alkyl part of the —N(R$^{35}$)-(alkyl) is substituted with one, two, three, four or five independently selected R$^{20a}$ substituents;

in which R$^{5a}$ is alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), or R$^{81}$;

R$^{20A}$ is cycloalkyl, halo, —CN, —OH, —SH, =O, —OR$^{30}$, —SR$^{30}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —NHC(NH)NH$_2$, —NHC(NH)NHNO$_2$, —OC(O)NH(R$^{35}$), —OC(O)N(R$^{35}$)(R$^{36}$), —SO$_2$NH$_2$, —SO$_2$NH(R$^{35}$), —SO$_2$N(R$^{35}$)(R$^{36}$), —CH=CH$_2$, or R$^{72}$; and R$^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NRC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

In a preferred ninth embodiment, the bacterial protein synthesis is antibacterial-resistant bacterial protein synthesis.

A tenth embodiment of this invention is directed to a method for inhibiting bacterial growth in vitro or in a fish or a mammal, the method comprising administering to an administrant a therapeutically effective amount of a compound having formula (I)

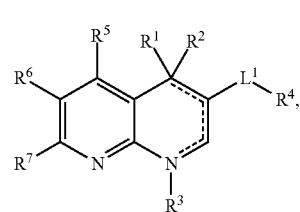

(I)

in which

═ is a single bond or a double bond;

one of R$^1$ and R$^2$ is absent or hydrogen and the other is hydrogen, —OH, —N(CH$_3$)$_2$, —NHR$^{12}$, or —NR$^{35}$R$^{12}$; or R$^1$ and R$^2$ together are =O;

R$^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one R$^{3a}$ substituent;

R$^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C≡CH, —C≡CR$^{3B}$, —CH=C=CH$_2$, —C(O)(aryl), or —CH=C=CHR$^{3B}$;

R$^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O—(alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

with the proviso that proper valencies are maintained for combinations of the forgoing variables;

L$^1$ is a covalent bond, —C(=O)—, or —(CH$_2$)$_m$—, in which m is 1, 2, 3, 4, or 5;

R$^4$ is hydrogen, aryl, —NH$_2$, —OH, —NH(R$^8$), —N(R$^8$)(R$^{10}$), —OR$^{11}$—N(R$^{12}$)$_2$, or —NHR$^{37}$;

R$^5$ is hydrogen, alkyl, aryl, heteroaryl, halo, —OH, —CF$_3$, —CH$_2$CF$_3$, —CF$_2$CF$_3$, —NH$_2$, —NHR$^{11}$, NR$^{11}$R$^{12}$, —NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;

R$^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or R$^5$ and R$^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{64}$;

R$^{64}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O—(alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

R$^7$ is halo, aryl, heteroaryl, heterocyclyl, bicyclic heterocycloalkyl, —NH(R$^{12}$), or —N(R$^{13}$)(R$^{14}$);

R$^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

R$^9$ and R$^{10}$ are independently methyl, ethyl, propyl, or iso-propyl, each of which is unsubstituted or substituted with one substituent selected from the group consisting of —OH and —O(alkyl); or R$^9$ and R$^{10}$ together are alkylene or heteroalkylene;

R$^{11}$ is alkyl, —(C$_1$-C$_4$-alkylene)-alkenyl, —(C$_1$-C$_4$-alkylene)-alkynyl, or alkyl substituted with one aryl substituent;

R$^{12}$ is alkyl, —NH$_2$, —NHR$^{6a}$, or alkyl substituted with one substituent selected from the group consisting of cycloalkenyl, aryl, heteroaryl, heterocyclyl, —NH$_2$, —N(R$^{15}$)(R$^{16}$), —NHC(=NH)NH$_2$, —OC(O)CF$_3$, —OH, —O-(alkyl), —S-(alkyl), and —C(O)NH$_2$;

R$^{13}$ and R$^{14}$ are independently alkyl or alkyl substituted with —N(CH$_3$)$_2$; or R$^{13}$ and R$^{14}$ together are alkylene;

R$^{15}$ and R$^{16}$ are independently alkyl or alkyl substituted with one substituent selected from the group consisting of —NH$_2$, —NH(alkyl), and —N(alkyl)$_2$;

R$^{30}$ is alkyl or alkyl substituted with one substituent selected from the group consisting of halo and —O(alkyl);

R$^{35}$, R$^{36}$, and R$^{37}$ are independently alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{40}$, cycloalkyl, —CO$_2$H, =O, —NH(C=NH)NHNO$_2$, and cycloalkyl substituted with —CH$_2$NH$_2$;

R$^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)NH$_2$, —O—(alkyl)-NR$^{70}$R$^{71}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

$R^{70}$ and $R^{71}$ are independently hydrogen, alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), $R^{80}$, cycloalkyl, —CO$_2$H, =O, —NH(C=NH)NHNO$_2$, and cycloalkyl substituted with —CH$_2$NH$_2$; and $R^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected $R^{5a}$ substituents, (b) alkyl substituted with one, two, three, four, or five independently selected $R^{20a}$ substituents, (c) —NH(alkyl), in which the alkyl part of the —NH(alkyl) is substituted with one, two, three, four, or five independently selected $R^{20a}$ substituents; and (d) —N($R^{35}$)-(alkyl), in which the alkyl part of the —N($R^{35}$)-(alkyl) is substituted with one, two, three, four or five independently selected $R^{20a}$ substituents;

in which $R^{5a}$ is alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{35}$)(R$^{36}$), C(O)R$^{35}$, —OC(O)OR$^{35}$, —OC(O)NH$_2$, —OC(O)NH(R$^{35}$)—OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), or $R^{81}$;

$R^{20A}$ is cycloalkyl, halo, —CN, —OH, —SH, =O, —OR$^{30}$, —SR$^{30}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —NHC(NH)NH$_2$, —NHC(NH)NHNO$_2$, —OC(O)NH(R$^{35}$), —OC(O)N(R$^{35}$)(R$^{36}$), —SO$_2$NH$_2$, —SO$_2$NH(R$^{35}$) —SO$_2$N(R$^{35}$)(R$^{36}$), —CH=CH$_2$, or $R^{72}$; and $R^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

In a preferred tenth embodiment, the bacterial growth is antibacterial-resistant bacterial growth.

In a another preferred tenth embodiment, the bacterial growth is quinolone-resistant bacterial growth.

In still another preferred tenth embodiment, the bacterial growth is bacterial growth in vitro.

In still yet another preferred tenth embodiment, the recipient is a fish or a mammal.

An eleventh embodiment of this invention is directed to a composition for the prophylaxis or treatment of antibacterial-resistant bacterial infection in a fish or a mammal, the composition comprising a therapeutically effective amount of compound having formula (I)

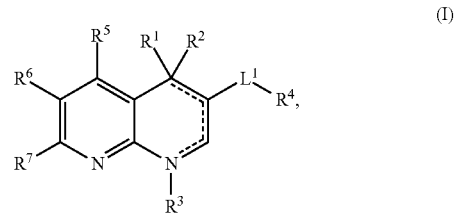

in which

--- is a single bond or a double bond;

one of $R^1$ and $R^2$ is absent or hydrogen and the other is hydrogen, —OH, —N(CH$_3$)$_2$, —NHR$^{12}$, or —NR$^{35}$R$^{12}$; or $R^1$ and $R^2$ together are =O;

$R^3$ is absent or is hydrogen, alkyl, —CH$_2$CF$_3$, —O—CH$_2$CH=CH$_2$, —CH=C=CH$_2$, —CH=C=CHR$^{40}$, —CH$_2$CH$_2$C(O)R$^{3a}$, or alkyl substituted with one $R^{3a}$ substituent;

$R^{3a}$ is bicyclic cycloalkyl, aryl, heteroaryl, heterocyclyl, benzofuranyl, benzodioxolyl, —NH$_2$, —NHR$^{35}$, —NR$^{35}$R$^{36}$, —C=CH, —C=CR$^{3B}$, —CH=C=CH$_2$, —C(O)(aryl), or —CH=C=CHR$^{3B}$;

$R^{3B}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3- triazolyl, pyridyl, quinolinyl, pyrazinyl, pyrimidinyl, cyclohexyl, pyrrolidinyl, pyrrolidinyl substituted with =O, uracilyl, imidazolidinyl, piperidinyl, piperazinyl, morpholinyl, thiomorpholinyl, or methyl optionally substituted with one, two or three independently selected substituents selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O— (alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

with the proviso that proper valencies are maintained for combinations of the forgoing variables;

L$^1$ is a covalent bond, —C(=O)—, or —(CH$_2$)$_m$—, in which m is 1, 2, 3, 4, or 5;

R$^4$ is hydrogen, aryl, —NH$_2$, —OH, —NH(R$^8$), —N(R$^9$)(R$^{10}$), —OR$^{11}$, —N(R$^{12}$)$_2$, or —NHR$^{37}$;

R$^5$ is hydrogen, alkyl, aryl, heteroaryl, halo, —OH, —CF$_3$, —CH$_2$CF$_3$, —CF$_2$CF$_3$, —NH$_2$, —NHR$^{11}$, —NR$^{11}$R$^{12}$, —NHC(O)R$^{11}$, —NR$^{11}$C(O)R$^{12}$, —NHS(O)$_2$R$^{11}$, —NR$^{11}$S(O)$_2$R$^{12}$, or —OR$^{11}$;

R$^6$ is hydrogen, halogen, alkyl, —N$_3$, —CN, —CH$_2$NH$_2$, —NO$_2$, —C(O)H, —C(O)R$^{35}$, —C≡CH, —C≡C-(alkyl), —C≡C-(aryl), —C≡C—CCl$_3$, —C≡C—CF$_3$, —CH=CH$_2$, or —OR$^{11}$; or R$^5$ and R$^6$ taken together are C$_2$-C$_5$-alkylene or C$_2$-C$_5$-heteroalkylene, each of which is unsubstituted or substituted with one, two, or three substituents independently selected from the group consisting of alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —O(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), and R$^{64}$;

R$^{64}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O-(alkyl)-NR$^{35}$R$^{36}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and phenyl substituted with alkyl;

R$^7$ is halo, aryl, heteroaryl, heterocyclyl, bicyclic heterocycloalkyl, —NH(R$^{12}$), or —N(R$^{13}$)(R$^{14}$);

R$^8$ is alkyl, cycloalkyl, aryl, heteroaryl, cycloalkyl fused with phenyl, or alkyl substituted with one or two substituents independently selected from the group consisting of aryl, heteroaryl, and —N(alkyl)$_2$;

R$^9$ and R$^{10}$ are independently methyl, ethyl, propyl, or iso-propyl, each of which is unsubstituted or substituted with one substituent selected from the group consisting of —OH and —O(alkyl); or R$^9$ and R$^{10}$ together are alkylene or heteroalkylene;

R$^{11}$ is alkyl, —(C$_1$-C$_4$-alkylene)-alkenyl, —(C$_1$-C$_4$-alkylene)-alkynyl, or alkyl substituted with one aryl substituent;

R$^{12}$ is alkyl, —NH$_2$, —NHR$^{6a}$, or alkyl substituted with one substituent selected from the group consisting of cycloalkenyl, aryl, heteroaryl, heterocyclyl, —NH$_2$, —N(R$^{15}$)(R$^{16}$), —NHC(=NH)NH$_2$, —OC(O)CF$_3$, —OH, —O-(alkyl), —S-(alkyl), and —C(O)NH$_2$;

R$^{13}$ and R$^{14}$ are independently alkyl or alkyl substituted with —N(CH$_3$)$_2$; or R$^{13}$ and R$^{14}$ together are alkylene;

R$^{15}$ and R$^{16}$ are independently alkyl or alkyl substituted with one substituent selected from the group consisting of —NH$_2$, —NH(alkyl), and —N(alkyl)$_2$;

R$^{30}$ is alkyl or alkyl substituted with one substituent selected from the group consisting of halo and —O(alkyl);

R$^{35}$, R$^{36}$, and R$^{37}$ are independently alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{40}$, cycloalkyl, —CO$_2$H, =O, —NH(C=NH)NHNO$_2$, and cycloalkyl substituted with —CH$_2$NH$_2$;

R$^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)NH$_2$, —O— (alkyl)-NR$^{70}$R$^{71}$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

R$^{70}$ and R$^{71}$ are independently hydrogen, alkyl, alkenyl, alkyl substituted with four or five hydroxyl substituents, or alkyl substituted with one, two, or three substituents independently selected from the group consisting of —NH(=NH)NH$_2$, —OH, —NH$_2$, —NH(alkyl), —N(alkyl)$_2$, —NH(CH$_2$(phenyl)), —S(alkyl), R$^{80}$, cycloalkyl, —CO$_2$H, =O, —NH(C=NH)NHNO$_2$, and cycloalkyl substituted with —CH$_2$NH$_2$; and R$^{80}$ is phenyl, naphthyl, furyl, thienyl, pyrrolyl, oxazolyl, thiazolyl, imidazolyl, pyrazolyl, isoxazolyl, isothiazolyl, 1,2, 3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O—(alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected $R^{5a}$ substituents, (b) alkyl substituted with one, two, three, four, or five independently selected $R^{20a}$ substituents, (c) —NH(alkyl), in which the alkyl part of the —NH(alkyl) is substituted with one, two, three, four, or five independently selected $R^{20a}$ substituents; and (d) —N($R^{35}$)-(alkyl), in which the alkyl part of the —N($R^{35}$)-(alkyl) is substituted with one, two, three, four or five independently selected $R^{20a}$ substituents;

in which $R^{5a}$ is alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)OR$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$, —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), or R$^{81}$;

$R^{20A}$ is cycloalkyl, halo, —CN, —OH, —SH, =O, —OR$^{30}$, —SR$^{30}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —NHC(NH)NH$_2$, —NHC(NH)NHNO$_2$, —OC(O)NH(R$^{35}$), —OC(O)N(R$^{35}$)(R$^{36}$), —SO$_2$NH$_2$, —SO$_2$NH(R$^{35}$)—SO$_2$N(R$^{35}$)(R$^{36}$), —CH=CH$_2$, or R$^{72}$; and $R^{81}$ is phenyl, naphthyl, furyl, thienyl, pyrrolyl, oxazolyl, thiazolyl, imidazolyl, pyrazolyl, isoxazolyl, isothiazolyl 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O-(alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

In a preferred eleventh embodiment, the antibacterial-resistant bacterial infection is quinolone-resistant bacterial infection.

DETAILED DESCRIPTION OF THE INVENTION

The compounds of the invention comprise a parent moiety and variable moieties, the latter of which are identified by a capital letter and accompanying numerical and/or alphabetical superscript, for which the following terms have the meanings indicated.

The term "alkenyl" means a monovalent, straight or branched hydrocarbon having two to eight carbon atoms and at least one carbon-carbon double bond.

The term "alkyl" means a monovalent, saturated, straight or branched hydrocarbon, having one to eight carbon The term "alkylene" means a divalent, saturated, straight or branched hydrocarbon, having one to eight carbon atoms.

The term "alkynyl" means a monovalent, straight or branched hydrocarbon having two to eight carbon atoms and at least one carbon-carbon triple bond.

The term "aryl" means phenyl which is unfused or fused with cycloalkyl, cycloalkenyl, heteroaryl, another phenyl, naphthyl, or the saturated part of indan.

The term "benzyl" means —CH$_2$-(phenyl).

The term "bicyclic cycloalkyl" means a monovalent five-, six-, seven-, or eight-membered carbocyclic ring having two non-adjacent carbon carbons connected by a covalent bond, —CH$_2$—, or —CH$_2$CH$_2$—;

The term "bicyclic heterocyclyl" means a monovalent six-membered ring having one or two nitrogen atoms and the remaining atoms are carbon, zero double bonds, and two non-adjacent carbons connected by a covalent bond or —CH$_2$—, attached through a carbon atom or nitrogen atom;

a monovalent or divalent, seven- or eight-membered ring with one, two, or three nitrogen atoms and the remaining atoms are carbon, zero or one double bonds, and two non-adjacent carbons connected by a covalent bond, attached through a carbon atom or nitrogen atom;

a monovalent seven- or eight-membered ring with one nitrogen atom and with or without an additional nitrogen, oxygen, or sulfur atom and the remaining atoms are carbon, zero double bonds, and two non-adjacent carbons connected by a covalent bond, attached through a carbon atom or a nitrogen atom; and a monovalent, nine-membered ring with one nitrogen atom or one nitrogen atom and an additional nitrogen, oxygen, or sulfur atom and with or without an additional nitrogen, oxygen, or sulfur atom and the remaining atoms are carbon, zero or one double bonds, and two non-adjacent carbons or a non-adjacent carbon and nitrogen atom connected by a covalent bond, attached through one or two atoms.

The term "cycloalkyl" means a monovalent, saturated cyclic hydrocarbon, having three to eight carbon atoms.

The term "halo" or "halogen" means fluoro (—F), chloro (—Cl), bromo (—Br), or iodo (—I).

The'term "heteroalkylene" means an alkylene of two to seven atoms, in which one, two, or three —CH$_2$— moieties have been independently replaced by a moiety independently selected from the group consisting of —B(alkyl)-, —NH—, —N(alkyl)-, —O—, —P(alkyl)-, —P(=O)(alkyl)-, —S—, —(C=O)—, —(S=O)—, and —SO$_2$—.

The term "heteroaryl" means a monovalent, aromatic, five-membered ring having two double bonds and one oxygen or one sulfur atom, one, two, three, or four nitrogen atoms, or one or two nitrogen atoms and one oxygen or one sulfur atom and the remaining atoms are carbon atoms, attached through a carbon atom or a nitrogen atom, and unfused or fused with a moiety selected from the group consisting of phenyl, cycloalkyl, cycloalkenyl, heterocycle, and another heteroaryl, and a monovalent aromatic, six-membered ring having three double bonds and one, two, or three nitrogen atoms and the remaining atoms are carbon atoms, attached through a carbon atom and unfused or fused with phenyl, cycloalkyl, cycloalkenyl, heterocycle, or another heteroaryl.

The term "heterocyclyl" means a monovalent, non-aromatic three- or four-membered ring having one nitrogen, oxygen, or sulfur atom and the remaining atoms are carbon atoms, zero double bonds, attached through a carbon atom or a nitrogen atom, and unfused or fused with phenyl or heteroaryl; a monovalent, non-aromatic five-membered ring having one or two nitrogen, oxygen, or sulfur atoms and the remaining atoms are carbon atoms, and zero or one double bonds, attached through a carbon or nitrogen atom, and unfused or fused with phenyl or heteroaryl; and a monovalent, non-aromatic six or seven-membered ring having one, two, or three nitrogen, oxygen, or sulfur atoms and the remaining atoms are carbon, and zero, one, or two double bonds, attached through a carbon or a nitrogen atom, and unfused or fused with phenyl or heteroaryl.

In a preferred embodiment for the practice of this invention, R$^1$ is absent and R$^2$ is 3-(aminomethyl)-benzylamino, 2-(guanidinyl)ethylamino, or N-methyl-(2-(dimethylamino)ethyl)amino; or R$^1$ and R$^2$ together are =O.

In another preferred embodiment for the practice of this invention, R$^3$ is hydrogen, ((1R,2S,5R)-6,6-dimethylbicyclo (3.1.1)hept-2-yl)methyl, (5-methylpyrazin-2-yl)methyl, 1,3-benzodioxol-5-ylmethyl, 2-(2,5-dimethoxyphenyl)ethyl, 2-(2-fluorophenyl)ethyl, 2-(3-methoxyphenyl)ethyl, 2-(4-(aminosulfonyl)phenyl)ethyl, 2-(4-hydroxyphenyl)ethyl, 2-(4-methoxyphenyl)ethyl, 2-(methylthio)benzyl, 2,2,2-trifluoroethyl, 2,3-dihydro-1-benzofuran-5-ylmethyl, 2,3-dimethoxybenzyl, 2,4-dimethoxybenzyl, 2-methoxybenzyl, 2-pyridin-2-ylethyl, 2-pyridin-4-ylethyl, 3-(aminomethyl) benzyl, 3,4,5-trimethoxybenzyl, 3,4-dimethoxybenzyl, 3,5-dimethoxybenzyl, 3-aminobenzyl, 3-aminopyrrolidin-1-yl, 3-oxo-3-phenylpropyl, 3-phenylprop-2-ynyl, 3-phenylpropyl, 3-pyridin-4-ylprop-2-ynyl, 4-(dihydroxyboryl)benzyl, 4-(dimethylamino)benzyl, 4-(methylthio)benzyl, 3-amino propyl, 4-aminobutyl, 4-carboxybenzyl, 4-methoxybenzyl, 5-aminopentyl, benzyl, piperidin-3-ylmethyl, piperidin-4-ylmethyl, propa-1,2-dienyl, pyridin-2-ylmethyl, pyridin-3-ylmethyl, —O-allyl, —CH$_2$—C≡CH, —(CH$_2$)$_4$N(CH$_3$)$_2$, or pyridin-4-ylmethyl.

In still another preferred embodiment for the practice of this invention, -L$^1$-R$^4$ is ((1,2-diphenylethyl)amino)methyl, ((2,4-difluorobenzyl)amino)methyl, ((3-(diethylamino)propyl)amino)methyl, ((3,4-difluorobenzyl)amino)methyl, ((3-phenylpropyl)amino)methyl, (1,2,3,4-tetrahydronaphthalen-1-ylamino)methyl, (2,5-dimethyl-pyrrolidin-1-yl)carbonyl, (morpholin-4-yl)carbonyl, (pyrrolidin-1-yl)carbonyl, (thiomorpholin-4-yl)carbonyl, carbamoyl, carboxy, ethoxycarbonyl, hydrogen, N-(2-(methylthio)ethyl)carbamoyl, N-(2-isopropoxyethyl)carbamoyl, N-(2-methoxyethyl)-N-(methyl)-carbamoyl, N-(isopentyl)carbamoyl, N-(isopropyl)-N-(methyl)-carbamoyl, N-(pyridin-2-yl)carbamoyl, N'-(trifluoroacetyl)hydrazinocarbonyl, N,N-bis(2-methoxyethyl)-carbamoyl, N-phenylcarbamoyl, or phenylcarbonyl.

In still yet another preferred embodiment for the practice of this invention, R$^5$ is hydrogen, methyl, ethyl, trifluoromethyl, or iodo, and R$^6$ moiety is hydrogen, fluoro, bromo, chloro, —CN, methyl, phenylethynyl, prop-1-ynyl, —O(CH$_2$—(phenyl)), aminomethyl, or —(O)CH$_3$; or R$^5$ and R$^6$ together are C$_2$-C$_4$-alkylene or C$_2$-C$_4$-heteroalkylene.

In still even yet another preferred embodiment for the practice of this invention, R$^7$ is (1R,5R)-3-((benzyloxy)carbonyl)-3,6-diazabicyclo(3.2.0)hept-6-yl, (1R,5S)-6-amino-3-azabicyclo(3.1.0)hex-3-yl, (1S,4S)-2,5-diazabicyclo (2.2.1)hept-2-yl, (2-(dimethylamino)ethyl)(ethyl)amino, (2-aminoethyl)amino, (3-((3-aminopropyl)(methyl)amino) propyl)amino, (3-((trifluoroacetyl)oxy)propyl)amino, (3-(4-(3-aminopropyl)piperazin-1-yl)propyl)amino, (3-aminopropyl)amino, (3aS,6aS)-hexahydropyrrolo[3,4-c]pyrrol-5 (1H)-yl, (3aS,6aS)-1-benzylhexahydropyrrolo[3,4-b]pyrrol-5(1H)-yl, (3-pyrrolidin-1-ylpropyl)amino, (3R)-3-aminopyrrolidin-1-yl, (3R)-3-hydroxypyrrolidin-1-yl, (3R, 4R)-3-(benzylamino)-4-hydroxypyrrolidin-1-yl, (3R,4R)-3-amino-4-hydroxypyrrolidin-1-yl, (3R,4S)-3-(benzylamino)-4-hydroxypyrrolidin-1-yl, (3R,4S)-3-amino-4-hydroxypyrrolidin-1-yl, (3S)-3-aminopyrrolidin-1-yl, (4-aminobutyl)amino, (4aS,7aS)-octahydro-6H-pyrrolo[3,4-b]pyridin-6-yl, 2-furyl, 3-(((1R)-2-hydroxy-1-phenylethyl) amino)pyrrolidin-1-yl, 3-(((1S)-2-hydroxy-1-(1H-imidazol-4-ylmethyl)ethyl)amino)pyrrolidin-1-yl, 3-(((1S)-2-hydroxy-1-phenylethyl)amino)pyrrolidin-1-yl, 3-(((2,6-dioxo-1,2,3,6-tetrahydropyrimidin-4-yl)methyl)amino) pyrrolidin-1-yl, 3-(((3-(aminomethyl)cyclohexyl)methyl) amino)pyrrolidin-1-yl, 3-(((3-methylthien-2-yl)methyl) amino)pyrrolidin-1-yl, 3-(((5-methylthien-2-yl)methyl) amino)pyrrolidin-1-yl, 3-((1,2-dideoxy-D-arabino-hexitolyl)amino)pyrrolidin-1-yl, 3-((1,2-dideoxy-D-erythro-pentitoyl)amino)pyrrolidin-1-yl, 3-((1,2-dideoxy-D-ribo-hexitolyl)aminopyrrolidin-1-yl, 3-((1,6-dideoxy-D-galactitolyl)amino)pyrrolidin-1-yl, 3-((1-benzylpiperidin-4-yl)amino)pyrrolidin-1-yl, 3-((1-deoxy-D-galactitolyl) amino)pyrrolidin-1-yl, 3-((1-deoxy-D-mannitolyl)amino) pyrrolidin-1-yl, 3-((1-deoxy-D-ribitolyl)amino)pyrrolidin-1-yl, 3-((1-deoxy-D-xylitolyl)amino)pyrrolidin-1-yl, 3-((1-deoxy-L-arabinitolyl)amino)pyrrolidin-1-yl, 3-((1-deoxy-L-mannitolyl)amino)pyrrolidin-1-yl, 3-((1H-imidazol-2-ylmethyl)amino)pyrrolidin-1-yl, 3-((1H-imidazol-2-ylmethyl)amino)pyrrolidin-1-yl, 3-((1H-imidazol-4-ylmethyl)amino)pyrrolidin-1-yl, 3-((1H-pyrazol-5-ylmethyl)amino)pyrrolidin-1-yl, 3-((1-methyl-1-phenylethyl)amino)pyrrolidin-1-yl, 3-((1-phenylethyl) amino)pyrrolidin-1-yl, 3-((1-phenylethyl)amino)pyrrolidin-1-yl, 3-((1-thien-2-ylethyl)amino)pyrrolidin-1-yl, 3-((2-((amino(imino)methyl)amino)ethyl)amino)pyrrolidin-1-yl, 3-((2-(1H-imidazol-5-yl)ethyl)amino)pyrrolidin-1-yl, 3-((2-(1H-imidazol-5-yl)ethyl)amino)pyrrolidin-1-yl, 3-((2-(dimethylamino)ethyl)amino)pyrrolidin-1-yl, 3-((2,3-dihydroxypropyl)amino)pyrrolidin-1-yl, 3-((2,4-difluorobenzyl) amino)pyrrolidin-1-yl, 3-((2,6-difluorobenzyl)amino) pyrrolidin-1-yl, 3-((2-aminoethyl)amino)pyrrolidin-1-yl, 3-((2-carboxy-2-(1H-imidazol-4-yl)ethyl)amino)pyrrolidin- 1-yl, 3-((2-ethylbutyl)amino)pyrrolidin-1-yl, 3-((2-furylmethyl)amino)pyrrolidin-1-yl, 3-((2-methoxyethyl)amino)pyrrolidin-1-yl, 3-((2-pyridin-4-ylethyl)amino)pyrrolidin-1-yl, 3-((2-pyrrolidin-1-ylethyl)amino)pyrrolidin-1-yl, 3-((3-((amino(imino)methyl)amino)propyl)amino)pyrrolidin-1-yl, 3-((3-(1H-imidazol-1-yl)propyl)amino)pyrrolidin-1-yl, 3-((3-(1H-imidazol-1-yl)propyl)amino)pyrrolidin-1-yl, 3-((3-(2-oxopyrrolidin-1-yl)propyl)amino)pyrrolidin-1-yl, 3-((3-(2-oxopyrrolidin-1-yl)propyl)amino)pyrrolidin-1-yl, 3-((3-(aminomethyl)benzyl)amino)pyrrolidin-1-yl, 3-((3-(benzylamino)-2-hydroxypropyl)amino)pyrrolidin-1-yl, 3-((3-(methylthio)propyl)amino)pyrrolidin-1-yl, 3-((3,5-difluorobenzyl)amino)pyrrolidin-1-yl, 3-((3-amino-2-hydroxypropyl)amino)pyrrolidin-1-yl, 3-((3-fluoro-4-methoxybenzyl)amino)pyrrolidin-1-yl, 3-((3-hydroxybenzyl)amino)pyrrolidin-1-yl, 3-((3-methoxybenzyl)amino)pyrrolidin-1-yl, 3-((3-pyridin-4-ylbenzyl)amino)pyrrolidin-1-yl, 3-((4-((amino(imino)methyl)amino)butyl)amino)pyrrolidin-1-yl, 3-((4-(3-(dimethylamino)propoxy)benzyl)amino)pyrrolidin-1-yl, 3-((4-(acetylamino)benzyl)amino)pyrrolidin-1-yl, 3-((4-(aminomethyl)benzyl)amino)pyrrolidin-1-yl, 3-((4-(aminosulfonyl)benzyl)amino)pyrrolidin-1-yl, 3-((4-amino-4-carboxy-butyl)amino)pyrrolidin-1-yl, 3-((4-aminobenzyl)amino)pyrrolidin-1-yl, 3-((4-aminobutyl)amino)pyrrolidin-1-yl, 3-((4-hydroxybenzyl)amino)pyrrolidin-1-yl, 3-((4-hydroxybutyl)amino)pyrrolidin-1-yl, 3-((5-((amino(imino)methyl)amino)pentyl)amino)pyrrolidin-1-yl, 3-((5,6-dideoxy-D-arabino-hexitolyl)amino)pyrrolidin-1-yl, 3-((5-amino-3-oxopentyl)amino)pyrrolidin-1-yl, 3-((5-deoxy-D-ribitolyl)amino)pyrrolidin-1-yl, 3-((amino(imino)methyl)amino)pyrrolidin-1-yl, 3-((cyclopropylmethyl)amino)pyrrolidin-1-yl, 3-((piperidin-4-ylmethyl)amino)pyrrolidin-1-yl, 3-((pyridin-3-ylmethyl)amino)pyrrolidin-1-yl, 3-((quinolin-2-ylmethyl)amino)pyrrolidin-1-yl, 3-((thien-2-ylmethyl)amino)pyrrolidin-1-yl, 3-((thien-3-ylmethyl)amino)pyrrolidin-1-yl, 3-(2-(aminocarbonyl)ethylamino)pyrrolidin-1-yl, 3-(allylamino)pyrrolidin-1-yl, 3-(aminomethyl)pyrrolidin-1-yl, 3-(benzyl(2-(dimethylamino)ethyl)amino)pyrrolidin-1-yl, 3-(benzylamino)pyrrolidin-1-yl, 3-(bis(2-hydroxyethyl)amino)pyrrolidin-1-yl, 3-(dimethylamino)pyrrolidin-1-yl, 3-(methylamino)pyrrolidin-1-yl, 3-aminoazetidin-1-yl, 3-aminopyrrolidin-1-yl, 3-fluorophenyl, 3-fluoropyrrolidin-1-yl, 3-hydroxyazetidin-1-yl, 3-pyridin-2-ylpyrrolidin-1-yl, 3-pyridin-3-ylpyrrolidin-1-yl, 4-(methylamino)hexahydrocyclopenta(c)pyrrol-2(1H)-yl, 4-aminopiperidin-1-yl, 4-ethylpiperazin-1-yl, 4-methylpiperazin-1-yl, azetidin-1-yl, chloro, dimethylamino, phenyl, piperazin-1-yl, pyrrolidin-1-yl, or thien-2-yl.

These preferred embodiments may combine to form the following preferred first, sixth, seventh, eighth, ninth, and tenth embodiments of this invention:

A compound of the first, sixth, seventh, eighth, ninth, or tenth embodiment in which $\equiv\equiv\equiv$ is a single bond or a double bond;

one of $R^1$ and $R^2$ is absent or hydrogen and the other is —$N(CH_3)_2$, —$NHR^{12}$, or —$N(alkyl)(R^{12})$, in which $R^{12}$ is alkyl substituted with one substituent selected from the group consisting of —$NH_2$, —NH(alkyl), —$N(alkyl)_2$, —NH(C=NH)$NH_2$, and phenyl which is unsubstituted or substituted with alkyl which is unsubstituted substituted with a substituent selected from the group consisting of —$NH_2$, —NH(alkyl), and —$N(alkyl)_2$; or $R^1$ and $R^2$ together are =O;

$R^3$ is absent or is hydrogen, alkyl, —$CH_2CF_3$, —O—$CH_2CH$=$CH_2$, —CH=C=$CH_2$, or alkyl substituted with one $R^{3a}$ substituent;

$R^{3a}$ is pyridinyl, pyrrolidinyl, piperidinyl, morpholinyl, thiomorpholinyl, 2,3-dihydrobenzofuranyl, benzodioxolyl, —$NH_2$, —C≡$CR^{3B}$, —C(O)(phenyl), aryl, or bicyclic cycloalkyl, in which the bicyclic cycloalkyl is a five-, six-, seven-, or eight-membered, saturated carbocyclic ring having two non-adjacent carbon atoms connected by a —$CH_2$— or —$CH_2CH_2$— bridge and is unsubstituted or substituted with one, two, or three substituents independently selected from the group consisting of alkyl, halo, —CN, —OH, =O, —$CF_3$, and —$NH_2$, and the aryl is phenyl which is unsubstituted or substituted with one, two, or three substituents independently selected from the group consisting of alkyl, halo, —CN, —OH, —$NH_2$, —NH(alkyl), —$N(alkyl)_2$, —$NO_2$, —$B(OH)_2$, —$CO_2H$, —$CF_3$, —$CH_2CF_3$—$CF_2CF_3$, —$OCF_3$, —$OCH_2CF_3$, —$OCF_2CF_3$, —O(alkyl), —S(alkyl), —C(O)$NH_2$, and alkyl substituted with one or two substituents independently selected from the group consisting of halo, —CN, —OH, —$NH_2$, —NH(alkyl), —N(alkyl)$_2$, —C(O)$NH_2$, —$SO_2NH_2$, —$SO_2$NH(alkyl), and —$SO_2N(alkyl)_2$, and $R^{3B}$ is phenyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, pyrazinyl, or pyrimidinyl, each of which is unsubstituted or substituted with one, two, or three substituents independently selected from the group consisting of alkyl, halo, —CN, —OH, —$NO_2$, —$CF_3$, —$CH_2CF_3$, —$CF_2CF_3$, —O(alkyl), —S(alkyl), —$OCF_3$, —$OCH_2CF_3$, —$OCF_2CF_3$, —$NH_2$, —NH(alkyl), —$N(alkyl)_2$, —C(O)$NH_2$, —$SO_2NH_2$, —$SO_2$NH(alkyl), and —$SO_2N(alkyl)_2$;

with the proviso that proper valencies are maintained for combinations of the foregoing variables;

$L^1$ is a covalent bond or —C(=O)—;

$R^4$ is hydrogen, —OH, —O(alkyl), phenyl, —$NH_2$, —NH($R^8$), or —N($R^9$)($R^{10}$), in which $R^8$ is alkyl, phenyl, pyridyl, —NHC(O)$CF_3$, cycloalkyl fused with phenyl, alkyl substituted with one or two substituents independently selected from the group consisting of —S(alkyl), —O(alkyl), —N(alkyl)$_2$, and phenyl which is unsubstituted or substituted with one or two independently selected halo substituents, and in which $R^9$ and $R^{10}$ are independently alkyl or alkyl substituted with —O(alkyl); or $R^9$ and $R^{10}$ are taken together and are morpholinyl, thiomorpholinyl, pyrrolidinyl, or pyrrolidinyl substituted with two alkyl substituents;

$R^5$ is hydrogen, alkyl, aryl, heteroaryl, halo, —OH, —$CF_3$, —$CH_2CF_3$, —$CF_2CF_3$, —$NH_2$, —$NHR^{11}$, —$NR^{11}R^{12}$, —NHC(O)$R^{11}$, —$NR^{11}C(O)R^{12}$, —NHS(O)$NR^{11}S(O)_2R^{12}$, or —O(alkyl);

$R^6$ is hydrogen, halogen, alkyl, —$N_3$, —CN, —$CH_2NH_2$, —$NO_2$, —C(O)H, —C(O)(alkyl), —CH=$CH_2$—C≡CH, —C≡C-(alkyl), —C≡C-(phenyl), or —$OR^{11}$, in which $R^{11}$ is alkyl or alkyl substituted with phenyl; or $R^5$ and $R^6$ taken together are $C_3$-$C_4$-alkylene or $C_3$-$C_4$-heteroalkylene, both of which are unsubstituted or substituted with one or two substituents independently selected from the group consisting of alkyl, halo, —CN, —OH, —$NH_2$, =O, —$CF_3$, —O(alkyl), and —C(O)$NH_2$;

$R^7$ is halo, aryl, heteroaryl, heterocyclyl, bicyclic heterocyclyl, NH($R^{12}$), or N($R^{13}$)($R^{14}$), in which the aryl is phenyl which is unsubstituted or substituted with one, two, or three halo substituents, the heteroaryl is furyl or thienyl, the heterocyclyl is azetidinyl, pyrrolidinyl, piperidinyl, or piperazinyl, each of which is unsubstituted or substituted with one substituent selected from the group consisting of halo, —NH(=NH)$NH_2$, —OH, —$NH_2$, —NH($R^{35}$) and —NH($R^{35}$)($R^{36}$), in which the $R^{35}$ part of the —NH($R^{35}$) is (a) $C_1$-$C_3$-alkyl, (b) $C_3$-alkenyl, (c) $C_5$-$C_6$-alkyl substituted with four or five hydroxyl substituents, (d) $C_1$-$C_5$-alkyl substituted with one or two substituents independently selected from the group consisting of —NH(=NH)NH$_2$, —OH, —O($C_1$-alkyl), —NH$_2$, —NH(alkyl), —N(alkyl)$_2$, phenyl, —NH(CH$_2$-phenyl), —S(alkyl), imidazolyl, pyridyl, thienyl, pyrazolyl, uracilyl, quinolinyl, pyrrolidinyl which is unsubstituted or substituted with =O, piperidinyl which is unsubstituted or substituted with —CH$_2$-(phenyl), cycloalkyl, —CO$_2$H, =O, and —NH(C=NH)NHNO$_2$, and cycloalkyl substituted with —CH$_2$NH$_2$, and (e) methyl substituted with phenyl, in which the phenyl is substituted with one or two substituents independently selected from the group consisting of —CH$_2$NH$_2$, —OH, —O(alkyl), —NH$_2$, —NH(alkyl), —N(alkyl)$_2$, halo, —O(alkyl), —O(alkylene)-NH$_2$, —O(alkylene)-NH(alkyl), —O(alkylene)-N(alkyl)$_2$, —SO$_2$NH$_2$, pyridyl, and —NHC(O)(alkyl), and in which the $R^{35}$ and $R^{36}$ of the —N($R^{35}$)($R^{36}$) are independently alkyl or alkyl substituted with one substituent selected from the group consisting of phenyl, —OH and —N(alkyl)$_2$;

the bicyclic heterocyclyl is six-membered with one or two nitrogen atoms and two non-adjacent carbons attached by a covalent bond or —CH$_2$—, seven-membered with two nitrogen atoms, eight-membered with 1 nitrogen atom and zero double bonds, eight-membered with two nitrogen atoms, or nine-membered with two nitrogen atoms and zero double bonds, in which each bicyclic heterocyclyl is unsubstituted or substituted with a substituent selected from the group consisting of —NH$_2$, —NH($R^{35}$), and —C(O)O$R^{35}$, in which the $R^{35}$ of the —NH($R^{35}$) and —C(O)O$R^{35}$ is alkyl or alkyl substituted with phenyl;

$R^{12}$ is alkyl substituted with a substituent selected from the group consisting of heterocyclyl, —NH$_2$, —N($R^{15}$)($R^{16}$), and —OC(O)CF$_3$, in which the heterocyclyl is piperazinyl or pyrrolidinyl, each of which is unsubstituted or substituted with alkyl substituted with —NH$_2$;

$R^{13}$ and $R^{14}$ are independently alkyl or alkyl substituted with —N(alkyl)$_2$; and $R^{15}$ and $R^{16}$ are independently alkyl or alkyl substituted with —NH$_2$.

A compound of the first, sixth, seventh, eighth, ninth, or tenth embodiment in which ---is a single bond or a double bond;

one of $R^1$ and $R^2$ is absent or hydrogen and the other is —N(CH$_3$)$_2$, —NHR$^{12}$, or —N (alkyl)($R^{12}$), in which $R^{12}$ is alkyl substituted with one substituent selected from the group consisting of —N(alkyl)$_2$, —NH(C=NH)NH$_2$, and phenyl substituted with alkyl substituted with —NH$_2$; or $R^1$ and $R^2$ together are =O;

$R^3$ is absent or is hydrogen, —CH$_2$CF$_3$, —CH=C=CH$_2$, or alkyl optionally substituted with $R^{3a}$;

$R^{3a}$ is pyridinyl, piperidinyl, 2,3-dihydrobenzofuranyl, benzodioxolyl, —N(alkyl)(alkyl), —NH$_2$, —C≡CR$^{3B}$, —C(O) (phenyl), aryl, or bicyclic cycloalkyl, in which the bicyclic cycloalkyl is a six-membered, saturated carbocyclic ring having two non-adjacent carbon atoms connected by a —CH$_2$— bridge and is substituted with two independently selected alkyl substituents, and the aryl is phenyl which is unsubstituted or substituted with one, two, or three substituents independently selected from the group consisting of halo, —OH, —NH$_2$, —N(alkyl)$_2$, —B(OH)$_2$, —CO$_2$H, —O(alkyl), —S(alkyl), and alkyl substituted with one substituent selected from the group consisting of —NH$_2$ and —SO$_2$NH$_2$, and $R^{3B}$ is phenyl or pyridyl;

with the proviso that proper valencies are maintained for combinations of the foregoing variables;

$L^1$ is a covalent bond or —C(=O)—;

$R^4$ is hydrogen, —OH, —O(alkyl), phenyl, —NH$_2$, —NH($R^8$), —N($R^9$)($R^{10}$), in which $R^8$ is alkyl, phenyl, pyridyl, —NHC(O)CF$_3$, cycloalkyl fused with phenyl, alkyl substituted with one or two substituents independently selected from the group consisting of —S(alkyl), —O(alkyl), —N(alkyl)$_2$, and phenyl which is unsubstituted or substituted with one or two independently selected halo substituents, and in which $R^9$ and $R^{10}$ are independently alkyl or alkyl substituted with —O(alkyl); or $R^9$ and $R^{10}$ are taken together and are morpholinyl, thiomorpholinyl, pyrrolidinyl, or pyrrolidinyl substituted with two alkyl substituents;

$R^5$ is hydrogen, alkyl, aryl, halogen, or —CF$_3$;

$R^6$ is hydrogen, halogen, alkyl, —N$_3$, —CN, —CH$_2$NH$_2$, —C(O)(alkyl), —C≡C-(alkyl), —C≡C-(phenyl), or —O-alkylene-phenyl; or $R^5$ and $R^6$ taken together are $C_3$-$C_4$-alkylene or $C_3$-$C_4$-heteroalkylene;

$R^7$ is halo, aryl, heteroaryl, heterocyclyl, bicyclic heterocyclyl, NH($R^{12}$), or N($R^{13}$)($R^{14}$), in which the aryl is phenyl which is unsubstituted or substituted with one halo substituent, the heteroaryl is furyl or thienyl, the heterocyclyl is azetidinyl, pyrrolidinyl, piperidinyl, or piperazinyl, each of which is unsubstituted or substituted with one substituent selected from the group consisting of halo, —NH(=NH)NH$_2$, —OH, —NH$_2$, —NH($R^{35}$), and —NH($R^{35}$)($R^{36}$), in which the $R^{35}$ is (a) alkyl, (b) alkyl substituted with four or five hydroxyl substituents, (c) alkyl substituted with one or two substituents independently selected from the group consisting of —NH(=NH)NH$_2$, —OH, —O(alkyl), —NH$_2$, phenyl, —NH(CH$_2$-phenyl), —S(alkyl), imidazolyl, pyridyl, thienyl, pyrazolyl, uracilyl, quinolinyl, pyrrolyl which is unsubstituted or substituted with =O, piperidinyl which is unsubstituted or substituted with —CH$_2$-phenyl, cycloalkyl, cycloalkyl substituted with —CH$_2$NH$_2$, —CO$_2$H, =O, and —NH(C=NH)NHNO$_2$, (d) alkenyl, and (e) alkyl substituted with phenyl in which the phenyl is substituted with one or two substituents independently selected from the group consisting of —CH$_2$NH$_2$, —OH, —O(alkyl), —NH$_2$, halo, —O(alkyl), —O(alkylene)-N(alkyl)$_2$, pyridyl, and —NHC(O)(alkyl), in which the $R^{35}$ and $R^{36}$ of the —N($R^{35}$)($R^{36}$) are independently alkyl, alkyl substituted with phenyl, or alkyl substituted with a substituent selected from the group consisting of —N(alkyl)$_2$ and —OH;

the bicyclic heterocyclyl is six-membered with one or two nitrogen atoms and two non-adjacent carbons attached by a covalent bond or CH$_2$, seven-membered with two nitrogen atoms, eight-membered with 1 nitrogen atom and zero double bonds, eight-membered with two nitrogen atoms, or nine-membered with two nitrogen atoms and zero double bonds, each of which is unsubstituted or substituted with a substituent selected from the group consisting of —NH$_2$, —NH($R^{35}$), and —C(O)O$R^{35}$, in which the $R^{35}$ of the —NH($R^{35}$) and —C(O)O$R^{35}$ is alkyl or alkyl substituted with phenyl;

$R^{12}$ is alkyl substituted with a substituent selected from the group consisting of heterocyclyl, —NH$_2$, —N($R^{15}$)($R^{16}$), and —OC(O)CF$_3$, in which the heterocyclyl is piperazinyl or pyrrolidinyl, each of which is unsubstituted or substituted with alkyl substituted with —NH$_2$;

$R^{13}$ and $R^{14}$ are independently alkyl or alkyl substituted with —N(alkyl)$_2$; and $R^{15}$ and $R^{16}$ are independently alkyl or alkyl substituted with —NH$_2$.

A compound of the first, sixth, seventh, eighth, ninth, or tenth embodiment in which --- is a single bond or a double bond;

one of $R^1$ and $R^2$ is absent or hydrogen and the other is —N(CH$_3$)$_2$, —NHR$^{12}$, or —N(alkyl)(R$^{12}$), in which R$^{12}$ is alkyl substituted with one substituent selected from the group consisting of —N(alkyl)$_2$, —NH(C=NH)NH$_2$, and phenyl substituted with alkyl substituted with —NH$_2$; or $R^1$ and $R^2$ together are =O;

$R^3$ is absent or is hydrogen, —CH$_2$CF$_3$, —CH=C=CH$_2$, or alkyl optionally substituted with $R^{3a}$;

$R^{3a}$ is pyridinyl, piperidinyl, 2,3-dihydrobenzofuranyl, benzodioxolyl, —N(alkyl)(alkyl), —NH$_2$, —C≡CR$^{3B}$, —C(O)(phenyl), aryl, or bicyclic cycloalkyl, in which the bicyclic cycloalkyl is a six-membered, saturated carbocyclic ring having two non-adjacent carbon atoms connected by a —CH$_2$— bridge and is substituted with two independently selected C$_1$-alkyl substituents, and the aryl is phenyl which is unsubstituted or substituted with one, two, or three substituents independently selected from the group consisting of halo, —OH, —NH$_2$, —N(alkyl)$_2$, —B(OH)$_2$, —CO$_2$H, —O(alkyl), —S(alkyl), and alkyl substituted with one substituent selected from the group consisting of —NH$_2$ and —SO$_2$NH$_2$, and R$^{3B}$ is phenyl or pyridyl;

with the proviso that proper valencies are maintained for combinations of the foregoing variables;

$L^1$ is a covalent bond or —C(=O)—;

$R^4$ is hydrogen, —OH, —O(alkyl), phenyl, —NH$_2$, —NH(R$^8$), —N(R$^9$)(R$^{10}$), in which R$^8$ is alkyl, phenyl, pyridyl, —NHC(O)CF$_3$, cycloalkyl fused with phenyl, alkyl substituted with one or two substituents independently selected from the group consisting of —S(alkyl), —O(alkyl), —N(alkyl)$_2$, and phenyl which is unsubstituted or substituted with one or two independently selected halo substituents, and in which R$^9$ and R$^{10}$ are independently alkyl or alkyl substituted with —O(alkyl); or R$^9$ and R$^{10}$ are taken together and are morpholinyl, thiomorpholinyl, pyrrolidinyl, or pyrrolidinyl substituted with two alkyl substituents;

$R^5$ is hydrogen, alkyl, aryl, halogen, or —CF$_3$;

$R^6$ is hydrogen, halogen, alkyl, —N$_3$, —CN, —CH$_2$NH$_2$, —C(O)(alkyl), —C≡C-(alkyl), —C≡C-(phenyl), or —OR$^{11}$, in which R$^{11}$ is alkyl substituted with phenyl; or $R^5$ and $R^6$ taken together are C$_2$-C$_5$-alkylene or C$_2$-C$_5$-heteroalkylene;

$R^7$ is halo, aryl, heteroaryl, heterocyclyl, bicyclic heterocyclyl, NH(R$^{12}$), or N(R$^{13}$)(R$^{14}$), in which the aryl is phenyl which is unsubstituted or substituted with one halo substituent, the heteroaryl is furyl or thienyl, the heterocyclyl is azetidinyl, pyrrolidinyl, piperidinyl, or piperazinyl, each of which is unsubstituted or substituted with one substituent selected from the group consisting of halo, —NH(=NH)NH$_2$, —OH, —NH$_2$, —NH(R$^{35}$), and —NH(R$^{35}$)(R$^{36}$), in which the R$^{35}$ is (a) C$_1$-C$_3$-alkyl, (b) C$_5$-C$_6$-alkyl substituted with four or five hydroxyl substituents, (c) C$_1$-C$_5$-alkyl substituted with one or two substituents independently selected from the group consisting of —NH(=NH)NH$_2$, —OH, —O(C$_1$-alkyl), —NH$_2$, phenyl, —NHC(H$_2$—(phenyl)), —S(C$_1$-alkyl), imidazolyl, pyridyl, thienyl, pyrazolyl, uracilyl, quinolinyl, pyrrolyl which is unsubstituted or substituted with =O, piperidinyl which is unsubstituted or substituted with —CH$_2$-phenyl, C$_3$-C$_6$-cycloalkyl, C$_6$-cycloalkyl substituted with —CH$_2$NH$_2$, —CO$_2$H, =O, and —NH(C=NH)NHNO$_2$, (d) C$_3$-alkenyl, and (e) C$_1$-alkyl substituted with phenyl in which the phenyl is substituted with one or two substituents independently selected from the group consisting of —CH$_2$NH$_2$, —OH, —O(C$_1$-alkyl), —NH$_2$, halo, —O(C$_1$-alkyl), —O(alkylene)-N(C$_1$-alkyl), pyridyl, and —NHC(O)(C$_1$-alkyl), in which the R$^{35}$ and R$^{36}$ of the —N(R$^{35}$)(R$^{36}$) are independently C$_1$-alkyl, C$_1$-alkyl substituted with phenyl, or C$_2$-alkyl substituted with a substituent selected from the group consisting of —N(C$_1$-alkyl)$_2$ and —OH;

the bicyclic heterocyclyl is six-membered with one or two nitrogen atoms and two non-adjacent carbons attached by a covalent bond or —CH$_2$—, seven-membered with two nitrogen atoms, eight-membered with 1 nitrogen atom and zero double bonds, eight-membered with two nitrogen atoms, or nine-membered with two nitrogen atoms and zero double bonds, each of which is unsubstituted or substituted with a substituent selected from the group consisting of —NH$_2$, —NH(R$^{35}$), and —C(O)OR$^{35i}$, in which the R$^{35}$ of the —NH(R$^{35}$) and —C(O)OR$^{35}$ is alkyl or C$_1$-alkyl substituted with phenyl;

$R^{12}$ is C$_3$-alkyl substituted with a substituent selected from the group consisting of heterocyclyl, —NH$_2$, —N(R$^{15}$)(R$^{16}$), and —OC(O)CF$_3$, in which the heterocyclyl is piperazinyl or pyrrolidinyl, each of which is unsubstituted or substituted with alkyl substituted with —NH$_2$;

$R^{13}$ and $R^{14}$ are independently C$_1$-alkyl or C$_2$-alkyl substituted with —N(C$_1$-alkyl)$_2$; and $R^{15}$ and $R^{16}$ are independently C$_1$-C$_2$-alkyl or C$_2$-C$_4$-alkyl substituted with —NH$_2$.

Preferred compounds of this invention include 7-((3R)-3-aminopyrrolidin-1-yl)-6-fluoro-5-methyl-4-oxo-1,4-dihydro-1,8-naphthyridine-3-carboxylic acid, 7-(3-aminopyrrolidin-1-yl)-6-fluoro-5-methyl-4-oxo-1,4-dihydro-1,8-naphthyridine-3-carboxylic acid, 7-(3-aminopyrrolidin-1-yl)-5-ethyl-6-fluoro-4-oxo-1,4-dihydro-1,8-naphthyridine-3-carboxylic acid, 7-((3S)-3-aminopyrrolidin-1-yl)-6-fluoro-5-methyl-4-oxo-1,4-dihydro-1,8-naphthyridine-3-carboxylic acid, 7-azetidin-1-yl-6-fluoro-5-methyl-4-oxo-1,4-dihydro-1,8-naphthyridine-3-carboxylic acid, 7-(3-aminopyrrolidin-1-yl)-6-fluoro-5-iodo-4-oxo-1,4-dihydro-1,8-naphthyridine-3-carboxylic acid, 7-azetidin-1-yl-6-fluoro-4-oxo-1,4-dihydro-1,8-naphthyridine-3-carboxylic acid, 7-azetidin-1-yl-4-oxo-5-(trifluoromethyl)-1,4-dihydro-1,8-naphthyridine-3-carboxylic acid, 7-((3S)-3-aminopyrrolidin-1-yl)-6-fluoro-4-oxo-1,4-dihydro-1,8-naphthyridine-3-carboxylic acid, 7-((1R,5S)-cis-6-amino-3-azabicyclo(3.1.0)hex-3-yl)-6-fluoro-5-methyl-4-oxo-1,4-dihydro-1,8-naphthyridine-3-carboxylic acid, 7-(3-aminopyrrolidin-1-yl)-6-fluoro-4-oxo-N-phenyl-1,4-dihydro-1,8-naphthyridine-3-carboxamide, 7-((3R)-3-aminopyrrolidin-1-yl)-6-fluoro-4-oxo-1,4-dihydro-1,8-naphthyridine-3-carboxylic acid, 6-fluoro-5-methyl-7-(4-(methylamino)hexahydrocyclopenta(c)pyrrol-2(1H)-yl)-4-oxo-1,4-dihydro-1,8-naphthyridine-3-carboxylic acid, 7-azetidin-1-yl-5-methyl-4-oxo-1,4-dihydro-1,8-naphthyridine-3-carboxylic acid, 6-fluoro-5-methyl-7-octahydro-6H-pyrrolo[3,4-b]pyridin-6-yl-4-oxo-1,4-dihydro-1,8-naphthyridine-3-carboxylic acid,
7-(3-aminoazetidin-1-yl)-6-fluoro-4-oxo-1,4-dihydro-1,8-naphthyridine-3-carboxylic acid,
7-(3-aminopyrrolidin-1-yl)-6-fluoro-4-oxo-1,4-dihydro-1,8-naphthyridine-3-carboxylic acid,
6-fluoro-7-(3-(methylamino)pyrrolidin-1-yl)-4-oxo-1,4-dihydro-1,8-naphthyridine-3-carboxylic acid,
7-((3aR,6aS)-hexahydropyrrolo[3,4-c]pyrrol-2(1H)-yl)-6-fluoro-5-methyl-4-oxo-1,4-dihydro-1,8-naphthyridine-3-carboxylic acid,
7-(3-aminopyrrolidin-1-yl)-6-fluoro-5-methyl-4-oxo-1,4-dihydro-1,8-naphthyridine-3-carboxamide,
6-fluoro-4-oxo-7-pyrrolidin-1-yl-1,4-dihydro-1,8-naphthyridine-3-carboxylic acid,
7-(3-aminopyrrolidin-1-yl)-4-oxo-5-(trifluoromethyl)-1,4-dihydro-1,8-naphthyridine-3-carboxylic acid,
6-fluoro-7-(3-hydroxyazetidin-1-yl)-4-oxo-1,4-dihydro-1,8-naphthyridine-3-carboxylic acid,
6-fluoro-7-(2-furyl)-4-oxo-1,4-dihydro-1,8-naphthyridine-3-carboxylic acid,
4-oxo-7-pyrrolidin-1-yl-5-(trifluoromethyl)-1,4-dihydro-1,8-naphthyridine-3-carboxylic acid,
6-fluoro-4-oxo-7-(3-pyridin-3-ylpyrrolidin-1-yl)-1,4-dihydro-1,8-naphthyridine-3-carboxylic acid,
5-methyl-4-oxo-7-(3-pyridin-3-ylpyrrolidin-1-yl)-1,4-dihydro-1,8-naphthyridine-3-carboxylic acid,
7-((2-(dimethylamino)ethyl)(methyl)amino)-6-fluoro-5-methyl-4-oxo-1,4-dihydro-1,8-naphthyridine-3-carboxylic acid,
ethyl 7-(3-aminopyrrolidin-1-yl)-6-fluoro-4-oxo-1,4-dihydro-1,8-naphthyridine-3-carboxylate,
7-((3-(4-(3-aminopropyl)piperazin-1-yl)propyl)amino)-6-fluoro-5-methyl-4-oxo-1,4-dihydro-1,8-naphthyridine-3-carboxylic acid,
7-((3-aminopropyl)amino)-6-fluoro-5-methyl-4-oxo-1,4-dihydro-1,8-naphthyridine-3-carboxylic acid,
6-fluoro-7-(3-fluorophenyl)-4-oxo-1,4-dihydro-1,8-naphthyridine-3-carboxylic acid,
7-(3-aminopyrrolidin-1-yl)-6-fluoro-4-oxo-1,4-dihydro-1,8-naphthyridine-3-carboxamide,
7-((3-((3-aminopropyl)(methyl)amino)propyl)amino)-6-fluoro-5-methyl-4-oxo-1,4-dihydro-1,8-naphthyridine-3-carboxylic acid,
7-((2-(dimethylamino)ethyl)(ethyl)amino)-6-fluoro-5-methyl-4-oxo-1,4-dihydro-1,8-naphthyridine-3-carboxylic acid,
7-((4aS,7aS)-octahydro-6H-pyrrolo[3,4-b]pyridin-6-yl)-6-fluoro-4-oxo-1,4-dihydro-1,8-naphthyridine-3-carboxylic acid,
6-fluoro-4-oxo-7-(3-pyridin-2-ylpyrrolidin-1-yl)-1,4-dihydro-1,8-naphthyridine-3-carboxylic acid,
6-fluoro-5-methyl-4-oxo-7-pyrrolidin-1-yl-1,4-dihydro-1,8-naphthyridine-3-carboxylic acid,
7-((2-(dimethylamino)ethyl)(methyl)amino)-5-methyl-4-oxo-1,4-dihydro-1,8-naphthyridine-3-carboxylic acid,
7-(3-aminopyrrolidin-1-yl)-6-fluoro-5-methyl-3-(morpholin-4-ylcarbonyl)-1,8-naphthyridin-4(1H)-one,
7-((2-aminoethyl)amino)-6-fluoro-5-methyl-4-oxo-1,4-dihydro-1,8-naphthyridine-3-carboxylic acid,
6-fluoro-4-oxo-N-pyridin-2-yl-7-pyrrolidin-1-yl-1,4-dihydro-1,8-naphthyridine-3-carboxamide,
7-((4-aminobutyl)amino)-6-fluoro-5-methyl-4-oxo-1,4-dihydro-1,8-naphthyridine-3-carboxylic acid,
6-fluoro-4-oxo-7-thien-2-yl-1,4-dihydro-1,8-naphthyridine-3-carboxylic acid,
6-fluoro-7-((3R)-3-hydroxypyrrolidin-1-yl)-4-oxo-1,4-dihydro-1,8-naphthyridine-3-carboxylic acid,
6-fluoro-5-methyl-4-oxo-7-((3-((trifluoroacetyl)oxy)propyl)amino)-1,4-dihydro-1,8-naphthyridine-3-carboxylic acid,
6-fluoro-7-(4-(methylamino)hexahydrocyclopenta(c)pyrrol-2(1H)-yl)-4-oxo-1,4-dihydro-1,8-naphthyridine-3-carboxylic acid,
7-chloro-5-methyl-4-oxo-1,4-dihydro-1,8-naphthyridine-3-carboxylic acid,
7-(4-aminopiperidin-1-yl)-6-fluoro-4-oxo-1,4-dihydro-1,8-naphthyridine-3-carboxylic acid,
6-fluoro-4-oxo-7-phenyl-1,4-dihydro-1,8-naphthyridine-3-carboxylic acid,
6-fluoro-5-methyl-4-oxo-7-((3-pyrrolidin-1-ylpropyl)amino)-1,4-dihydro-1,8-naphthyridine-3-carboxylic acid,
7-(dimethylamino)-6-fluoro-4-oxo-1,4-dihydro-1,8-naphthyridine-3-carboxylic acid,
7-((1R,5R)-3-((benzyloxy)carbonyl)-3,6-diazabicyclo(3.2.0)hept-6-yl)-6-fluoro-4-oxo-1,4-dihydro-1,8-naphthyridine-3-carboxylic acid,
7-(3-aminopyrrolidin-1-yl)-4-oxo-1,4-dihydro-1,8-naphthyridine-3-carboxylic acid,
4-oxo-7-pyrrolidin-1-yl-1,4-dihydro-1,8-naphthyridine-3-carboxylic acid,
7-((3S)-3-aminopyrrolidin-1-yl)-6-fluoro-4-oxo-1,4-dihydro-1,8-naphthyridine-3-carboxamide,
7-(3-aminopyrrolidin-1-yl)-5-ethyl-6-fluoro-4-oxo-1,4-dihydro-1,8-naphthyridine-3-carboxamide,
6-fluoro-7-(3-(methylamino)pyrrolidin-1-yl)-4-oxo-1,4-dihydro-1,8-naphthyridine-3-carboxamide,
6-bromo-4-oxo-7-pyrrolidin-1-yl-1,4-dihydro-1,8-naphthyridine-3-carboxylic acid,
6-chloro-4-oxo-7-pyrrolidin-1-yl-1,4-dihydro-1,8-naphthyridine-3-carboxylic acid,
7-azetidin-1-yl-6-chloro-4-oxo-1,4-dihydro-1,8-naphthyridine-3-carboxylic acid,
7-azetidin-1-yl-6-bromo-4-oxo-1,4-dihydro-1,8-naphthyridine-3-carboxylic acid,
7-azetidin-1-yl-6-cyano-4-oxo-1,4-dihydro-1,8-naphthyridine-3-carboxylic acid,
7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylic acid,
6-(3-aminopyrrolidin-1-yl)-1-oxo-4,7,8,9-tetrahydro-1H-cyclopenta(c)-1,8-naphthyridine-2-carboxylic acid,
6-chloro-5-methyl-7-(3-(methylamino)pyrrolidin-1-yl)-4-oxo-1,4-dihydro-1,8-naphthyridine-3-carboxylic acid,
7-(3-aminopyrrolidin-1-yl)-6-chloro-5-methyl-4-oxo-1,4-dihydro-1,8-naphthyridine-3-carboxylic acid,
6-azetidin-1-yl-1-oxo-4,7,8,9-tetrahydro-1H-cyclopenta(c)-1,8-naphthyridine-2-carboxylic acid,
6-bromo-5-methyl-7-(3-(methylamino)pyrrolidin-1-yl)-4-oxo-1,4-dihydro-1,8-naphthyridine-3-carboxylic acid,
7-(3-aminopyrrolidin-1-yl)-5,6-dimethyl-4-oxo-1,4-dihydro-1,8-naphthyridine-3-carboxylic acid,
1-(3-(aminomethyl)benzyl)-7-(3-aminopyrrolidin-1-yl)-6-fluoro-4-oxo-1,4-dihydro-1,8-naphthyridine-3-carboxylic acid,
6-((1S,4S)-2,5-diazabicyclo(2.2.1)hept-2-yl)-1-oxo-4,7,8,9-tetrahydro-1H-cyclopenta(c)-1,8-naphthyridine-2-carboxylic acid,
1-(3-(aminomethyl)benzyl)-7-((1S,4S)-2,5-diazabicyclo(2.2.1)hept-2-yl)-6-fluoro-4-oxo-1,4-dihydro-1,8-naphthyridine-3-carboxylic acid,
7-(3-(aminomethyl)pyrrolidin-1-yl)-6-bromo-5-methyl-4-oxo-1,4-dihydro-1,8-naphthyridine-3-carboxylic acid, 7-(3-aminopyrrolidin-1-yl)-6-bromo-5-methyl-4-oxo-1,4-dihydro-1,8-naphthyridine-3-carboxylic acid,
7-(3-aminopyrrolidin-1-yl)-6-bromo-5-methyl-4-oxo-1,4-dihydro-1,8-naphthyridine-3-carboxylic acid,
7-azetidin-1-yl-4-oxo-5-(trifluoromethyl)-1,4-dihydro-1,8-naphthyridine-3-carboxylic acid,
7-(3-((4-((amino(imino)methyl)amino)butyl)amino)pyrrolidin-1-yl)-6-fluoro-4-oxo-1,4-dihydro-1,8-naphthyridine-3-carboxylic acid,
5-methyl-7-(3-(methylamino)pyrrolidin-1-yl)-4-oxo-1,4-dihydro-1,8-naphthyridine-3-carboxylic acid,
6-fluoro-7-(3-((3-(1H-imidazol-1-yl)propyl)amino)pyrrolidin-1-yl)-4-oxo-1,4-dihydro-1,8-naphthyridine-3-carboxylic acid,
6-bromo-7-((1S,4S)-2,5-diazabicyclo(2.2.1)hept-2-yl)-5-methyl-4-oxo-1,4-dihydro-1,8-naphthyridine-3-carboxylic acid,
7-(3-aminopyrrolidin-1-yl)-6-fluoro-4-oxo-1-propa-1,2-dienyl-1,4-dihydro-1,8-naphthyridine-3-carboxylic acid,
((3aS,6aS)-1-benzylhexahydropyrrolo[3,4-b]pyrrol-5(1H)-yl)-6-fluoro-4-oxo-1,4-dihydro-1,8-naphthyridine-3-carboxylic acid,
6-(4-aminopiperidin-1-yl)-1-oxo-4,7,8,9-tetrahydro-1H-cyclopenta(c)-1,8-naphthyridine-2-carboxylic acid,
7-(3-((4-((amino(imino)methyl)amino)butyl)amino)pyrrolidin-1-yl)-1-(2,4-dimethoxybenzyl)-6-fluoro-4-oxo-1,4-dihydro-1,8-naphthyridine-3-carboxylic acid,
7-(3-((4-aminobutyl)amino)pyrrolidin-1-yl)-6-fluoro-4-oxo-1,4-dihydro-1,8-naphthyridine-3-carboxylic acid,
6-bromo-4-oxo-7-piperazin-1-yl-1,4-dihydro-1,8-naphthyridine-3-carboxylic acid,
1-oxo-6-pyrrolidin-1-yl-4,7,8,9-tetrahydro-1H-cyclopenta(c)-1,8-naphthyridine-2-carboxylic acid,
7-(4-aminopiperidin-1-yl)-6-bromo-4-oxo-1,4-dihydro-1,8-naphthyridine-3-carboxylic acid,
7-(3-((5-amino-3-oxopentyl)amino)pyrrolidin-1-yl)-6-fluoro-4-oxo-1,4-dihydro-1,8-naphthyridine-3-carboxylic acid,
7-(3-((3-(aminomethyl)benzyl)amino)pyrrolidin-1-yl)-6-fluoro-4-oxo-1,4-dihydro-1,8-naphthyridine-3-carboxylic acid,
7-(3-aminopyrrolidin-1-yl)-6-cyano-4-oxo-1,4-dihydro-1,8-naphthyridine-3-carboxylic acid,
7-(3-(3-((amino(imino)methyl)amino)propyl)amino)pyrrolidin-1-yl)-1-(2,4-dimethoxybenzyl)-6-fluoro-4-oxo-1,4-dihydro-1,8-naphthyridine-3-carboxylic acid,
7-(3-((5-((amino(imino)methyl)amino)pentyl)amino)pyrrolidin-1-yl)-1-(2,4-dimethoxybenzyl)-6-fluoro-4-oxo-1,4-dihydro-1,8-naphthyridine-3-carboxylic acid,
7-(3-((3-(benzylamino)-2-hydroxypropyl)amino)pyrrolidin-1-yl)-6-fluoro-4-oxo-1,4-dihydro-1,8-naphthyridine-3-carboxylic acid,
1-((1-(6-carboxy-3-fluoro-5-oxo-5,8-dihydro-1,8-naphthyridin-2-yl)pyrrolidin-3-yl)amino)-1,6-dideoxy-D-galactitol,
6-(3-(benzylamino)pyrrolidin-1-yl)-1-oxo-4,7,8,9-tetrahydro-1H-cyclopenta(c)-1,8-naphthyridine-2-carboxylic acid,
6-fluoro-7-(3-((3-(methylthio)propyl)amino)pyrrolidin-1-yl)-4-oxo-1,4-dihydro-1,8-naphthyridine-3-carboxylic acid,
6-fluoro-7-(3-((2-(1H-imidazol-5-yl)ethyl)amino)pyrrolidin-1-yl)-4-oxo-1,4-dihydro-1,8-naphthyridine-3-carboxylic acid,
6-((1S,4S)-2,5-diazabicyclo(2.2.1)hept-2-yl)-4-(2,4-dimethoxybenzyl)-1-oxo-4,7,8,9-tetrahydro-1H-cyclopenta(c)-1,8-naphthyridine-2-carboxylic acid,
7-(4-aminopiperidin-1-yl)-6-chloro-4-oxo-1,4-dihydro-1,8-naphthyridine-3-carboxylic acid,
7-(3-((4-(aminomethyl)benzyl)amino)pyrrolidin-1-yl)-6-fluoro-4-oxo-1,4-dihydro-1,8-naphthyridine-3-carboxylic acid,
7-(3-(((3-(aminomethyl)cyclohexyl)methyl)amino)pyrrolidin-1-yl)-6-fluoro-4-oxo-1,4-dihydro-1,8-naphthyridine-3-carboxylic acid,
6-fluoro-7-(3-((1H-imidazol-2-ylmethyl)amino)pyrrolidin-1-yl)-4-oxo-1,4-dihydro-1,8-naphthyridine-3-carboxylic acid,
6-(3-aminopyrrolidin-1-yl)-1-oxo-1,4,7,8,9,10-hexahydrobenzo(c)-1,8-naphthyridine-2-carboxylic acid,
7-(3-((3-amino-2-hydroxypropyl)amino)pyrrolidin-1-yl)-6-fluoro-4-oxo-1,4-dihydro-1,8-naphthyridine-3-carboxylic acid,
7-(3-(4-amino-4-carboxy-butylamino)-pyrrolidin-1-yl)-6-fluoro-4-oxo-1,4-dihydro-(1,8)naphthyridine-3-carboxylic acid,
1-((1-(6-carboxy-3-fluoro-5-oxo-5,8-dihydro-1,8-naphthyridin-2-yl)pyrrolidin-3-yl)amino)-1-deoxy-D-mannitol,
1-((1-(6-carboxy-3-fluoro-5-oxo-5,8-dihydro-1,8-naphthyridin-2-yl)pyrrolidin-3-yl)amino)-1-deoxy-D-xylitol,
6-chloro-7-((1S,4S)-2,5-diazabicyclo(2.2.1)hept-2-yl)-5-methyl-4-oxo-1,4-dihydro-1,8-naphthyridine-3-carboxylic acid,
6-chloro-7-(3-(dimethylamino)pyrrolidin-1-yl)-5-methyl-4-oxo-1,4-dihydro-1,8-naphthyridine-3-carboxylic acid,
6-fluoro-7-(3-((3-hydroxybenzyl)amino)pyrrolidin-1-yl)-4-oxo-1,4-dihydro-1,8-naphthyridine-3-carboxylic acid,
7-(3-((2-aminoethyl)amino)pyrrolidin-1-yl)-6-fluoro-4-oxo-1,4-dihydro-1,8-naphthyridine-3-carboxylic acid,
1-((1-(6-carboxy-3-fluoro-5-oxo-5,8-dihydro-1,8-naphthyridin-2-yl)pyrrolidin-3-yl)amino)-1-deoxy-D-galactitol,
6-((1-(6-carboxy-3-fluoro-5-oxo-5,8-dihydro-1,8-naphthyridin-2-yl)pyrrolidin-3-yl)amino)-1,6-dideoxy-D-galactitol,
6-fluoro-4-oxo-7-(3-((2-pyridin-4-ylethyl)amino)pyrrolidin-1-yl)-1,4-dihydro-1,8-naphthyridine-3-carboxylic acid,
1-((1-(6-carboxy-3-fluoro-5-oxo-5,8-dihydro-1,8-naphthyridin-2-yl)pyrrolidin-3-yl)amino)-1,2-dideoxy-D-erythro-pentitol,
1-((1-(6-carboxy-3-fluoro-5-oxo-5,8-dihydro-1,8-naphthyridin-2-yl)pyrrolidin-3-yl)amino)-1-deoxy-L-mannitol,
6-((1-(6-carboxy-3-fluoro-5-oxo-5,8-dihydro-1,8-naphthyridin-2-yl)pyrrolidin-3-yl)amino)-5,6-dideoxy-D-arabino-hexitol,
7-(3-((4-(3-(dimethylamino)propoxy)benzyl)amino)pyrrolidin-1-yl)-6-fluoro-4-oxo-1,4-dihydro-1,8-naphthyridine-3-carboxylic acid,
6-chloro-4-oxo-7-piperazin-1-yl-1,4-dihydro-1,8-naphthyridine-3-carboxylic acid,
1-((1-(6-carboxy-3-fluoro-5-oxo-5,8-dihydro-1,8-naphthyridin-2-yl)pyrrolidin-3-yl)amino)-1,2-dideoxy-D-arabino-hexitol,
7-(3-aminopyrrolidin-1-yl)-4-oxo-6-(phenylethynyl)-1,4-dihydro-1,8-naphthyridine-3-carboxylic acid,
1-((1-(6-carboxy-3-fluoro-5-oxo-5,8-dihydro-1,8-naphthyridin-2-yl)pyrrolidin-3-yl)amino)-1-deoxy-D-ribitol,
5-((1-(6-carboxy-3-fluoro-5-oxo-5,8-dihydro-1,8-naphthyridin-2-yl)pyrrolidin-3-yl)amino)-5-deoxy-D-ribitol,
7-(3-(aminomethyl)pyrrolidin-1-yl)-5-methyl-4-oxo-1,4-dihydro-1,8-naphthyridine-3-carboxylic acid,
6-fluoro-4-oxo-7-(3-((thien-3-ylmethyl)amino)pyrrolidin-1-yl)-1,4-dihydro-1,8-naphthyridine-3-carboxylic acid, 6-fluoro-7-(3-((1H-imidazol-4-ylmethyl)amino)pyrrolidin-1-yl)-4-oxo-1,4-dihydro-1,8-naphthyridine-3-carboxylic acid,
1-oxo-6-piperazin-1-yl-4,7,8,9-tetrahydro-1H-cyclopenta(c)-1,8-naphthyridine-2-carboxylic acid,
6-fluoro-4-oxo-7-(3-((1-phenylethyl)amino)pyrrolidin-1-yl)-1,4-dihydro-1,8-naphthyridine-3-carboxylic acid,
6-fluoro-7-(3-((1-methyl-1-phenylethyl)amino)pyrrolidin-1-yl)-4-oxo-1,4-dihydro-1,8-naphthyridine-3-carboxylic acid,
6-fluoro-7-(3-((4-hydroxybenzyl)amino)pyrrolidin-1-yl)-4-oxo-1,4-dihydro-1,8-naphthyridine-3-carboxylic acid,
1-((1-(6-carboxy-3-fluoro-5-oxo-5,8-dihydro-1,8-naphthyridin-2-yl)pyrrolidin-3-yl)amino)-1-deoxy-L-arabinitol,
1-((1-(6-carboxy-3-fluoro-5-oxo-5,8-dihydro-1,8-naphthyridin-2-yl)pyrrolidin-3-yl)amino)-1,2-dideoxy-D-ribohexitol,
7-((1S,4S)-2,5-diazabicyclo(2.2.1)hept-2-yl)-1-(2,4-dimethoxybenzyl)-5,6-dimethyl-4-oxo-1,4-dihydro-1,8-naphthyridine-3-carboxylic acid,
7-(3-aminopyrrolidin-1-yl)-1-(2-(4-(aminosulfonyl)phenyl)ethyl)-6-fluoro-5-methyl-4-oxo-1,4-dihydro-1,8-naphthyridine-3-carboxylic acid,
7-(3-aminopyrrolidin-1-yl)-6-fluoro-4-oxo-1-(3-pyridin-4-ylprop-2-ynyl)-1,4-dihydro-1,8-naphthyridine-3-carboxylic acid,
7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylic acid,
7-(3-((2-(((amino(imino)methyl)amino)ethyl)amino)pyrrolidin-1-yl)-1-(2,4-dimethoxybenzyl)-6-fluoro-4-oxo-1,4-dihydro-1,8-naphthyridine-3-carboxylic acid,
7-(3-((4-aminobenzyl)amino)pyrrolidin-1-yl)-6-fluoro-4-oxo-1,4-dihydro-1,8-naphthyridine-3-carboxylic acid,
1-(3-aminobenzyl)-7-((1S,4S)-2,5-diazabicyclo(2.2.1)hept-2-yl)-6-fluoro-4-oxo-1,4-dihydro-1,8-naphthyridine-3-carboxylic acid,
7-(3-aminopyrrolidin-1-yl)-6-fluoro-1-(2-(4-hydroxyphenyl)ethyl)-5-methyl-4-oxo-1,4-dihydro-1,8-naphthyridine-3-carboxylic acid,
6-(4-aminopiperidin-1-yl)-4-(2,4-dimethoxybenzyl)-1-oxo-4,7,8,9-tetrahydro-1H-cyclopenta(c)-1,8-naphthyridine-2-carboxylic acid,
7-(3-(allylamino)pyrrolidin-1-yl)-6-fluoro-4-oxo-1,4-dihydro-1,8-naphthyridine-3-carboxylic acid,
6-fluoro-7-(3-((4-hydroxybutyl)amino)pyrrolidin-1-yl)-4-oxo-1,4-dihydro-1,8-naphthyridine-3-carboxylic acid,
6-fluoro-4-oxo-7-(3-((1H-pyrazol-5-ylmethyl)amino)pyrrolidin-1-yl)-1,4-dihydro-1,8-naphthyridine-3-carboxylic acid,
ethyl 7-(3-aminopyrrolidin-1-yl)-6-fluoro-4-oxo-1-(3-pyridin-4-ylprop-2-ynyl)-1,4-dihydro-1,8-naphthyridine-3-carboxylate,
7-(3-aminopyrrolidin-1-yl)-6-fluoro-1-(2-(4-methoxyphenyl)ethyl)-5-methyl-4-oxo-1,4-dihydro-1,8-naphthyridine-3-carboxylic acid,
6-fluoro-4-oxo-7-(3-((1-thien-2-ylethyl)amino)pyrrolidin-1-yl)-1,4-dihydro-1,8-naphthyridine-3-carboxylic acid,
7-(3-((2-(dimethylamino)ethyl)amino)pyrrolidin-1-yl)-6-fluoro-4-oxo-1,4-dihydro-1,8-naphthyridine-3-carboxylic acid,
7-((1S,4S)-2,5-diazabicyclo(2.2.1)hept-2-yl)-1-(2,3-dihydro-1-benzofuran-5-ylmethyl)-6-fluoro-4-oxo-1,4-dihydro-1,8-naphthyridine-3-carboxylic acid,
6-fluoro-7-(3-(((1S)-2-hydroxy-1-(1H-imidazol-4-ylmethyl)ethyl)amino)pyrrolidin-1-yl)-4-oxo-1,4-dihydro-1,8-naphthyridine-3-carboxylic acid,
7-(3-((2,3-dihydroxypropyl)amino)pyrrolidin-1-yl)-6-fluoro-4-oxo-1,4-dihydro-1,8-naphthyridine-3-carboxylic acid,
7-(3-aminopyrrolidin-1-yl)-6-fluoro-4-oxo-1-(3-oxo-3-phenylpropyl)-1,4-dihydro-1,8-naphthyridine-3-carboxylic acid,
ethyl 6-fluoro-7-(3-((4-hydroxybenzyl)amino)pyrrolidin-1-yl)-4-oxo-1,4-dihydro-1,8-naphthyridine-3-carboxylate,
6-fluoro-7-(3-((3-fluoro-4-methoxybenzyl)amino)pyrrolidin-1-yl)-4-oxo-1,4-dihydro-1,8-naphthyridine-3-carboxylic acid,
7-((1S,4S)-2,5-diazabicyclo(2.2.1)hept-2-yl)-6-fluoro-1-(4-methoxybenzyl)-4-oxo-1,4-dihydro-1,8-naphthyridine-3-carboxylic acid,
6-fluoro-4-oxo-7-(3-((quinolin-2-ylmethyl)amino)pyrrolidin-1-yl)-1,4-dihydro-1,8-naphthyridine-3-carboxylic acid,
7-((1S,4S)-2,5-diazabicyclo(2.2.1)hept-2-yl)-1-(4-(dihydroxyboryl)benzyl)-6-fluoro-4-oxo-1,4-dihydro-1,8-naphthyridine-3-carboxylic acid,
N-(3-(aminomethyl)benzyl)-6-fluoro-7-pyrrolidin-1-yl-1,8-naphthyridin-4-amine,
6-acetyl-7-(3-aminopyrrolidin-1-yl)-4-oxo-1,4-dihydro-1,8-naphthyridine-3-carboxylic acid,
6-fluoro-4-oxo-7-(3-((piperidin-4-ylmethyl)amino)pyrrolidin-1-yl)-1,4-dihydro-1,8-naphthyridine-3-carboxylic acid,
ethyl 7-(3-aminopyrrolidin-1-yl)-6-fluoro-4-oxo-1-(3-phenylprop-2-ynyl)-1,4-dihydro-1,8-naphthyridine-3-carboxylate,
7-(3-aminopyrrolidin-1-yl)-6-fluoro-1-(4-methoxybenzyl)-4-oxo-1,4-dihydro-1,8-naphthyridine-3-carboxylic acid,
4-(2,4-dimethoxybenzyl)-1-oxo-6-piperazin-1-yl-4,7,8,9-tetrahydro-1H-cyclopenta(c)-1,8-naphthyridine-2-carboxylic acid,
7-((1S,4S)-2,5-diazabicyclo(2.2.1)hept-2-yl)-6-fluoro-4-oxo-1-(pyridin-4-ylmethyl)-1,4-dihydro-1,8-naphthyridine-3-carboxylic acid,
7-(3-aminopyrrolidin-1-yl)-4-oxo-6-prop-1-ynyl-1,4-dihydro-1,8-naphthyridine-3-carboxylic acid,
7-((1S,4S)-2,5-diazabicyclo(2.2.1)hept-2-yl)-1-(3,4-dimethoxybenzyl)-6-fluoro-4-oxo-1,4-dihydro-1,8-naphthyridine-3-carboxylic acid,
6-fluoro-7-(3-(((1R)-2-hydroxy-1-phenylethyl)amino)pyrrolidin-1-yl)-4-oxo-1,4-dihydro-1,8-naphthyridine-3-carboxylic acid,
7-(3-((4-(aminosulfonyl)benzyl)amino)pyrrolidin-1-yl)-6-fluoro-4-oxo-1,4-dihydro-1,8-naphthyridine-3-carboxylic acid,
6-fluoro-7-(3-((3-methoxybenzyl)amino)pyrrolidin-1-yl)-4-oxo-1,4-dihydro-1,8-naphthyridine-3-carboxylic acid,
1-(2,4-dimethoxybenzyl)-6-fluoro-7-(3-((2-(1H-imidazol-5-yl)ethyl)amino)pyrrolidin-1-yl)-4-oxo-1,4-dihydro-1,8-naphthyridine-3-carboxylic acid,
1-(2,4-dimethoxybenzyl)-6-fluoro-7-(3-((3-(1H-imidazol-1-yl)propyl)amino)pyrrolidin-1-yl)-4-oxo-1,4-dihydro-1,8-naphthyridine-3-carboxylic acid,
7-(3-(2-carbamoyl-ethylamino)-pyrrolidin-1-yl)-6-fluoro-4-oxo-1,4-dihydro-1,8-naphthyridine-3-carboxylic acid
6-fluoro-4-oxo-7-(3-((2-pyrrolidin-1-ylethyl)amino)pyrrolidin-1-yl)-1,4-dihydro-1,8-naphthyridine-3-carboxylic acid,
7-(3-aminopyrrolidin-1-yl)-6-fluoro-3-(((3-phenylpropyl)amino)methyl)-1,8-naphthyridin-4(1H)-one,
6-fluoro-7-(3-(((1S)-2-hydroxy-1-phenylethyl)amino)pyrrolidin-1-yl)-4-oxo-1,4-dihydro-1,8-naphthyridine-3-carboxylic acid, 7-(3-(benzyl(2-(dimethylamino)ethyl)amino)pyrrolidin-1-yl)-6-fluoro-4-oxo-1,4-dihydro-1,8-naphthyridine-3-carboxylic acid,
7-((3R,4S)-3-(benzylamino)-4-hydroxypyrrolidin-1-yl)-6-fluoro-4-oxo-1,4-dihydro-1,8-naphthyridine-3-carboxylic acid,
7-(3-aminopyrrolidin-1-yl)-3-(((3-(diethylamino)propyl)amino)methyl)-6-fluoro-1,8-naphthyridin-4(1H)-one
6-fluoro-4-oxo-7-(3-(((3-pyridin-4-ylbenzyl)amino)pyrrolidin-1-yl)-1,4-dihydro-1,8-naphthyridine-3-carboxylic acid,
1-(4-aminobutyl)-7-((1S,4S)-2,5-diazabicyclo(2.2.1)hept-2-yl)-6-fluoro-4-oxo-1,4-dihydro-1,8-naphthyridine-3-carboxylic acid,
6-fluoro-7-(3-((2-methoxyethyl)amino)pyrrolidin-1-yl)-4-oxo-1,4-dihydro-1,8-naphthyridine-3-carboxylic acid,
7-(3-aminopyrrolidin-1-yl)-6-fluoro-5-methyl-4-oxo-1-(2,2,2-trifluoroethyl)-1,4-dihydro-1,8-naphthyridine-3-carboxylic acid,
7-azetidin-1-yl-4-oxo-6-prop-1-ynyl-1,4-dihydro-1,8-naphthyridine-3-carboxylic acid,
7-((3R,4R)-3-amino-4-hydroxypyrrolidin-1-yl)-6-fluoro-4-oxo-1,4-dihydro-1,8-naphthyridine-3-carboxylic acid,
N-(2-((6-fluoro-7-pyrrolidin-1-yl-1,8-naphthyridin-4-yl)amino)ethyl)guanidine,
7-((1S,4S)-2,5-diazabicyclo(2.2.1)hept-2-yl)-6-fluoro-1-(2-(methylthio)benzyl)-4-oxo-1,4-dihydro-1,8-naphthyridine-3-carboxylic acid,
1-(1,3-benzodioxol-5-ylmethyl)-7-((1S,4S)-2,5-diazabicyclo(2.2.1)hept-2-yl)-6-fluoro-4-oxo-1,4-dihydro-1,8-naphthyridine-3-carboxylic acid,
7-(3-aminopyrrolidin-1-yl)-6-fluoro-1-(2-(3-methoxyphenyl)ethyl)-5-methyl-4-oxo-1,4-dihydro-1,8-naphthyridine-3-carboxylic acid,
7-(3-((cyclopropylmethyl)amino)pyrrolidin-1-yl)-6-fluoro-4-oxo-1,4-dihydro-1,8-naphthyridine-3-carboxylic acid
7-((1S,4S)-2,5-diazabicyclo(2.2.1)hept-2-yl)-1-(2,4-dimethoxybenzyl)-5-ethyl-6-fluoro-4-oxo-1,4-dihydro-1,8-naphthyridine-3-carboxylic acid,
1-(5-aminopentyl)-7-((1S,4S)-2,5-diazabicyclo(2.2.1)hept-2-yl)-6-fluoro-4-oxo-1,4-dihydro-1,8-naphthyridine-3-carboxylic acid,
7-((1S,4S)-2,5-diazabicyclo(2.2.1)hept-2-yl)-6-fluoro-1-(4-(methylthio)benzyl)-4-oxo-1,4-dihydro-1,8-naphthyridine-3-carboxylic acid,
7-(3-aminopyrrolidin-1-yl)-6-fluoro-4-oxo-1-(3-phenylpropyl)-1,4-dihydro-1,8-naphthyridine-3-carboxylic acid,
7-((1S,4S)-2,5-diazabicyclo(2.2.1)hept-2-yl)-1-(4-(dimethylamino)benzyl)-6-fluoro-4-oxo-1,4-dihydro-1,8-naphthyridine-3-carboxylic acid,
7-(3-aminopyrrolidin-1-yl)-3-(((3,4-difluorobenzyl)amino)methyl)-6-fluoro-1,8-naphthyridin-4(1H)-one,
7-(3-((3,5-difluorobenzyl)amino)pyrrolidin-1-yl)-6-fluoro-4-oxo-1,4-dihydro-1,8-naphthyridine-3-carboxylic acid,
ethyl 7-(3-aminopyrrolidin-1-yl)-6-fluoro-1-(2-(2-fluorophenyl)ethyl)-5-methyl-4-oxo-1,4-dihydro-1,8-naphthyridine-3-carboxylate,
6-(benzyloxy)-7-((1S,4S)-2,5-diazabicyclo(2.2.1)hept-2-yl)-1-(2,4-dimethoxybenzyl)-4-oxo-1,4-dihydro-1,8-naphthyridine-3-carboxylic acid,
6-fluoro-4-oxo-7-(3-(((thien-2-ylmethyl)amino)pyrrolidin-1-yl)-1,4-dihydro-1,8-naphthyridine-3-carboxylic acid,
7-((1S,4S)-2,5-diazabicyclo(2.2.1)hept-2-yl)-6-fluoro-4-oxo-1-propa-1,2-dienyl-1,4-dihydro-1,8-naphthyridine-3-carboxylic acid,
7-(3-(bis(2-hydroxyethyl)amino)pyrrolidin-1-yl)-6-fluoro-4-oxo-1,4-dihydro-1,8-naphthyridine-3-carboxylic acid,
6-fluoro-7-(3-(((3-methylthien-2-yl)methyl)amino)pyrrolidin-1-yl)-4-oxo-1,4-dihydro-1,8-naphthyridine-3-carboxylic acid,
6-fluoro-7-(3-(((5-methylthien-2-yl)methyl)amino)pyrrolidin-1-yl)-4-oxo-1,4-dihydro-1,8-naphthyridine-3-carboxylic acid,
7-(3-((4-(acetylamino)benzyl)amino)pyrrolidin-1-yl)-6-fluoro-4-oxo-1,4-dihydro-1,8-naphthyridine-3-carboxylic acid,
7-((3R,4S)-3-amino-4-hydroxypyrrolidin-1-yl)-6-fluoro-4-oxo-1,4-dihydro-1,8-naphthyridine-3-carboxylic acid,
7-((1S,4S)-2,5-diazabicyclo(2.2.1)hept-2-yl)-1-(((1S,2R,5S)-6,6-dimethylbicyclo(3.1.1)hept-2-yl)methyl)-6-fluoro-4-oxo-1,4-dihydro-1,8-naphthyridine-3-carboxylic acid,
ethyl 7-(3-aminopyrrolidin-1-yl)-6-fluoro-1-(2-(4-hydroxyphenyl)ethyl)-5-methyl-4-oxo-1,4-dihydro-1,8-naphthyridine-3-carboxylate,
ethyl 6-fluoro-7-(3-(((1H-imidazol-2-yl)methyl)amino)pyrrolidin-1-yl)-4-oxo-1,4-dihydro-1,8-naphthyridine-3-carboxylate,
7-((1S,4S)-2,5-diazabicyclo(2.2.1)hept-2-yl)-6-fluoro-4-oxo-1-(pyridin-3-ylmethyl)-1,4-dihydro-1,8-naphthyridine-3-carboxylic acid,
7-(3-((amino(imino)methyl)amino)pyrrolidin-1-yl)-6-fluoro-4-oxo-1,4-dihydro-1,8-naphthyridine-3-carboxylic acid,
7-(3-(((2,6-dioxo-1,2,3,6-tetrahydropyrimidin-4-yl)methyl)amino)pyrrolidin-1-yl)-6-fluoro-4-oxo-1,4-dihydro-1,8-naphthyridine-3-carboxylic acid,
6-fluoro-4-oxo-7-(3-((pyridin-3-ylmethyl)amino)pyrrolidin-1-yl)-1,4-dihydro-1,8-naphthyridine-3-carboxylic acid,
6-fluoro-7-(3-((2-furylmethyl)amino)pyrrolidin-1-yl)-4-oxo-1,4-dihydro-1,8-naphthyridine-3-carboxylic acid,
6-(aminomethyl)-7-(3-aminopyrrolidin-1-yl)-4-oxo-1,4-dihydro-1,8-naphthyridine-3-carboxylic acid,
N-(6-fluoro-7-pyrrolidin-1-yl-1,8-naphthyridin-4-yl)-N,N',N'-trimethylethane-1,2-diamine,
7-((1S,4S)-2,5-diazabicyclo(2.2.1)hept-2-yl)-6-fluoro-4-oxo-1-(piperidin-4-ylmethyl)-1,4-dihydro-1,8-naphthyridine-3-carboxylic acid,
ethyl 7-((1S,4S)-2,5-diazabicyclo(2.2.1)hept-2-yl)-6-fluoro-4-oxo-1-(3-phenylprop-2-ynyl)-1,4-dihydro-1,8-naphthyridine-3-carboxylate,
7-((1S,4S)-2,5-diazabicyclo(2.2.1)hept-2-yl)-6-fluoro-1-((5-methylpyrazin-2-yl)methyl)-4-oxo-1,4-dihydro-1,8-naphthyridine-3-carboxylic acid,
ethyl 7-(3-aminopyrrolidin-1-yl)-6-fluoro-5-methyl-4-oxo-1-(2-pyridin-4-ylethyl)-1,4-dihydro-1,8-naphthyridine-3-carboxylate,
7-(3-((2,6-difluorobenzyl)amino)pyrrolidin-1-yl)-6-fluoro-4-oxo-1,4-dihydro-1,8-naphthyridine-3-carboxylic acid,
7-((3R,4R)-3-(benzylamino)-4-hydroxypyrrolidin-1-yl)-6-fluoro-4-oxo-1,4-dihydro-1,8-naphthyridine-3-carboxylic acid,
6-fluoro-4-oxo-7-(3-((3-(2-oxopyrrolidin-1-yl)propyl)amino)pyrrolidin-1-yl)-1,4-dihydro-1,8-naphthyridine-3-carboxylic acid,
7-((1S,4S)-2,5-diazabicyclo(2.2.1)hept-2-yl)-1-(3,5-dimethoxybenzyl)-6-fluoro-4-oxo-1,4-dihydro-1,8-naphthyridine-3-carboxylic acid,
7-(3-aminopyrrolidin-1-yl)-6-fluoro-3-((1,2,3,4-tetrahydronaphthalen-1-ylamino)methyl)-1,8-naphthyridin-4(1H)-one, ethyl 7-(3-aminopyrrolidin-1-yl)-1-(2-(4-(aminosulfonyl)phenyl)ethyl)-6-fluoro-5-methyl-4-oxo-1,4-dihydro-1,8-naphthyridine-3-carboxylate,
1-(3-(aminomethyl)benzyl)-7-azetidin-1-yl-6-fluoro-4-oxo-1,4-dihydro-1,8-naphthyridine-3-carboxylic acid,
7-((1S,4S)-2,5-diazabicyclo(2.2.1)hept-2-yl)-6-fluoro-4-oxo-1-(3,4,5-trimethoxybenzyl)-1,4-dihydro-1,8-naphthyridine-3-carboxylic acid,
7-((1S,4S)-2,5-diazabicyclo(2.2.1)hept-2-yl)-1-(2,3-dimethoxybenzyl)-6-fluoro-4-oxo-1,4-dihydro-1,8-naphthyridine-3-carboxylic acid,
7-(3-((2,4-difluorobenzyl)amino)pyrrolidin-1-yl)-6-fluoro-4-oxo-1,4-dihydro-1,8-naphthyridine-3-carboxylic acid,
7-((1S,4S)-2,5-diazabicyclo(2.2.1)hept-2-yl)-6-fluoro-4-oxo-1-(pyridin-2-ylmethyl)-1,4-dihydro-1,8-naphthyridine-3-carboxylic acid,
ethyl 7-(3-aminopyrrolidin-1-yl)-6-fluoro-5-methyl-4-oxo-1-(2-pyridin-2-ylethyl)-1,4-dihydro-1,8-naphthyridine-3-carboxylate,
7-(3-aminopyrrolidin-1-yl)-6-fluoro-4-oxo-1-(piperidin-3-ylmethyl)-1,4-dihydro-1,8-naphthyridine-3-carboxylic acid,
ethyl 6-fluoro-4-oxo-7-(3-((1-phenylethyl)amino)pyrrolidin-1-yl)-1,4-dihydro-1,8-naphthyridine-3-carboxylate,
ethyl 7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylate,
7-(3-aminopyrrolidin-1-yl)-3-(((1,2-diphenylethyl)amino)methyl)-6-fluoro-1,8-naphthyridin-4(1H)-one,
$N^2$-(1-(6-carboxy-3-fluoro-5-oxo-5,8-dihydro-1,8-naphthyridin-2-yl)pyrrolidin-3-yl)-$N^5$-(imino(nitroamino)methyl)-L-ornithine,
7-(3-((1-benzylpiperidin-4-yl)amino)pyrrolidin-1-yl)-6-fluoro-4-oxo-1,4-dihydro-1,8-naphthyridine-3-carboxylic acid,
7-((1S,4S)-2,5-diazabicyclo(2.2.1)hept-2-yl)-6-fluoro-1-(2-methoxybenzyl)-4-oxo-1,4-dihydro-1,8-naphthyridine-3-carboxylic acid,
7-(3-aminopyrrolidin-1-yl)-1-(4-carboxybenzyl)-6-fluoro-4-oxo-1,4-dihydro-1,8-naphthyridine-3-carboxylic acid,
6-fluoro-7-(3-fluoropyrrolidin-1-yl)-4-oxo-1,4-dihydro-1,8-naphthyridine-3-carboxylic acid,
1-benzyl-7-((1S,4S)-2,5-diazabicyclo(2.2.1)hept-2-yl)-6-fluoro-4-oxo-1,4-dihydro-1,8-naphthyridine-3-carboxylic acid,
7-(3-((2-ethylbutyl)amino)pyrrolidin-1-yl)-6-fluoro-4-oxo-1,4-dihydro-1,8-naphthyridine-3-carboxylic acid,
7-(3-aminopyrrolidin-1-yl)-3-benzoyl-1-(2,4-dimethoxybenzyl)-6-fluoro-1,8-naphthyridin-4(1H)-one,
7-(3-((2-carboxy-2-(1H-imidazol-4-yl)ethyl)amino)pyrrolidin-1-yl)-6-fluoro-4-oxo-1,4-dihydro-1,8-naphthyridine-3-carboxylic acid,
7-(3-aminopyrrolidin-1-yl)-3-(((2,4-difluorobenzyl)amino)methyl)-6-fluoro-1,8-naphthyridin-4(1H)-one,
1-(2,4-dimethoxybenzyl)-6-fluoro-4-oxo-7-(3-((3-(2-oxopyrrolidin-1-yl)propyl)amino)pyrrolidin-1-yl)-1,4-dihydro-1,8-naphthyridine-3-carboxylic acid,
ethyl 7-(3-aminopyrrolidin-1-yl)-1-(2-(2,5-dimethoxyphenyl)ethyl)-6-fluoro-5-methyl-4-oxo-1,4-dihydro-1,8-naphthyridine-3-carboxylate,
7-(3-aminopyrrolidin-1-yl)-6-fluoro-4-oxo-1-(piperidin-4-ylmethyl)-1,4-dihydro-1,8-naphthyridine-3-carboxylic acid, and
7-(3-aminopyrrolidin-1-yl)-1-(((1R,2S,5R)-6,6-dimethylbicyclo(3.1.1)hept-2-yl)methyl)-6-fluoro-4-oxo-1,4-dihydro-1,8-naphthyridine-3-carboxylic acid.

As used herein, the terms "S" and "R" configuration are as defined by the IUPAC 1974 Recommendations for Section E, Fundamental Stereochemistry, Pure Appl. Chem. (1976) 45, 13-30.

The compounds of the invention may comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers.

By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

Geometric isomers, assigned E or Z, may result from the arrangement of substituents around the carbon-carbon or carbon-nitrogen double bond in the compounds. Double bonds with an excess of one arrangement over the other are assigned the arrangement in the higher amount, preferably an excess of about 85%-90%, more preferably an excess of about 95%-99%, and still more preferably an excess of greater than about 99%. The compounds may also exist as an equilibrium mixture comprising two geometric isomers.

In addition, solvates and hydrates of the compounds are meant to be included in this invention.

When any variable (for example $R^1$, $R^2$, and $R^3$, etc.) occurs more than one time in any substituent or in a compound of the invention, its definition on each occurrence is independent of its definition at every other occurrence. In addition, combinations of substituents are permissible only if such combinations result in stable compounds. Stable compounds are compounds which can be isolated in a useful degree of purity from a reaction mixture. This invention is intended to encompass compounds when prepared by synthetic processes or by metabolic processes. Preparation of the compounds of the invention by metabolic processes include those occurring in the human or animal body (in vivo) or processes occurring in vitro.

Compounds containing hydroxyl, amino, or carboxylic acids may have attached thereto prodrug-forming moieties. The prodrug-forming moieties are removed by metabolic processes and release the compounds having the freed hydroxyl, amino, or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

The compounds may exist as acid addition salts, basic addition salts, or zwitterions. Salts of the compounds are prepared during their isolation or following their purification. Acid addition salts of the compounds are those derived from the reaction of the compounds with an acid. For example, the acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, lactate, maleate, mesitylenesulfonate, methanesulfonate, naphthylenesulfonate, nicotinate, oxalate, pamoate, pectinate, persulfate, picrate, propionate, succinate, tartrate, thiocyanate, trichloroacetic, trifluoroacetic, phosphate, glutamate, bicarbonate, para-toluenesulfonate, lactobionate, and undecanoate salts of the compounds and prodrugs thereof are contemplated as being within the scope of the invention. When the compounds contain carboxylic acids, basic addition salts may be prepared therefrom by reaction with a base such as the hydroxide, carbonate, or bicarbonate of cations such as lithium, sodium, potassium, calcium, and magnesium.

The compounds may be administrated with or without another antibacterials and with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds in solid dosage forms include agar, alginic acid, cocoa butter, gelatin, isotonic saline, malt, powdered tragacanth, Ringer's solution, talc, water, aluminum hydroxide, magnesium hydroxide, sodium and potassium phosphate salts, cellulose, cellulose acetate, ethyl cellulose, sodium carboxymethyl cellulose, ethyl laureate, ethyl oleate, magnesium stearate, sodium lauryl sulfate, castor oil, corn oil, cottonseed oil, germ oil, groundnut oil, olive oil, peanut oil, safflower oil, sesame oil, soybean oil, benzyl alcohol, benzyl benzoate, 1,3-butylene glycol, ethanol, ethyl acetate, ethyl carbonate, glycerol, isopropanol, propylene glycol, tetrahydrofurfuryl alcohol, corn starch, potato starch, lactose, glucose sucrose, and mixtures thereof. Excipients for ophthalmically and orally administered compounds in liquid dosage forms include water, ethanol, isopropanol, ethyl carbonate, ethyl acetate, benzyl alcohol, benzyl benzoate, propylene glycol, 1,3-butylene glycol, cottonseed oil, groundnut oil, corn oil, germ oil, olive oil, castor oil, sesame oil, glycerol, tetrahydrofurfuryl alcohol, polyethylene glycols, fatty acid esters of sorbitan, and mixtures thereof. Excipients for osmotically administered compounds include water, ethanol, isopropanol, chlorofluorohydrocarbons, and mixtures thereof. Excipients for parenterally administered compounds include water, 1,3-butanediol, Ringer's solution, U.S.P. or isotonic sodium chloride solution, oleic acid, castor oil, corn oil, cottonseed oil, germ oil, groundnut oil, olive oil, peanut oil, safflower oil, sesame oil, soybean oil, liposomes, and mixtures thereof. Excipients for rectally and vaginally administered compounds include cocoa butter, polyethylene glycol, wax, and mixtures thereof.

The compounds may be administered parenterally (subcutaneously, intravenously, intramuscularly, and intrasternally), orally, osmotically, ophthalmically, rectally, topically, and vaginally. Orally administered compounds in solid dosage forms may be administered as capsules, dragees, granules, pills, powders, and tablets. Ophthalmically and orally administered compounds in liquid dosage forms may be administered as elixirs, emulsions, microemulsions, solutions, suspensions, and syrups. Osmotically and topically administered compounds may be administered as creams, gels, inhalants, lotions, ointments, pastes, powders, solutions, and sprays. Parenterally administered compounds may be administered as aqueous or oleaginous solutions or aqueous or oleaginous suspensions, the latter of which contains crystalline, amorphous, or otherwise insoluble forms of the compounds. Rectally and vaginally administered compounds may be administered as creams, gels, lotions, ointments, and pastes.

Dosage forms for the compounds depend on the species being treated, the disorder being treated and the severity thereof, the composition comprising the compounds, the time of administration, the route of administration, the duration of treatment, the potency of the compounds, and the rate of excretion of the compounds. The daily therapeutically effective amount of the compounds administered to a patient in single or divided doses range from about 0.1 to about 200 mg/kg body weight, preferably from about 0.25 to about 100 mg/kg body weight. Single dose compositions contain these amounts of the compounds or combinations of submultiples thereof.

Antibacterial activity of the compounds against *Streptococcus pneumoniae* was determined visually by the broth microdilution method described in the National Committee for Clinical Laboratory Standards (1997), "Methods For Dilution Antimicrobial Susceptibility Tests For Bacteria That Grow Aerobically," approved standard M7-A4 (Wayne, Pa., USA). All strains tested were from the Abbott Laboratories culture collection and were either clinical isolates or reference strains obtained from the American Type Culture Collection (Manassas, Va., USA).

Twelve petri dishes, each containing successive aqueous dilutions of test compounds in sterilized Brain Heart Infusion agar (Difco 0418-01-5) (10 mL), were inoculated with 1:100 dilutions of the microorganisms in TABLE 1 using a Steers replicator block (or 1:10 dilutions for slow-growing *Streptococcus* strains), co-incubated at 35-37° C. for 20-24 hours with plates containing three commercially-available quinolones one commercially-available oxazolidinone, and a control plate with no compound, and inspected visually to provide the minimum inhibitory concentration (MIC), in µg/mL, by which is meant the lowest concentration of the test compound which yielded no growth, a slight haze, or sparsely isolated colonies on the inoculum spot as compared to growth in the control plate.

TABLE 1

| Microorganism | Code |
|---|---|
| Quinolone-Succeptable *Streptococcus pneumoniae* ATCC 6303 | AA |
| Quinolone-Resistant *Streptococcus pneumoniae* 7257 | BB |

TABLE 2

| Example | AA MIC | BB MIC |
|---|---|---|
| Ciprofloxacin | 1 | 16 |
| Norfloxacin | 1 | 32 |
| Trovafloxacin | 0.06 | 4 |
| Linezolid | 2 | 0.5 |

The antibacterial activity of the compounds was superior to the control containing no compound and in the range of about 2-8 μM against AA and about 0.25-1 μM against BB. These data demonstrate that the compounds are antibacterials and are therefore useful for the prophylaxis and treatment of bacterial infections.

Bacterial protein synthesis inhibitory activity of the compounds and the aforementioned commercially-available antibacterials was determined by translation assays performed using the firefly luciferase reporter system described by Murray et al., (2001), "*Staphylococcus aureus* Cell Extract Transcription-Translation Assay: Firefly Luciferase Reporter System for Evaluating Protein Translation Inhibitors," Antimicrob. Agents Chemother. 45(6): 1900-1904, replacing the *Staphylococcus aureus* S30 extract described therein with S30 *Streptococcus pneumoniae* extract from quinolone-succeptable *Streptococcus pneumoniae* ATCC 46919, and replacing plasmid coding for the luciferase gene with mRNA (encoding produced by in vitro transcription from the plasmid pAS10rbs3) which encoded the luciferase gene with an upstream *Streptococcus pneumoniae* promoter and Shine-Dalgarno site.

The $IC_{50}$'s of the compounds, defined as concentrations of the same which caused 50% inhibition of bacterial protein synthesis, was in the range of about 0.01-40 μM.

The $IC_{50}$'s of the commercially-available quinolones tested were greater than about 100 μM compared to the $IC_{50}$ of Linezolid which is about 3 μM.

These data demonstrate that the commercially-available quinolones tested do not inhibit bacterial protein synthesis in *Streptococcus pneumoniae*, even at high concentrations, and that inhibition of bacterial protein synthesis by the compounds is comparable to Linezolid.

Thus, while not being limited to a particular theory, the compounds function by a mechanism more similar to Linezolid (which inhibits bacterial protein synthesis) than quinolones (which inhibit DNA gyrase).

Because the compounds inhibit the growth of quinolone resistant bacteria at least as well as the growth of quinolone susceptible bacteria, and because they function by a mechanism which differs from quinolones, they are useful not only for prophylaxis and treatment of bacterial infections but also for prophylaxis and treatment of bacterial infections for which quinolones would be ineffective or only partially effective.

The following schemes illustrate representative processes by which the compounds may be made. It is meant to be understood that the order of the steps in the processes may be varied, other reagents may be substituted for those specifically mentioned, and vulnerable substituents may be protected and deprotected during the process.

Abbreviations used are DME for 1,2-dimethoxyethane; DMF for N,N-dimethylformamide; DMSO for dimethylsulfoxide; and THF for tetrahydrofuran.

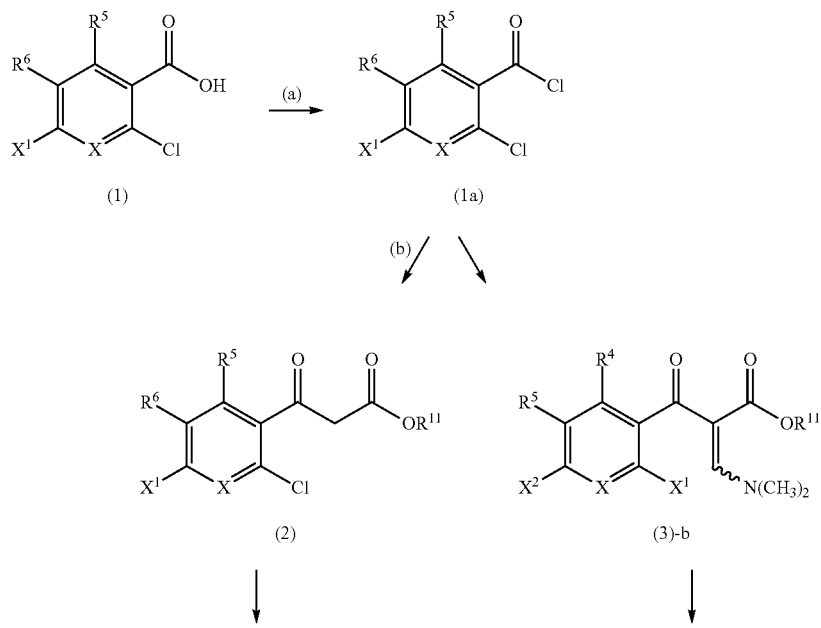

SCHEME 1

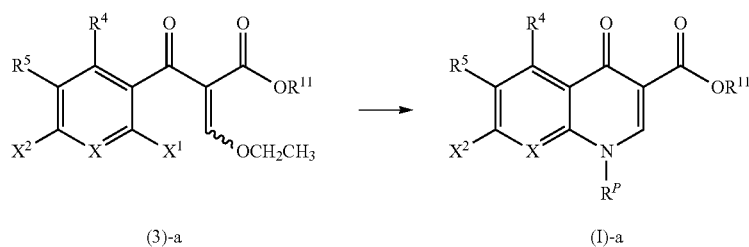

(3)-a    (I)-a

Compounds having formula (1), in which $X^1$ is —Br or —Cl, may be converted to compounds having formula (2) by reacting the former and a halogenating agent to provide an acid chloride (1a) and subsequently reacting (1a) and a compound having formula (i)

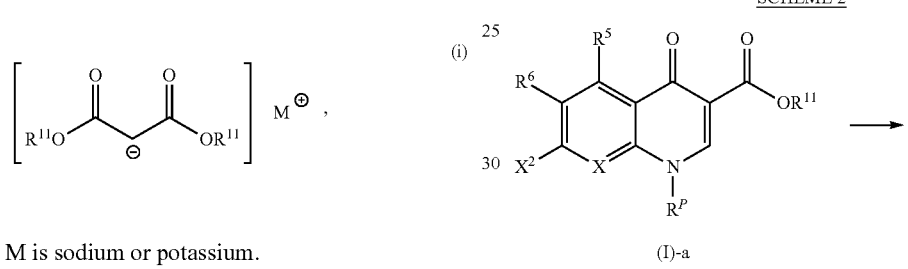

in which M is sodium or potassium.

Halogenating agents include oxalyl chloride/DMF and thionyl chloride. Step (a) is typically conducted at about 25° C. to 50° C., over about 1 to 6 hours, in solvents such as dichloromethane and chloroform. Step (b) is typically conducted at about 0° C. to 25° C., over about 1 to 24 hours, in solvents such as dichloromethane, chloroform, THF, and mixtures thereof.

Compounds having formula (2) may be converted to compounds having formula (3)-a by reacting the former, triethyl orthoformate, and acetic anhydride. The reaction is typically conducted from about 1 to 6 hours, at about 80° C. to 140° C., in acetic anhydride.

Compounds of formula (Ia) may be converted to compounds of formula (3)-b by reacting the former, 3,3-dimethylaminoacrylate, and triethylamine.

The reaction is typically conducted from about 1 to 3 hours, at about 80° C. to 110° C., in solvents such as benzene, toluene, or THF.

Compounds having formulas (3)-a or (3)-b may be converted to compounds having formula (I)-a by (a) reacting the former and compounds having formula (ii)

$R^P$—NH$_2$    (ii), in which $R^P$ is a nitrogen protecting group, and (b) reacting the product of step (a) with a second base. Nitrogen protecting groups include allyloxy, 2,4-dimethoxybenzyl, 2-cyanoethyl, 4-methoxybenzyl, trimethylsilyl, tert-butyl, and triphenylmethyl. Second bases include potassium carbonate, sodium carbonate, sodium hydride, and potassium hydride. The reaction is typically conducted from about ½ hour to 7 days, at about 0° C. to 100° C., in solvents such as dichloromethane, acetonitrile, THF, and mixtures thereof.

SCHEME 2

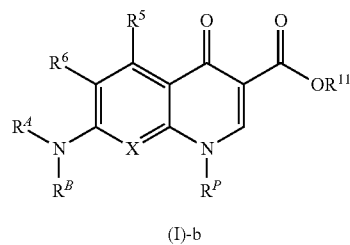

(I)-a

(I)-b

Compounds having formula (I)-a may be converted to compounds having formula (I)-b by reacting the former and compounds having formula (iii)

NHR$^A$R$^B$    (iii)

in which $R^A$ and $R^B$ combine to form groups embraced by $R^7$ which are attached through a nitrogen atom, and a third base. Third bases include potassium bicarbonate, sodium-bicarbonate, potassium phosphate, potassium carbonate, triethylamine, diisopropylethylamine, and 1,8-diazabicyclo-(5.4.0)undec-7-ene. The reaction is typically conducted from about 5 hours to 7 days, at about 25° C. to 160° C., in solvents such as acetonitrile, dichloromethane, DMSO, DMF, dimethylacetamide, N-methylpyrrolidine, water, and mixtures thereof.

SCHEME 3

(I)-c → (I)-d → (I)-e

Compounds having formula (I)-c may be converted to compounds having formula (I)-d by reacting the former and a fourth base. Fourth bases include lithium hydroxide, sodium hydroxide, and potassium hydroxide. The reaction is typically conducted from about 3 to 24 hours, at about 25° C. to 110° C., and at atmospheric or elevated pressures, in solvents such as THF, 1,4-dioxane, methanol, ethanol, iso-propanol, dichloromethane, water, and mixtures thereof.

Compounds having formula (I)-d can be converted to compounds having formula (I)-e by reacting the former and compounds having formula (iv)

$$NHR^C R^D \quad (iv),$$

in which $R^C$ and $R^D$ combine to form the groups represented by $R^4$ which are connected through a nitrogen atom, a coupling agent, the first base, and, optionally, a first additive. Coupling agents include 1,3-dicyclohexylcarbodiimide and 1-(3-dimethylaminopropyl)-3-ethylcarbodiimide, 1-hydroxy-7-azobenzotriazole, O-(7-azabenzotriazol-1-yl)-N,N,N',N'-tetramethyluronium hexafluorophosphate, iso-butyl chloroformate, and iso-propenyl chloroformate. First additives include trimethylaluminum, 1-hydroxybenzotriazole, and 4,4-dimethylaminopyridine. The reaction is typically conducted from about 12 to 24 hours, at about −25° C. to 25° C., in solvents such as N,N-dimethylacetamide, dichloromethane, chloroform, DMF, and THF.

SCHEME 4

(I)-f →

-continued (I)

Compounds having formula (I)-f may be converted to compounds having formula (I) by reacting the former and a compound having formula (v), $$R^7\text{-}Q^1 \quad (v),$$

in which $R^7$ is aryl or heteroaryl,
$Q^1$ is $B(V^1)_2$ or $Sn(alkyl)_3$, and
$V^1$ is alkyl, —O(alkyl), or —OH,
a coupling catalyst, a fifth base, and, optionally, a second additive. Coupling catalysts include tetrakis(triphenylphosphine)palladium(0), tris(dibenzylideneacetone)dipalladium (0), (1,1'-bis(diphenylphosphino)ferrocene)dichloropalladium (II), and dichlorobis(triphenylphosphine)palladium(II). Fifth bases include potassium bicarbonate, sodium bicarbonate, potassium phosphate, potassium carbonate, cesium carbonate, cesium fluoride, triethylamine, diisopropylethylamine, and 1,8-diazabicyclo-(5.4.0)undec-7-ene. Second additives include phosohines such as tributylphosphine, tricyclohexylphosphine, triphenylphosphine, trinaphthylphosphine, tri(fury-2-yl)phosphine, tri(pyrid-3-yl)phosphine, triphenylarsine, 1,4-bis(diphenylphosphino)butane (dppb), 1,2-bis(diphenyl-phosphino)ethane (dppe), 1,1-bis(diphenylphosphino)methane (dppm), 1,2-bis(dimethylphosphino) ethane (dmpe), and 1,1'-bis(diphenylphosphino)ferrocene (dppf), and salts such as copper(I) iodide and copper(I) chloride. The reaction is typically conducted from about 3 to 24 hours, at about 80° C. to 150° C., in solvents such as benzene, toluene, xylenes, 1,4-dioxane, THF and DMF.

SCHEME 5

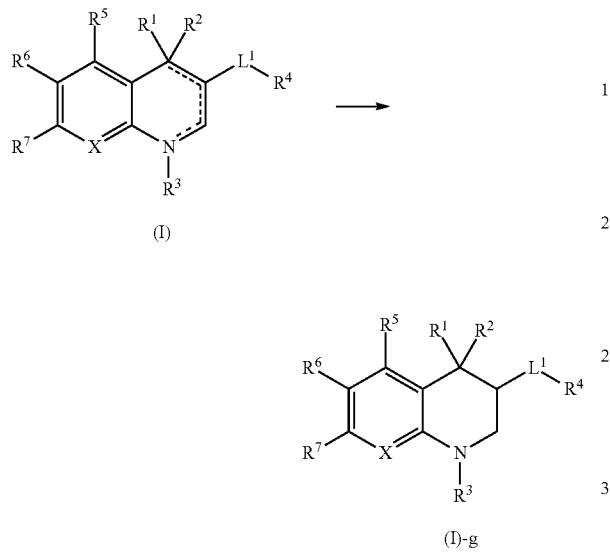

SCHEME 6

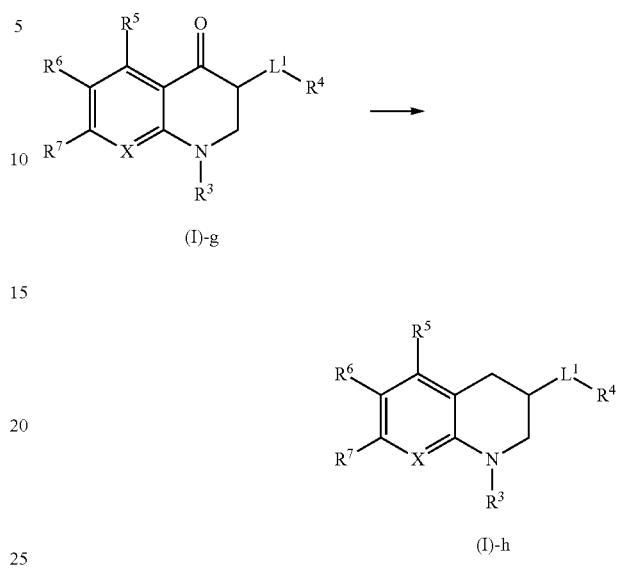

Compounds having formula (I) can be converted to compounds having formula (I)-g by reacting the former and a hydrogenation catalyst. Hydrogenation catalysts include platinum on carbon with hydrogen gas and triethylsilane with trifluoroacetic acid. The reaction is typically conducted from about 3 to 24 hours, at about 0° C. to 35° C., in solvents such as dichloromethane, chloroform, and carbon tetrachloride.

Compounds having formula (I) can be converted to compounds having formula (I)-g by reacting the former and a reducing agent. Reducing agents include sodium borohydride and sodium cyanoborohydride. The reaction is typically conducted from about 1 to 18 hours, at about 0° C. to 35° C., in solvents such as methanol, ethanol, THF, water, and mixtures thereof.

In the foregoing description of the invention, it is understood by those skilled in the art, that when $R^3$ is hydrogen and ⁼⁼⁼ is a double bond, then various tautomeric forms of formula (I) are understood to be equivalent representations of the compound. One example of this tautomeric equilibrium is shown below.

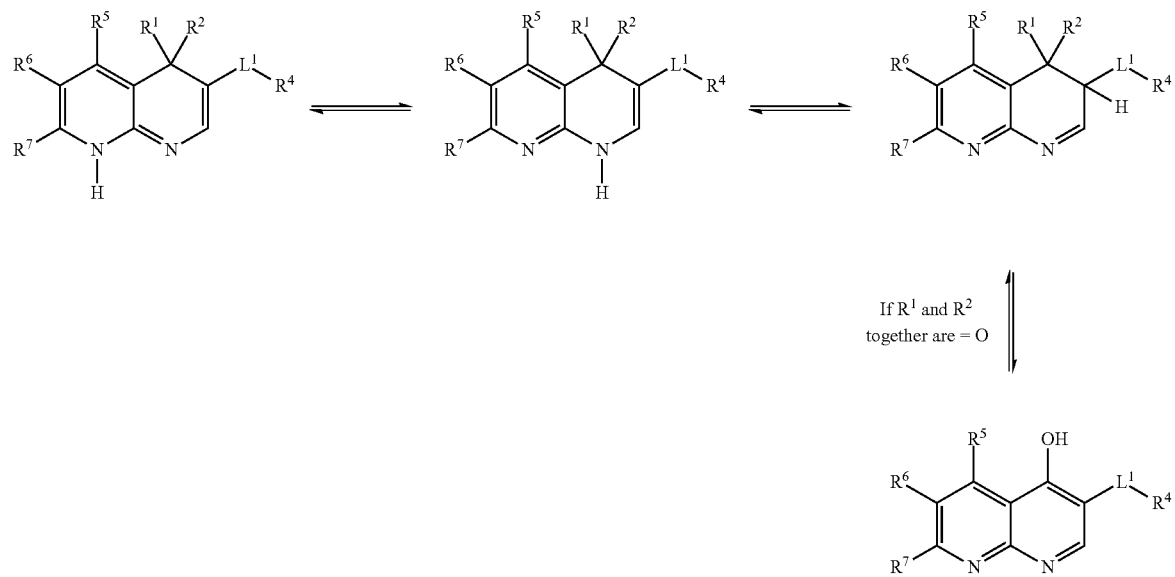

The following examples illustrate methods by which certain preferred first embodiments of the invention may be prepared.

Example 1

7-((3R)-3-aminopyrrolidin-1-yl)-6-fluoro-5-methyl-4-oxo-1,4-dihydro-1,8-naphthyridine-3-carboxylic acid

Example 1A 2,6-dichloro-5-fluoro-4-methylnicotinic acid and 2,6-dichloro-5-fluoro-4-ethylnicotinic acid A solution of 2,6-dichloro-5-fluoronicotinic acid (1.99 g) in THF (40 mL) at −78° C. was treated with 1.4M methyllithium in diethyl ether (14 mL), stirred at −25° C. for 1.5 hours then at −78° C. for one hour, treated with iodomethane (1.4 mL), stirred at 0° C. for 2 hours and −20° C. for 18 hours, treated with water, concentrated to remove the THF, diluted with water, washed with diethyl ether, acidified with 1M HCl, and extracted with diethyl ether; and the extract was dried (MgSO$_4$), filtered, and concentrated.

Example 1B ethyl 3-(2,6-dichloro-5-fluoro-4-methyl-pyrid-3-yl)-3-oxopropanoate and ethyl 3-(2,6-dichloro-5-fluoro-4-ethyl-pyrid-3-yl)-3-oxopropanoate A solution of EXAMPLE 1A (9.48 mmol) in dichloromethane (20 mL) was treated with oxalyl chloride (8 mL) and DMF (2 drops), stirred for 1 hour, and concentrated; and the concentrate was dissolved in THF (25 mL) to provide an acid chloride solution. A slurry of the mono-potassium salt of ethyl malonate (4.0 g) in acetonitrile (40 mL) at 0° C. was treated with triethylamine (3.3 mL) and magnesium chloride (3.2 g), warmed to ambient temperature, stirred for 4 hours, treated with the acid chloride solution, stirred for 1 hour, treated with 1M HCl, and extracted with ethyl acetate. The extract was washed with brine, dried (Na$_2$SO$_4$), filtered, and concentrated; and the concentrate was flash chromatographed on silica gel with 90:10 hexanes/ethyl acetate.

Example 1C ethyl (2E/Z)-2-((2,6-dichloro-5-fluoro-4-methylpyridin-3-yl)carbonyl)-3-ethoxy-2-propenoate and ethyl (2E/Z)-2-((2,6-dichloro-5-fluoro-4-ethylpyridin-3-yl)carbonyl)-3-ethoxy-2-propenoate A solution of Example 1B (1.8 g) and triethyl orthoformate (1.25 mL) in acetic anhydride (5 mL) was heated at 110° C. for 4 hours then cooled and concentrated.

Example 1D ethyl 7-chloro-1-(2,4-dimethoxybenzyl)-6-fluoro-5-methyl-4-oxo-1,4-dihydro-1,8-naphthyridine-3-carboxylate and ethyl 7-chloro-1-(2,4-dimethoxybenzyl)-6-fluoro-5-ethyl-4-oxo-1,4-dihydro-1,8-naphthyridine-3-carboxylate A solution of Example 1C (6 mmol) in dichloromethane (20 mL) at 0° C. was treated with dimethoxybenzylamine (0.96 mL), stirred at ambient temperature for 90 minutes, and concentrated. The concentrate was dissolved in acetonitrile (10 mL), treated with potassium carbonate (2.3 g), refluxed for 7 days then cooled, stirred at ambient temperature for 2 days, diluted with dichloromethane, washed with water, 10% citric acid, and brine, and dried (Na$_2$SO$_4$), filtered, and concentrated; and the concentrate was flash chromatographed on silica gel with a hexanes/ethyl acetate gradient to provide the desired products.

Example 1E ethyl 7-((3R)-3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxylate A solution of ethyl 7-chloro-1-(2,4-dimethoxybenzyl)-6-fluoro-5-methyl-4-oxo-1,4-dihydro-1,8-naphthyridine-3-carboxylate (250 mg), potassium carbonate (126 mg), and (3R)-(3-tert-butoxycarbonylamino)pyrrolidine (212 mg) in dichloromethane (2.85 mL) was stirred for 3 days, diluted with dichloromethane, washed with water and 10% citric acid, and dried (Na$_2$SO$_4$), filtered, and concentrated.

Example 1F 7-((3R)-3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxylic acid A solution of Example 1E (332 mg) in 1M LiOH (3 mL) and THF (7 mL) was stirred at ambient temperature for 18 hours, diluted with dichloromethane, washed with 1M HCl, and dried (Na$_2$SO$_4$), filtered, and concentrated.

Example 1G 7-((3R)-3-aminopyrrolidin-1-yl)-6-fluoro-5-methyl-4-oxo-1,4-dihydro-1,8-naphthyridine-3-carboxylic acid A solution of Example 1F (334 mg) in trifluoroacetic acid (25 mL) was refluxed for 3 hours then cooled and concentrated. The concentrate was azeotroped with toluene and dissolved in water (250 mL); and this solution was washed with diethyl ether, filtered through a 0.45 µm syringe membrane filter, and lyophilized. NMR (300 MHz, DMSO-d$_6$) δ 8.46 (s, 1H), 4.01-3.75 (m, 5H), 2.71 (m, 3H), 2.30 (m, 1H), 2.10 (m, 1H).

Example 2

7-(3-aminopyrrolidin-1-yl)-6-fluoro-5-methyl-4-oxo-1,4-dihydro-1,8-naphthyridine-3-carboxylic acid

Example 2A ethyl 7-(3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxylate This example was prepared by substituting 3-(tert-butoxycarbonylamino)pyrrolidine for (3R)-(3-tert-butoxycarbonylamino)pyrrolidine in EXAMPLE 1E.

Example 2B 7-(3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxylic acid This example was prepared by substituting EXAMPLE 2A for EXAMPLE 1E in EXAMPLE 1F.

Example 2C 7-(3-aminopyrrolidin-1-yl)-6-fluoro-5-methyl-4-oxo-1,4-dihydro-1,8-naphthyridine-3-carboxylic acid This example was prepared by substituting EXAMPLE 2B for EXAMPLE 1F in EXAMPLE 1G and purified by reverse phase HPLC ($C_{18}$ column with a continuous water/0.5% trifluoroacetic acid to acetonitrile/0.5% trifluoroacetic acid gradient followed by lypholization of appropriate fractions). NMR (300 MHz, $CD_3CO_2D$) δ 8.69 (s, 1H), 4.29 (m, 1H), 4.21 (m, 1H), 4.08 (m, 2H), 3.95 (m, 1H), 2.74 (m, 3H), 2.45 (m, 2H).

Example 3

7-(3-aminopyrrolidin-1-yl)-5-ethyl-6-fluoro-4-oxo-1,4-dihydro-1,8-naphthyridine-3-carboxylic acid

Example 3A ethyl 7-(3-((tert-butoxycarbonyl)amino)pyrrolidin-1-yl)-1-(2,4-dimethoxybenzyl)-5-ethyl-6-fluoro-4-oxo-1,4-dihydro-1,8-naphthyridine-3-carboxylate This example was prepared by substituting ethyl 7-chloro-1-(2,4-dimethoxybenzyl)-6-fluoro-5-ethyl-4-oxo-1,4-dihydro-1,8-naphthyridine-3-carboxylate for ethyl 7-chloro-1-(2,4-dimethoxybenzyl)-6-fluoro-5-methyl-4-oxo-1,4-dihydro-1,8-naphthyridine-3-carboxylate and 3-(tert-butoxycarbonylamino)pyrrolidine for (3R)-3-(tert-butoxycarbonylamino)pyrrolidine in EXAMPLE 1E.

Example 3B 7-(3-((tert-butoxycarbonyl)amino)pyrrolidin-1-yl)-1-(2,4-dimethoxybenzyl)-5-ethyl-6-fluoro-4-oxo-1,4-dihydro-1,8-naphthyridine-3-carboxylic acid This example was prepared by substituting EXAMPLE 3A for EXAMPLE 1E in EXAMPLE 1F.

Example 3C 7-(3-aminopyrrolidin-1-yl)-5-ethyl-6-fluoro-4-oxo-1,4-dihydro-1,8-naphthyridine-3-carboxylic acid This example was prepared by substituting EXAMPLE 3B for EXAMPLE 1F in EXAMPLE 1G. NMR (300 MHz, DMSO-$d_6$) δ 9.47 (s, 1H), 4.02-3.77 (m, 5H), 3.29 (m, 2H), 2.30 (m, 1H), 2.10 (m, 1H), 1.20 (m, 3H).

Example 4

7-((3S)-3-aminopyrrolidin-1-yl)-6-fluoro-5-methyl-4-oxo-1,4-dihydro-1,8-naphthyridine-3-carboxylic acid

Example 4A ethyl 7-((3S)-3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxylate This example was prepared by substituting (3S)-3-(tert-butoxycarbonylamino)pyrrolidine for (3R)-3-(tert-butoxycarbonylamino)pyrrolidine in EXAMPLE 1E.

Example 4B 7-((3S)-3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxylic acid This example was prepared by substituting EXAMPLE 4A for EXAMPLE 1E in EXAMPLE 1F.

Example 4C 7-((3S)-3-aminopyrrolidin-1-yl)-6-fluoro-5-methyl-4-oxo-1,4-dihydro-1,8-naphthyridine-3-carboxylic acid This example was prepared by substituting EXAMPLE 4B for EXAMPLE 1F in EXAMPLE 1G. NMR (300 MHz, DMSO-$d_6$) δ 8.46 (s, 1H), 4.05-3.70 (m, 5H), 2.71 (m, 3H), 2.30 (m, 1H), 2.10 (m, 1H).

Example 5

7-azetidin-1-yl-6-fluoro-5-methyl-4-oxo-1,4-dihydro-1,8-naphthyridine-3-carboxylic acid

Example 5A ethyl 7-azetidin-1-yl-1-(2,4-dimethoxybenzyl)-6-fluoro-5-methyl-4-oxo-1,4-dihydro-1,8-naphthyridine-3-carboxylate A mixture of ethyl 7-chloro-1-(2,4-dimethoxybenzyl)-6-fluoro-5-methyl-4-oxo-1,4-dihydro-1,8-naphthyridine-3-carboxylate (254 mg), azetidine (0.085 mL), and potassium carbonate (160 mg) in dichloromethane (5 mL) was stirred for 3 days, diluted with dichloromethane, washed with water and 10% citric acid, filtered through a cotton plug, and concentrated.

Example 5B ethyl 7-azetidin-1-yl-6-fluoro-5-methyl-4-oxo-1,4-dihydro-1,8-naphthyridine-3-carboxylate A solution of Example 5A (267 mg) in trifluoroacetic acid (11 mL) was stirred at 40° C. for 3 hours and concentrated; and the concentrate was azeotroped with toluene.

Example 5C 7-azetidin-1-yl-6-fluoro-5-methyl-4-oxo-1,4-dihydro-1,8-naphthyridine-3-carboxylic acid A solution of Example 5B (0.58 mmol) in THF (10 mL) was treated with 1M LiOH (30 mL), stirred for 12 hours, heated at 70° C. for 8 hours then cooled, stirred at ambient temperature for 2 days, heated at 70° C. for 8 hours then cooled, treated with 10% citric acid, and filtered.

Example 5D 7-azetidin-1-yl-6-fluoro-5-methyl-4-oxo-1,4-dihydro-1,8-naphthyridine-3-carboxylic acid, sodium salt A suspension of Example 5C (81 mg) in water (100 mL) was treated with 0.2014M NaOH (1.3 mL), sonicated for 1 hour, and filtered first through filter paper and then a 0.45 μm membrane; and the filtrate was lyophilized. NMR (300 MHz, DMSO-$d_6$) δ 8.6 (s, 1H), 4.2 (m, 4H), 2.7 (m, 3H), 2.3 (m, 2H).

Example 6

7-(3-aminopyrrolidin-1-yl)-6-fluoro-5-iodo-4-oxo-1,4-dihydro-1,8-naphthyridine-3-carboxylic acid

Example 6A 2,6-dichloro-5-fluoro-4-iodonicotinic acid

A solution of 2,6-dichloro-5-fluoronicotinic acid (10 g) in THF (100 mL) at −78° C. was treated with 1.6M methyllithium in diethyl ether (62.5 mL), stirred at −25° C. for 1.5 hours, cooled to −78° C., treated with trifluoromethyl iodide (22.6 g) over 30 minutes, stirred at −78° C. for 1.5 hours, −25° C. for 1.5 hours, and 0° C. for two hours, treated with water, concentrated to remove the organic solvents, washed with diethyl ether, acidified with 1M HCl, and extracted with diethyl ether; and the extract was dried ($Na_2SO_4$), filtered, and concentrated.

Example 6B ethyl 3-(2,6-dichloro-5-fluoro-4-iodopyridin-3-yl)-3-oxopropanoate This example was prepared by substituting EXAMPLE 6A for EXAMPLE 1A in EXAMPLE 1B and flash chromatographed on silica gel with 15:85 ethyl acetate/hexane.

Example 6C ethyl (2Z)-2-((2,6-dichloro-5-fluoro-4-iodopyridin-3-yl)carbonyl)-3-ethoxyacrylate This example was prepared by substituting EXAMPLE 6B for EXAMPLE 1B in EXAMPLE 10.

Example 6D ethyl 7-chloro-1-(2,4-dimethoxybenzyl)-6-fluoro-5-iodo-4-oxo-1,4-dihydro-1,8-naphthyridine-3-carboxylate This example was prepared by substituting EXAMPLE 6C for EXAMPLE 10 in EXAMPLE 1D and flash chromatographed on silica gel with a hexane/ethyl acetate gradient then on silica gel with a methanol/dichloromethane gradient.

Example 6E ethyl 7-(3-((tert-butoxycarbonyl)amino)pyrrolidin-1-yl)-1-(2,4-dimethoxybenzyl)-6-fluoro-5-iodo-4-oxo-1,4-dihydro-1,8-naphthyridine-3-carboxylate This example was prepared by substituting EXAMPLE 6D for EXAMPLE 1D in EXAMPLE 1E, 3-(tert-butoxycarbonylamino)pyrrolidine for (3R)-3-(tert-butoxycarbonylamino)pyrrolidine, and 1:1 DMSO/methanol for dichloromethane, and flash chromatographed on silica gel with a methanol/dichloromethane gradient.

Example 6F 7-(3-((tert-butoxycarbonyl)amino)pyrrolidin-1-yl)-1-(2,4-dimethoxybenzyl)-6-fluoro-5-iodo-4-oxo-1,4-dihydro-1,8-naphthyridine-3-carboxylic acid This example was prepared by substituting EXAMPLE 6E for EXAMPLE 1E in EXAMPLE 1F and flash chromatographed on silica gel with a methanol/dichloromethane gradient.

Example 6G 7-(3-Amino-pyrrolidin-1-yl)-6-fluoro-5-iodo-4-oxo-1,4-dihydro-(1,8)naphthyridine-3-carboxylic acid This example was prepared by substituting EXAMPLE 6F for EXAMPLE 1F in EXAMPLE 1G. NMR (300 MHz, DMSO-$d_6$) δ 8.05 (s, 1H), 4.00-3.79 (m, 4H), 3.27 (m, 1H), 2.30 (m, 1H), 2.10 (m, 1H).

Example 7

7-azetidin-1-yl-6-fluoro-4-oxo-1,4-dihydro-1,8-naphthyridine-3-carboxylic acid

Example 7A ethyl (2E/Z)-2-((2,6-dichloro-5-fluoropyridin-3-yl)carbonyl)-3-(ethoxy)prop-2-enoate A solution of ethyl 3-(2,6-dichloro-5-fluoropyridin-3-yl)-3-oxopropanoate (40 g) and triethyl orthoformate (26.1 mL) in acetic anhydride (100 mL) was heated at 85° C. for 6.5 hours then cooled and concentrated; and the concentrate was azeotroped with toluene and crystallized from hexanes, with a small amount of diethyl ether and dichloromethane.

Example 7B ethyl (2E/Z)-2-((2,6-dichloro-5-fluoropyridin-3-yl)carbonyl)-3-(dimethylamino)prop-2-enoate A solution of 2,6-dichloro-5-fluoronicotinoyl chloride (62.5 g), ethyl 3,3-dimethylaminoacrylate (58.8 g), and triethylamine (69 g) in toluene (600 mL) was heated at 90° C. for 1 hour then cooled and concentrated. The concentrate was dissolved in dichloromethane (60 mL), diluted with diethyl ether, and filtered. The filtrate was concentrated, and the concentrate was crystallized from hexanes:diethyl ether.

Example 7C ethyl 7-chloro-1-(2-cyanoethyl)-6-fluoro-4-oxo-1,4-dihydro-1,8-naphthyridine-3-carboxylate A solution of Example 7A (20 g) in acetonitrile (400 mL) at 0° C. was treated with 3-aminopropionitrile (4.6 mL), stirred at 0° C. for 15 minutes and ambient temperature for 30 minutes, treated with potassium carbonate (15 g), heated at 75° C. for 18 hours then cooled, diluted with ethyl acetate, washed with water, 10% citric acid, water, and brine, and dried (MgSO$_4$), filtered, and concentrated; and the concentrate was plug filtered through silica gel with 9:1 ethyl acetate/dichloromethane.

Example 7C (Alternative)

The desired product may be prepared by substituting EXAMPLE 7B for EXAMPLE 7A in EXAMPLE 7C.

Example 7D ethyl 7-azetidin-1-yl-1-(2-cyanoethyl)-6-fluoro-4-oxo-1,4-dihydro-1,8-naphthyridine-3-carboxylate A solution of Example 7C (13.26 g), azetidine hydrochloride (9.58 g) and triethylamine (17.2 mL) in dichloromethane (650 mL) was stirred for 2 hours, treated with triethylamine (900 mg), stirred for 1 hour, diluted with dichloromethane, washed with water and brine, dried (MgSO$_4$), filtered, and concentrated; and the concentrate was triturated with refluxing dichloromethane, treated with diethyl ether and hexanes, and filtered.

Example 7E 7-azetidin-1-yl-6-fluoro-4-oxo-1,4-dihydro-1,8-naphthyridine-3-carboxylic acid A suspension of EXAMPLE 7D in THF (400 mL) and methanol (200 mL) at reflux was treated with 1M LiOH (200 mL), stirred for an 3 hours then cooled, concentrated to half volume, acidified with 10% citric acid, and filtered.

Example 7F ethyl 7-chloro-1-(2,4-dimethoxybenzyl)-6-fluoro-4-oxo-1,4-dihydro-1,8-naphthyridine-3-carboxylate The desired compound was prepared by substituting 2,4-dimethoxybenzylamine for 3-aminopropionitrile in EXAMPLE 7C.

Example 7G ethyl 7-azetidin-1-yl-1-(2,4-dimethoxybenzyl)-6-fluoro-4-oxo-1,4-dihydro-1,8-naphthyridine-3-carboxylate This example was prepared by substituting EXAMPLE 7F for EXAMPLE 7C in EXAMPLE 7D.

Example 7H 7-azetidin-1-yl-1-(2,4-dimethoxybenzyl)-6-fluoro-4-oxo-1,4-dihydro-1,8-naphthyridine-3-carboxylic acid The desired compound was prepared by substituting EXAMPLE 7G for EXAMPLE 7D in EXAMPLE 7E.

Example 7I 7-azetidin-1-yl-6-fluoro-4-oxo-1,4-dihydro-1,8-naphthyridine-3-carboxylic acid A solution of EXAMPLE 7H (1 g) in trifluoroacetic acid (10 mL) was heated at 50° C. for 3 hours and concentrated; and the concentrate was azeotroped with toluene and triturated with acetonitrile. NMR (300 MHz, DMSO-d$_6$) δ 15.51 (s, 1H), 13.28 (br s, 1H), 8.42 (s, 1H), 7.92 (m, 1H), 4.40-4.20 (m, 4H), 2.43 (m, 2H).

Example 8

7-azetidin-1-yl-4-oxo-5-(trifluoromethyl)-1,4-dihydro-1,8-naphthyridine-3-carboxylic acid

Example 8A 2,6-dichloro-4-(trifluoromethyl)nicotinic acid

This example was prepared by substituting 2,6-dichloro-4-(trifluoromethyl)nicotinamide for 2,6-dichloro-4-methylnicotinamide in EXAMPLE 65A.

Example 8B ethyl 3-(2,6-dichloro-4-(trifluoromethyl)pyridin-3-yl)-3-oxopropanoate This example was prepared by substituting EXAMPLE 8A for EXAMPLE 65A in EXAMPLE 65B.

Example 8C ethyl (2E/Z)-2-((2,6-dichloro-4-(trifluoromethyl)pyridin-3-yl)carbonyl)-3-(ethoxy)prop-2-enoate This example was prepared by substituting EXAMPLE 8B for EXAMPLE 65B in EXAMPLE 65C.

Example 8D ethyl 7-chloro-1-(2,4-dimethoxybenzyl)-4-oxo-5-(trifluoromethyl)-1,4-dihydro-1,8-naphthyridine-3-carboxylate This example was prepared by substituting EXAMPLE 8C for EXAMPLE 65C in EXAMPLE 65D and flash chromatographed on silica gel with 40% ethyl acetate/hexanes.

Example 8E ethyl 7-azetidin-1-yl-1-(2,4-dimethoxybenzyl)-4-oxo-5-(trifluoromethyl)-1,4-dihydro-1,8-naphthyridine-3-carboxylate This example was prepared by substituting EXAMPLE 8D for EXAMPLE 65D in EXAMPLE 18A.

Example 8F 7-azetidin-1-yl-4-oxo-5-(trifluoromethyl)-1,4-dihydro-1,8-naphthyridine-3-carboxylic acid This example was prepared by substituting EXAMPLE 8E for EXAMPLE 65D in EXAMPLE 65E. NMR (300 MHz, DMSO-$d_6$) δ 15.53 (s, 1H), 13.20 (m, 1H), 8.43 (m, 1H), 6.89 (m, 1H), 4.35-4.16 (m, 4H), 2.42 (m, 2H).

Example 9

7-((3S)-3-aminopyrrolidin-1-yl)-6-fluoro-4-oxo-1,4-dihydro-1,8-naphthyridine-3-carboxylic acid A solution of Example 7C (32.4 mg) and (3S)-3-(tert-butoxycarbonylamino)pyrrolidine (55.8 mg) in acetonitrile (1 mL) in a sealed vial was heated for 24 hours then cooled and concentrated. The concentrate was dissolved in 1:1 DMSO/methanol (1 mL) and chromatographed by reverse phase HPLC. The product was suspended in 2-propanol (1 mL), treated with 1M LiOH (1.2 mL), heated at 80° C. for 18 hours in a sealed vial for 24 hours, and concentrated. The concentrate was treated with 10% citric acid to pH 4-6 and filtered. The filtrant was dissolved in 4M HCl/dioxane (1.5 mL), and this solution was stirred for 2 hours and concentrated. NMR (500 MHz DMSO-$d_6$) δ 13.4 (m, 1H), 8.50 (m, 1H), 8.45 (s, 2H), 8.00 (m, 1H), 4.00-3.40 (m, 5H), 2.38 (m, 1H), 2.18 (m, 1H).

Example 10

7-((1R,5S)-cis-6-amino-3-azabicyclo(3.1.0)hex-3-yl)-6-fluoro-5-methyl-4-oxo-1,4-dihydro-1,8-naphthyridine-3-carboxylic acid

Example 10A tert-butyl (1R,5S)-3-azabicyclo(3.1.0)hex-6-ylcarbamate

This compound was prepared as described by Norris et al. in J. Chem. Soc. Perkin Trans. 1, 2000, 10, 1615-1622:

Example 10B ethyl 7-((1R,5S)-cis-6-((tert-butoxycarbonyl)amino)-3-azabicyclo(3.1.0)hex-3-yl)-1-(2,4-dimethoxybenzyl)-6-fluoro-5-methyl-4-oxo-1,4-dihydro-1,8-naphthyridine-3-carboxylate This example was prepared by substituting EXAMPLE 10A for (3R)-3-(tert-butoxycarbonylamino)pyrrolidine in EXAMPLE 1E.

Example 10C 7-((1R,5S)-cis-6-((tert-butoxycarbonyl)amino)-3-azabicyclo(3.1.0)hex-3-yl)-1-(2,4-dimethoxybenzyl)-6-fluoro-5-methyl-4-oxo-1,4-dihydro-1,8-naphthyridine-3-carboxylic acid This example was prepared by substituting EXAMPLE 10B for EXAMPLE 1E in EXAMPLE 1F.

Example 10D 7-((1R,5S)-cis-6-amino-3-azabicyclo(3.1.0)hex-3-yl)-6-fluoro-5-methyl-4-oxo-1,4-dihydro-1,8-naphthyridine-3-carboxylic acid This example was prepared by substituting EXAMPLE 10C for EXAMPLE 1F in EXAMPLE 1G and conducting the reaction at reflux for 18 hours. NMR (300 MHz, DMSO-$d_6$) δ 8.43 (s, 1H), 4.03 (m, 2H), 3.83 (m, 2H), 2.68 (m, 3H), 2.14 (m, 2H).

Example 11

7-(3-aminopyrrolidin-1-yl)-6-fluoro-4-oxo-N-phenyl-1,4-dihydro-1,8-naphthyridine-3-carboxamide

Example 11A 7-(3-((tert-butoxycarbonyl)amino)pyrrolidin-1-yl)-1-(2,4-dimethoxybenzyl)-6-fluoro-4-oxo-1,4-dihydro-1,8-naphthyridine-3-carboxylic acid This example was prepared by substituting EXAMPLE 36A for EXAMPLE 7D in EXAMPLE 7E.

Example 11B 7-(3-aminopyrrolidin-1-yl)-6-fluoro-4-oxo-N-phenyl-1,4-dihydro-1,8-naphthyridine-3-carboxamide A solution of EXAMPLE 11A (50 mg), hydroxyazobenzotriazole (20 mg), 0-(7-azabenzotriazol-1-yl)-N,N,N',N'-tetramethyluronium hexafluorophosphate (50 mg), diisopropylethylamine (0.025 mL), N,N-dimethylaminopyridine (100 mg), and dimethylacetamide (2 mL) was stirred for 30 minutes, treated with aniline (12.6 mg), stirred for 18 hours, treated with trisamine resin (0.26 g), stirred for 2 hours, treated with carbonate resin (0.090 g), stirred for 2 hours, and filtered. The filtrate was concentrated, and the concentrate was dissolved in dichloromethane, applied to a silica gel-containing solid-phase extraction cartridge, and eluted with 25% ethyl acetate/hexanes then 10% methanol/dichloromethane. The product was dissolved in trifluoroacetic acid, stirred at 80° C. for 18 hours in a sealed vial, and concentrated. This concentrate was dissolved in methanol, treated with anion exchange resin, and filtered. The filtrate was concentrated, and the concentrate was purified by reverse phase HPLC. NMR (300 MHz, CD$_3$OD) δ 8.65 (s, 1H), 8.05 (m, 1H), 7.60-7.70 (m, 2H), 7.30-7.40 (m, 2H), 7.10-7.15 (m, 1H), 3.85-4.15 (m, 5H), 2.40-2.55 (m, 1H), 2.10-2.50 (m, 1H).

Example 15

7-((3R)-3-aminopyrrolidin-1-yl)-6-fluoro-4-oxo-1,4-dihydro-1,8-naphthyridine-3-carboxylic acid

Example 15A ethyl 1-tert-butyl-7-chloro-6-fluoro-4-oxo-1,4-dihydro-1,8-naphthyridine-3-carboxylate This example was prepared by substituting tert-butylamine for 3-aminopropionitrile in EXAMPLE 7C.

Example 15B ethyl 7-((3R)-3-((tert-butoxycarbonyl)amino)pyrrolidin-1-yl)-1-tert-butyl-6-fluoro-4-oxo-1,4-dihydro-1,8-naphthyridine-3-carboxylate A solution of Example 15A (300 mg) in acetonitrile (40 mL) at 0° C. was treated with potassium carbonate (1 g), heated at 60° C. for 18 hours then cooled, diluted with ethyl acetate, washed with water, 10% citric acid, water and brine, dried (MgSO$_4$), filtered, and concentrated; and the concentrate was flash chromatographed on silica gel with ethyl acetate.

Example 15C 7-((3R)-3-aminopyrrolidin-1-yl)-6-fluoro-4-oxo-1,4-dihydro-1,8-naphthyridine-3-carboxylic acid hydrochloride A suspension of EXAMPLE 15B (260 mg) in ethanol (60 mL) was treated with HCl gas to saturation, heated at 120° C. for 18 hours then cooled, treated with diethyl ether and filtered to provide the desired product. NMR (300 MHz, DMSO-d$_6$) δ 13.32 (d, 1H), 8.42 (d, 1H), 8.36 (br s, 3H), 8.02 (d, 1H), 4.05-3.83 (m, 5H), 2.44-2.25 (m, 1H), 2.20-2.12 (m, 1H).

Example 17

6-fluoro-5-methyl-7-(4-(methylamino)hexahydrocyclopenta(c)pyrrol-2(1H)-yl)-4-oxo-1,4-dihydro-1,8-naphthyridine-3-carboxylic acid This example was prepared by substituting EXAMPLE 1D for EXAMPLE 7C in EXAMPLE 9, tert-butyl methyl(octahydrocyclopenta(c)pyrrol-4-yl)carbamate for (3S)-3-(tert-butoxycarbonylamino)pyrrolidine, and dimethylacetamide for acetonitrile and conducting the reaction at 100° C. for 18 hours; the deprotection step substituted trifluoroacetic acid for hydrochloric acid and was conducted at 70° C. for 18 hours; and the concentrate was triturated with diethyl ether to provide the desired product. NMR (500 MHz, DMSO-d$_6$) δ 15.8 (br s, 1H), 12.9 (br s, 1H), 8.80 (m, 1H), 8.4 (m, 1H), 3.40-4.00 (m, 5H), 3.05 (m, 1H), 2.85, (m, 1H), 2.65 (m, 3H), 2.60 (s, 3H), 2.05 (m, 1H), 1.95 (m, 1H), 1.78 (m, 1H), 1.65 (m, 1H).

Example 18

7-azetidin-1-yl-5-methyl-4-oxo-1,4-dihydro-1,8-naphthyridine-3-carboxylic acid

Example 18A ethyl 7-(azetidin-1-yl)-1-(2,4-dimethoxybenzyl)-5-methyl-4-oxo-1,4-dihydro-1,8-naphthyridine-3-carboxylate A solution of Example 65D (400 mg), azetidine hydrochloride (108 mg), and N,N-diisopropylethylamine (0.503 mL) in acetonitrile (10 mL) was heated at 60° C. for 18 hours then cooled, diluted with dichloromethane, washed with 0.1M HCl, saturated sodium bicarbonate, and brine, and dried (MgSO$_4$), filtered, and concentrated; and the concentrate was recrystallized from diethyl ether to provide the desired product.

Example 18B 7-(azetidin-1-yl)-1-(2,4-dimethoxybenzyl)-5-methyl-4-oxo-1,4-dihydro-1,8-naphthyridine-3-carboxylic acid A solution of EXAMPLE 18A (0.320 g) in 1,4-dioxane (7.3 mL) was treated with lithium hydroxide monohydrate (0.0919° g), heated at 60° C. for 18 hours then cooled, poured into 1M HCl, and filtered to provide the desired product.

Example 18C 7-azetidin-1-yl-5-methyl-4-oxo-1,4-dihydro-1,8-naphthyridine-3-carboxylic acid A solution of Example 18B (0.230 g) in trifluoroacetic acid (5.6 mL) was heated at 60° C. for 1.5 hours then cooled, poured into water, and filtered. NMR (300 MHz, DMSO-d$_6$) δ 12.88 (m, 1H), 8.33 (m, 1H), 6.32 (m, 1H), 4.14 (m, 4H), 2.72 (s, 3H), 2.38 (m, 2H). (C(O)OH not observed).

Example 19

6-fluoro-5-methyl-7-octahydro-6H-pyrrolo(3,4-b)pyridin-6-yl-4-oxo-1,4-dihydro-1,8-naphthyridine-3-carboxylic acid This example was prepared by substituting 1-tert-butoxycarbonyloctahydro-1H-pyrrolo[3,4-b]pyridine for tert-butyl methyl(octahydrocyclopenta(c)pyrrol-4-yl)carbamate in EXAMPLE 17. NMR (500 MHz DMSO-d$_6$) δ 15.85 (br s, 1H), 13.1 (br. s 1H), 8.60 (br s, 1H), 8.45 (m, 1H), 3.60-4.20 (m, 5H), 3.25 (m, 1H), 2.90 (m, 1H), 2.75 (m, 1H), 2.50 (m, 3H), 1.65-1.90 (m, 4H).

Example 20

7-(3-aminoazetidin-1-yl)-6-fluoro-4-oxo-1,4-dihydro-1,8-naphthyridine-3-carboxylic acid

Example 20A ethyl 7-(3-((tert-butoxycarbonyl)amino)azetidin-1-yl)-1-(2-cyanoethyl)-6-fluoro-4-oxo-1,4-dihydro-1,8-naphthyridine-3-carboxylate A solution of Example 7C (0.3 g) and 3-(tert-butoxycarbonylamino)azetidine (0.46 g) in dichloromethane (60 mL) was stirred for 2 hours, diluted with dichloromethane, washed with water, 10% citric acid, and brine, and dried (MgSO$_4$), filtered, and concentrated.

Example 20B 7-(3-((tert-butoxycarbonyl)amino)azetidin-1-yl)-1-(2-cyanoethyl)-6-fluoro-4-oxo-1,4-dihydro-1,8-naphthyridine-3-carboxylic acid A suspension of EXAMPLE 20A (0.41 g) in THF (60 mL) and methanol (30 mL) at reflux was treated with 1M LiOH (100 mL), stirred for 3 hours then cooled, concentrated to half volume, acidified with 10% citric acid (90 mL), and filtered.

Example 20C 7-(3-aminoazetidin-1-yl)-6-fluoro-4-oxo-1,4-dihydro-1,8-naphthyridine-3-carboxylic acid A solution of EXAMPLE 20B (0.12 g) in trifluoroacetic acid (6 mL) was stirred for 10 minutes and concentrated; and the concentrate was azeotroped with toluene to provide the desired product. NMR (300 MHz, DMSO-$d_6$) δ 8.51 (s, 1H), 8.03 (m, 1H), 4.58 (m, 2H), 4.26 (m, 2H), 4.16 (br s, 1H).

Example 21

7-(3-aminopyrrolidin-1-yl)-6-fluoro-4-oxo-1,4-dihydro-1,8-naphthyridine-3-carboxylic acid

Example 21A ethyl 7-(3-((tert-butoxycarbonyl)amino)pyrrolidin-1-yl)-1-tert-butyl-6-fluoro-4-oxo-1,4-dihydro-1,8-naphthyridine-3-carboxylate This example was prepared by substituting 3-(tert-butoxycarbonylamino)pyrrolidine for (3R)-3-(tert-butoxycarbonylamino)pyrrolidine in EXAMPLE 15B.

Example 21B 7-(3-aminopyrrolidin-1-yl)-6-fluoro-4-oxo-1,4-dihydro-1,8-naphthyridine-3-carboxylic acid This example was prepared by substituting EXAMPLE 21A for EXAMPLE 15B in EXAMPLE 15C and purified by reverse phase HPLC. NMR (300 MHz, DMSO-$d_6$) δ 13.32 (d, 1H), 8.42 (d, 1H), 8.36 (br s, 3H), 8.02 (d, 1H), 4.05-3.83 (m, 5H), 2.44-2.25 (m, 1H), 2.20-2.12 (m, 1H).

Example 22

6-fluoro-7-(3-(methylamino)pyrrolidin-1-yl)-4-oxo-1,4-dihydro-1,8-naphthyridine-3-carboxylic acid

Example 22A ethyl 7-(3-((tert-butoxycarbonyl)(methyl)amino) pyrrolidin-1-yl)-1-(2,4-dimethoxybenzyl)-6-fluoro-4-oxo-1,4-dihydro-1,8-naphthyridine-3-carboxylate This example was prepared by substituting EXAMPLE 7F and tert-butyl methyl(pyrrolidin-3-yl)carbamate for EXAMPLE 1D and (3R)-3-tert-butoxycarbonyl-amino)pyrrolidine, respectively, in EXAMPLE 1E.

Example 22B 7-(3-((tert-butoxycarbonyl)(methyl)amino)pyrrolidin-1-yl)-1-(2,4-dimethoxybenzyl)-6-fluoro-4-oxo-1,4-dihydro-1,8-naphthyridine-3-carboxylic acid This example was prepared by substituting EXAMPLE 22A for EXAMPLE 1E in EXAMPLE 1F.

Example 22C 6-fluoro-7-(3-(methylamino)pyrrolidin-1-yl)-4-oxo-1,4-dihydro-1,8-naphthyridine-3-carboxylic acid This example was prepared by substituting EXAMPLE 22B for EXAMPLE 1F in EXAMPLE 1G, conducting the reaction at reflux for 18 hours, and purifying the product by reverse phase HPLC. NMR (300 MHz, DMSO-$d_6$) δ 8.52 (s, 1H), 8.03 (d, 1H), 4.09-3.78 (m, 5H), 2.66 (s, 3H), 2.33 (m, 1H), 2.21 (m, 1H).

Example 24

7-((3aR,6aS)-hexahydropyrrolo[3,4-c]pyrrol-2(1H)-yl)-6-fluoro-5-methyl-4-oxo-1,4-dihydro-1,8-naphthyridine-3-carboxylic acid This example was prepared by substituting (3aR,6aS)-octahydropyrrolo(3,4-cl pyrrole for tert-butyl methyl(octahydrocyclopenta(c)pyrrol-4-yl)carbamate in Example 17. NMR (500 MHz DMSO-$d_6$) δ 15.75 (br s, 1H), 13.15 (br s. 1H), 8.90 (br s, 1H), 8.45 (m, 1H), 3.15-4.40 (m, 8H), 2.60 (m, 3H), 2.18 (m, 1H), 1.95 (m, 1H).

Example 25

7-(3-aminopyrrolidin-1-yl)-6-fluoro-5-methyl-4-oxo-1,4-dihydro-1,8-naphthyridine-3-carboxamide

Example 25A 7-(3-((tert-butoxycarbonyl)amino)pyrrolidin-1-yl)-1-(2,4-dimethoxybenzyl)-6-fluoro-5-methyl-4-oxo-1,4-dihydro-1,8-naphthyridine-3-carboxamide A suspension of EXAMPLE 2B (235 mg) and triethylamine (0.088 mL) in dichloromethane (8.4 mL) at 0° C. was treated with isopropenyl chloroformate (0.069 mL), stirred for 30 minutes, treated with concentrated ammonium hydroxide (0.114 mL), stirred for 18 hours at ambient temperature, and concentrated; and the concentrate was flash chromatographed on silica gel with a methanol/dichloromethane gradient.

Example 25B 7-(3-aminopyrrolidin-1-yl)-1-(2,4-dimethoxybenzyl)-6-fluoro-5-methyl-4-oxo-1,4-dihydro-1,8-naphthyridine-3-carboxamide This example was prepared by substituting EXAMPLE 2B for EXAMPLE 1F in EXAMPLE 1G, conducting the reaction at reflux for 18 hours, and purifying the product by reverse phase HPLC. NMR (300 MHz, DMSO-$d_6$) δ 12.25 (m, 1H), 9.33 (m, 1H), 8.37 (m, 1H), 8.09 (m, 2H), 7.34 (m, 1H), 4.00-3.75 (m, 5H), 2.71 (m, 3H), 2.30 (m, 1H), 2.08 (m, 1H).

Example 26

6-fluoro-4-oxo-7-pyrrolidin-1-yl-1,4-dihydro-1,8-naphthyridine-3-carboxylic acid

Example 26A ethyl 1-tert-butyl-6-fluoro-4-oxo-7-pyrrolidin-1-yl-1,4-dihydro-1,8-naphthyridine-3-carboxylate This example was prepared by substituting pyrrolidine for (3R)-3-(tert-butoxycarbonylamino)pyrrolidine in EXAMPLE 15B.

Example 26B 6-fluoro-4-oxo-7-pyrrolidin-1-yl-1,4-dihydro-1,8-naphthyridine-3-carboxylic acid This example was prepared by substituting EXAMPLE 26A for EXAMPLE 15B in EXAMPLE 15C. NMR (300 MHz, DMSO-$d_6$) δ 15.52 (br s, 1H), 8.43 (s, 1H), 7.92 (d, 1H), 3.78-3.60-3.83 (m, 4H), 1.98-1.93 (m, 4H).

Example 28

7-(3-aminopyrrolidin-1-yl)-4-oxo-5-(trifluoromethyl)-1,4-dihydro-1,8-naphthyridine-3-carboxylic acid

Example 28A ethyl 7-(3-((tert-butoxycarbonyl)amino)pyrrolidin-1-yl)-1-(2,4-dimethoxybenzyl)-4-oxo-5-(trifluoromethyl)-1,4-dihydro-1,8-naphthyridine-3-carboxylate This example was prepared by substituting EXAMPLE 8D and 3-(tert-butoxycarbonylamino)pyrrolidine for EXAMPLE 65D and azetidine hydrochloride, respectively, in EXAMPLE 18A.

Example 28B 7-(3-aminopyrrolidin-1-yl)-4-oxo-5-(trifluoromethyl)-1,4-dihydro-1,8-naphthyridine-3-carboxylic acid, trifluoroacetic acid salt This example was prepared by substituting EXAMPLE 28A for EXAMPLE 65D in EXAMPLE 65E.

Example 29

6-fluoro-7-(3-hydroxyazetidin-1-yl)-4-oxo-1,4-dihydro-1,8-naphthyridine-3-carboxylic acid

Example 29A ethyl 1-(2-cyanoethyl)-6-fluoro-7-(3-hydroxyazetidin-1-yl)-4-oxo-1,4-dihydro-1,8-naphthyridine-3-carboxylate This example was prepared by substituting 3-azetidinol hydrochloride for azetidine hydrochloride in EXAMPLE 7D.

Example 29B 6-fluoro-7-(3-hydroxyazetidin-1-yl)-4-oxo-1,4-dihydro-1,8-naphthyridine-3-carboxylic acid This example was prepared by substituting EXAMPLE 29A for EXAMPLE 7D in EXAMPLE 7E. NMR (300 MHz, DMSO-$d_6$) δ 15.46 (s, 1H), 13.29 (br s, 1H), 8.43 (s, 1H), 7.93 (d, 1H), 5.86 (d, 1H), 4.70-4.62 (m, 1H), 4.61-4.53 (m, 2H), 4.13-4.06 (m, 2H).

Example 30

6-fluoro-7-(2-furyl)-4-oxo-1,4-dihydro-1,8-naphthyridine-3-carboxylic acid

Example 30A ethyl 1-(2,4-dimethoxybenzyl)-6-fluoro-7-(2-furyl)-4-oxo-1,4-dihydro-1,8-naphthyridine-3-carboxylate A solution of Example 7F (210 mg), 2-(tributylstannyl)furan (220 µL) and dichlorobis(triphenyl-phosphine)palladium(II) (10.5 mg) in toluene (8 mL) was heated at 80° C. for 3 hours then cooled and filtered through diatomaceous earth (Celite®) with ethyl acetate. The filtrate was dried ($Na_2SO_4$), filtered, and concentrated; and the concentrate was flash chromatographed on silica gel with heptane then dichloromethane.

Example 30B 1-(2,4-dimethoxybenzyl)-6-fluoro-7-(2-furyl)-4-oxo-1,4-dihydro-1,8-naphthyridine-3-carboxylic acid A solution of EXAMPLE 30A (166 mg) in THF (8 mL) was treated with lithium hydroxide monohydrate (155 mg) in water (7.4 mL), stirred at ambient temperature for 3 hours, diluted with 10% ammonium chloride (20 mL), adjusted to pH 3 with 1M HCl, and extracted with dichloromethane. The extract was dried ($Na_2SO_4$), filtered, and concentrated.

Example 30C 6-fluoro-7-(2-furyl)-4-oxo-1,4-dihydro-1,8-naphthyridine-3-carboxylic acid A solution of EXAMPLE 30B (130 mg) in trifluoroacetic acid (8 mL) was heated at 50° C. for 2 hours then cooled and concentrated. The concentrate was diluted with diethyl ether, stirred at ambient temperature for 4 hours, and filtered to provide the desired product. NMR (300 MHz, DMSO-$d_6$) δ 14.05 (br s, 1H), 8.78 (s, 1H), 8.53 (m, 1H), 8.14 (m, 1H), 7.48 (m, 1H), 6.87 (m, 1H), 6.55 (s, 1H).

Example 32

4-oxo-7-pyrrolidin-1-yl-5-(trifluoromethyl)-1,4-dihydro-1,8-naphthyridine-3-carboxylic acid

Example 32A ethyl 1-(2,4-dimethoxybenzyl)-4-oxo-7-pyrrolidin-1-yl-5-(trifluoromethyl)-1,4-dihydro-1,8-naphthyridine-3-carboxylate A solution of EXAMPLE 8D (0.580 g) and pyrrolidine (0.309 mL) in acetonitrile (12.3 mL) was stirred for 18 hours and concentrated. The concentrate was dissolved in dichloromethane (50 mL), and the solution was washed with 1M HCl, saturated sodium bicarbonate, and brine, dried (MgSO$_4$), filtered, and concentrated; and the concentrate was recrystallized from ethyl acetate/diethyl ether.

Example 32B 1-(2,4-dimethoxybenzyl)-4-oxo-7-pyrrolidin-1-yl-5-(trifluoromethyl)-1,4-dihydro-1,8-naphthyridine-3-carboxylic acid This example was prepared by substituting EXAMPLE 32A for EXAMPLE 18A in EXAMPLE 18B.

Example 32C 4-oxo-7-pyrrolidin-1-yl-5-(trifluoromethyl)-1,4-dihydro-1,8-naphthyridine-3-carboxylic acid This example was prepared by substituting EXAMPLE 32B for EXAMPLE 18B in EXAMPLE 18C. NMR (300 MHz, DMSO-d$_6$) δ 15.57 (s, 1H), 13.10 (m, 1H), 8.46 (m, 1H), 7.07 (s, 1H), 3.67-3.58 (m, 4H), 2.06-1.94 (m, 4H).

Example 33

6-fluoro-4-oxo-7-(3-pyridin-3-ylpyrrolidin-1-yl)-1,4-dihydro-1,8-naphthyridine-3-carboxylic acid This example was prepared by substituting 3-(3-pyrrolidinyl)pyridine for (3S)-3-(tert-butoxycarbonylamino)pyrrolidine in EXAMPLE 9 and omitting HCl/dioxane. NMR (500 MHz DMSO-d$_6$) δ 15.55 (br s, 1H), 8.60 (m, 1H), 8.50 (m, 1H), 8.45 (s, 1H), 7.95 (m, 1H), 7.80 (m, 1H), 7.40 (m, 1H), 4.25 (m, 1H), 4.05 (m, 1H), 3.85 (m, 1H), 3.70 (m, 1H), 3.58 (m, 1H), 2.45 (m, 1H), 2.15 (m, 1H).

Example 34

5-methyl-4-oxo-7-(3-pyridin-3-ylpyrrolidin-1-yl)-1,4-dihydro-1,8-naphthyridine-3-carboxylic acid Example 34A ethyl 1-(2,4-dimethoxybenzyl)-5-methyl-4-oxo-7-(3-pyridin-3-ylpyrrolidin-1-yl)-1,4-dihydro-1,8-naphthyridine-3-carboxylate This example was prepared by substituting 3-(3-pyrrolidinyl)pyridine dihydrochloride for azetidine hydrochloride in EXAMPLE 18A.

Example 34B 5-methyl-4-oxo-7-(3-pyridin-3-ylpyrrolidin-1-yl)-1,4-dihydro-1,8-naphthyridine-3-carboxylic acid, trifluoroacetic acid salt This example was prepared by substituting EXAMPLE 34A for EXAMPLE 65D in EXAMPLE 65E. NMR (300 MHz, DMSO-d$_6$) δ 12.79 (s, 1H), 8.76 (s, 1H), 8.66 (m, 1H), 8.39 (m, 1H), 8.18 (m, 1H), 7.71 (m, 1H), 6.62 (m, 1H), 4.21-4.02 (m, 1H), 3.96-3.52 (m, 4H), 3.35 (s, 3H), 2.50-2.42 (m, 1H), 2.30-2.12 (m, 1H); (C(O)OH not observed).

Example 35

7-((2-(dimethylamino)ethyl)(methyl)amino)-6-fluoro-5-methyl-4-oxo-1,4-dihydro-1,8-naphthyridine-3-carboxylic acid This example was prepared by substituting N,N,N'-trimethylethane-1,2-diamine for tert-butyl methyl(octahydrocyclopenta(c)pyrrol-4-yl)carbamate in EXAMPLE 17. NMR (500 MHz DMSO-d$_6$) δ 15.70 (br s, 1H), 13.0 (br s, 1H), 8.58 (m, 1H), 4.00 (m, 2H), 3.30 (m, 3H) 2.90 (2, 6H), 2.70 (m, 3H).

Example 36 ethyl 7-(3-aminopyrrolidin-1-yl)-6-fluoro-4-oxo-1,4-dihydro-1,8-naphthyridine-3-carboxylate Example 36A ethyl 7-(3-((tert-butoxycarbonyl)amino)pyrrolidin-1-yl)-1-(2,4-dimethoxybenzyl)-6-fluoro-4-oxo-1,4-dihydro-1,8-naphthyridine-3-carboxylate This example was prepared by substituting EXAMPLE 7F for EXAMPLE 15A and 3-(tert-butoxycarbonylamino)pyrrolidine for (3R)-3-(tert-butoxycarbonylamino)pyrrolidine in EXAMPLE 15B.

Example 36B ethyl 7-(3-aminopyrrolidin-1-yl)-6-fluoro-4-oxo-1,4-dihydro-1,8-naphthyridine-3-carboxylate, trifluoroacetic acid salt A solution of EXAMPLE 36A (115 mg) in trifluoroacetic acid (10 mL) was refluxed for 18 hours and concentrated; and the concentrate was purified by reverse phase HPLC. NMR (300 MHz, DMSO-d$_6$) δ 12.29 (br s, 1H), 8.26 (s, 1H), 8.09 (br s, 3H), 7.85 (d, 1H), 4.20 (q, 2H), 4.12-3.80 (m, 5H), 2.44-2.11 (m, 4H), 1.26 (m, 3H).

Example 37

7-((3-(4-(3-aminopropyl)piperazin-1-yl)propyl)amino)-6-fluoro-5-methyl-4-oxo-1,4-dihydro-1,8-naphthyridine-3-carboxylic acid A mixture of p-nitrophenylcarbonate resin (Nova Biochem Inc., substitution 0.92 mmoles/g) (8.5 g) and 3-(4-(3-aminopropyl)piperazin-1-yl)propylamine (15.64 mmole) was stirred for 18 hours and decanted. The remainder was washed with DMF, methanol, dichloromethane, dimethylformamide, methanol (twice), and dichloromethane and dried to provide the desired resin.

A mixture of EXAMPLE 1D, the resin (300 mg), and diisopropylethylamine (90 µL) was heated at 100° C. for 18 hours then cooled and decanted. The remainder was washed five times with each of dimethylacetamide, methanol, dimethylacetamide, methanol, and dichloromethane, dried, treated with 50% trifluoroacetic acid/dichloromethane, stirred for 2 hours, decanted, and filtered with dichloromethane. The filtrate was concentrated, dissolved in 50% DMSO/methanol (1.5 mL), and purified by reverse phase HPLC. The product was suspended in iso-propanol (1 mL), treated with 1M LiOH (1.2 mL), heated at 80° C. for 18 hours in a sealed vial then cooled, and concentrated. The concentrate was acidified to pH 4-6 with 1-2 mL of 10% citric acid and filtered. The filtrant was treated with trifluoroacetic acid (1.5 mL), heated at 70° C. for 18 hours then cooled and concentrated. The concentrate was triturated with diethyl ether and filtered. NMR (500 MHz DMSO-$d_6$) δ 15.95 (br s, 1H), 13.1 (br s, 1H), 8.42 (m, 1H), 8.10 (m, 1H), 7.75 (br s, 2H), 3.0-4.0 (m, 12H), 2.70 (m, 3H), 2.00 (br s, 2H), 1.75 (br s, 2H).

Example 38

7-((3-aminopropyl)amino)-6-fluoro-5-methyl-4-oxo-1,4-dihydro-1,8-naphthyridine-3-carboxylic acid This example was prepared by substituting propane-1,3-diamine for 3-4-(3-aminopropyl)piperazin-1-yl)propylamine in EXAMPLE 37. NMR (500 MHz DMSO-$d_6$) δ 15.95 (s, 1H), 8.45 (s, 1H), 8.15 (m, 1H), 7.70 (br s, 2H), 3.50 (m, 2H), 2.85 (m, 2H), 2.70 (m, 3H), 1.90 (m, 2H).

Example 39

6-fluoro-7-(3-fluorophenyl)-4-oxo-1,4-dihydro-1,8-naphthyridine-3-carboxylic acid

Example 39A ethyl 1-(2,4-dimethoxybenzyl)-6-fluoro-7-(3-fluorophenyl)-4-oxo-1,4-dihydro-1,8-naphthyridine-3-carboxylate A solution of EXAMPLE 7F (210 mg), potassium acetate (176 mg), 3-fluorobenzeneboronic acid (84 mg), and (1,1'-bis(diphenylphosphino)ferrocene)dichloropalladium (II) (12 mg) in DMF (6 mL) was heated at 90° C. for 3 hours then cooled, diluted with dichloromethane, washed with water, and dried ($Na_2SO_4$), filtered, and concentrated; and the concentrate was flash chromatographed on silica gel with 0-2% methanol/dichloromethane.

Example 39B 1-(2,4-dimethoxybenzyl)-6-fluoro-7-(3-fluorophenyl)-4-oxo-1,4-dihydro-1,8-naphthyridine-3-carboxylic acid This example was prepared by substituting EXAMPLE 39A for EXAMPLE 30A in EXAMPLE 30B and conducting the reaction for 4 hours.

Example 39C 6-fluoro-7-(3-fluorophenyl)-4-oxo-1,4-dihydro-1,8-naphthyridine-3-carboxylic acid This example was prepared by substituting EXAMPLE 39B for EXAMPLE 30B in EXAMPLE 30C and conducting the reaction for 3 hours. NMR (300 MHz, DMSO-$d_6$) δ 14.5 (br s, 1H), 14.05 (br s, 1H), 8.84 (s, 1H), 8.60 (m, 1H), 7.92 (m, 1H), 7.83 (m, 1H), 7.68 (m, 1H), 7.49 (m, 1H).

Example 40

7-(3-aminopyrrolidin-1-yl)-6-fluoro-4-oxo-1,4-dihydro-1,8-naphthyridine-3-carboxamide

Example 40A 7-(3-((tert-butoxycarbonyl)amino)pyrrolidin-1-yl)-1-(2,4-dimethoxybenzyl)-6-fluoro-4-oxo-1,4-dihydro-1,8-naphthyridine-3-carboxamide A suspension of ammonium chloride (19 mg) in toluene (5 mL) was treated with 2M trimethylaluminum in toluene (350 µL), stirred for 30 minutes, treated with EXAMPLE 36A (200 mg) heated at 65° C. for 18 hours, diluted with dichloromethane (40 mL), washed with 10% citric acid, water, and brine, and dried ($MgSO_4$), filtered, and concentrated; and the concentrate was crystallized from dichloromethane/diethyl ether.

Example 40B 7-(3-aminopyrrolidin-1-yl)-6-fluoro-4-oxo-1,4-dihydro-1,8-naphthyridine-3-carboxamide, trifluoroacetic acid salt This example was prepared by substituting EXAMPLE 40A for EXAMPLE 36A in EXAMPLE 36B. NMR (500 MHz, DMSO-$d_6$) δ 13.3 (br s, 1H), 9.24 (d, 2H), 8.42 (s, 1H), 8.11 (br s, 3H), 7.94 (d, 1H), 7.38 (d, 2H), 3.95-3.88 (m, 3H), 3.83-3.71 (m, 2H), 2.34-2.27 (m, 1H), 2.10-2.07 (m, 1H).

Example 41

7-((3-((3-aminopropyl)(methyl)amino)propyl)amino)-6-fluoro-5-methyl-4-oxo-1,4-dihydro-1,8-naphthyridine-3-carboxylic acid This example was prepared by substituting N-(3-aminopropyl)-N-methylpropane-1,3-diamine for 3-(4-(3-aminopropyl)piperazin-1-yl)propylamine in EXAMPLE 37. NMR (500 MHz DMSO-$d_6$) δ 15.95 (br s, 1H), 13.10 (br s, 1H), 8.45 (s, 1H), 8.15 (m, 1H), 7.90 (br s, 2H), 2.80-4.00 (m, 8H), 2.75 (s, 3H), 2.65 (m, 3H), 1.90-2.05 (m, 4H).

Example 43

7-((2-(dimethylamino)ethyl)(ethyl)amino)-6-fluoro-5-methyl-4-oxo-1,4-dihydro-1,8-naphthyridine-3-carboxylic acid This example was prepared by substituting N-ethyl-N',N'-dimethylethane-1,2-diamine for tert-butyl methyl(octahydrocyclopenta(c)pyrrol-4-yl)carbamate in EXAMPLE 17. NMR (500 MHz DMSO-$d_6$) δ 15.70 (br s, 1H), 13.05 (br s, 1H), 8.60 (s, 1H), 3.95 (m, 2H), 3.65 (m, 2H), 3.40 (m, 2H), 2.90 (s, 6H), 2.70 (m, 3H), 1.25 (m, 3H).

Example 44

7-((4aS,7aS)-octahydro-6H-pyrrolo[3,4-b]pyridin-6-yl)-6-fluoro-4-oxo-1,4-dihydro-1,8-naphthyridine-3-carboxylic acid This example was prepared by substituting (4aS,7aS)-octahydro-1H-pyrrolo[3,4-b]pyridine for (3S)-3-(tert-butoxycarbonylamino)pyrrolidine in EXAMPLE 9. NMR (500 MHz DMSO-d$_6$) δ 13.3 (s, 1H), 8.80 (br s, 1H), 8.50 (m, 1H), 8.00 (m, 1H), 3.40-4.00 (m, 6H), 3.20 (m, 1H), 2.90 (m, 1H), 1.60-1.90 (m, 4H).

Example 45

6-fluoro-4-oxo-7-(3-pyridin-2-ylpyrrolidin-1-yl)-1,4-dihydro-1,8-naphthyridine-3-carboxylic acid This example was prepared by substituting 2-pyrrolidin-3-ylpyridine for (3S)-3-(tert-butoxycarbonylamino)pyrrolidine in EXAMPLE 9 and omitting HCl/dioxane. NMR (500 MHz DMSO-d$_6$) δ 15.82 (br s, 1H), 13.2 (br s, 1H), 8.55 (m, 1H), 8.50 (s, 1H), 7.95 (m, 1H), 7.78 (m, 1H), 7.40 (m, 1H), 7.25 (m, 1H), 4.20 (m, 1H), 3.90-4.00 (m, 2H), 3.85 (m, 1H), 3.75 (m, 1H), 2.40 (m, 1H), 2.20 (m, 1H).

Example 46

6-fluoro-5-methyl-4-oxo-7-pyrrolidin-1-yl-1,4-dihydro-1,8-naphthyridine-3-carboxylic acid Example 46A ethyl 1-(2,4-dimethoxybenzyl)-6-fluoro-5-methyl-4-oxo-7-pyrrolidin-1-yl-1,4-dihydro-1,8-naphthyridine-3-carboxylate This example was prepared by substituting pyrrolidine for (3R)-3-(tert-butoxycarbonylamino)pyrrolidine in EXAMPLE 1E.

Example 46B 6-fluoro-5-methyl-4-oxo-7-pyrrolidin-1-yl-1,4-dihydro-1,8-naphthyridine-3-carboxylic acid, sodium salt A solution of Example 46A (260 mg) in trifluoroacetic acid (30 mL) was refluxed for 3 hours and concentrated. The concentrate was azeotroped with toluene, suspended in water (200 mL) and 1M NaOH (0.48 mL), sonicated for 3 hours (in an unsuccessful attempt to make the sodium salt), and filtered through filter paper and a 0.2μ syringe filter. The filtrate was acidified and filtered; and the filtrate was suspended in DMSO (5 mL), treated with 1M NaOH (0.337 mL), filtered through a 0.2μ syringe filter and concentrated.

NMR (300 MHz, DMSO-d$_6$) δ 8.60 (s, 1H), 3.64 (m, 4H), 2.70 (m, 3H), 1.96 (m, 4H).

Example 47

7-((2-(dimethylamino)ethyl)(methyl)amino)-5-methyl-4-oxo-1,4-dihydro-1,8-naphthyridine-3-carboxylic acid Example 47A ethyl 1-(2,4-dimethoxybenzyl)-7-((2-(dimethylamino)ethyl)(methyl)amino)-5-methyl-4-oxo-1,4-dihydro-1,8-naphthyridine-3-carboxylate This example was prepared by substituting N,N,N'-trimethylethane-1,2-diamine for azetidine hydrochloride in EXAMPLE 18A.

Example 47B 7-((2-(dimethylamino)ethyl)(methyl)amino)-5-methyl-4-oxo-1,4-dihydro-1,8-naphthyridine-3-carboxylic acid, trifluoroacetic acid salt This example was prepared by substituting EXAMPLE 47A for EXAMPLE 65D in EXAMPLE 65E. NMR (300 MHz, DMSO-d$_6$) δ 12.83 (s, 1H), 9.33 (s, 1H), 8.53 (m, 1H), 6.79 (s, 1H), 4.01 (m, 2H), 3.14 (s, 3H), 2.89 (s, 6H), 2.79 (s, 3H). (One methylene group is obscured by HOD at δ 3.5-3.3 ppm).

Example 48

7-(3-aminopyrrolidin-1-yl)-6-fluoro-5-methyl-3-(morpholin-4-ylcarbonyl)-1,8-naphthyridin-4(1H)-one This example was prepared by substituting EXAMPLE 2B and morpholine for EXAMPLE 11A and aniline, respectively, in EXAMPLE 11B. After coupling, the solution was concentrated, and the concentrate was dissolved in dichloroethane. This solution was washed with water, 10% citric acid, and 0.5M NaOH, and dried (MgSO$_4$), filtered, and concentrated. The concentrate was purified as described in EXAMPLE 11B, and the 2,4-dimethoxybenzyl group was removed as described in EXAMPLE 11B. NMR (500 MHz DMSO-d$_6$) δ 11.78 (m, 1H), 8.00 (br s, 2H), 7.65 (m, 1H), 3.90 (m, 2H), 3.78 (m, 3H), 3.55 (m, 4H), 3.25 (m, 4H), 2.30 (m, 1H), 2.08 (m, 1H).

7-((2-aminoethyl)amino)-6-fluoro-5-methyl-4-oxo-1,4-dihydro-1,8-naphthyridine-3-carboxylic acid This example was prepared by substituting ethylenediamine for 3-(4-(3-aminopropyl)piperazin-1-yl)propylamine in EXAMPLE 37. NMR (500 MHz DMSO-d$_6$) δ 15.83 (s, 1H), 12.95 (s, 1H), 8.50 (s, 1H), 8.05 (m, 1H), 7.80 (s, 2H), 3.65 (m, 2H), 3.18 (m, 2H), 2.70 (m, 3H).

Example 51

6-fluoro-4-oxo-N-pyridin-2-yl-7-pyrrolidin-1-yl-1,4-dihydro-1,8-naphthyridine-3-carboxamide Example 51A ethyl 7-chloro-1-(2,4-dimethoxybenzyl)-6-fluoro-4-oxo-1,4-dihydro-1,8-naphthyridine-3-carboxylate This example was prepared by substituting 2,4-dimethoxybenzylamine for 3-aminopropionitrile in EXAMPLE 7C.

Example 51B ethyl 1-(2,4-dimethoxybenzyl)-6-fluoro-4-oxo-7-pyrrolidin-1-yl-1,4-dihydro-1,8-naphthyridine-3-carboxylate A suspension of EXAMPLE 51A (30 g), potassium carbonate (25 g), and pyrrolidine (15.2 g) in acetonitrile (750 mL) was stirred for two days and concentrated. The concentrate was dissolved in dichloromethane, washed with water, 10% citric acid, water, and brine, and dried (MgSO$_4$), filtered, and concentrated; and the concentrate was recrystallized from dichloromethane/diethyl ether/hexane.

Example 51C 1-(2,4-dimethoxybenzyl)-6-fluoro-4-oxo-7-pyrrolidin-1-yl-1,4-dihydro-1,8-naphthyridine-3-carboxylic acid A solution of Example 51B (17.9 g) in THF (750 mL) and methanol (70 mL) was treated with 1M LiOH (196 mL), stirred for 1.5 hours, and filtered. The filtrant was dissolved in 2:1 methanol/water (1.5 L), and this solution was treated with 1M HCl and water (500 mL total) and filtered.

Example 51D 6-fluoro-4-oxo-N-pyridin-2-yl-7-pyrrolidin-1-yl-1,4-dihydro-1,8-naphthyridine-3-carboxamide This example was prepared by substituting EXAMPLE 51D and 2-aminopyridine for EXAMPLE 11A and aniline, respectively, in EXAMPLE 11B. After coupling, the solution was concentrated, and the concentrate was dissolved in dichloroethane. This solution was washed with distilled water, 10% citric acid, and 0.5M NaOH, and dried (MgSO$_4$), filtered, and concentrated. The concentrate was purified as described in EXAMPLE 11B, and the 2,4-dimethoxybenzyl group was removed as described in EXAMPLE 11B. NMR (500 MHz DMSO-d$_6$) δ 12.70 (m, 2H), 8.55 (m, 1H), 8.35 (m, 1H), 8.25 (m, 1H), 7.90 (m, 1H), 7.80 (m, 1H), 7.15 (m, 1H), 3.70 (s, 4H), 1.95 (s, 4H).

Example 55

7-((4-aminobutyl)amino)-6-fluoro-5-methyl-4-oxo-1,4-dihydro-1,8-naphthyridine-3-carboxylic acid This example was prepared by substituting butane-1,4-diamine for 3-(4-(3-aminopropyl)piperazin-1-yl)propylamine in EXAMPLE 37. NMR (500 MHz DMSO-d$_6$) δ 15.95 (s, 1H), 12.95 (s, 1H), 8.40 (m, 1H), 8.10 (m, 1H), 7.70 (br s, 2H), 3.70 (m, 2H), 2.82 (m, 2H), 2.65 (m, 3H), 1.50-1.70 (m, 4H).

Example 56

6-fluoro-4-oxo-7-thien-2-yl-1,4-dihydro-1,8-naphthyridine-3-carboxylic acid

Example 56A ethyl 1-(2,4-dimethoxybenzyl)-6-fluoro-4-oxo-7-thien-2-yl-1,4-dihydro-1,8-naphthyridine-3-carboxylate This example was prepared by substituting 2-(tributylstannyl)thiophene for 2-(tributylstannyl)furan in EXAMPLE 30A and conducting the reaction for 23 hours.

Example 56B 1-(2,4-dimethoxybenzyl)-6-fluoro-4-oxo-7-thien-2-yl-1,4-dihydro-1,8-naphthyridine-3-carboxylic acid This example was prepared by substituting EXAMPLE 56A for EXAMPLE 30A in EXAMPLE 30B.

Example 56C 6-fluoro-4-oxo-7-thien-2-yl-1,4-dihydro-1,8-naphthyridine-3-carboxylic acid This example was prepared by substituting EXAMPLE 56B for EXAMPLE 30B in EXAMPLE 30C and conducting the reaction for 18 hours. NMR (300 MHz, DMSO-d$_6$) δ 14.05 (br s, 1H), 10.00 (s, 1H), 8.52 (m, 1H), 8.08 (m, 1H), 8.03 (m, 1H), 7.32 (m, 1H), 6.52 (s, 1H).

Example 58

6-fluoro-7-((3R)-3-hydroxypyrrolidin-1-yl)-4-oxo-1,4-dihydro-1,8-naphthyridine-3-carboxylic acid

Example 58A ethyl 1-tert-butyl-6-fluoro-7-((3R)-3-hydroxypyrrolidin-1-yl)-4-oxo-1,4-dihydro-1,8-naphthyridine-3-carboxylate This example was prepared by substituting (3R)-3-pyrrolidinol hydrochloride for (3R)-3-(tert-butoxycarbonylamino)pyrrolidine in EXAMPLE 15B.

Example 58B 6-fluoro-7-((3R)-3-hydroxypyrrolidin-1-yl)-4-oxo-1,4-dihydro-1,8-naphthyridine-3-carboxylic acid A solution of Example 58A (100 mg) in 6M HCl (6 mL) was heated at 90° C. for 28 hours then cooled and concentrated; and the concentrate was recrystallized from methanol. NMR (300 MHz, DMSO-d$_6$) δ 15.40 (br s, 1H), 13.15 (d, 1H), 8.45 (s, 1H), 7.95 (s, 1H), 4.42-4.39 (m, 1H), 3.80-3.64 (m, 4H), 2.30-1.95 (m, 2H).

Example 62

6-fluoro-5-methyl-4-oxo-7-((3-((trifluoroacetyl)oxy)propyl)amino)-1,4-dihydro-1,8-naphthyridine-3-carboxylic acid

Example 62A 7-azetidin-1-yl-1-(2,4-dimethoxybenzyl)-6-fluoro-5-methyl-4-oxo-1,4-dihydro-1,8-naphthyridine-3-carboxylic acid A solution of Example 5A (250 mg) in THF (30 mL) dichloromethane (10 mL) was treated with 1M LiOH (15 mL), stirred for 18 hours, treated with 10% citric acid, and extracted with dichloromethane; and the extract was concentrated.

Example 62B 6-fluoro-5-methyl-4-oxo-7-((3-((trifluoroacetyl)oxy)propyl)amino)-1,4-dihydro-1,8-naphthyridine-3-carboxylic acid A solution of Example 62A (0.55 mmol) in trifluoroacetic acid (15 mL) was heated to 80° C. for 16 hours and concentrated. The concentrate was dissolved in dichloromethane, washed with water, and filtered; and the filtrate was concentrated to provide the desired product and a small amount of 6-fluoro-5-methyl-4-oxo-7-(azetidin-1-yl)-1,4-dihydro-1,8-naphthyridine-3-carboxylic acid 7-azetidin-1-yl compound. NMR (300 MHz, DMSO-$d_6$) δ 8.4 (s, 1H), 8.15 (m, 1H), 4.5 (m, 2H), 3.55 (m, 2H), 2.7 (m, 3H), 2.1 (m, 2H).

Example 63

6-fluoro-7-(4-(methylamino)hexahydrocyclopenta(c)pyrrol-2(1H)-yl)-4-oxo-1,4-dihydro-1,8-naphthyridine-3-carboxylic acid This example was prepared by substituting tert-butyl methyl(octahydrocyclopenta(c)pyrrol-4-yl)carbamate for (3S)-3-(tert-butoxycarbonylamino)pyrrolidine in EXAMPLE 9.

Example 65

7-chloro-5-methyl-4-oxo-1,4-dihydro-1,8-naphthyridine-3-carboxylic acid

Example 65A 2,6-dichloro-4-methylnicotinic acid

A solution of 2,6-dichloro-4-methyl-nicotinamide (6.40 g) in 2:1 acetic anhydride/acetic acid (156 mL) was treated with sodium nitrite (21.5 g), stirred for 18 hours, poured into diethyl ether (600 mL) and filtered. The filtrate was concentrated with a toluene azeotrope, and the concentrate was treated with brine and extracted with ethyl acetate. The extract was dried (MgSO$_4$), filtered, and concentrated; and this concentrate was suspended in hexane, sonicated and filtered.

Example 65B ethyl 3-(2,6-dichloro-4-methylpyridin-3-yl)-3-oxopropanoate

A solution of EXAMPLE 65A (4.07 g) and oxalyl chloride (1.82 mL) in dichloromethane (80 mL) was treated with N,N-dimethylformamide (0.0459 mL), stirred for 2 hours, concentrated, and dissolved in dichloromethane (30 mL) to provide an acid chloride solution. A suspension of the potassium salt of diethyl malonate (8.41 g) in acetonitrile (80 mL) at 0° C. was treated with magnesium chloride (6.58 g) and triethylamine (6.88 mL), warmed to ambient temperature, stirred for three hours, treated with the acid chloride solution, stirred for 1 hour, and concentrated. The concentrate was treated with 1M HCl (100 mL) and extracted with ethyl acetate. The extract was washed with 1M HCl, saturated sodium bicarbonate and brine, dried (MgSO$_4$), filtered, and concentrated; and the concentrate was flash chromatographed on silica gel with 25% ethyl acetate/hexanes.

Example 65C ethyl (2E/Z)-2-((2,6-dichloro-4-methylpyridin-3-yl)carbonyl)-3-(ethyloxy)prop-2-enoate A solution of Example 65B (4.1 g) and triethylorthoformate (2.72 mL) in acetic anhydride (30 mL) were heated at 130° C. for 1.5 hours then cooled and concentrated; and the concentrate was azeotroped with toluene.

Example 65D ethyl 1-((2,4-bis(methyloxy)phenyl)methyl)-7-chloro-5-methyl-4-oxo-1,4-dihydro-1,8-naphthyridine-3-carboxylate A solution of Example 65C (4.93 g) and 2,4-dimethoxybenzylamine (2.34 mL) in dichloromethane (60 mL) was stirred at ambient temperature for 30 minutes and concentrated. The concentrate was dissolved in THF (60 mL), cooled to 0° C., treated with 60% oily sodium hydride (0.623 g) over 5 minutes, stirred at ambient temperature for 1 hour, treated with water, poured into 0.1M HCl (500 mL), and filtered; and the filtrant was recrystallized from diethyl ether to provide the desired product.

Example 65E 7-chloro-5-methyl-4-oxo-1,4-dihydro-1,8-naphthyridine-3-carboxylic acid A solution of Example 65D (0.200 g) in 1.4-dioxane (5 mL) was treated with lithium hydroxide monohydrate (0.100 g), stirred for 16 hours, and concentrated. The concentrate was dissolved in trifluoroacetic acid (8 mL), heated at 60° C. for 12 hours, and concentrated; and this concentrate was purified by reverse phase HPLC to afford the desired product. NMR (300 MHz, DMSO-$d_6$) δ 14.95 (s, 1H), 13.79 (s, 1H), 8.72 (s, 1H), 7.57 (s, 1H), 2.89 (s, 3H).

Example 66

7-(4-aminopiperidin-1-yl)-6-fluoro-4-oxo-1,4-dihydro-1,8-naphthyridine-3-carboxylic acid Example 66A ethyl 7-(4-((tert-butoxycarbonyl)amino)piperidin-1-yl)-1-(2-cyanoethyl)-6-fluoro-4-oxo-1,4-dihydro-1,8-naphthyridine-3-carboxylate A solution of EXAMPLE 7C (0.5 g) and 1,1-dimethylethyl piperidin-4-ylcarbamate in dichloromethane (100 mL) was stirred for 2 hours, diluted with dichloromethane (100 mL), washed with water, 10% citric acid, and brine, and dried (MgSO$_4$), filtered, and concentrated.

Example 66B 7-(4-((tert-butoxycarbonyl)amino)piperidin-1-yl)-1-(2-cyanoethyl)-6-fluoro-4-oxo-1,4-dihydro-1,8-naphthyridine-3-carboxylic acid A suspension of EXAMPLE 66A (0.71 g) in THF (100 mL) and methanol (50 mL) at reflux was treated with 1M LiOH (100 mL), stirred for 3 hours, concentrated to half volume, acidified with 10% citric acid, and filtered.

Example 66C 7-(4-aminopiperidin-1-yl)-6-fluoro-4-oxo-1,4-dihydro-1,8-naphthyridine-3-carboxylic acid A solution of Example 66B was treated with trifluoroacetic acid (20 mL), stirred for 10 minutes and concentrated; and the concentrate was azeotroped with toluene and dried under vacuum. NMR (300 MHz, DMSO-$d_6$) δ 15.26 (s, 1H), 13.36

(br s, 1H), 8.57 (s, 1H), 8.09 (m, 1H), 7.91 (br s, 3H), 4.46 (m, 2H), 4.02 (br s, 1H), 3.22 (m, 2H), 2.04 (m, 2H), 1.61 (m, 2H).

Example 67

6-fluoro-4-oxo-7-phenyl-1,4-dihydro-1,8-naphthyridine-3-carboxylic acid

Example 67A ethyl 1-(2,4-dimethoxybenzyl)-6-fluoro-4-oxo-7-phenyl-1,4-dihydro-1,8-naphthyridine-3-carboxylate This example was prepared by substituting phenylboronic acid for 3-fluorophenylboronic acid in EXAMPLE 39A and conducting the reaction for 18 hours.

Example 67B 1-(2,4-dimethoxybenzyl)-6-fluoro-4-oxo-7-phenyl-1,4-dihydro-1,8-naphthyridine-3-carboxylic acid This example was prepared by substituting EXAMPLE 67A for EXAMPLE 30A in EXAMPLE 30B and conducting the reaction for 2 hours.

Example 67C 6-fluoro-4-oxo-7-phenyl-1,4-dihydro-1,8-naphthyridine-3-carboxylic acid This example was prepared by substituting EXAMPLE 67B for EXAMPLE 30B in EXAMPLE 30C. NMR (300 MHz, DMSO-$d_6$) δ 14.50 (brs, 1H), 8.85 (s, 1H), 8.57 (m, 1H), 8.04 (m, 2H), 7.63 (m, 3H), 6.03 (s, 1H).

Example 68

6-fluoro-5-methyl-4-oxo-7-((3-pyrrolidin-1-ylpropyl)amino)-1,4-dihydro-1,8-naphthyridine-3-carboxylic acid This example was prepared by substituting 3-pyrrolidin-1-ylpropan-1-amine for tert-butyl methyl(octahydrocyclopenta (c)pyrrol-4-yl)carbamate in EXAMPLE 17. NMR (500 MHz DMSO-$d_6$) δ 15.9 (s, 1H), 13.0 (br s, 1H), 8.45 (s, 1H), 8.10 (m, 1H), 3.55 (m, 4H), 3.20 (m, 4H), 2.70 (m, 3H), 1.80-2.05 (m, 6H).

Example 69

7-(dimethylamino)-6-fluoro-4-oxo-1,4-dihydro-1,8-naphthyridine-3-carboxylic acid

Example 69A ethyl 1-tert-butyl-7-(dimethylamino)-6-fluoro-4-oxo-1,4-dihydro-1,8-naphthyridine-3-carboxylate This example was prepared using EXAMPLE 15A and substituting 2M dimethylamine in methanol for (3R)-3-(tert-butoxycarbonylamino)pyrrolidine in EXAMPLE 15B.

Example 69B 7-(dimethylamino)-6-fluoro-4-oxo-1,4-dihydro-1,8-naphthyridine-3-carboxylic acid A solution of EXAMPLE 69A (155 mg) in 6M HCl (10 mL) was heated at 110° C. for 18 hours then cooled and filtered. NMR (300 MHz, CDCl$_3$) δ 8.64 (d, 1H), 8.00 (d, 1H), 3.32 (d, 6H).

Example 70

7-((1R,5R)-3-((benzyloxy)carbonyl)-3,6-diazabicyclo(3.2.0)hept-6-yl)-6-fluoro-4-oxo-1,4-dihydro-1,8-naphthyridine-3-carboxylic acid This example was prepared by substituting (1R,5R)-3-benzyloxycarbonyl-3,6-diazabicyclo(3.2.0)heptane for (3S)-3-(tert-butoxycarbonylamino)pyrrolidine in EXAMPLE 9.

Example 73

7-(3-aminopyrrolidin-1-yl)-4-oxo-1,4-dihydro-1,8-naphthyridine-3-carboxylic acid

Example 73A ethyl 3-(2,6-dichloropyridin-3-yl)-3-oxopropanoate

This example was prepared by substituting 2,6-dichloronicotinic acid for 2,6-dichloro-4-methyl-nicotinic acid in EXAMPLE 65B.

Example 73B ethyl (2E/Z)-2-((2,6-dichloropyridin-3-yl)carbonyl)-3-(ethyloxy)prop-2-enoate This example was prepared by substituting EXAMPLE 73A for EXAMPLE 65B in EXAMPLE 65C.

Example 73C ethyl 1-tert-butyl-7-chloro-4-oxo-1,4-dihydro-1,8-naphthyridine-3-carboxylate A solution of Example 73B (6.34 g), tert-butylamine (2.21 mL), and potassium carbonate (13.8 g) in DMF (80 mL) at 80° C. was stirred for 16 hours then cooled, diluted with water and extracted with ethyl acetate. The extract was washed with 1M HCl, saturated sodium bicarbonate and brine (500 mL), and dried (MgSO$_4$), filtered, and concentrated; and the concentrate was flash chromatographed on silica gel with 40% ethyl acetate/hexanes.

Example 73D ethyl 7-(3-((tert-butoxycarbonyl)amino)pyrrolidin-1-yl)-1-tert-butyl-4-oxo-1,4-dihydro-1,8-naphthyridine-3-carboxylate A solution of Example 73C (0.19 g), 3-(tert-butoxycarbonylamino)pyrrolidine (0.344 g), and potassium carbonate (0.255 g) in dichloromethane (6.2 mL) was refluxed for 4 hours then cooled, stirred for 18 hours, diluted with dichloromethane (50 mL), washed with 0.1M HCl, saturated sodium bicarbonate, and brine, and dried (MgSO₄), filtered, and concentrated; and the concentrate was recrystallized from diethyl ether.

Example 73E 7-(3-aminopyrrolidin-1-yl)-4-oxo-1,4-dihydro-1,8-naphthyridine-3-carboxylic acid A solution of Example 73D (120 mg) in ethanol (5 mL), and 6M HCl (5 mL) was heated in a sealed tube at 130° C. for 18 hours then cooled, concentrated to remove the ethanol, diluted with diethyl ether, cooled to 0° C., and filtered; and the filtrant was washed with ether, dried, and purified by reverse phase HPLC. NMR (300 MHz, DMSO-$d_6$) δ 8.54 (s), 8.32 (m), 6.83 (m), 4.12 (m), 3.98 (m), 3.83 (m), 2.55 (m), 2.27 (m).

Example 74

4-oxo-7-pyrrolidin-1-yl-1,4-dihydro-1,8-naphthyridine-3-carboxylic acid

Example 74A ethyl 1-tert-butyl-4-oxo-7-pyrrolidin-1-yl-1,4-dihydro-1,8-naphthyridine-3-carboxylate A solution of Example 73C (210 mg), potassium carbonate (150 mg), and pyrrolidine (113 µl) in dichloromethane was stirred for 3 days, treated with potassium carbonate (150 mg) and pyrrolidine (113 µL), stirred for 3 more days, and concentrated; and the concentrate was purified by flash column chromatography on silica gel with a methanol/dichloromethane gradient.

Example 74B 4-oxo-7-pyrrolidin-1-yl-1,4-dihydro-1,8-naphthyridine-3-carboxylic acid A solution of Example 74A (63.2 mg) in ethanol (2.5 mL) and 6M HCl (2.5 mL) was heated in a sealed tube at 130° C. for 18 hours then cooled, diluted with diethyl ether, and filtered. NMR (300 MHz, DMSO-$d_6$) δ 8.43 (s, 1H), 8.22 (m, 1H), 6.80 (m, 1H), 3.55 (m, 4H), 2.00 (m, 4H).

Example 75

7-((3S)-3-aminopyrrolidin-1-yl)-6-fluoro-4-oxo-1,4-dihydro-1,8-naphthyridine-3-carboxamide

Example 75A ethyl 7-((3S)-3-((tert-butoxycarbonyl)amino)pyrrolidin-1-yl)-1-(2,4-dimethoxybenzyl)-6-fluoro-4-oxo-1,4-dihydro-1,8-naphthyridine-3-carboxylate A solution of Example 7F (0.5 g), (3S)-(tert-butoxycarbonylamino)pyrrolidine (0.44 g), and potassium carbonate (0.25 g) in dichloromethane was stirred for 3 days at ambient temperature, loaded onto a flash silica gel column, and eluted with a 0-6% methanol/dichloromethane gradient.

Example 75B 7-((3S)-3-((tert-butoxycarbonyl)amino)pyrrolidin-1-yl)-1-(2,4-dimethoxybenzyl)-6-fluoro-4-oxo-1,4-dihydro-1,8-naphthyridine-3-carboxylic acid A solution of Example 75A (678 mg) and 1M LiOH (4.75 mL) in THF (20 mL) was stirred for 18 hours, diluted with 10% citric acid, and extracted with dichloromethane. The extract was dried (Na₂SO₄), filtered, and concentrated.

Example 75C 7-((3S)-3-((tert-butoxycarbonyl)amino)pyrrolidin-1-yl)-1-(2,4-dimethoxybenzyl)-6-fluoro-4-oxo-1,4-dihydro-1,8-naphthyridine-3-carboxamide A suspension of EXAMPLE 75B (350 mg) and triethylamine (0.098 mL) in dichloromethane (4 mL) and THF (3 mL) at 0° C. was treated with isopropenyl chloroformate (0.077 mL), stirred for 30 minutes, treated with concentrated ammonium hydroxide (0.100 mL), stirred for 18 hours at ambient temperature, loaded onto a flash silica gel column, and eluted with a methanol/dichloromethane gradient.

Example 75D 7-((3S)-3-aminopyrrolidin-1-yl)-6-fluoro-4-oxo-1,4-dihydro-1,8-naphthyridine-3-carboxamide This example was prepared by substituting EXAMPLE 75C for EXAMPLE 1F in EXAMPLE 1G, conducting the reaction at reflux for 18 hours, and crystallizing the concentrate from methanol/diethyl ether. NMR (300 MHz, DMSO-$d_6$) δ 9.26 (m, 1H), 8.44 (s, 1H), 7.96 (m, 1H), 7.41 (m, 1H), 4.09-3.57 (m, 5H), 2.30 (m, 1H), 2.10 (m, 1H).

Example 77

7-(3-aminopyrrolidin-1-yl)-5-ethyl-6-fluoro-4-oxo-1,4-dihydro-1,8-naphthyridine-3-carboxamide

Example 77A 7-(3-((tert-butoxycarbonyl)amino)pyrrolidin-1-yl)-1-(2,4-dimethoxybenzyl)-5-ethyl-6-fluoro-4-oxo-1,4-dihydro-1,8-naphthyridine-3-carboxamide This example was prepared by substituting EXAMPLE 3B for EXAMPLE 2B in EXAMPLE 25A.

Example 77B 7-(3-aminopyrrolidin-1-yl)-5-ethyl-6-fluoro-4-oxo-1,4-dihydro-1,8-naphthyridine-3-carboxamide The title compound was prepared by substituting EXAMPLE 77A for EXAMPLE 1F in EXAMPLE 1G, conducting the reaction at reflux for 18 hours, and purifying the product by reverse phase HPLC. NMR (300 MHz, DMSO-$d_6$) δ 12.26 (m, 1H), 9.35 (m, 1H), 8.39 (m, 1H), 8.07 (m, 2H), 7.34 (m, 1H), 4.00-3.75 (m, 5H), 3.32 (m, 2H), 2.29 (m, 1H), 2.09 (m, 1H), 1.19 (m, 3H).

Example 78

6-fluoro-7-(3-(methylamino)pyrrolidin-1-yl)-4-oxo-1,4-dihydro-1,8-naphthyridine-3-carboxamide

Example 78A 7-(3-((tert-butoxycarbonyl)(methyl)amino)pyrrolidin-1-yl)-1-(2,4-dimethoxybenzyl)-6-fluoro-4-oxo-1,4-dihydro-1,8-naphthyridine-3-carboxamide A suspension of EXAMPLE 22B (410 mg) and triethylamine (0.113 mL) in dichloromethane (4 mL) and THF (3.5 mL) at 0° C. was treated with isopropenyl chloroformate (0.088 mL), stirred for 30 minutes, treated with concentrated ammonium hydroxide (0.114 mL), stirred for 18 hours at ambient temperature, loaded onto a flash silica gel column, and eluted with a methanol/dichloromethane gradient.

Example 78B 6-fluoro-7-(3-(methylamino)pyrrolidin-1-yl)-4-oxo-1,4-dihydro-1,8-naphthyridine-3-carboxamide This example was prepared by substituting EXAMPLE 78A for EXAMPLE 1F in EXAMPLE 1G, conducting the reaction at reflux for 18 hours, and purifying the concentrate by reverse phase HPLC. NMR (300 MHz, DMSO-$d_6$) δ 9.25 (m, 1H), 8.80 (m, 1H), 8.43 (s, 1H), 7.97 (m, 1H), 7.42 (m, 1H), 4.05-3.73 (m, 5H), 2.67 (s, 3H), 2.34 (m, 1H), 2.21 (m, 1H).

Example 79

6-bromo-4-oxo-7-pyrrolidin-1-yl-1,4-dihydro-1,8-naphthyridine-3-carboxylic acid

Example 79A ethyl 6-bromo-1-tert-butyl-4-oxo-7-pyrrolidin-1-yl-1,4-dihydro-1,8-naphthyridine-3-carboxylate A solution of Example 74A (343.42 mg) and 1,3-dibromo-5,5-dimethylhydantoin (171.5 mg) in dichloromethane (15 mL) was stirred for 15 minutes, treated with 10% sodium bisulfite, and extracted with dichloromethane (50 mL). The extract was washed with water and brine, dried (MgSO$_4$), filtered, and concentrated; and the concentrate was crystallized from dichloromethane/diethyl ether.

Example 79B 6-bromo-4-oxo-7-pyrrolidin-1-yl-1,4-dihydro-1,8-naphthyridine-3-carboxylic acid A solution of Example 79A (128 mg) in 1:1 6M HCl/ethanol (15 mL) was refluxed for 24 hours then cooled, diluted with water, and filtered. NMR (300 MHz, DMSO) δ 15.22 (s, 1H), 13.11 (br s, 1H), 8.47 (s, 1H), 8.38 (s, 1H), 3.84-3.80 (m, 4H), 1.95-1.91 (m, 4H).

Example 80

6-chloro-4-oxo-7-pyrrolidin-1-yl-1,4-dihydro-1,8-naphthyridine-3-carboxylic acid

Example 80A ethyl 1-tert-butyl-6-chloro-4-oxo-7-pyrrolidin-1-yl-1,4-dihydro-1,8-naphthyridine-3-carboxylate A solution of Example 74A (448 mg) and 1,3-dichloro-5,5-dimethylhydantoin (282 mg) in dichloromethane (15 mL) was stirred for 8 hours, diluted with 10% sodium bisulfite (30 mL), and extracted with dichloromethane. The extract was washed with water and brine (30 mL), and dried (MgSO$_4$), filtered, and concentrated.

Example 80B 6-chloro-4-oxo-7-pyrrolidin-1-yl-1,4-dihydro-1,8-naphthyridine-3-carboxylic acid A solution of EXAMPLE 80A (160 mg) in 1:1 9M HCl/1,4-dioxane (15 mL) was heated in a sealed tube at 115° C. for 15 minutes and at 95° C. for 24 hours then cooled, diluted with water (20 mL), and filtered. NMR (300 MHz, DMSO-$d_6$) δ 15.25 (s, 1H), 13.11 (br s, 1H), 8.47 (s, 1H), 8.18 (s, 1H), 3.84-3.80 (m, 4H), 1.96-1.91 (m, 4H).

Example 81

7-azetidin-1-yl-6-chloro-4-oxo-1,4-dihydro-1,8-naphthyridine-3-carboxylic acid

Example 81A ethyl (2Z)-2-((2,6-dichloropyridin-3-yl)carbonyl)-3-(dimethylamino)prop-2-enoate A solution of 2,6-dichloronicotinoyl chloride (62.5 g), ethyl 3,3-dimethylaminoacrylate (58.8 g) and triethylamine (69 g) in toluene (600 mL) was stirred at 90° C. for 1 hour then cooled and concentrated. The concentrate was dissolved in dichloromethane (60 mL), diluted with diethyl ether, and filtered. The filtrate was concentrated, and the concentrate was crystallized from dichloromethane/diethyl ether/hexanes.

Example 81B ethyl 7-chloro-1-(2-cyanoethyl)-4-oxo-1,4-dihydro-1,8-naphthyridine-3-carboxylate A solution of EXAMPLE 81A (20 g) and 3-aminopropionitrile (4.9 mL) in 1:1 ethanol/diethyl ether (400 mL) was stirred for 15 minutes, diluted with hexanes (1 L), and filtered. The filtrant was dissolved in acetonitrile (400 mL), and the resulting solution was treated with potassium carbonate (17.4 g), heated at 75° C. for 18 hours then cooled, diluted with water (1.5 L), stirred for 1 hour, and filtered.

Example 81C ethyl 7-azetidin-1-yl-1-(2-cyanoethyl)-4-oxo-1,4-dihydro-1,8-naphthyridine-3-carboxylate A solution of EXAMPLE 81B (16 g), azetidine hydrochloride (12.2 g) and triethylamine (21.9 mL) in acetonitrile (500 mL) was stirred for 2 hours, treated with triethylamine (900 mg), stirred for one hour, diluted with water (1.5 L), stirred for 1 hour, and filtered.

Example 81D ethyl 7-azetidin-1-yl-6-chloro-1-(2-cyanoethyl)-4-oxo-1,4-dihydro-1,8-naphthyridine-3-carboxylate A solution of EXAMPLE 81C (0.50 g) and 1,3-dichloro-5,5-dimethylhydantoin (0.30 g) in chloroform (100 mL) was refluxed for 2 hours then cooled, diluted with chloroform,

Example 81E 7-azetidin-1-yl-6-chloro-4-oxo-1,4-dihydro-1,8-naphthyridine-3-carboxylic acid A suspension of EXAMPLE 81D (0.50 g) in methanol (100 mL) at reflux was treated with a 1M LiOH (50 mL), stirred for 3 hours then cooled, treated with 10% citric acid, and filtered. NMR (300 MHz, DMSO-$d_6$) δ 8.67 (s, 1H), 8.13 (s, 1H), 4.28 (m, 4H), 2.28 (m, 2H).

Example 82

7-azetidin-1-yl-6-bromo-4-oxo-1,4-dihydro-1,8-naphthyridine-3-carboxylic acid

Example 82A ethyl 7-azetidin-1-yl-6-bromo-1-(2-cyanoethyl)-4-oxo-1,4-dihydro-1,8-naphthyridine-3-carboxylate A solution of EXAMPLE 81C (0.50 g) and 1,3-dibromo-5,5-dimethylhydantoin (0.26 g) in chloroform (100 mL) was refluxed for 10 minutes then cooled, diluted with chloroform, washed with 10% sodium bisulfate and brine, dried (MgSO$_4$), filtered, and concentrated; and the concentrate was crystallized from dichloromethane/ethyl acetate/hexanes.

Example 82B 7-azetidin-1-yl-6-bromo-4-oxo-1,4-dihydro-1,8-naphthyridine-3-carboxylic acid A suspension of EXAMPLE 82A (0.50 g) in methanol (100 mL) at reflux was treated with 1M LiOH (50 mL), stirred for 3 hours then cooled, treated with 10% citric acid, and filtered to provide the desired product. NMR (300 MHz, DMSO-$d_6$) δ 17.21 (s, 1H), 8.68 (s, 1H), 8.32 (s, 1H), 4.29 (m, 4H), 2.26 (m, 2H).

Example 83

7-azetidin-1-yl-6-cyano-4-oxo-1,4-dihydro-1,8-naphthyridine-3-carboxylic acid

Example 83A ethyl 7-azetidin-1-yl-6-cyano-1-(2-cyanoethyl)-4-oxo-1,4-dihydro-1,8-naphthyridine-3-carboxylate A solution of EXAMPLE 82A (0.50 g), dicyanozinc (0.29 g), 2-(di-tert-butylphosphino)biphenyl (0.15 g), and tris(dibenzylideneacetone)dipalladium(0) (0.11 g) in acetonitrile (20 mL) was refluxed for 1 hour then cooled and filtered; and the filtrate was diluted with water and filtered.

Example 83B 7-azetidin-1-yl-6-cyano-4-oxo-1,4-dihydro-1,8-naphthyridine-3-carboxylic acid A solution of EXAMPLE 83A (0.38 g) in methanol (100 mL) was treated with 1M LiOH (50 mL), stirred for 18 hours, treated with 10% citric acid, and filtered. NMR (300 MHz, DMSO-$d_6$) δ 14.83 (s, 1H), 13.27 (br s, 1H), 8.67 (s, 1H), 8.48 (s, 1H), 4.43 (br s, 4H), 2.40 (m, 2H).

Example 84

7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylic acid

Example 84A ethyl 7-((1S,4S)-5-(tert-butoxycarbonyl)-2,5-diazabicyclo(2.2.1)hept-2-yl)-1-(2,4-dimethoxybenzyl)-6-fluoro-4-oxo-1,4-dihydro-1,8-naphthyridine-3-carboxylate A solution of EXAMPLE 7F (500 mg), tert-butyl (1S,4S)-(−)-2,5-diazabicyclo(2.2.1)heptane-2-carboxylate (0.259 g), and diisopropylethylamine (0.622 mL) in acetonitrile (11.9 mL) was heated at 50° C. for 18 hours then cooled, diluted with dichloromethane, washed with saturated ammonium chloride and brine, and dried (MgSO$_4$), filtered, and concentrated; and the concentrate was recrystallized from diethyl ether.

Example 84B 7-((1S,4S)-5-(tert-butoxycarbonyl)-2,5-diazabicyclo(2.2.1)hept-2-yl)-1-(2,4-dimethoxybenzyl)-6-fluoro-4-oxo-1,4-dihydro-1,8-naphthyridine-3-carboxylic acid A solution of EXAMPLE 84A in 1:1 ethanol/1M NaOH (20 mL) was heated at 80° C. for 18 hours then cooled, poured into saturated ammonium chloride (100 mL), and filtered.

Example 84C 7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylic acid, trifluoroacetic acid salt A solution of EXAMPLE 84B in trifluoroacetic acid (10 mL) was heated at 50° C. for 18 hours then cooled and concentrated; and the concentrate was purified by reverse phase HPLC. NMR (300 MHz, DMSO-$d_6$): δ 15.25 (br s, 1H), 9.13 (br s, 1H), 8.97 (s, 1H), 8.13 (d, 1H), 7.20 (d, 1H), 6.60 (d, 1H), 6.52 (dd, 1H), 5.55 (q, 2H), 5.19 (br s, 1H), 4.54 (br s, 1H), 3.91 (br s, 2H), 3.78 (s, 3H), 3.75 (s, 3H), 3.35-3.30 (m, 2H), 2.20 (d, 1H), 1.99 (d, 1H).

Example 85

6-(3-aminopyrrolidin-1-yl)-1-oxo-4,7,8,9-tetrahydro-1H-cyclopenta(c)-1,8-naphthyridine-2-carboxylic acid

Example 85A

A suspension of methyl 2-oxocyclopentanecarboxylate (83.8 g) in methanol (220 mL) at 25° C. was treated with 2-cyanoacetamide (49.57 g) and potassium hydroxide (35 g) in methanol (75 mL), stirred for 2 hours, heated at reflux for 18 hours and cooled, treated with water (1.5 L), acidified with concentrated HCl to a pH of less than 1, and filtered.

Example 85B

A suspension of EXAMPLE 85A (30 g) in phosphorous oxychloride (130.5 g) at 170° C. was stirred in sealed tube for 5 hours, poured over ice, and filtered; and the filtrant was flash chromatographed on silica gel with dichloromethane.

Example 85C

A suspension of EXAMPLE 85B (27.7 g) in concentrated sulfuric acid (80 mL) was heated at 110° C. for 4 hours and cooled, poured over ice, and filtered.

Example 85D

A suspension of EXAMPLE 85C (29.2 g) in acetic anhydride (200 mL) at 0° C. was treated with acetic acid (100 mL) and sodium nitrite (69 g), stirred for 18 hours at 25° C., treated with water (1.3 L), acidified with concentrated HCl, and filtered.

Example 85E

A suspension of EXAMPLE 85D (15.7 g) in dichloromethane (120 mL) at 25° C. was treated with oxalyl chloride (9 mL) and N,N-dimethylformamide (2 drops), stirred for 3.5 hours, and concentrated.

Example 85F

A suspension of potassium monoethyl malonate (27.4 g) in acetonitrile (200 mL) at 0° C. was treated with $MgCl_2$ (21.5 g) and triethylamine (22.5 mL), stirred for 3 hours at 25° C. The reaction mixture was treated with EXAMPLE 85E (16.9 g) in tetrahydrofuran (60 mL), stirred for 18 hours (250 mL), acidified with concentrated HCl, concentrated to half volume, and extracted with ethyl acetate (400 mL). The extract was washed with 1M HCl, water, aqueous sodium bicarbonate, water, and brine and dried ($MgSO_4$), filtered through silica gel with ethyl acetate, and concentrated.

Example 85G

A solution of EXAMPLE 85F (11 g) in acetic anhydride (25 mL) at 25° C. was treated with triethylorthoformate (7 mL), heated for 2 hours at 70° C. and 2 hours at 100° C., and concentrated with a toluene azeotrope.

Example 85H

A solution of EXAMPLE 85G (13.0 g) in dichloromethane (75 mL) at 25° C. was treated with tert-butylamine (4.01 mL), stirred for 15 minutes, and concentrated.

Example 85I

A solution of EXAMPLE 85H (14 g) in acetonitrile was treated with potassium carbonate (11 g), heated for 48 hours at reflux and cooled, treated with ethyl acetate, washed with 10% citric acid and brine, and dried ($MgSO_4$), filtered, and concentrated; the concentrate was flash chromatographed on silica gel with dichloromethane and ethyl acetate.

Example 85J

A suspension of EXAMPLE 85I (370 mg) in acetonitrile (30 mL) was treated with potassium carbonate (1.2 g) and tert-butyl pyrrolidin-3-ylcarbamate (987 mg), heated for 18 hours at reflux and cooled, treated with water, and filtered.

Example 85K

A solution of the EXAMPLE 85J (498.6 mg) in methanol (50 mL) at 25° C. was treated with 1M LiOH (7 mL), stirred for 18 hours, concentrated to one quarter volume, treated with 10% citric acid, and filtered.

Example 85

A solution of EXAMPLE 85K (374 mg) in trifluoroacetic acid (5 mL) at 25° C. was treated with concentrated sulfuric acid (0.5 mL), stirred for 3 hours, treated with ether, and filtered. NMR (300 MHz, DMSO-$d_6$) δ ppm 8.41 (s, 1H), 3.94 (m, 5H), 3.38 (t, 2H), 3.16 (t, 2H), 2.07 (m, 3H), 2.28 (m, 1H).

Example 86

6-chloro-5-methyl-7-(3-(methylamino)pyrrolidin-1-yl)-4-oxo-1,4-dihydro-1,8-naphthyridine-3-carboxylic acid

Example 86A

A solution of EXAMPLE 65C (9.5 g) in dichloromethane (35 mL) at 25° C. was treated with 3-aminopropanenitrile (2.2 mL), stirred for 10 minutes, washed with 10% citric acid and brine, and dried ($MgSO_4$), filtered, and concentrated. A solution of the concentrate (9.9 g) in tetrahydrofuran (175 mL) at 25° C. was treated with 60% suspension of sodium hydride in mineral oil (1.167 g) and 10% citric acid and extracted with ethyl acetate. The extract was washed with water and brine and dried ($MgSO_4$), filtered, and concentrated; and the concentrate was flash chromatographed on silica gel with 25-50% ethyl acetate/hexanes.

Example 86B

A suspension of EXAMPLE 86A (456 mg) in acetonitrile (12 mL) at 25° C. was treated with tert-butyl methyl(pyrrolidin-3-yl)carbamate (1.14 g), stirred for 18 hours, treated with 10% citric acid, and extracted with dichloromethane; and the extract was washed with 10% citric acid and brine and dried ($MgSO_4$), filtered, and concentrated.

Example 86C

A solution of EXAMPLE 86B (250 mg) in chloroform (10 mL) at 25° C. was treated with 1,3-dichloro-5,5-dimethylimidazolidine-2,4-dione (107 mg), stirred for 30 minutes, treated with chloroform, washed with 10% sodium bisulfite, water, and brine, and dried ($MgSO_4$), filtered, and concentrated.

Example 86D

A solution of EXAMPLE 86C (245 mg) in ethanol (15 mL) at 25° C. was treated with 1M LiOH (3 mL), stirred for 5 hours at 80° C. and cooled, treated with water (35 mL) and 10% citric acid (50 mL), and filtered.

Example 86

A solution of EXAMPLE 86D (140 mg) in trifluoroacetic acid (5 mL) at 25° C. was stirred for 18 minutes, treated with diethyl ether, and filtered. NMR (300 MHz, DMSO-$d_6$) δ ppm 15.63 (s, 1H), 13.11 (d, 1H), 8.80 (bs, 2H), 8.52 (d, 1H), 3.98 (m, 5H), 2.95 (s, 3H), 2.66 (t, 3H), 2.16 (m, 1H), 2.32 (m, 1H).

Example 87

7-(3-aminopyrrolidin-1-yl)-6-chloro-5-methyl-4-oxo-1,4-dihydro-1,8-naphthyridine-3-carboxylic acid Example 87A A suspension of EXAMPLE 86A (1.2 g) in acetonitrile (20 mL) at 25° C. was treated with tert-butyl pyrrolidin-3-ylcarbamate (2.1 g), stirred for 18 hours at 45° C. and cooled, treated with 10% citric acid, and extracted with dichloromethane. The extract was washed with 10% citric acid, water and brine, dried (MgSO$_4$), filtered, and concentrated.

Example 87B

A solution of EXAMPLE 87A (358 mg) in acetonitrile (10 mL) at 25° C. was treated with 1,3-dichloro-5,5-dimethylimidazolidine-2,4-dione (158 mg), stirred for 90 minutes, treated with diethyl ether, and filtered; and the filtrant was rinsed with diethyl ether, 10% sodium bisulfite, and water.

Example 87C

A solution of EXAMPLE 87B (265 mg) in ethanol (15 mL) at 25° C. was treated with 1M LiOH (3 mL), heated for 6 hours at 80° C. and cooled, treated with water (35 mL) and 10% citric acid (50 mL), and filtered.

Example 87

A solution of EXAMPLE 87C (139 mg) in trifluoroacetic acid (5 mL) at 25° C. was stirred for 10 minutes and concentrated with a toluene azeotrope; and the concentrate was triturated with diethyl ether and filtered. NMR (300 MHz, DMSO-d$_6$) δ ppm 15.64 (s, 1H), 13.09 (d, 1H), 8.50 (d, 1H), 8.14 (s, 3H), 3.97 (m, 5H), 2.94 (s, 3H), 2.29 (m, 1H), 2.06 (d, 1H).

Example 88

6-azetidin-1-yl-1-oxo-4,7,8,9-tetrahydro-1H-cyclopenta(c)-1,8-naphthyridine-2-carboxylic acid Example 88A A suspension of EXAMPLE 85l (360 mg) in acetonitrile (30 mL) was treated with potassium carbonate (1.2 g) and azetidine hydrochloride (482 mg), heated for 18 hours at reflux and cooled, treated with water, and extracted with dichloromethane; and the extract was washed with water and brine and dried (MgSO$_4$), filtered, and concentrated.

Example 88B

A solution of EXAMPLE 88A (293 mg) in methanol (50 mL) at 25° C. was treated with 1M LiOH (8 mL), stirred for 18 hours, concentrated to one quarter volume, treated with 10% citric acid, and filtered.

Example 88

A solution of EXAMPLE 88B (243 mg) in trifluoroacetic acid (5 mL) at 25° C. was treated with concentrated sulfuric acid (0.2 mL), stirred for 2.5 hours, treated with diethyl ether, and filtered. NMR (500 MHz, DMSO-d$_6$) δ ppm 8.34 (s, 1H), 4.32 (t, 4H), 3.35 (t, 2H), 2.92 (t, 2H), 2.35 (m, 2H), 2.09 (m, 2H).

Example 89

6-bromo-5-methyl-7-(3-(methylamino)pyrrolidin-1-yl)-4-oxo-1,4-dihydro-1,8-naphthyridine-3-carboxylic acid Example 89A A solution of EXAMPLE 86A (590 mg) in acetonitrile (30 mL) at 25° C. was treated with tert-butyl methyl(pyrrolidin-3-yl)carbamate (1.1 g), stirred for 5 hours at 55° C. and cooled, concentrated to half volume, treated with water, and extracted with dichloromethane; and the extract was washed with water and brine and dried (MgSO$_4$), filtered, and concentrated.

Example 89B

A solution of EXAMPLE 89A (185 mg) in chloroform (10 mL) at 25° C. was treated with 1,3-dibromo-5,5-dimethylimidazolidine-2,4-dione (65.6 mg), stirred for 30 minutes, treated with chloroform, washed with 10% sodium bisulfite, water, and brine, and dried (MgSO$_4$), filtered, and concentrated.

Example 89C

A solution of EXAMPLE 89B (200 mg) in ethanol (15 mL) at 25° C. was treated with lithium hydroxide (1M, 2 mL), heated for 4 hours at 80° C. and cooled, treated with water (35 mL) and 10% citric acid (50 mL), and filtered.

Example 89

A solution of EXAMPLE 89C (110 mg) in trifluoroacetic acid (5 mL) at 25° C. was stirred for 16 minutes, treated with diethyl ether, and filtered. NMR (300 MHz, DMSO-d$_6$) δ ppm 15.60 (s, 1H), 13.11 (s, 1H), 8.77 (s, 2H), 8.54 (d, 1H), 3.97 (m, 5H) 3.01 (s, 3H), 2.66 (br. s. 3H), 2.31 (m, 1H), 2.13 (m, 1H).

Example 90

7-(3-aminopyrrolidin-1-yl)-5,6-dimethyl-4-oxo-1,4-dihydro-1,8-naphthyridine-3-carboxylic acid Example 90A A suspension of methyl 2-methyl-3-oxobutanoate (83.8 g) in methanol (220 mL) at 25° C. was treated with 2-cyanoacetamide (49.57 g) and potassium hydroxide (35 g) in methanol (75 mL), stirred for 2 hours, heated at reflux for 18 hours and cooled, treated with water (1.5 L), acidified with concentrated HCl to a pH of less than 1, and filtered.

Example 90B

A solution of EXAMPLE 90A (27.17 g) in phosphorous oxychloride (71 mL) at 170° C. was stirred in sealed tube for 5 hours, poured over ice, and filtered; and the filtrant was flash chromatographed on silica gel with dichloromethane.

Example 90C

A suspension of EXAMPLE 90B (60 mL) in sulfuric acid (60 mL) was heated at 110° C. for 1 hour, poured over ice, and filtered.

Example 90D

A suspension of EXAMPLE 90C (23 g) in acetic anhydride (150 mL) at 0° C. was treated with acetic acid (75 mL) and sodium nitrite (52 g) over 1.5 hours, stirred for 18 hours at 25° C., treated with water (1.3 L), acidified with concentrated HCl, and filtered.

Example 90E

A suspension of EXAMPLE 90D (18.6 g) in dichloromethane (150 mL) at 25° C. was treated with oxalyl chloride (11.2 mL) and N,N-dimethylformamide (3 drops), stirred for 4 hours, and concentrated.

Example 90F

A suspension of potassium monoethyl malonate (36 g) in acetonitrile (200 mL) at 0° C. was treated with $MgCl_2$ (28.16 g) and triethylamine (29.5 mL), stirred for 3 hours at 25° C., treated with EXAMPLE 90E (20.1 g) in tetrahydrofuran (60 mL), stirred for 18 hours at 25° C., treated with water (250 mL), acidified with concentrated HCl, concentrated to half volume, and extracted with ethyl acetate; and the extract was washed with 1M HCl, water, sodium bicarbonate, water, and brine, and dried ($MgSO_4$), filtered through silica gel with ethyl acetate, and concentrated.

Example 90G

A solution of EXAMPLE 90F (21.5 g) in acetic anhydride (40 mL) at 25° C. was treated with triethylorthoformate (14 mL), stirred for 2.5 hours at 70° C., 2 hours at 90° C., 2 hours at 110° C., and 30 minutes at 130° C., cooled, and concentrated with a toluene azeotrope.

Example 90H

A solution of EXAMPLE 90G (4.05 g) in dichloromethane (75 mL) at 25° C. was treated with 2,4-dimethoxybenzylamine (4.01 mL), stirred for 15 minutes, and concentrated.

Example 90I

A solution of EXAMPLE 90H (5.46 g) in tetrahydrofuran (200 mL) at 0° C. was treated with 60% suspension of sodium hydride in mineral oil (468 mg), stirred for 1 hour, treated with more 60% suspension of sodium hydride in mineral oil (93.5 mg), stirred for another hour at 25° C., treated with 1M HCl, and filtered.

Example 90J

A suspension of EXAMPLE 90I (455 mg) in acetonitrile (30 mL) was treated with triethylamine (0.5 mL) and tert-butyl pyrrolidin-3-ylcarbamate (393 mg), heated at reflux for 18 hours, treated with 10% citric acid, and extracted with dichloromethane. The extract was washed with water and brine and dried ($MgSO_4$), filtered, and concentrated; and the concentrate was flash chromatographed on silica gel with ethyl acetate.

Example 90K

A solution of EXAMPLE 90J (210 mg) in methanol (25 mL) at 25° C. was treated with 1M LiOH (7 mL), stirred for 3.5 hours at 50° C., treated with 10% citric acid and water, and filtered.

Example 90

A solution of EXAMPLE 90K (180 mg) in trifluoroacetic acid (6 mL) at 25° C. was stirred for 48 hours and concentrated; and the concentrate was purified by reverse phase high performance liquid chromatography (HPLC) on a C18 column with 5-25% of acetonitrile in water containing 0.1% trifluoroacetic acid.

NMR (300 MHz, DMSO-$d_6$) δ ppm 16.07 (s, 1H), 12.91 (d, Hz, 1H), 8.46 (d, 1H), 8.11 (s, 3H), 3.76 (m, 5H), 2.82 (s, 3H), 2.28 (s, 3H), 2.22 (m, 1H), 2.01 (m, 1H).

Example 91

1-(3-(aminomethyl)benzyl)-7-(3-aminopyrrolidin-1-yl)-6-fluoro-4-oxo-1,4-dihydro-1,8-naphthyridine-3-carboxylic acid

Example 91A

A solution of EXAMPLE 7A (1.68 g) in acetonitrile (15 mL) at 0° C. was treated with tert-butyl 3-(aminomethyl)benzylcarbamate (1.24 g) and triethylamine (3.48 mL), stirred for 30 minutes at 0° C., 24 hours at 25° C., and 24 hours at 85° C., cooled, and filtered.

Example 91B

A solution of EXAMPLE 91A (250 mg) in acetonitrile (5 mL) at 25° C. was treated with triethylamine (142 µL) and tert-butyl pyrrolidin-3-ylcarbamate (113.9 mg), stirred for 24 hours, treated with 1M NaOH (2.6 mL) and methanol (2 mL), stirred for 18 hours, treated with water, acidified with 1M HCl to pH 3.5, and filtered.

Example 91

A solution of EXAMPLE 91B (100 mg) in 4N HCl/dioxane (5 mL) at 25° C. was stirred for 2 hours, centrifuged, and decanted; and the solid remaining was triturated with diethyl ether and dichloromethane and filtered. NMR (300 MHz, DMSO-$d_6$) δ ppm 15.40 (bs, 1H), 9.13 (bs, 1H), 8.58 (bs, 3H), 8.40 (bs, 3H), 8.06 (d, 1H), 7.39 (m, 4H), 5.71 (bs, 2H), 3.92 (m, 5H), 3.37 (m, 2H) (obscured by water peak), 2.24 (m, 2H).

Example 92

6-((1S,4S)-2,5-diazabicyclo(2.2.1)hept-2-yl)-1-oxo-4,7,8,9-tetrahydro-1H-cyclopenta(c)-1,8-naphthyridine-2-carboxylic acid

Example 92A

A solution of EXAMPLE 85G (12.09 g) in tetrahydrofuran (200 mL) at 0° C. was treated with 2,4-dimethoxybenzylamine (5.3 g), stirred for 1 hour, treated with 60% oily sodium hydride (0.85 g), stirred for 1 hours at 0° C., treated with 1M HCl and water, and filtered.

Example 92B

A solution of EXAMPLE 92A (300 mg) and tert-butyl (1S,4S)-2,5-diazabicyclo(2.2.1)heptane-2-carboxylate (269 mg) in acetonitrile (20 mL) at 25° C. was treated with triethylamine (1 mL), heated at reflux for 5 days and cooled, treated with dichloromethane (100 mL), washed with water, 10% citric acid, and brine, and dried (MgSO$_4$), filtered, and concentrated; and the concentrate was chromatographed on silica gel with 3% methanol/ethyl acetate.

Example 92C

A solution of EXAMPLE 92B (0.357 g) in methanol (20 mL) at reflux was treated with 1M LiOH (5 mL), stirred for 4 hours and cooled, treated with 10% citric acid, and filtered.

Example 92

A solution of EXAMPLE 92C (0.226 g) in trifluoroacetic acid (15 mL) was heated at reflux for 6 hours and cooled, treated with diethyl ether (200 mL), and filtered. NMR (300 MHz, DMSO-d$_6$) δ ppm 15.81 (s, 1H), 12.97 (bs, 1H), 9.16 (bs, 1H), 8.64 (bs, 1H), 8.45 (d, 1H), 5.10 (s, 1H), 4.50 (s, 1H), 3.91 (s, 2H), 3.43-3.32 (m, 4H), 3.08-2.96 (m, 2H), 2.18-1.94 (m, 4H).

Example 93

1-(3-(aminomethyl)benzyl)-7-((1S,4S)-2,5-diazabicyclo(2.2.1)hept-2-yl)-6-fluoro-4-oxo-1,4-dihydro-1,8-naphthyridine-3-carboxylic acid

Example 93A

A solution of EXAMPLE 91A (250 mg) in acetonitrile (5 mL) at 25° C. was treated with triethylamine (142 μl) and tert-butyl (1S,4S)-2,5-diazabicyclo(2.2.1)heptane-2-carboxylate (121.4 mg), stirred for 24 hours at 50° C., treated with 1M NaOH (2.6 mL) and methanol (2 mL), stirred for 18 hours at 25° C., treated with water, acidified with 1M HCl to pH 3.5, and filtered.

Example 93

A solution of EXAMPLE 93A (100 mg) in 4N HCl/dioxane (5 mL) at 25° C. was stirred for 2 hours, centrifuged, and decanted; and the remaining solid was triturated with diethyl ether and dichloromethane. NMR (300 MHz, DMSO-d$_6$) δ ppm 9.63 (bs, 1H), 9.18 (bs, 1H), 9.16 (s, 1H), 8.30 (bs, 3H), 8.13 (d, 1H), 7.40 (m, 3H), 7.24 (br, 1H), 5.74 (m, 2H), 5.00 (bs, 1H), 4.46 (bs, 1H), 4.07 (m, 1H), 3.97 (dd, 2H), 3.85 (m, 1H), 3.12 (bs, 1H), 2.88 (bs, 1H), 2.03 (dd, 2H).

Example 94

7-(3-(aminomethyl)pyrrolidin-1-yl)-6-bromo-5-methyl-4-oxo-1,4-dihydro-1,8-naphthyridine-3-carboxylic acid

Example 94A

A solution of EXAMPLE 86A (785 mg) in acetonitrile (30 mL) at 25° C. was treated with triethylamine (342 μL) and tert-butyl pyrrolidin-3-ylmethylcarbamate (737 mg), stirred for 36 hours at 55° C. and cooled, concentrated to half volume, treated with water and 10% citric acid, and extracted with dichloromethane. The extract was washed with water and brine and dried (MgSO$_4$), filtered, and concentrated; and the concentrate was flash chromatographed on silica gel with 50-100% ethyl acetate/hexanes.

Example 94B

A solution of EXAMPLE 94A (155 mg) in chloroform (8 mL) at 25° C. was treated with 1,3-dibromo-5,5-dimethylimidazolidine-2,4-dione (55 mg), stirred for 30 minutes at 25° C., treated with chloroform, washed with 10% sodium bisulfite, water, and brine, and dried (MgSO$_4$), filtered, and concentrated; and the concentrate was flash chromatographed on silica gel with 50-100% ethyl acetate/hexane.

Example 94C

A solution of EXAMPLE 94B (115 mg) in ethanol (15 mL) at 25° C. was treated with 1M LiOH (1.5 mL), stirred for 5 hours at 70° C., treated with water (35 mL) and 10% citric acid (50 mL), and filtered.

Example 94

A solution of EXAMPLE 94C (75 mg) in trifluoroacetic acid (4 mL) at 25° C. was stirred for 14 minutes, treated with diethyl ether, and filtered. NMR (300 MHz, DMSO-d$_6$) δ ppm 15.69 (s, 1H), 13.00 (d, 1H), 8.50 (d, 1H), 7.86 (s, 3H), 3.93 (m, 2H), 3.81 (m, 2H), 3.65 (m, 2H), 2.99 (s, 3H), 2.91 (m, 1H), 2.12 (m, 1H), 1.76 (m, 1H).

Example 95

7-(3-aminopyrrolidin-1-yl)-6-bromo-5-methyl-4-oxo-1,4-dihydro-1,8-naphthyridine-3-carboxylic acid

Example 95A

A solution of EXAMPLE 87A (358 mg) in acetonitrile (8 mL) at 25° C. was treated with 1,3-dibromo-5,5-dimethylimidazolidine-2,4-dione (120 mg), stirred for 15 minutes, treated with diethyl ether, and filtered; and the filtrant washed with diethyl ether, 10% sodium bisulfite, and water.

Example 95B

A solution of EXAMPLE 95A (229 mg) in ethanol (10 mL) was treated with 1M LiOH (3 mL), heated at 80° C. for 8 hours, treated with water (25 mL) and 10% citric acid (30 mL), and filtered.

Example 95

A solution of EXAMPLE 95B (122 mg) in trifluoroacetic acid (5 mL) at 25° C. was stirred for 10 minutes and concentrated with a toluene azeotrope; and the concentrate was triturated with diethyl ether and filtered. NMR (300 MHz, DMSO-d$_6$) δ ppm 8.53 (s, 1H), 3.96 (m, 5H), 3.01 (s, 3H), 2.28 (m, 1H), 2.05 (m, 1H).

Example 96

7-(3-(aminomethyl)pyrrolidin-1-yl)-6-chloro-5-methyl-4-oxo-1,4-dihydro-1,8-naphthyridine-3-carboxylic acid

Example 96A

A solution of EXAMPLE 94A (193 mg) in chloroform (8 mL) at 25° C. was treated with 1,3-dichloro-5,5-dimethylimidazolidine-2,4-dione (86 mg), stirred for 9 hours, treated with dichloromethane, washed with 10% sodium bisulfite, water and brine, and dried (MgSO$_4$), filtered, and concentrated.

Example 96B

A solution of EXAMPLE 96A (190 mg) in ethanol (15 mL) at 25° C. was treated with 1M LiOH (2 mL), stirred for 5 hours at 70° C. and 12 hours at 55° C., treated with water (20 mL) and 10% citric acid (30 mL), and filtered.

Example 96

A solution of EXAMPLE 96B (100 mg) in trifluoroacetic acid (4 mL) was stirred at 25° C. for 15 minutes, treated with diethyl ether, and filtered. NMR (300 MHz, DMSO-d$_6$) δ ppm 15.70 (s, 1H), 12.98 (d, 1H), 1.76 (m, 1H), 8.46 (d, 1H), 7.91 (s, 3H), 3.97 (m, 1H), 3.83 (m, 2H), 3.64 (m, 1H), 2.97 (m, 1H), 2.91 (s, 3H), 2.50 (m, 2H), 2.13 (m, 1H).

Example 97

7-azetidin-1-yl-4-oxo-5-(trifluoromethyl)-1,4-dihydro-1,8-naphthyridine-3-carboxylic acid

Example 97A

A solution of EXAMPLE 8C (7.24 g) in dichloromethane (75 mL) at 25° C. was treated with 2,4-dimethoxybenzylamine (2.96 mL), stirred for 30 minutes, and concentrated. A solution of the concentrate in tetrahydrofuran (75 mL) at 0° C. was treated with 60% oily sodium hydride (788 mg) over 5 minutes, stirred for 1 hour at 25° C., treated with water, poured into 0.1M HCl (500 mL), stirred for 18 hours, and filtered; and the filtrant was recrystallized from diethyl ether.

Example 97B

A mixture of EXAMPLE 97A (0.50 g) and azetidine hydrochloride (0.119 g) in acetonitrile (11 mL) at 25° C. was treated with N,N-diisopropylethylamine (0.742 mL), stirred for 18 hours at 50° C., cooled, treated with dichloromethane, washed with 1M HCl, saturated ammonium chloride, and brine, and dried (MgSO$_4$), filtered, and concentrated; and the concentrate was crystallized from diethyl ether.

Example 97

7-azetidin-1-yl-4-oxo-5-(trifluoromethyl)-1,4-dihydro-1,8-naphthyridine-3-carboxylic acid A solution of EXAMPLE 97B (463 mg) in dioxane (10 mL) at 25° C. was treated with lithium hydroxide monohydrate (210 mg), stirred for 18 hours at 60° C., cooled, and concentrated. A solution of the concentrate in trifluoroacetic acid (8 mL) at 25° C. was stirred for 12 hours, poured into water, and filtered; and the filtrant was rinsed with water, dried, triturated with diethyl ether, and filtered. NMR (300 MHz, DMSO-d$_6$) δ ppm 15.53 (bs, 1H), 13.20 (d, 1H), 8.43 (d, 1H), 6.89 (s, 1H), 4.35-4.16 (m, 4H), 2.42 (pentet, 2H).

Example 98

7-(3-((4-((amino(imino)methyl)amino)butyl)amino)pyrrolidin-1-yl)-6-fluoro-4-oxo-1,4-dihydro-1,8-naphthyridine-3-carboxylic acid, trifluoroacetic acid salt

Example 98A

A solution of EXAMPLE 51A (15 g) and pyrrolidin-3-ol (4.67 g) in acetonitrile (450 mL) at 25° C. was treated with triethylamine (10 mL), stirred for 4 hours, and concentrated. The concentrate was dissolved in dichloromethane, and the solution was washed with 1M HCl and brine and dried (Na$_2$SO$_4$), filtered, and concentrated.

Example 98B

A solution of EXAMPLE 98A (8 g) and 1-(3-(dimethylamino)propyl)-3-ethylcarbodiimide hydrochloride (9.86 g) in dichloromethane (250 mL) and dimethylsulfoxide (12 mL) at 25° C. was treated with pyridinium trifluoroacetate (9.83 g) over 10 minutes, stirred for 16 hours, treated with dichloromethane, washed with saturated NaHCO$_3$, water, and brine, and dried (Na$_2$SO$_4$), filtered, and concentrated; and the concentrate was flash chromatographed on silica gel with 30% ethyl acetate/hexanes.

Example 98C

A solution of EXAMPLE 98B (120 mg) and N-(4-aminobutyl)guanidine in methanol (1.5 mL) and dichloromethane (0.5 mL) at 25° C. was treated with acetic acid (150 µL) and sodium triacetoxyborohydride (108 mg), stirred for 12 hours, treated with dichloromethane, washed with saturated sodium bicarbonate and brine, and dried (Na$_2$SO$_4$), filtered, and concentrated; and the concentrate purified by reverse phase high performance liquid chromatography (HPLC) on a C8 column with 10-100% acetonitrile in water containing 0.1% trifluoroacetic acid.

Example 98D

A suspension of EXAMPLE 98C (80 mg) in ethanol (2 mL) at 25° C. was treated with 2M LiOH (340 µL), stirred for 1 hour, and concentrated. The concentrate was acidified to pH 4 with 1M HCl and extracted with dichloromethane. The extract was washed with brine and dried (Na$_2$SO$_4$), filtered, and concentrated; and the concentrate was purified by reverse phase high performance liquid chromatography (HPLC) on a C8 column with 10-100% acetonitrile in water containing 0.1% trifluoroacetic acid.

Example 98

A solution of EXAMPLE 98D (50 mg) in trifluoroacetic acid (1 mL) at 25° C. was treated with concentrated sulfuric acid (10 µL), stirred for 12 hours, and concentrated; and the concentrate was dissolved in dimethylsulfoxide (1.5 mL) and purified by reverse phase high performance liquid chromatography (HPLC) on a C8 column with 10-100% acetonitrile in water containing 0.1% trifluoroacetic acid. NMR (300 MHz, CD$_3$OD) δ ppm 8.54 (s, 1H), 7.96 (d, 1H), 4.25-3.88 (m, 5H), 3.27-3.18 (m, 4H), 2.60-2.45 (m, 1H), 2.38-2.25 (m, 1H), 1.88-1.65 (m, 4H).

Example 99

5-methyl-7-(3-(methylamino)pyrrolidin-1-yl)-4-oxo-1,4-dihydro-1,8-naphthyridine-3-carboxylic acid trifluoroacetic acid salt

Example 99A

A solution of EXAMPLE 65C (4.93 g) in dichloromethane (60 mL) at 25° C. was treated with 2,4-dimethoxybenzylamine (2.34 mL), stirred for 30 minutes, and concentrated. A solution of the concentrate in tetrahydrofuran (60 mL) at 0° C.

was treated with 60% oily sodium hydride (0.623 g) over 5 minutes, stirred for 1 hour at 25° C., treated with water, poured into 0.1M hydrochloric acid (500 mL), and filtered; and the filtrant was rinsed with water, dried, and recrystallized from diethyl ether.

Example 99B

A mixture of EXAMPLE 99A (500 mg) and tert-butyl methyl(pyrrolidin-3-yl)carbamate (0.353 mL) in acetonitrile (12 mL) at 25° C. was treated with N,N-diisopropylethylamine (0.838 mL), stirred for 18 hours at 50° C. and cooled, treated with dichloromethane, washed with saturated ammonium chloride, and dried ($MgSO_4$), filtered, and concentrated; and the concentrate was recrystallized from diethyl ether.

Example 99

5-methyl-7-(3-(methylamino)pyrrolidin-1-yl)-4-oxo-1,4-dihydro-1,8-naphthyridine-3-carboxylic acid trifluoroacetic acid salt A solution of EXAMPLE 99B (0.50 g) in 1:1 ethanol/1M sodium hydroxide (15 mL) at 60° C. was stirred for 18 hours and cooled, poured into saturated ammonium chloride, and filtered. A solution of the filtrant in trifluoroacetic acid (5 mL) was heated for 18 hours at 50° C. and cooled, concentrated, dissolved in 1:1 dimethylsulfoxide/water, filtered, and purified by reverse phase high performance liquid chromatography (HPLC) on a C8 column with 10-100% acetonitrile in water containing 0.1% trifluoroacetic acid. NMR (300 MHz, DMSO-$d_6$) δ ppm 2.23 (m, 1H), 2.39 (m, 1H), 2.66 (t, 3H), 2.78 (s, 3H), 3.80 (m, 5H), 6.62 (s, 1H), 8.42 (d, 1H), 8.81 (bs, 2H), 12.88 (s, 1H), 15.98 (bs, 1H).

Example 100

6-fluoro-7-(3-((3-(1H-imidazol-1-yl)propyl)amino) pyrrolidin-1-yl)-4-oxo-1,4-dihydro-1,8-naphthyridine-3-carboxylic acid, trifluoroacetic acid salt This example was prepared as in EXAMPLE 98 but substituting 3-(1H-imidazol-1-yl)propan-1-amine for N-(4-aminobutyl)guanidine in EXAMPLE 98C. NMR (300 MHz, $CD_3OD$) δ ppm 9.01 (s, 1H), 8.52 (s, 1H), 7.90 (d, 1H), 7.70 (t, 1H), 7.62 (t, 1H), 4.45 (t, 2H), 4.21-3.87 (m, 5H), 3.33-3.21 (m, 2H), 2.60-2.27 (m, 4H).

Example 101

6-bromo-7-((1S,4S)-2,5-diazabicyclo(2.2.1)hept-2-yl)-5-methyl-4-oxo-1,4-dihydro-1,8-naphthyridine-3-carboxylic acid Example 101A A solution of EXAMPLE 86A (430 mg) in acetonitrile (30 mL) at 25° C. was treated with potassium carbonate (1 g) and tert-butyl (1S,4S)-2,5-diazabicyclo(2.2.1)heptane-2-carboxylate (666 mg), stirred for 24 hours at 40° C., cooled, concentrated to half volume, diluted with water, acidified with 10% aqueous citric acid, and extracted with dichloromethane. The extract was washed with water and brine and dried ($MgSO_4$), filtered, and concentrated.

Example 101B

A solution of EXAMPLE 101A (165 mg) in chloroform (8 mL) at 25° C. was treated with 1,3-dibromo-5,5-dimethylimidazolidine-2,4-dione (59 mg), stirred for 30 minutes, diluted with chloroform, washed with 10% sodium bisulfite, water and brine. The organic phase was dried ($MgSO_4$), filtered and concentrated.

Example 101C

A solution of EXAMPLE 101B (150 mg) in ethanol (15 mL) at 25° C. was treated with a solution of 1N LiOH in water (2.5 mL), stirred for 5 hours at 80° C., cooled, treated with water (35 mL), acidified with trifluoroacetic acid (4 mL), and filtered.

Example 101

Example 101C (77 mg) in trifluoroacetic acid (4 mL) was stirred for 30 minutes at 25° C., treated with diethyl ether, and filtered. NMR (500 MHz, DMSO-$d_6$) δ ppm 15.50 (s, 1H), 13.20 (d, 1H), 9.08 (s, 1H), 8.60 (d, 1H), 8.39 (s, 1H), 5.02 (s, 1H), 4.47 (s, 1H), 4.21 (d, 1H), 3.78 (d, 1H), 3.57 (m, 1H), 3.37 (m, 1H), 3.01 (s, 3H), 2.07 (dd, 2H).

Example 102

7-(3-aminopyrrolidin-1-yl)-6-fluoro-4-oxo-1-propa-1,2-dienyl-1,4-dihydro-1,8-naphthyridine-3-carboxylic acid Example 102A A solution of EXAMPLE 7A (1.64 g) in dichloromethane (15 mL) at 25° C. was treated with propargyl amine (0.352 mL), stirred for one hour, and concentrated. A solution of the concentrate in tetrahydrofuran (35 mL) at 0° C. was treated with sodium hydride as a 60% mineral oil dispersion (206 mg), stirred for 5 minutes, treated with dilute HCl (300 mL), and filtered.

Example 102B

A mixture of EXAMPLE 102A (0.5 g) and tert-butyl pyrrolidin-3-ylcarbamate (0.32 g) in acetonitrile (15 mL) at 25° C. was treated with diisopropylethylamine (0.310 mL), heated at 55° C. for one hour, cooled, and concentrated. The residue suspended in dilute aqueous HCl, and filtered.

Example 102

A solution of EXAMPLE 102B (0.15 g) in 2/1 tetrahydrofuran/methanol (9 mL) at 25° C. was treated with 2N NaOH (0.48 mL), stirred for one hour, stirred for ninety minutes at 55° C., 1 hour at 70° C., cooled and concentrated. The residue was partitioned with dilute aqueous HCl and chloroform. The organic extract was concentrated and the concentrate was purified by reverse phase high performance liquid chromatography (HPLC) on a C8 column with 10-95% acetonitrile in water containing 1.0% trifluoroacetic acid. The product was treated with 1N HCl in acetic acid (1 mL) at 25° C. for fifteen minutes, and lyophilized. NMR (500 MHz, DMSO-$d_6$) δ ppm 8.65 (s, 1H), 7.98 (db, 1H), 7.91 (t, 1H), 5.94 (db, 2H), 4.2-3.8 (m, 5H), 2.46-2.18 (m, 2H).

Example 103

7-((3aS,6aS)-1-benzylhexahydropyrrolo[3,4-b]pyrrol-5(1H)-yl)-6-fluoro-4-oxo-1,4-dihydro-1,8-naphthyridine-3-carboxylic acid, trifluoroacetic acid salt

Example 103A

EXAMPLE 103A was prepared according to the procedure as described in WO0181347, EXAMPLE 15E.

Example 103B

EXAMPLE 103B was prepared according to the procedure described in EXAMPLE 98A substituting EXAMPLE 103A for pyrrolidin-3-ol.

Example 103C

EXAMPLE 103B (200 mg) at 25° C. was treated with 4M HCl in dioxane (12 mL), stirred for 2 hours, concentrated, neutralized with saturated $Na_2CO_3$, and extracted with dichloromethane. The extract was dried ($Na_2SO_4$), filtered, and concentrated.

Example 103D

A mixture of EXAMPLE 103C (120 mg) and benzaldehyde (27 mg) in methanol (1.5 mL) and dichloromethane (0.5 mL) at 25° C. was treated with acetic acid (135 μl) and sodium triacetoxyborohydride (108 mg), stirred for 12 hours, diluted with dichloromethane, washed with saturated sodium bicarbonate and brine, dried ($Na_2SO_4$), filtered and concentrated; and the concentrate purified by reverse phase high performance liquid chromatography (HPLC) on a C8 column with 10-100% acetonitrile in water containing 0.1% trifluoroacetic acid.

Example 103E

EXAMPLE 103E was prepared according to the procedure described in EXAMPLE 98D substituting EXAMPLE 103D for EXAMPLE 98C.

Example 103

EXAMPLE 103F was prepared according to procedure described in EXAMPLE 98E substituting EXAMPLE 103E for EXAMPLE 98D. NMR (300 MHz, DMSO-$d_6$) δ ppm 13.27 (s, 1H), 10.22 (s, 1H), 8.54 (d, 1H), 8.05 (d, 1H), 7.61-7.45 (m, 5H), 4.61-4.30 (m, 3H), 4.07-3.76 (m, 4H), 3.40-3.20 (m, 3H), 2.48-2.37 (m, 1H), 1.90-1.76 (m, 1H).

Example 104

6-(4-aminopiperidin-1-yl)-1-oxo-4,7,8,9-tetrahydro-1H-cyclopenta(c)-1,8-naphthyridine-2-carboxylic acid

Example 104A

A solution of EXAMPLE 92A (1.0 g), tert-butyl piperidin-4-ylcarbamate (0.904 g) and triethylamine (1 mL) in acetonitrile (50 mL) was heated at reflux for 5 days, diluted with dichloromethane, washed with water, 10% citric acid and brine. The organic phase was dried (MgSO$_4$), filtered and concentrated. The concentrate was chromatographed on silica gel with 3% methanol/ethyl acetate.

Example 104B

A refluxing solution of EXAMPLE 104A (0.357 g) in methanol (20 mL) was treated with aqueous 1M LiOH (5 mL), heated at reflux for 4 hours, cooled, acidified with 10% citric acid and filtered.

Example 104

EXAMPLE 104B (0.208 g) in trifluoroacetic acid (15 mL) was heated at reflux for 6 hours, cooled, treated with diethyl ether (200 mL) and filtered. NMR (300 MHz, DMSO-$d_6$) δ ppm 15.77 (s, 1H), 13.00 (bs, 1H), 8.48 (s, 1H), 7.90 (bs, 3H), 4.42-4.38 (d, 2H), 3.42-3.33 (m, 3H), 3.11 (t, 2H), 2.96 (t, 2H), 2.11-1.98 (m, 4H), 1.61-1.50 (m, 2H).

Example 105

7-(3-((4-((amino(imino)methyl)amino)butyl)amino) pyrrolidin-1-yl)-1-(2,4-dimethoxybenzyl)-6-fluoro-4-oxo-1,4-dihydro-1,8-naphthyridine-3-carboxylic acid, trifluoroacetic acid salt This compound was prepared according to the procedure described in EXAMPLE 98D. NMR (300 MHz, CD$_3$OD) δ ppm 8.60 (s, 1H), 7.98 (d, 1H), 7.32 (d, 1H), 6.62-6.50 (m, 2H), 5.5 (s, 2H), 4.30-3.91 (m, 5H), 3.81 (s, 3H), 3.79 (s, 3H), 3.30-3.15 (m, 4H), 2.63-2.48 (m, 1H), 2.41-2.25 (m, 1H), 1.88-1.65 (m, 4H).

Example 106

7-(3-((4-aminobutyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting butane-1,4-diamine for N-(4-aminobutyl) guanidine in EXAMPLE 98C. NMR (300 MHz, CD$_3$OD) ppm 8.22 (s, 1H), 7.80 (d, 1H), 4.20-3.82 (m, 5H), 3.30-3.15 (m, 4H), 2.59-2.46 (m, 1H), 2.39-2.21 (m, 1H), 1.96-1.60 (m, 4H).

Example 107

6-bromo-4-oxo-7-piperazin-1-yl-1,4-dihydro-1,8-naphthyridine-3-carboxylic acid

Example 107A

A solution of EXAMPLE 141A (0.60 g) and 1,3-dibromo-5,5-dimethylimidazolidine-2,4-dione (0.224 g) in chloroform (100 mL) was refluxed for 1 hour, cooled, washed with 10% NaHSO$_3$, water and brine. The organic phase was dried (MgSO$_4$), filtered, and concentrated; and the concentrate was crystallized from dichloromethane/diethyl ether/hexanes.

Example 107B

A refluxing solution of EXAMPLE 107A (0.549 g) in methanol (30 mL) was treated with aqueous 1M LiOH (10 mL), heated at reflux for 4 hours, cooled, acidified with 10% aqueous citric acid, and filtered.

Example 107

Example 107B (0.45 g) was refluxed in trifluoroacetic acid (20 mL) and sulfuric acid (5 drops, 16M) for 6 hours, cooled, treated with diethyl ether (200 mL), and filtered. NMR (300 MHz, DMSO-$d_6$) δ ppm 8.73 (s, 1H), 8.62 (s, 1H), 3.74 (m, 4H), 3.31 (bm, 4H).

Example 108

1-oxo-6-pyrrolidin-1-yl-4,7,8,9-tetrahydro-1H-cyclopenta[c]-1,8-naphthyridine-2-carboxylic acid

Example 108A

A suspension of EXAMPLE 851 (410 mg) in acetonitrile (30 mL) at 25° C. was treated with potassium carbonate (1.2 g) and pyrrolidine (0.5 mL), heated at reflux for 18 hours, concentrated, treated with water (80 mL) and ethanol (5 mL), and filtered.

Example 108B

A solution of EXAMPLE 108A (383.5 mg) in methanol (50 mL) at 25° C. was treated with 1N aqueous LiOH (8 mL), stirred for 18 hours, concentrated to 10 mL, treated with 10% citric acid, and filtered.

Example 108

A solution of EXAMPLE 108B in trifluoroacetic acid (5.0 mL) at 25° C. was treated with concentrated sulfuric acid (0.2 mL), stirred for 2.5 hours, treated with diethyl ether, and filtered. NMR (500 MHz, DMSO-$d_6$) δ ppm 8.35 (s, 1H), 3.76 (m, 4H), 3.37 (t, 2H), 3.18 (t, 2H), 2.06 (dd, 2H), 1.93 (m, 4H).

Example 109

7-(4-aminopiperidin-1-yl)-6-bromo-4-oxo-1,4-dihydro-1,8-naphthyridine-3-carboxylic acid

Example 109A

A solution of EXAMPLE 121A (0.60 g) and 1,3-dibromo-5,5-dimethylimidazolidine-2,4-dione (0.218 g) in chloroform (100 mL) was heated at reflux for 1 hour, cooled, washed with 10% NaHSO$_3$, water and brine. The organic phase was dried (MgSO$_4$), filtered, and concentrated; and the concentrate was crystallized from dichloromethane/diethyl ether/hexanes.

Example 109B

A refluxing solution of EXAMPLE 109A (0.634 g) in methanol (30 mL) at 25° C. was treated with 1M LiOH (10 mL), heated at reflux for 4 hours, cooled, acidified with 10% aqueous citric acid and filtered.

Example 109

EXAMPLE 109B (0.56 g) was refluxed in trifluoroacetic acid (20 mL) and sulfuric acid (5 drops, 16M) for 6 hours. The mixture was cooled, treated with diethyl ether (200 mL), and filtered. NMR (300 MHz, DMSO-$d_6$) δ ppm 8.71 (s, 1H), 8.56 (s, 1H), 4.15 (d, 2H), 3.05 (t, 2H), 2.03 (d, 2H), 1.76-1.68 (m, 2H).

Example 110

7-(3-((5-amino-3-oxopentyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting 1,5-diaminopentan-3-one for N-(4-aminobutyl)guanidine in EXAMPLE 98C. NMR (300 MHz, CD$_3$OD) δ ppm 8.46 (s, 1H), 7.82 (d, 1H), 4.26-3.84 (m, 5H), 3.81-3.72 (m, 2H), 3.71-3.64 (t, 2H), 3.58-3.38 (m, 2H), 3.23-3.08 (m, 2H), 2.67-2.48 (m, 2H).

Example 111

7-(3-((3-(aminomethyl)benzyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting 3-(aminomethyl)benzylamine for N-(4-aminobutyl)guanidine in EXAMPLE 98C. NMR (300 MHz, CD$_3$OD) δ ppm 8.48 (s, 1H), 7.88 (d, 1H), 7.70-7.54 (m, 4H), 4.44 (s, 2H), 4.25-4.04 (m, 6H), 3.97-3.87 (m, 1H), 2.63-2.52 (m, 1H), 2.48-2.35 (m, 1H).

Example 112

7-(3-aminopyrrolidin-1-yl)-6-cyano-4-oxo-1,4-dihydro-1,8-naphthyridine-3-carboxylic acid

Example 112A

A solution of EXAMPLE 81B (3.0 g) and tert-butyl pyrrolidin-3-ylcarbamate (5.4 g) in acetonitrile (150 mL) at 25° C. was treated with triethylamine (10 mL), heated at reflux for 3 days, cooled, treated with dichloromethane (100 mL), washed with water, 10% citric acid and brine, dried (MgSO$_4$), filtered and concentrated.

Example 112B

A solution of EXAMPLE 112A (1.5 g) and 1,3-dibromo-5,5-dimethylimidazolidine-2,4-dione (0.56 g) in chloroform (300 mL) was refluxed for 1 hour, cooled, washed with 10% NaHSO$_3$, water and brine, dried (MgSO$_4$), filtered, and concentrated; and the concentrate chromatographed on silica gel with 3% methanol/ethyl acetate.

Example 112C

A solution of EXAMPLE 112B (0.692 g), Zn(CN)$_2$ (0.329 g), tris(dibenzylideneacetone)-dipalladium(0) (0.064 g) and 2-(di-t-butylphosphino)biphenyl (0.084 g) in acetonitrile (60 mL) was heated at reflux for 4 hours, filtered, diluted with dichloromethane (100 mL), washed with water and brine, dried (MgSO$_4$), filtered, and concentrated; and the concentrate crystallized from dichloromethane/diethyl ether/hexanes.

Example 112D

A solution of EXAMPLE 112C (0.114 g) in methanol (15 mL) at 25° C. was treated with 1M LiOH (5 mL), stirred for 12 hours, acidified with 10% aqueous citric acid, and filtered.

Example 112

EXAMPLE 112D (0.066 g) at 25° C. was treated with trifluoroacetic acid (5 mL), stirred for 5 minutes, treated with diethyl ether (200 mL), and filtered. NMR (300 MHz, DMSO-$d_6$) δ ppm 14.72 (bs, 1H), 13.32 (bs, 1H), 8.76 (s, 1H), 8.57 (s, 1H), 8.11 (bs, 3H), 4.01 (bm, 5H), 2.34 (bm, 1H), 2.16 (bm, 1H).

Example 113

7-(3-((3-((amino(imino)methyl)amino)propyl)amino)pyrrolidin-1-yl)-1-(2,4-dimethoxybenzyl)-6-fluoro-4-oxo-1,4-dihydro-1,8-naphthyridine-3-carboxylic acid, trifluoroacetic acid salt Example 113A A solution of EXAMPLE 98B (320 mg) and tert-butyl 3-aminopropylcarbamate in methanol (4.5 mL) and dichloromethane (1.5 mL) at 25° C. was treated with acetic acid (250 µL) and sodium triacetoxyborohydride (288 mg), stirred for 12 hours, and concentrated. A solution of the concentrate in dichloromethane was washed with saturated sodium bicarbonate and brine, dried ($Na_2SO_4$), filtered and concentrated. The concentrate was flash chromatographed on silica gel with 40% ethyl acetate/hexanes.

Example 113B

EXAMPLE 113A (300 mg) at 25° C. was treated with 4M HCl in dioxane (18 mL), stirred for 2 hours, concentrated, neutralized with saturated $Na_2CO_3$, and extracted with dichloromethane; the extract was dried ($Na_2SO_4$), filtered and concentrated.

Example 113C

A mixture of EXAMPLE 113B (120 mg) and 2-ethyl isothiourea hydrobromide (86 mg) in methanol (8 mL) at 25° C. was treated with triethylamine (100 ul), stirred for 16 hours, and filtered. The filtrate was concentrated and purified by reverse phase high performance liquid chromatography (HPLC) on a C8 column with 10-100% acetonitrile in water containing 0.1% trifluoroacetic acid.

Example 113

A suspension of EXAMPLE 113C (40 mg) in ethanol (1.5 mL) at 25° C. was treated with 2M LiOH (180 µL), stirred for 1 hour, and concentrated. The concentrate was acidified to pH4 with 1N HCl, and extracted with dichloromethane. The extract was washed with brine, dried ($Na_2SO_4$), filtered, and concentrated; and the concentrate was purified by reverse phase high performance liquid chromatography (HPLC) on a C8 column with 10-100% acetonitrile in water containing 0.1% trifluoroacetic acid. NMR (300 MHz, $CD_3OD$) δ ppm 8.80 (s, 1H), 7.99 (d, 1H), 7.32 (d, 1H), 6.62-6.50 (m, 2H), 5.2 (s, 2H), 4.28-3.97 (m, 5H), 3.81 (s, 3H), 3.79 (s, 3H), 3.38-3.33 (m, 2H), 3.27-3.19 (m, 2H), 2.66-2.48 (m, 1H), 2.43-2.29 (m, 1H), 2.11-1.97 (m, 2H).

Example 114

7-(3-((5-((amino(imino)methyl)amino)pentyl)amino)pyrrolidin-1-yl)-1-(2,4-dimethoxybenzyl)-6-fluoro-4-oxo-1,4-dihydro-1,8-naphthyridine-3-carboxylic acid, trifluoroacetic acid salt This compound was prepared as described in EXAMPLE 113 substituting tert-butyl 5-aminopentylcarbamate. for tert-butyl 3-aminopropylcarbamate in EXAMPLE 113A. NMR (300 MHz, $CD_3OD$) δ ppm 8.80 (s, 1H), 8.01 (d, 1H), 7.32 (d, 1H), 6.62-6.50 (m, 2H), 5.51 (s, 2H), 4.30-3.96 (m, 5H), 3.81 (s, 3H), 3.79 (s, 3H), 3.25-3.10 (m, 4H), 2.64-2.48 (m, 1H), 2.44-2.25 (m, 1H), 1.87-1.40 (m, 6H).

Example 115

7-(3-((3-(benzylamino)-2-hydroxypropyl)amino)pyrrolidin-1-yl)-6-fluoro-4-oxo-1,4-dihydro-1,8-naphthyridine-3-carboxylic acid Example 115A A mixture of EXAMPLE 36A (4 g) and epibromohydrin (1.80 mL) in N,N-dimethylformamide (50 mL) at 25° C. was treated with 60% oily sodium hydride (0.337 g), stirred for 2 hours, treated with 60% oily sodium hydride (0.337 g), stirred for additional 3 hours, quenched with saturated ammonium chloride, and filtered; and the solid was triturated with diethyl ether and filtered.

Example 115B

A solution of EXAMPLE 115A (0.340 g) and benzylamine (0.621 mL) in chloroform (6 mL) was heated at 75° C. for 18 hours, cooled, and concentrated. The concentrate was taken up in saturated ammonium chloride, sonicated, and filtered.

Example 115

7-(3-(3-Benzylamino-2-hydroxy-propylamino)-pyrrolidin-1-yl)-6-fluoro-4-oxo-1,4-dihydro-(1,8)naphthyridine-3-carboxylic acid trifluoroacetic acid salt A mixture of EXAMPLE 115B (0.200 g) and trifluoroacetic acid (6 mL) was heated at 50° C. for 36 hours, cooled, and concentrated. The concentrate was treated with methanol/diethyl ether and filtered. NMR (300 MHz, DMSO-$d_6$) δ ppm 2.04-2.35 (m, 2H), 2.84-3.07 (m, 2H), 3.60-4.11 (m, 12H), 7.43-7.52 (m, 5H), 8.03 (d, 1H), 8.51 (s, 1H), 8.98 (bs, 2H), 15.43 (bs, 1H).

Example 116

1-((1-(6-carboxy-3-fluoro-5-oxo-5,8-dihydro-1,8-naphthyridin-2-yl)pyrrolidin-3-yl)amino)-1,6-dideoxy-D-galactitol Example 116A A solution of EXAMPLE 118A (8.00 g) in 1M hydrochloric acid in dioxane (100 mL) was stirred at 25° C. for 18 hours, and filtered.

Example 116

1-((1-(6-carboxy-3-fluoro-5-oxo-5,8-dihydro-1,8-naphthyridin-2-yl)pyrrolidin-3-yl)amino)-1,6-dideoxy-D-galactitol A mixture of EXAMPLE 116A (0.250 g), D-fucose (0.200 g), pyridine-borane (0.381 mL) and acetic acid (0.175 mL) in 1:1 methanol/water (12.2 mL) was heated at 70° C. for 18 hours, cooled, and azeotroped with 1-butanol. The residue was taken up in methanol and concentrated (2×), then the product recrystallized from methanol. The conctrate was treated with 1.002 M sodium hydroxide volumetric solution (1.61 mL) and water (4.0 mL), stirred at 70° C. for 18 hours, cooled, and concentrated; and the concentrate was purified by reverse phase high performance liquid chromatography (HPLC) on a C8 column with 10-100% acetonitrile in water containing 0.1% trifluoroacetic acid. After purification, the product was dissolved in water and lyophilized. NMR (300 MHz, DMSO-$d_6$) δ ppm 1.08 (d, 3H), 1.83 (m, 1H), 2.08 (m, 1H), 2.72 (m, 2H), 3.21 (dd, 1H), 3.40 (m, 2H), 3.52 (m, 2H), 3.65-3.91 (m, 9H), 7.84 (d, 1H), 8.61 (s, 1H).

Example 117

6-(3-(benzylamino)pyrrolidin-1-yl)-1-oxo-4,7,8,9-tetrahydro-1H-cyclopenta(c)-1,8-naphthyridine-2-carboxylic acid

Example 117A

A solution of EXAMPLE 85J (1.08 g) in dichloromethane (30 mL) at 25° C. was treated with trifluoroacetic acid (10 mL), stirred for 5.5 hours, and concentrated. The residue was treated with methanol and diethyl ether and filtered.

Example 117B

A solution of EXAMPLE 117A (220 mg) in 1:1 dichloromethane:methanol (15 mL) at 25° C. was treated with benzaldehyde (0.046 mL), acetic acid (0.123 mL) and sodium cyanoborohydride (27 mg), stirred for 5 hours, quenched with water and concentrated. The concentrate was purified using reverse phase high performance liquid chromatography (HPLC) on a C18 column with 0-15% of acetonitrile in water containing 0.1% trifluoroacetic acid.

Example 117C

A solution of EXAMPLE 117B (200 mg) in ethanol (20 mL) at 25° C. was treated with aqueous 1M LiOH (4 mL), stirred for 1 hour at 80° C., 18 hours at 50° C., quenched with trifluoroacetic acid, and concentrated. The concentrate was treated with sufficient water, and filtered.

Example 117

A solution of EXAMPLE 117C (140 mg) in trifluoroacetic acid (10 mL) at 25° C. was treated with concentrated sulfuric acid (4 drops), stirred for 1 hour, diluted with water, and purified by reverse phase high performance liquid chromatography (HPLC) on a C18 column with 0 to 15% acetonitrile in water containing 0.1% trifluoroacetic acid. NMR (300 MHz, DMSO-$d_6$) δ ppm 15.92 (s, 1H), 12.86 (d, 1H), 9.14 (s, 2H), 8.42 (d, 1H), 7.50 (m, 5H), 4.30 (m, 2H), 4.00 (m, 5H), 3.38 (t, 2H), 3.18 (t, 2H), 2.32 (m, 2H), 2.08 (m, 2H).

Example 118

6-fluoro-7-(3-((3-(methylthio)propyl)amino)pyrrolidin-1-yl)-4-oxo-1,4-dihydro-1,8-naphthyridine-3-carboxylic acid, hemicitric acid salt

Example 118A

A solution of EXAMPLE 7C (12 g) and tert-butyl pyrrolidin-3-ylcarbamate (13.8 g) in acetonitrile (250 mL) was heated at 72° C. for 4 hours and concentrated. A solution of the concentrate in dichloromethane was washed with 10% citric acid, water and brine and dried ($Na_2SO_4$), filtered and concentrated.

Example 118B

A suspension of EXAMPLE 118A (8.9 g) in dichloromethane (75 mL) at 25° C. was treated with trifluoroacetic acid (25 mL) over 5 minutes, stirred for 4 hours and concentrated. The concentrate at 25° C. was treated with diethyl ether, stirred for 30 minutes and filtered. A suspension of the solid in dichloromethane (75 mL) and methanol (75 mL) at 0° C. was treated with triethylamine (5 mL), stirred for 2 hours at 25° C., concentrated and dried.

Example 118C

A solution of EXAMPLE 118B (150 mg) and 3-(methylthio)propanal (33 mg) in dichloromethane (2.5 mL) and methanol (2.5 mL) was stirred at 25° C. for 30 minutes, treated with acetic acid (69 mg) and sodium cyanoborohydride (16 mg), stirred for 40 minutes at 25° C., diluted with dichloromethane, washed with saturated sodium bicarbonate and brine, dried ($Na_2SO_4$), filtered and concentrated. The concentrate was purified by reverse phase high performance liquid chromatography (HPLC) on a C8 column with 10-100% acetonitrile in water containing 0.1% trifluoroacetic acid.

Example 118

A suspension of EXAMPLE 118C (47 mg) in ethanol (1.5 mL) at 75° C. was treated with aqueous 1M LiOH (0.815 mL), stirred for 4 hours, cooled, concentrated to half volume, acidified with 10% citric acid, and filtered. NMR (300 MHz, DMSO-$d_6$/$CF_3COOD$) δ ppm 8.48 (s, 1H), 7.95 (d, 1H), 4.15-3.75 (m, 5H), 3.15-3.05 (m, 2H), 2.80-2.60 (m, 2H), 2.55 (t, 2H), 2.40-2.17 (m, 2H), 2.0 (s, 3H), 1.87 (pentet, 2H).

Example 119

6-fluoro-7-(3-((2-(1H-imidazol-5-yl)ethyl)amino)pyrrolidin-1-yl)-4-oxo-1,4-dihydro-1,8-naphthyridine-3-carboxylic acid, trifluoroacetic acid salt This compound was prepared as described in EXAMPLE 98 substituting 2-(1H-imidazol-5-yl)ethanamine for N-(4-aminobutyl)guanidine in EXAMPLE 98C. NMR (300 MHz, $CD_3OD$) δ ppm 8.88 (d, 1H), 8.52 (s, 1H), 7.94 (d, 1H), 7.49 (s, 1H), 4.25-3.88 (m, 5H), 3.6-3.5 (t, 2H), 3.3-3.2 (d, 2H), 2.62-2.31 (m, 2H).

Example 120

6-((1S,4S)-2,5-diazabicyclo(2.2.1)hept-2-yl)-4-(2,4-dimethoxybenzyl)-1-oxo-4,7,8,9-tetrahydro-1H-cyclopenta(c)-1,8-naphthyridine-2-carboxylic acid Example 92C (0.050 g) at 25° C. was treated with trifluoroacetic acid (5 mL), stirred for 5 minutes, treated with diethyl ether (200 mL), and filtered. NMR (300 MHz, DMSO-$d_6$) δ ppm 15.79 (bs, 1H), 9.09 (bs, 1H), 8.88 (s, 1H), 8.55 (bs, 1H), 7.03 (d, 1H), 6.61 (d, 1H), 6.49-6.46 (dd, 1H), 5.53 (q, 2H), 5.07 (s, 1H), 4.49 (s, 1H), 3.90 (s, 2H), 3.78 (s, 3H), 3.74 (s, 3H), 3.64 (m, 2H), 3.03 (m, 2H), 2.15-1.93 (m, 3H).

Example 121

7-(4-aminopiperidin-1-yl)-6-chloro-4-oxo-1,4-dihydro-1,8-naphthyridine-3-carboxylic acid

Example 121A

A solution of EXAMPLE 143B (2.0 g) and tert-butyl piperidin-4-ylcarbamate (3.9 g) in acetonitrile (100 mL) was treated with triethylamine (6 mL), heated at reflux for 3 days, diluted with dichloromethane (200 mL), washed with water, 10% citric acid and brine, dried ($MgSO_4$), filtered and concentrated.

Example 121B

A solution of EXAMPLE 121A (0.50 g) and 1,3-dichloro-5,5-dimethylimidazolidine-2,4-dione (0.21 g) in chloroform (100 mL) was heated for 1 hour at reflux, cooled, washed with 10% $NaHSO_3$, water and brine, dried ($MgSO_4$), filtered, and concentrated; and the concentrate was recrystallized from dichloromethane/diethyl ether/hexanes.

Example 121C

A refluxing solution of EXAMPLE 121B (0.37 g) in methanol (30 mL) was treated with aqueous 1M LiOH (10 mL), heated at reflux for 4 hours, cooled, acidified with 10% aqueous citric acid, and filtered.

Example 121

Example 121C (0.344 g) in trifluoroacetic acid (20 mL) and concentrated sulfuric acid (5 drops) was heated at reflux for 6 hours, cooled, treated with diethyl ether (200 mL), and filtered. NMR (300 MHz, DMSO-$d_6$) δ ppm 8.71 (s, 1H), 8.37 (s, 1H), 4.15 (d, 2H), 3.25 (m, 1H), 3.06 (t, 2H), 2.02 (d, 2H), 1.75-1.67 (m, 2H).

Example 122

7-(3-((4-(aminomethyl)benzyl)amino)pyrrolidin-1-yl)-6-fluoro-4-oxo-1,4-dihydro-1,8-naphthyridine-3-carboxylic acid

Example 122A

A solution of EXAMPLE 7C (15 g) and pyrrolidin-3-ol (6.06 g) in acetonitrile (450 mL) at 25° C. was treated with triethylamine (12 ml), stirred for 4 hours and concentrated. A solution of the concentrate in dichloromethane was washed with 1N HCl and brine, dried ($Na_2SO_4$), filtered, and concentrated.

Example 122B

A solution of EXAMPLE 122A (8 g), dimethylsulfoxide (14 mL), and 1-(3-(dimethylamino)propyl)-3-ethylcarbodiimide hydrochloride (EDCI) (11.12 g) in dichloromethane (250 mL) at 25° C. was treated portionwise with pyridinium trifluoroacetate (10.99 g), stirred for 16 hours, diluted with dichloromethane, washed with saturated $NaHCO_3$, water, and brine, dried ($Na_2SO_4$), filtered, and concentrated; and the concentrate was flash chromatographed on silica gel with 30% ethyl acetate/hexanes.

Example 122C

A solution of EXAMPLE 122B (120 mg), and 4-(aminomethyl)benzylamine in methanol (1.5 mL) and dichloromethane (0.5 mL) at 25° C. was treated with acetic acid (160 μL) and sodium triacetoxyborohydride (115 mg), stirred for 12 hours, diluted with dichloromethane, washed sequentially with saturated sodium bicarbonate and brine, dried ($Na_2SO_4$), filtered and concentrated. The concentrate was purified by reverse phase high performance liquid chromatography (HPLC) on a C8 column with 10-95% acetonitrile in water containing 0.1% trifluoroacetic acid.

Example 122

A solution of EXAMPLE 122C (60 mg) in ethanol (1.5 mL) at 75° C. was treated with aqueous 2M LiOH (0.35 mL), stirred for 6 hours, cooled, and centrifuged. The supernatant was concentrated and purified by reverse phase high performance liquid chromatography (HPLC) (conditions?). NMR (300 MHz, $CD_3OD$) δ ppm 8.58 (s, 1H), 7.88 (d, 1H), 7.70-7.54 (m, 4H), 4.39 (s, 2H), 4.25-4.03 (m, 6H), 3.96-3.89 (m, 1H), 2.61-2.53 (m, 1H), 2.47-2.34 (m, 1H).

Example 123

7-(3-(((3-(aminomethyl)cyclohexyl)methyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 122 substituting (3-(aminomethyl)cyclohexyl)methylamine for 4-(aminomethyl)benzylamine in EXAMPLE 122C. NMR (300 MHz, $CD_3OD$) δ ppm 8.48 (s, 1H), 7.91 (d, 1H), 4.21-4.03 (m, 5H), 2.63-2.55 (m, 1H), 2.43-2.25 (m, 4H), 1.85-1.66 (m, 3H), 1.46-1.06 (m, 6H), 0.81-0.45 (m, 2H).

Example 124

6-fluoro-7-(3-((1H-imidazol-2-ylmethyl)amino)pyrrolidin-1-yl)-4-oxo-1,4-dihydro-1,8-naphthyridine-3-carboxylic acid This compound was prepared according to the procedure described in EXAMPLE 118 substituting 1H-imidazole-2-carbaldehyde for 3-(methylthio)propanal in EXAMPLE 118C. NMR (500 MHz, DMSO-$d_6$/$CF_3COOD$) δ ppm 8.46 (s, 1H), 7.91 (d, 1H), 7.59 (s, 2H), 4.67-4.60 (m, 2H), 4.15-3.80 (m, 5H), 2.43-2.35 (m, 1H), 2.33-2.25 (m, 1H).

Example 125

6-(3-aminopyrrolidin-1-yl)-1-oxo-1,4,7,8,9,10-hexahydrobenzo(c)-1,8-naphthyridine-2-carboxylic acid

Example 125A

A solution of ethyl 2-oxocyclohexanecarboxylate (81.5 g) in methanol (250 mL) at 25° C. was treated with 2-cyanoacetamide (44.0 g) and potassium hydroxide (30.8 g) in methanol (100 mL), stirred for 24 hours, treated with water (300 mL), and filtered.

Example 125B

A suspension of EXAMPLE 125A (33 g) in phosphorous oxychloride (87 mL) was heated in sealed tube for 5 hours at 170° C., cooled, poured over ice, and filtered. The filtrant washed with water, dried and chromatographed on silica gel with dichloromethane.

Example 125C

A suspension of EXAMPLE 125B (30 g) in concentrated sulfuric acid (150 mL) was heated at 115° C. for an hour, cooled, poured over ice, and filtered.

Example 125D

A suspension of EXAMPLE 125C (31 g) in acetic anhydride (200 mL) at 0° C. was treated with acetic acid (100 mL), and sodium nitrite (69 g) over 1.5 hour, stirred for 18 hours at 25° C., treated with water (800 mL), and filtered. The filtrate was acidified with concentrated HCl, and filtered.

Example 125E

A suspension of EXAMPLE 125D (20 g) in dichloromethane (150 mL) at 25° C. was treated with oxalyl chloride (10.8 mL) and N,N-dimethylforamide (2 drops), stirred for 4 hours, and concentrated.

Example 125F

A suspension of potassium ethoxycarbonylacetate (34.6 g) in acetonitrile (200 mL) at 0° C. was treated with magnesium chloride (27.1 g) and triethylamine (28.3 mL), stirred for 3 hours at 25° C., treated with EXAMPLE 125E (21.49 g) in dichloromethane (60 mL), stirred for 18 hours, treated with water (250 mL), acidified with concentrated HCl, concentrated to half volume and extracted with ethyl acetate (400 mL). The extract was washed with 1N HCl, water, sodium bicarbonate, water and brine, dried ($MgSO_4$), filtered and concentrated.

Example 125G

A solution of EXAMPLE 125F (24 g) in acetic anhydride (40 mL) at 25° C. was treated with triethylorthoformate (14 mL), stirred for 2.5 hours at 70° C., 2 hours at 90° C., 2 hours at 110° C., and 30 minutes at 130° C., and concentrated with a toluene azeotrope.

Example 125H

A solution of EXAMPLE 125G (11.0 g) in dichloromethane (100 mL) at 25° C. was treated with 3-aminopropanenitrile (2.29 mL), stirred 15 minutes, and concentrated.

Example 125I

A solution of EXAMPLE 125H (11.7 g) in tetrahydrofuran (300 mL) at 0° C. was treated with 60% oily sodium hydride (2.2 g), stirred for 30 minutes, 2 hours at 25° C., treated with aqueous HCl and water, and filtered.

Example 125J

A suspension of EXAMPLE 125I (392 mg) in acetonitrile (30 mL) at 25° C. was treated with triethylamine (0.152 mL) and tert-butyl pyrrolidin-3-ylcarbamate (507 mg), heated for 18 hours at reflux, cooled, diluted with water, and filtered.

Example 125K

A solution of EXAMPLE 125J (305 mg) in methanol (30 mL) at 25° C. was treated with 1M lithium hydroxide (5 mL), heated for 18 hours at reflux, cooled, acidified with 10% aqueous citric acid, treated with water, and filtered.

Example 125

A solution of EXAMPLE 125K (200 mg) in dichloromethane (4 mL) at 25° C. was treated with trifluoroacetic acid (5.0 mL), stirred for 30 minutes, and concentrated. A solution of the concentrate in methanol (10 mL) was treated with diethyl ether, and filtered. NMR (300 MHz, DMSO-$d_6$) δ ppm 16.16 (s, 1H), 12.86 (s, 1H), 1.75 (m, 2H), 8.43 (s, 1H), 8.09 (s, 3H), 3.91 (m, 4H), 3.73 (m, 3H), 3.47 (m, 2H), 2.73 (s, 2H), 2.26 (m, 1H), 2.04 (d, 1H).

Example 126

7-(3-((3-amino-2-hydroxypropyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 122 substituting 1,3-diaminopropan-2-ol for 4-(aminomethyl)benzylamine in EXAMPLE 122C. NMR (300 MHz, $CD_3OD$) δ ppm 8.60 (s, 1H), 7.95 (d, 1H), 4.41-4.03 (m, 5H), 3.94-3.82 (m, 2H), 3.72-3.63 (m, 1H), 3.29-3.13 (m, 2H), 3.03-2.94 (m, 1H), 2.68-2.62 (m, 1H).

Example 127

7-(3-(4-Amino-4-carboxy-butylamino)-pyrrolidin-1-yl)-6-fluoro-4-oxo-1,4-dihydro-(1,8)naphthyridine-3-carboxylic acid A solution of EXAMPLE 122B (120 mg) and W-(tert-butoxycarbonyl)ornithine in methanol (1.5 mL) and dichloromethane (0.5 mL) at 25° C. was treated with acetic acid (160 μL) and sodium triacetoxyborohydride (115 mg), stirred for 12 hours, diluted with dichloromethane, washed with saturated sodium bicarbonate and brine, dried ($Na_2SO_4$), filtered and concentrated. The concentrate was treated with 4M HCl in dioxane (3 mL), stirred at 25° C. for 2 hours, and concentrated. The concentrate was purified by reverse phase high performance liquid chromatography (HPLC) on a C18 column with 10-95% acetonitrile in water containing 0.1% trifluoroacetic acid. NMR (300 MHz, $CD_3OD$) δ ppm 8.48 (s, 1 H), 7.89 (d, 1H), 4.20-4.00 (m, 4H), 3.97-3.88 (m, 1H), 3.55-3.45 (m, 1H), 3.29-3.20 (m, 2H), 2.60-2.459 (m, 1H), 2.42-2.29 (m, 1H), 2.15-1.88 (m, 4H).

Example 128

1-((1-(6-carboxy-3-fluoro-5-oxo-5,8-dihydro-1,8-naphthyridin-2-yl)pyrrolidin-3-yl)amino)-1-deoxy-D-mannitol The title compound is prepared by the method described for EXAMPLE 116B, substituting D-mannose for D-fucose.

Example 129

1-((1-(6-carboxy-3-fluoro-5-oxo-5,8-dihydro-1,8-naphthyridin-2-yl)pyrrolidin-3-yl)amino)-1-deoxy-D-xylitol The title compound is prepared by the method described for EXAMPLE 116B, substituting D-xylose for D-fucose.

Example 130

6-chloro-7-((1S,4S)-2,5-diazabicyclo(2.2.1)hept-2-yl)-5-methyl-4-oxo-1,4-dihydro-1,8-naphthyridine-3-carboxylic acid

Example 130A

A solution of EXAMPLE 101A (190 mg) in chloroform (10 mL) at 25° C. was treated with 1,3-dichloro-5,5-dimethylimidazolidine-2,4-dione (81.6 mg), stirred for 90 minutes, treated with diethyl ether, and filtered.

Example 130B

A solution of EXAMPLE 130A (180 mg) in ethanol (15 mL) at 25° C. was treated with 1M LiOH (2.5 mL), heated for 6 hours at 80° C., treated with water (35 mL) and 10% citric acid (50 mL), and filtered.

Example 130

A solution of EXAMPLE 130B (97 mg) in trifluoroacetic acid (10 mL) was stirred for 30 minutes at 25° C., concentrated and azeotroped with toluene (20 mL). The resulting solid was suspended in diethyl ether, filtered, washed with diethyl ether, and dried. NMR (300 MHz, DMSO-$d_6$) δ ppm 15.53 (s, 1H), 13.19 (d, 1H), 9.15 (s, 1H), 8.57 (d, 1H), 8.45 (s, 1H), 5.06 (s, 1H), 4.48 (s, 1H), 4.14 (d, 1H), 3.86 (d, 1H), 3.55 (m, 1H), 3.36 (m, 1H), 2.95 (s, 3H), 2.07 (dd, 2H)

Example 131

6-chloro-7-(3-(dimethylamino)pyrrolidin-1-yl)-5-methyl-4-oxo-1,4-dihydro-1,8-naphthyridine-3-carboxylic acid

Example 131A

A suspension of the EXAMPLE 86A (379 mg) in acetonitrile (15 mL) at 25° C. was treated with N,N-dimethylpyrrolidin-3-amine (541 mg), stirred for 18 hours, treated with 10% aqueous citric acid, and extracted with dichloromethane. The extract was washed with 10% aqueous citric acid and brine, dried (MgSO$_4$), filtered and concentrated.

Example 131B

A solution of EXAMPLE 131A (120 mg) in acetonitrile (8 mL) at 25° C. was treated with 1,3-dichloro-5,5-dimethylimidazolidine-2,4-dione (59.5 mg), stirred for 30 minutes, treated with diethyl ether and filtered.

Example 131

A solution of EXAMPLE 131B (110 mg) in ethanol (10 mL) at 25° C. was treated with 1N LiOH in water (1.25 mL), heated for 3 hours at 80° C., cooled, treated with trifluoroacetic acid and water and filtered. NMR (300 MHz, DMSO-$d_6$) δ ppm 15.67 (s, 1H), 1.96 (m, 1H), 8.49 (s, 1H), 3.91 (m, 5H), 2.94 (s, 3H), 2.51 (m, 6H), 2.27 (m, 1H)

Example 132

6-fluoro-7-(3-((3-hydroxybenzyl)amino)pyrrolidin-1-yl)-4-oxo-1,4-dihydro-1,8-naphthyridine-3-carboxylic acid, citric acid salt This compound was prepared according to the procedure described in EXAMPLE 118 substituting 3-acetoxybenzaldehyde for 3-(methylthio)propanal in EXAMPLE 118C. NMR (500 MHz, DMSO-$d_6$/CF$_3$COOD) δ ppm 8.49 (s, 1H), 7.94 (d, 1H), 7.19 (t, 1H), 6.92 (m, 2H), 6.82 (dd, 1H), 4.20-3.08 (m, 2H), 4.06-3.97 (m, 4H), 3.80 (m, 1H), 2.77-2.63 (m, 2H), 2.37-2.27 (m, 2H).

Example 133

7-(3-((2-aminoethyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 122 substituting ethane-1,2-diamine for 4-aminomethylbenzylamine in EXAMPLE 122C. NMR (300 MHz, CD$_3$OD) δ ppm 8.58 (s, 1H), 7.87 (d, 1H), 4.23-4.02 (m, 2H), 3.88-3.79 (t, 2H), 3.55-3.42 (m, 3H), 3.08-2.92 (m, 2H), 2.69-2.61 (m, 1H), 2.47-2.41 (m, 1H).

Example 134

1-((1-(6-carboxy-3-fluoro-5-oxo-5,8-dihydro-1,8-naphthyridin-2-yl)pyrrolidin-3-yl)amino)-1-deoxy-D-galactitol The title compound is prepared by the method described for EXAMPLE 116B, substituting D-galactose for D-fucose.

Example 135

6-((1-(6-carboxy-3-fluoro-5-oxo-5,8-dihydro-1,8-naphthyridin-2-yl)pyrrolidin-3-yl)amino)-1,6-dideoxy-D-galactitol The title compound is prepared by the method described for EXAMPLE 116B, substituting L-fucose for D-fucose.

Example 136

6-fluoro-4-oxo-7-(3-((2-pyridin-4-ylethyl)amino)pyrrolidin-1-yl)-1,4-dihydro-1,8-naphthyridine-3-carboxylic acid, trifluoroacetic acid salt This compound was prepared as described in EXAMPLE 122 substituting 2-pyridin-4-ylethanamine for 4-aminomethylbenzylamine in EXAMPLE 122C. NMR (300 MHz, CD$_3$OD) δ ppm 8.82 (d, 2H), 8.49 (s, 1H), 8.06 (d, 2H), 7.90 (d, 1H), 4.26-3.89 (m, 5H), 3.70-3.60 (t, 2H), 3.47-3.38 (t, 2H), 2.62-2.48 (m, 1H), 2.47-2.34 (m, 1H).

Example 137

1-((1-(6-carboxy-3-fluoro-5-oxo-5,8-dihydro-1,8-naphthyridin-2-yl)pyrrolidin-3-yl)amino)-1,2-dideoxy-D-erythro-pentitol The title compound is prepared by the method described for EXAMPLE 116B, substituting 2-deoxy-D-ribose for D-fucose.

Example 138

1-((1-(6-carboxy-3-fluoro-5-oxo-5,8-dihydro-1,8-naphthyridin-2-yl)pyrrolidin-3-yl)amino)-1-deoxy-L-mannitol The title compound is prepared by the method described for EXAMPLE 116B, substituting L-mannose for D-fucose.

Example 139

6-((1-(6-carboxy-3-fluoro-5-oxo-5,8-dihydro-1,8-naphthyridin-2-yl)pyrrolidin-3-yl)amino)-5,6-dideoxy-D-arabino-hexitol The title compound is prepared by the method described for EXAMPLE 116B, substituting 2-deoxy-D-galactose for D-fucose.

Example 140

7-(3-((4-(3-(dimethylamino)propoxy)benzyl)amino) pyrrolidin-1-yl)-6-fluoro-4-oxo-1,4-dihydro-1,8-naphthyridine-3-carboxylic acid, trifluoroacetic acid salt

Example 140A

The compound was prepared according to the procedure described in EXAMPLE 118C substituting 4-(3-(dimethylamino)propoxy)benzaldehyde for 3-(methylthio)propanal.

Example 140

A suspension of EXAMPLE 140A (106 mg) in ethanol (3 mL) at 75° C. was treated with 1M LiOH (1.5 mL), stirred for 4 hours, concentrated, and purified by reverse phase high performance liquid chromatography on a C8 column with 10-100% acetonitrile in water containing 0.1% trifluoroacetic acid. NMR (300 MHz, DMSO-$d_6$/CF$_3$COOD) δ ppm 8.55 (s, 1H), 8.04 (d, J=12.87 Hz, 1H), 7.50 (d, J=8.82 Hz, 1H), 7.03 (d, J=8.82 Hz, 1H), 4.30-4.20 (m, 2H), 4.10-3.80 (m, 7H), 3.30-3.22 (m, 2H), 2.86 (s, 6H), 2.45-2.30 (m, 2H), 2.18-2.08 (m, 2H).

Example 141

6-chloro-4-oxo-7-piperazin-1-yl-1,4-dihydro-1,8-naphthyridine-3-carboxylic acid

Example 141A

A solution of Example 143B (2.0 g) and tert-butyl piperazine-1-carboxylate (3.61 g) in acetonitrile (100 mL) and triethylamine (6 mL) was heated at reflux for 3 days, cooled, treated with dichloromethane (200 mL), washed with water, 10% aqueous citric acid and brine, dried (MgSO$_4$), filtered, and concentrated.

Example 141B

A solution of Example 141A (0.50 g) and 1,3-dichloro-5,5-dimethylimidazolidine-2,4-dione (0.21 g) in chloroform (100 mL) was refluxed for 1 hour, cooled, washed with aqueous 10% NaHSO$_3$, water and brine, dried (MgSO$_4$), filtered, and concentrated; and the concentrate was crystallized from dichloromethane/diethyl ether/hexanes.

Example 141C

A refluxing solution of EXAMPLE 141B (0.411 g) in methanol (30 mL) was treated with aqueous 1M LiOH (10 mL), heated for 4 hours at reflux, cooled, acidified with 10% aqueous citric acid, and filtered.

Example 141

Example 141C (0.361 g) at 25° C. was treated with trifluoroacetic acid (20 mL) and concentrated sulfuric acid (5 drops), heated at reflux for 6 hours, cooled, treated with diethyl ether (200 mL), and filtered. NMR (300 MHz, DMSO-$d_6$) δ ppm 8.73 (s, 1H), 8.44 (s, 1H), 3.73 (m, 4H), 3.31 (bm, 4H).

Example 142

1-((1-(6-carboxy-3-fluoro-5-oxo-5,8-dihydro-1,8-naphthyridin-2-yl)pyrrolidin-3-yl)amino)-1,2-dideoxy-D-arabino-hexitol The title compound is prepared by the method described for EXAMPLE 116B, substituting 2-deoxy-D-glucose for D-fucose.

Example 143

7-(3-aminopyrrolidin-1-yl)-4-oxo-6-(phenylethynyl)-1,4-dihydro-1,8-naphthyridine-3-carboxylic acid

Example 143A

A solution of 2,6-dichloronicotinic acid (25 g) in dichloromethane (300 mL) and N,N-dimethylformamide (several drops) at 25° C. was treated with 2M oxalyl chloride in dichloromethane (98 mL), stirred till the evolution of gas ceased, and concentrated. A solution of triethylamine (27 mL) and ethyl-3,3-dimethylaminoacrylate (20.5 g) in toluene (150 mL) at 25° C. was treated with a solution of the concentrate in toluene (75 mL), stirred for 2.5 hours, and thirty minutes at 85° C., cooled, stand for 18 hours at 25° C., and partitioned with 10% aqueous HCl and ethyl acetate. The organic extracts were concentrated. A solution of the concentrate in a mixture of diethyl ether (400 mL) and ethanol (200 mL) at 25° C. was treated with tert-butylamine (14.4 mL), stirred for 5 hours, and concentrated; and the concentrate was flash chromatographed on silica gel with 20% ethyl acetate/hexane.

Example 143B

A solution of EXAMPLE 143A (6.93 g) in anhydrous tetrahydrofuran (125 mL) at 0° C. was treated in portions with sodium hydride as a 60% mineral oil dispersion (0.84 g), stirred for thirty minutes, treated with dilute HCl (1400 mL), and filtered. The filtrant was washed with water, dried, and flash chromatographed on silica gel with 50% ethyl acetate/hexane.

Example 143C

A mixture of EXAMPLE 143B (1.0 g) and 3 tert-butyl pyrrolidin-3-ylcarbamate (0.63 g) in acetonitrile (25 mL) at 25° C. was treated with N,N-diisopropylethylamine (0.62 mL), stirred for 18 hours at 55° C., treated with tert-butyl pyrrolidin-3-ylcarbamate (0.100 g) and N,N-diisopropylethylamine (0.1 mL), stirred for 24 hours at 55° C., cooled and concentrated. The concentrate was suspended in dilute aqueous HCl, and filtered.

Example 143D

A solution of EXAMPLE 143C (1.42 g) in tetrahydrofuran (50 mL) at 25° C. was treated with 1,3-dibromo-5,5-dimethylimidazolidine-2,4-dione (0.56 g) in one portion, stirred for 1 hour, and concentrated; and the concentrate was suspended in sodium bisulfite solution, and filtered.

Example 143E

A solution of EXAMPLE 143D (0.193 g) in N,N-dimethylformamide (4 mL) at 25° C. was treated with triethylamine (0.06 mL), ethynylbenzene (0.086 mL), bis(triphenylphosphine)palladium(II) chloride (0.092 g) and copper(I)iodide (0.021 g), stirred in a sealed tube under inert atmosphere for one hour at 85-90° C., cooled and concentrated. The concentrate was flash chromatographed on silica gel with 50% ethyl acetate-hexane.

Example 143

A solution of EXAMPLE 143E (0.092 g) in 2:1 tetrahydrofuran/methanol (6 mL) at 25° C. was treated with 2N NaOH (0.170 mL), stirred for two hours at 55° C., cooled, concentrated, and partitioned with dilute citric acid and chloroform. The combined organic phase was concentrated. The concentrate was treated with trifluoroacetic acid (3 mL) and concentrated sulfuric acid (three drops) at 25° C., stirred for 3.5 hours, and concentrated; and the concentrate purified by reverse phase high performance liquid chromatography (HPLC) on a C8 column with 10-95% acetonitrile in water containing 1.0% trifluoroacetic acid. NMR (500 MHz, DMSO-$d_6$) δ ppm 8.49 (s, 1H), 8.38 (s, 1H), 8.3-8.1 (s, 3H), 7.67-7.55 (m, 2H), 7.5-7.4 (m, 3H), 4.3-3.9 (m, 5H), 2.4-2.27 (m, 1H), 2.2-2.05 (m, 1H).

Example 144

1-((1-(6-carboxy-3-fluoro-5-oxo-5,8-dihydro-1,8-naphthyridin-2-yl)pyrrolidin-3-yl)amino)-1-deoxy-D-ribitol The title compound is prepared by the method described for EXAMPLE 116B, substituting D-ribose for D-fucose.

Example 145

5-((1-(6-carboxy-3-fluoro-5-oxo-5,8-dihydro-1,8-naphthyridin-2-yl)pyrrolidin-3-yl)amino)-5-deoxy-L-ribitol The title compound is prepared by the method described for EXAMPLE 116B, substituting L-ribose for D-fucose.

Example 146

7-(3-(aminomethyl)pyrrolidin-1-yl)-5-methyl-4-oxo-1,4-dihydro-1,8-naphthyridine-3-carboxylic acid

Example 146A

A mixture of EXAMPLE 99A (0.380 g) and tert-butyl pyrrolidin-3-ylmethylcarbamate (0.201 g) in acetonitrile (9 mL) at 25° C. was treated with N,N-diisopropylethylamine (0.478 mL), stirred for 18 hours at 50° C., cooled, treated with dichloromethane, washed with 0.1 M hydrochloric acid, dried (MgSO$_4$), filtered, and concentrated; and the concentrate was recrystallized from diethyl ether.

Example 146B

A solution of EXAMPLE 146A (0.440 g) in 1:1 ethanol/1M sodium hydroxide (15 mL) was stirred for 18 hours at 80° C., poured into saturated ammonium chloride, and filtered.

Example 146

7-(3-(aminomethyl)pyrrolidin-1-yl)-5-methyl-4-oxo-1,4-dihydro-1,8-naphthyridine-3-carboxylic acid A solution of EXAMPLE 146B in trifluoroacetic acid (5 mL) was heated at 50° C. for 18 hours, cooled, and concentrated. The residue was taken up in 1:1 dimethylsulfoxide/methanol, filtered and purified by reverse phase high performance liquid chromatography (HPLC) on a C8 column with 10-100% acetonitrile in water containing 0.1% trifluoroacetic acid. NMR (300 MHz, DMSO-$d_6$) δ ppm 1.84 (m, 1H) 2.17 (m, 1H) 2.58 (m, 1H) 2.75 (s, 3H) 2.96 (m, 2H) 3.32 (dd, 1H) 3.64 (m, 3H) 6.48 (s, 1H) 7.92 (s, 3H) 8.38 (d, 1H) 12.77 (s, 1H) 16.06 (s, 1H).

Example 147

6-fluoro-4-oxo-7-(3-((thien-3-ylmethyl)amino)pyrrolidin-1-yl)-1,4-dihydro-1,8-naphthyridine-3-carboxylic acid, citric acid salt This compound was prepared according to the procedure described in EXAMPLE 118 substituting thiophene-3-carbaldehyde for 3-(methylthio)propanal in EXAMPLE 118C. NMR (500 MHz, DMSO-$d_6$/CF$_3$COOD) δ ppm 8.26 (s, 1H), 7.63 (d, 1H), 7.34 (d, 1H), 7.18 (dd, 1H), 6.96, (d, 1H), 4.03-3.96 (m, 2H), 3.85-3.50 (m, 5H), 2.53-2.35 (m, 4H), 2.15-2.05 (m, 2H).

Example 148

6-fluoro-7-(3-((1H-imidazol-4-ylmethyl)amino)pyrrolidin-1-yl)-4-oxo-1,4-dihydro-1,8-naphthyridine-3-carboxylic acid

Example 148A

A solution of EXAMPLE 7C (5.5 g) in acetonitrile (120 mL) at 25° C. was treated with tert-butyl pyrrolidin-3-ylcarbamate (6.8 g) and triethylamine (4 mL), heated at reflux for 30 minutes, poured into water (1.5 L), acidified with a solution of 10% aqueous citric acid, and filtered. A solution of the filtrant in trifluoroacetic acid (35 mL) was stirred for 2 hours at 25° C., and concentrated; and the concentrate was treated with ethanol and diethyl ether, and filtered.

Example 148B

A solution of EXAMPLE 148A (290 mg) in methanol (10 mL) and dichloromethane (5 mL) at 25° C. was treated with 1H-imidazole-4-carbaldehyde (63 mg), sodium cyanoborohydride (30 mg) and acetic acid (0.170 mL), stirred for 5 hours, treated with 1H-imidazole-4-carbaldehyde (9 mg), stirred for 18 hours, treated with water, and concentrated; and the concentrate was purified by reverse phase high performance liquid chromatography (HPLC) on a C18 column using 0-85% acetonitrile in water containing 0.1% trifluoroacetic acid.

Example 148

A solution of EXAMPLE 148B (140 mg) in ethanol (10 mL) at 25° C. was treated with 1M LiOH (2 mL), heated for 3.5 hours at 70° C., and 18 hours at 50° C., cooled, acidified with trifluoroacetic acid, and concentrated. The product was isolated by reverse phase high performance liquid chromatograph (HPLC) on a C18 column using 0-85% acetonitrile in water containing 0.1% trifluoroacetic acid. NMR (300 MHz, DMSO-$d_6$) δ ppm 15.38 (s, 1H), 13.28 (s, 1H), 8.52 (s, 2H), 8.32 (s, 1H), 8.04 (d, 1H), 7.48 (s, 1H), 4.27 (s, 2H), 3.97 (m, 5H), 2.42 (m, 1H), 2.27 (m, 1H).

771400 Example 149

1-oxo-6-piperazin-1-yl-4,7,8,9-tetrahydro-1H-cyclopenta(c)-1,8-naphthyridine-2-carboxylic acid

Example 149A

A mixture of EXAMPLE 92A (0.30 g) and tert-butyl piperazine-1-carboxylate (0.252 g) in acetonitrile (20 mL) at 25° C. was treated with triethylamine (1 mL), heated at reflux for 3 days, cooled, treated with dichloromethane (100 mL), washed with water, 10% citric acid and brine, dried (MgSO$_4$), filtered and concentrated. The concentrate was chromatographed on silica gel with 3% methanol/ethyl acetate.

Example 149B

A refluxing solution of EXAMPLE 149A (0.274 g) in methanol (20 mL) at 25° C. was treated with aqueous 1M LiOH (5 ml), refluxed for 4 hours, cooled, acidified with 10% aqueous citric acid, and filtered.

Example 149

EXAMPLE 149B (0.166 g) was refluxed in trifluoroacetic acid (15 mL) for 6 hours, cooled, treated with diethyl ether (200 mL), and filtered. NMR (300 MHz, DMSO-$d_6$) δ ppm 15.65 (s, 1H), 13.09 (bs, 1H), 8.83 (bs, 2H), 8.52 (d, 1H), 3.86 (m, 4H), 3.31 (bm, 4H), 3.26 (bs, 2H), 2.98 (t, 2H), 2.10 (m, 2H).

Example 150

6-fluoro-4-oxo-7-(3-((1-phenylethyl)amino)pyrrolidin-1-yl)-1,4-dihydro-1,8-naphthyridine-3-carboxylic acid, trifluoroacetic acid salt This compound was prepared as described in Example 122 substituting 1-phenylethanamine for 4-aminomethylbenzylamine in Example 122C. NMR (300 MHz, CD$_3$OD) δ ppm 8.48 (s, 1H), 7.90 (d, 1H), 7.61-7.47 (m, 5H), 4.67-4.57 (q, 1H), 4.12-3.78 (m, 5H), 2.42-2.31 (m, 1H), 2.23-2.12 (m, 1H), 1.75 (d, 3H).

Example 151

6-fluoro-7-(3-((1-methyl-1-phenylethyl)amino)pyrrolidin-1-yl)-4-oxo-1,4-dihydro-1,8-naphthyridine-3-carboxylic acid, trifluoroacetic acid salt This compound was prepared as described in EXAMPLE 122 substituting 1-methyl-1-phenylethylamine for 4-aminomethylbenzylamine in EXAMPLE 122C.

NMR (300 MHz, DMSO-$d_6$) δ ppm 13.25 (d, 1H), 9.34-9.12 (m, 2H), 8.51 (d, 1H), 8.00 (d, 1H), 7.71-7.62 (d, 2H), 7.57-7.44 (m, 3H), 3.93-3.71 (m, 5H), 2.18-2.06 (m, 1H), 2.04-1.94 (m, 1H), 1.78 (s, 6H).

Example 152

6-fluoro-7-(3-((4-hydroxybenzyl)amino)pyrrolidin-1-yl)-4-oxo-1,4-dihydro-1,8-naphthyridine-3-carboxylic acid, hemicitric acid salt This compound was prepared according to the procedure described in EXAMPLE 118 substituting 4-hydroxybenzaldehyde for 3-(methylthio)propanal in EXAMPLE 118C. NMR (500 MHz, DMSO-$d_6$/CF$_3$COOD) δ ppm 8.47 (s, 1H), 7.93 (d, 1H), 7.29 (d, 2H), 6.80 (d, 2H), 4.15-4.07 (m, 2H), 3.75-4.25 (m, 5H), 2.76-2.62 (m, 2H), 2.40-2.25 (m, 2H).

Example 153

1-((1-(6-carboxy-3-fluoro-5-oxo-5,8-dihydro-1,8-naphthyridin-2-yl)pyrrolidin-3-yl)amino)-1-deoxy-L-arabinitol The title compound is prepared by the method described for EXAMPLE 116B, substituting L-arabinose for D-fucose.

Example 154

1-((1-(6-carboxy-3-fluoro-5-oxo-5,8-dihydro-1,8-naphthyridin-2-yl)pyrrolidin-3-yl)amino)-1,2-dideoxy-D-ribo-hexitol The title compound is prepared by the method described for EXAMPLE 116B, substituting 2-deoxy-D-ribohexopyranose for D-fucose.

Example 155

7-((1S,4S)-2,5-diazabicyclo(2.2.1)hept-2-yl)-1-(2,4-dimethoxybenzyl)-5,6-dimethyl-4-oxo-1,4-dihydro-1,8-naphthyridine-3-carboxylic acid

Example 155A

A suspension of EXAMPLE 90I (504 mg) in acetonitrile (20 mL) at 25° C. was treated with triethylamine (0.5 mL) and tert-butyl (1S,4S)-2,5-diazabicyclo(2.2.1)heptane-2-carboxylate (437 mg), heated at reflux for 72 hours, cooled, treated with 10% citric acid and extracted with dichloromethane. The extract was washed with water and brine, dried (MgSO$_4$), and filtered. The concentrate was chromatographed on silica gel with 0.5-1% methanol in ethyl acetate.

Example 155B

A solution of EXAMPLE 155A (200 mg) in methanol (25 mL) at 25° C. was treated with a solution of 1N LiOH (7 mL), stirred for 2 hours at 50° C., cooled, acidified with 10% citric acid, diluted with water, and filtered.

Example 155

A solution of EXAMPLE 155B (134 mg) in dichloromethane (6.5 mL) at 25° C. was treated with trifluoroacetic acid (1.5 mL), stirred for 7 hours, and concentrated. The resulting solid was treated with diethyl ether, and filtered.

NMR (300 MHz, DMSO-d$_6$) δ ppm 15.92 (s, 1H) 8.96 (s, 1H) 8.91 (s, 1H) 8.36 (s, 1H) 6.95 (d, 1H) 6.61 (d, 1H) 6.47 (dd, 1H) 4.79 (s, 1H) 5.54 (s, 2H) 4.42 (s, 1H) 3.99 (d, 1H) 3.78 (s, 3H) 3.74 (s, 3H) 3.52 (d, 1H) 3.24 (m, 1H) 3.15 (m, 1H) 2.83 (s, 3H) 2.17 (s, 3H) 2.01 (dd, 2H).

Example 156

7-(3-aminopyrrolidin-1-yl)-1-(2-(4-(aminosulfonyl) phenyl)ethyl)-6-fluoro-5-methyl-4-oxo-1,4-dihydro-1,8-naphthyridine-3-carboxylic acid Example 156A A solution of Example 1C (182 mg) in acetonitrile (4 mL) at 25° C. was treated with 4-(2-aminoethyl)benzenesulfonamide (100 mg) and N,N-diisopropylethyl amine (450 μL), heated in a microwave reactor for 10 min at 50° C., 1 hour at 200° C., cooled, treated with tert-butyl pyrrolidin-3-ylcarbamate (112 mg), heated in a microwave reactor for 30 min at 100° C., cooled, treated with aqueous lithium hydroxide (1M, 2.8 mL) and a small amount of methanol, stirred at 25° C. for 18 hours, diluted with water, acidified to a pH of about 1 with aqueous HCl, and filtered.

Example 156

A solution of EXAMPLE 156A (130 mg) in dioxane (3 mL) at 25° C. was treated with 4 M HCl in dioxane (2 mL), stirred for 2 hours, diluted with diethyl ether, and decanted. The residual solid was triturated with ethyl acetate and dichloromethane, and purified by reverse phase high performance liquid chromatography (HPLC) on a C8 column with 0-100% acetonitrile in water containing 0.1% trifluoroacetic acid. NMR (500 MHz, DMSO-d$_6$) δ ppm 8.83 (s, 1H); 7.73 (d, 2H); 7.40 (d, 2H); 4.59 (m, 2H); 3.90 (m, 5H); 3.15 (m, 2H); 2.67 (d, 3H); 2.29 (m, 1H); 2.09 (m, 1H).

Example 157

7-(3-aminopyrrolidin-1-yl)-6-fluoro-4-oxo-1-(3-pyridin-4-ylprop-2-ynyl)-1,4-dihydro-1,8-naphthyridine-3-carboxylic acid Example 157A A solution of 2,6-dichloro-5-fluoronicotinic acid (2.5 g) in dichloromethane (30 mL) and N,N-dimethylformamide (several drops) at 25° C. was treated dropwise with 2M oxalyl chloride in dichloromethane (9 mL), stirred till evolution of gas ceased, and concentrated.

Example 157B

A solution of mono-tert-butyl malonate (4 g) in anhydrous tetrahydrofuran (100 mL) at −30° C. was treated dropwise with 2.5M n-butyllithium in hexane (19 mL), warmed to −7° C., then cooled to −45° C., treated dropwise with a solution of EXAMPLE 157A (2.72 g) in tetrahydrofuran (30 mL), stirred for two hours at 25° C., treated with dilute aqueous HCl, and extracted with ethyl acetate. The extract was washed with 5% sodium bicarbonate, brine, dried (MgSO$_4$), filtered, and concentrated; and the concentrate was flash chromatographed on silica gel with 1% ethyl acetate/hexanes.

Example 157C

A solution of EXAMPLE 157B (0.1 g) in tetrahydrofuran (1 mL) at 25° C. was treated with dimethylformamide dimethyl acetal (0.09 mL), stirred in a sealed tube for 18 hours, and concentrated. A solution of the concentrate in 2:1 diethyl ether/ethanol (1.5 mL) at 25° C. was treated with propargyl amine (0.023 mL), stirred for 90 minutes, treated with more propargyl amine (0.006 ml), stirred for 18 hours, and concentrated. A solution of the concentrate in anhydrous tetrahydrofuran (2 mL) at 0° C. was treated in portions with sodium hydride as a 60% mineral oil dispersion (0.014 g), stirred for 5 minutes, treated with dilute aqueous HCl, and extracted with chloroform. The extract was dried (MgSO$_4$), filtered and concentrated.

Example 157D

A solution of EXAMPLE 157C (0.108 g) in acetonitrile (4 mL) at 25° C. was treated with tert-butyl pyrrolidin-3-ylcarbamate (0.065 g) and diisopropylethylamine (0.06 mL), stirred for five hours at 55° C., and 18 hours at 25° C., treated with 5% citric acid, and filtered.

Example 157E

A solution of 157D (0.126 g) in N,N-dimethylformamide (3 mL) at 25° C. was treated with 4-bromopyridine HCl salt (0.063 g), bis(triphenylphosphine)palladium(II) chloride (0.022 g), copper(I)iodide (0.015 g), and triethylamine (0.11 mL), stirred in a sealed tube under inert atmosphere for three hours at 55° C., and 18 hours at 25° C., and concentrated; and the concentrate purified by reverse phase high performance liquid chromatography (HPLC) on a C8 column with 0-95% acetonitrile in water containing 1.0% trifluoroacetic acid.

Example 157

EXAMPLE 157E (0.075 g) at 25° C. was treated with trifluoroacetic acid (2 mL), stirred for three hours, and concentrated. A solution of the concentrate in methanol (1 mL) was precipitated with diethyl ether, and filtered. NMR (500 MHz, DMSO-d$_6$) δ 9.11 (s, 1H), 8.65-8.55 (d, 2H), 8.28-8.10 (s, 3H), 8.07 (d, 1H), 7.45-7.35 (d, 2H), 5.59 (s, 2H), 4.2-3.6 (m, 5H), 2.4-2.25 (m, 1H), 2.2-2.02 (m, 1H).

Example 158

7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylic acid Example 158A A mixture of EXAMPLE 51A (0.500 g) and tert-butyl (1S,4S)-(−)-2,5-diazabicyclo(2.2.1)heptane-2-carboxylate (0.259 g) in acetonitrile (11.9 mL) at 25° C. was treated with N,N-diisopropylethylamine (0.622 mL), stirred for 18 hours at 50° C., cooled, treated with dichloromethane (50 mL), washed with saturated ammonium chloride and saturated sodium chloride, dried (MgSO$_4$), filtered, and concentrated; and the residue was recrystallized from diethyl ether.

Example 158B

A solution of EXAMPLE 158A (0.30 g) in 1:1 ethanol/1M sodium hydroxide (20 mL) was heated at 80° C. for 18 hours, cooled, poured into saturated ammonium chloride (100 mL), and filtered.

Example 158

A solution of EXAMPLE 158B (0.25 g) in trifluoroacetic acid (10 mL) was heated for 18 hours at 50° C., cooled, and concentrated; and the concentrate was purified by high performance liquid chromatography (HPLC) on a C8 column with 10-100% acetonitrile in water containing 0.1% trifluoroacetic acid. NMR (300 MHz, DMSO-$d_6$) δ ppm 15.25 (bs, 1H), 9.13 (b s, 1H), 8.97 (s, 1H), 8.13 (d, 1H), 7.20 (d, 1H), 6.60 (d, 1H), 6.52 (dd, 1H), 5.55 (q, 2H), 5.19 (br. s, 1H), 4.54 (bs, 1H), 3.91 (bs, 2H), 3.78 (s, 3H), 3.75 (s, 3H), 3.35-3.30 (m, 2H), 2.20 (d, 1H), 1.99 (d, 1H).

Example 159

7-(3-((2-((amino(imino)methyl)amino)ethyl)amino) pyrrolidin-1-yl)-1-(2,4-dimethoxybenzyl)-6-fluoro-4-oxo-1,4-dihydro-1,8-naphthyridine-3-carboxylic acid, trifluoroacetic acid salt This compound was prepared as described in EXAMPLE 113 substituting tert-butyl 2-aminoethylcarbamate for tert-butyl 3-aminopropylcarbamate in EXAMPLE 113A. NMR (300 MHz, CD$_3$OD) δ ppm 8.80 (s, 1H), 8.00 (d, 1H), 7.32 (d, 1H), 6.62-6.50 (m, 2H), 5.52 (s, 2H), 4.29-3.92 (m, 5H), 3.81 (s, 3H), 3.79 (s, 3H), 3.69-3.59 (t, 2H), 3.44-3.36 (t, 2H), 2.62-2.49 (m, 1H), 2.43-2.31 (m, 1H).

Example 160

7-(3-((4-aminobenzyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 122 substituting 4-aminobenzylamine for 4-(aminomethyl) benzylamine in EXAMPLE 122C. NMR (300 MHz, CD$_3$OD) δ ppm 8.44 (s, 1H), 7.84 (d, 1H), 7.60 (d, 2H), 7.25 (d, 2H), 4.39 (s, 2H), 4.17-3.88 (m, 5H), 2.62-2.49 (m, 1H), 2.48-2.32 (m, 1H).

Example 161

1-(3-aminobenzyl)-7-((1S,4S)-2,5-diazabicyclo (2.2.1)hept-2-yl)-6-fluoro-4-oxo-1,4-dihydro-1,8-naphthyridine-3-carboxylic acid Example 161A A solution of EXAMPLE 7A (170 mg) in acetonitrile (4 mL) at 25° C. was treated with tert-butyl 3-(aminomethyl) phenylcarbamate (107 mg) and N,N-diisopropylethyl amine (450 μL), heated in a microwave reactor for 10 min at 50° C., and 20 min at 190° C., cooled, treated with tert-butyl (1S,4S)-(–)-2,5-diaza-bicyclo(2.2.1)heptane-2-carboxylate (116 mg), heated in a microwave reactor for 30 min at 100° C., cooled, treated with aqueous lithium hydroxide (2M, 1.2 mL), heated in a microwave reactor for 15 min at 100° C., cooled, stirred for 18 hours at 25° C., diluted with water, acidified to pH 3 with aqueous HCl, and filtered.

Example 161

A solution of EXAMPLE 161A (162 mg) in dioxane (2 mL) at 25° C. was treated with HCl in dioxane (4M, 2.5 mL), stirred for 2 hours, diluted with diethyl ether, and decanted. The residual solid was triturated with ethyl acetate and dichloromethane, and dried. NMR (500 MHz, DMSO-$d_6$) δ ppm 9.19 (s, 1H), 8.07 (d, 1H), 7.44 (m, 2H), 7.29 (d, 1H), 7.19 (s, 1H), 5.75 (m, 2H), 4.98 (bs, 1H), 4.45 (s, 1H), 3.86 (m, 2H), 3.10 (m, 2H), 2.09 (d, 1H), 1.95 (d, 1H).

Example 162

7-(3-aminopyrrolidin-1-yl)-6-fluoro-1-(2-(4-hydroxyphenyl)ethyl)-5-methyl-4-oxo-1,4-dihydro-1,8-naphthyridine-3-carboxylic acid Example 162A A solution of EXAMPLE 1C (182 mg) in acetonitrile (4 mL) at 25° C. was treated with 4-(2-aminoethyl)phenol (76 mg) and N,N-diisopropylethylamine (450 μL), heated in a microwave reactor for 10 min at 50° C., and 1 hour at 200° C., cooled, treated with tert-butyl pyrrolidin-3-ylcarbamate (111 mg), heated in a microwave reactor for 30 min at 100° C., cooled, treated with aqueous lithium hydroxide (1M, 2.8 mL) and a small amount of methanol, stirred for 18 hours at 25° C., diluted with water, acidified to pH 1 with aqueous HCl, and filtered.

Example 162

A solution of EXAMPLE 162A (130 mg) in dioxane (3 mL) at 25° C. was treated with HCl in dioxane (4M, 2 mL), stirred for 2 hours, diluted with diethyl ether, and decanted. The residual solid was triturated with ethyl acetate and dichloromethane, and purified by reverse phase high performance liquid chromatography (HPLC) on a C8 column with 0-100% acetonitrile in water containing 0.1% trifluoroacetic acid. NMR (500 MHz, DMSO-$d_6$) δ ppm 8.39 (s, 1H), 6.75 (d, 2H), 6.47 (d, 2H), 4.35 (t, 2H), 3.76 (m, 5H), 2.79 (t, 2H), 2.49 (d, 3H), 2.13 (m, 1H), 1.96 (m, 1H).

Example 163

6-(4-aminopiperidin-1-yl)-4-(2,4-dimethoxybenzyl)-1-oxo-4,7,8,9-tetrahydro-1H-cyclopenta(c)-1,8-naphthyridine-2-carboxylic acid EXAMPLE 104B (0.079 g) at 25° C. was treated with trifluoroacetic acid (5 mL), stirred for 5 minutes, treated with diethyl ether (200 mL), and filtered. NMR (300 MHz, DMSO-$d_6$) δ ppm 15.77 (d, 1H), 13.00 (bs, 1H), 8.88 (s, 1H), 8.48 (bs, 1H), 7.88 (bs, 3H), 7.03 (d, 1H), 6.61 (d, 1H), 6.46 (dd, 1H), 5.54 (s, 2H), 4.41-4.38 (bd, 2H), 3.78 (s, 3H), 3.74 (s, 3H), 3.4 (t, 2H), 3.11 (m, 2H), 2.96 (t, 2H), 2.11-1.97 (m, 3H), 1.57-1.46 (m, 2H).

Example 164

7-(3-(allylamino)pyrrolidin-1-yl)-6-fluoro-4-oxo-1, 4-dihydro-1,8-naphthyridine-3-carboxylic acid, trifluoroacetic acid salt This compound was prepared as described in EXAMPLE 98 substituting allylamine for N-(4-aminobutyl)guanidine in EXAMPLE 98C. NMR (300 MHz, CD$_3$OD) δ ppm 8.48 (s, 1H), 7.91 (d, 1H), 6.08-5.92 (m, 1H), 5.67-5.51 (dd, 2H), 4.24-3.89 (m, 5H), 3.86-3.80 (d, 2H), 2.60-2.46 (m, 1H), 2.39-2.26 (m, 1H).

Example 165

6-fluoro-7-(3-((4-hydroxybutyl)amino)pyrrolidin-1-yl)-4-oxo-1,4-dihydro-1,8-naphthyridine-3-carboxylic acid, trifluoroacetic acid salt This compound was prepared as described in EXAMPLE 122 substituting 4-aminobutan-1-ol for 4-(aminomethyl)benzylamine in EXAMPLE 122C. NMR (300 MHz, CD$_3$OD) δ ppm 8.46 (s, 1H), 7.86 (d, 1H), 4.50-4.42 (m, 1H), 4.29-4.13 (m, 3H), 3.97-3.86 (m, 1H), 3.67-3.58 (t, 2H), 3.27-3.16 (t, 2H), 2.63-2.45 (m, 1H), 2.41-2.26 (m, 1H), 1.90-1.65 (m, 4H).

Example 166

6-fluoro-4-oxo-7-(3-((1H-pyrazol-5-ylmethyl)amino)pyrrolidin-1-yl)-1,4-dihydro-1,8-naphthyridine-3-carboxylic acid

Example 166A

A suspension of EXAMPLE 118B (467 mg) in methanol (4 mL) and dichloromethane (4 mL) at 25° C. was treated with 1H-pyrazole-5-carbaldehyde (111 mg), sodium cyanoborohydride (60 mg), and acetic acid (0.275 mL), stirred for 18 hours, and concentrated; and the concentrate was purified by reverse phase high performance liquid chromatography (HPLC) on a C$_{18}$ column with 0-80% of acetonitrile in water containing 0.1% trifluoroacetic acid.

Example 166

A solution of EXAMPLE 166A (400 mg) in ethanol (8 mL) at 25° C. was treated with 1M LiOH (2 mL), stirred for 5 hours at 70° C., 12 hours at 50° C., and 4 hours at 80° C., and concentrated; and the concentrate was purified by reverse phase high performance liquid chromatography (HPLC) on a C$_{18}$ column with 0-50% acetonitrile in water containing 0.1% trifluoroacetic acid). NMR (300 MHz, DMSO-d$_6$) δ ppm 15.41 (s, 1H) 13.11 (bs, 1H) 8.51 (s, 1H) 8.02 (d, 1H) 7.83 (s, 1H) 6.41 (d, 1H) 4.28 (m, 2H) 3.91 (m, 5H) 2.32 (m, 2H).

Example 167 ethyl 7-(3-aminopyrrolidin-1-yl)-6-fluoro-4-oxo-1-(3-pyridin-4-ylprop-2-ynyl)-1,4-dihydro-1,8-naphthyridine-3-carboxylate

Example 167A

A solution of EXAMPLE 7A (1.64 g) in dichloromethane (15 mL) at 25° C. was treated with propargyl amine (0.352 mL), stirred for one hour, and concentrated. A solution of the concentrate in tetrahydrofuran (35 mL) at 0° C. was treated in portions with sodium hydride as a 60% mineral oil dispersion (0.206 g), stirred for five minutes, treated with dilute HCl solution (300 mL), and filtered.

Example 167B

A mixture of EXAMPLE 167A (0.5 g) and tert-butyl pyrrolidin-3-ylcarbamate (0.32 g) in acetonitrile (15 mL) at 25° C. was treated with N,N-diisopropylethylamine (0.310 mL), stirred for 1 hour at 55° C., and concentrated; and the residue was suspended in dilute aqueous HCl, and filtered.

Example 167C

A solution of EXAMPLE 167B (0.077 g) in N,N-dimethylformamide (1 mL) at 25° C. was treated with 4-bromopyridine HCl salt (0.041 g), bis(triphenylphosphine)palladium (II) chloride (0.0146 g) copper(I)iodide (0.0084 g), and triethylamine (0.070 mL), stirred in a sealed tube under an inert atmosphere for 1.5 hours at 55° C., and concentrated; and the concentrate flash chromatographed on silica gel with 65% ethyl acetate-hexane followed by 5% methanol in ethyl acetate

Example 167D

EXAMPLE 167C (0.0168 g) at 25° C. was treated with 1N HCl in glacial acetic acid (1 ml), stirred for fifteen minutes, and lyophilized. NMR (500 MHz, DMSO-d$_6$) δ ppm 8.31 (s, 1H), 8.78-8.68 (s, 2H), 8.65-8.5 (s, 3H), 7.88 (d, 1H), 7.82-7.74 (d, 2H), 5.5 (s, 2H), 4.22 (q, 2H), 4.05-3.8 (m, 5H), 2.35-2.23 (m, 1H), 2.22-2.11 (m, 1H), 1.28 (t, 3H).

Example 168

7-(3-aminopyrrolidin-1-yl)-6-fluoro-1-(2-(4-methoxyphenyl)ethyl)-5-methyl-4-oxo-1,4-dihydro-1,8-naphthyridine-3-carboxylic acid

Example 168A

A solution of Example 1C (181 mg) in acetonitrile (4 mL) at 25° C. was treated with 2-(4-methoxyphenyl)ethanamine (76 mg) and N,N-diisopropylethylamine (450 µL), heated in a microwave reactor for 10 min at 50° C., 30 min at 190° C., and 1 hour at 210° C., cooled, treated with tert-butyl pyrrolidin-3-ylcarbamate (123 mg), heated in a microwave reactor for 30 min at 100° C., cooled, treated with aqueous lithium hydroxide (1M, 1.5 mL) and a small amount of methanol, stirred for 2 hours at 25° C., diluted with water, acidified to pH 1 with aqueous HCl, and filtered.

Example 168

A solution of EXAMPLE 168A (130 mg) in dioxane (2 mL) was treated with HCl in dioxane (4M, 2.5 mL), stirred for 2 hours, treated with diethyl ether, and decanted. The residual solid was triturated with ethyl acetate and dichloromethane. NMR (500 MHz, DMSO-d$_6$) δ ppm 8.73 (s, 1H), 7.13 (d, 2H), 6.85 (d, 2H), 4.57 (t, 2H), 3.98 (m, 5H), 3.69 (s, 3H), 3.03 (m, 2H), 2.71 (d, 3H), 2.34 (m, 1H), 2.15 (m, 1H).

Example 169

6-fluoro-4-oxo-7-(3-((1-thien-2-ylethyl)amino)pyrrolidin-1-yl)-1,4-dihydro-1,8-naphthyridine-3-carboxylic acid, trifluoroacetic acid salt This compound was prepared as described in EXAMPLE 118 substituting 1-thien-2-ylethanone for 3-(methylthio)propanal in EXAMPLE 118C. NMR (300 MHz, DMSO-d$_6$) δ ppm 13.26 (S, 1H), 9.40 (bs, 2H), 8.52 (s, 1H), 8.02 (d, 1H), 7.70 (t, 1H), 7.37 (t, 1H), 7.14 (m, 1H), 4.95 (s, 1H), 4.10-3.71 (m, 5H), 2.36-2.20 (m, 1H), 2.16-2.05 (m, 1H), 1.64 (d, 3H).

Example 170

7-(3-((2-(dimethylamino)ethyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting N,N-dimethylethane-1,2-diamine for N-(4-aminobutyl)guanidine in EXAMPLE 98C. NMR (300 MHz, $CD_3OD$) δ ppm 8.51 (s, 1H), 7.86 (d, 1H), 4.18-3.85 (m, 5H), 3.46 (bs, 4H), 2.96 (s, 6H), 2.52-2.37 (m, 1H), 2.35-2.22 (m, 1H).

Example 171

7-((1S,4S)-2,5-diazabicyclo(2.2.1)hept-2-yl)-1-(2,3-dihydro-1-benzofuran-5-ylmethyl)-6-fluoro-4-oxo-1,4-dihydro-1,8-naphthyridine-3-carboxylic acid A solution of EXAMPLE 7A (336.1 mg) in acetonitrile (10 mL) at 25° C. was treated with 1-(2,3-dihydro-1-benzofuran-5-yl)methanamine hydrochloride (194.9 mg) and potassium carbonate (150 mg), stirred for 2 hours at 25° C., and 16 hours at 50° C., cooled, treated with potassium carbonate (367.2 mg), stirred for 2 days at 85° C., cooled, treated with tert-butyl (1S,4S)-(−)-2,5-diazabicyclo(2.2.1)heptane-2-carboxylate (237.9 mg), stirred for 3 days at 50° C., cooled, treated with aqueous 1N NaOH (4 mL) and methanol (2 ml), stirred for 16 hours at 40° C., cooled, diluted with water, acidified to pH 3.5 with 1N HCl, and filtered. A solution of the solid (150 mg) in 4N HCl/dioxane (4 mL) was stirred for 2 hours at 25° C., diluted with diethyl ether, centrifuged, and decanted; and the solid was triturated with diethyl ether and dichloromethane. NMR (300 MHz, DMSO-$d_6$) δ ppm 15.30 (s, 1H), 9.52 (bs, 1H), 9.14 (s, 1H), 8.88 (bs, 1H), 8.12 (d, 1H), 7.20 (s, 1H), 7.12 (dd, 1H), 6.72 (d, 1H), 5.61 (dd, 2H), 5.18 (s, 1H), 4.48 (m, 3H), 4.01 (m, 1H), 3.90 (m, 1H), 3.31 (m, 1H) (obscured by water peak), 3.13 (m, 3H), 2.08 (dd, 2H).

Example 172

6-fluoro-7-(3-(((1S)-2-hydroxy-1-(1H-imidazol-4-ylmethyl)ethyl)amino)pyrrolidin-1-yl)-4-oxo-1,4-dihydro-1,8-naphthyridine-3-carboxylic acid, trifluoroacetic acid salt This compound was prepared as described in EXAMPLE 122 substituting (2S)-2-amino-3-(1H-imidazol-4-yl)propan-1-ol for 4-(aminomethyl)benzylamine in EXAMPLE 122C. NMR (300 MHz, $CD_3OD$) δ ppm 8.75 (d, 1H), 8.52 (d, 1H), 7.91 (d, 1H), 7.47 (d, 1H), 4.35-4.09 (m, 2H), 4.16-4.01 (m, 2H), 3.99-3.85 (d, 2H), 3.81-3.71 (m, 1H), 3.69-3.61 (dd, 1H), 3.30-3.22 (m, 2H), 2.65-2.48 (m, 1H), 2.42-2.28 (m, 1H).

Example 173

7-(3-((2,3-dihydroxypropyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting 2,2-dimethyl-1,3-dioxolane-4-methanamine for N-(4-aminobutyl)guanidine in EXAMPLE 98C. NMR (300 MHz, $CD_3OD$) δ ppm 8.52 (s, 1H), 7.94 (d, 1H), 4.30-3.85 (m, 6H), 3.65-3.57 (m, 2H), 3.42-3.33 (m, 1H), 3.22-3.08 (q, 1H), 2.62-2.48 (m, 1H), 2.40-2.24 (m, 1H).

Example 174

7-(3-aminopyrrolidin-1-yl)-6-fluoro-4-oxo-1-(3-oxo-3-phenylpropyl)-1,4-dihydro-1,8-naphthyridine-3-carboxylic acid

Example 174A

A solution of EXAMPLE 167B (0.075 g) in N,N-dimethylformamide (1 mL) at 25° C. was treated with iodobenzene (0.028 mL), triphenylphosphine (0.0077 g), copper (I) iodide (0.0027 g), triethylamine (0.050 mL) and palladium acetate (0.0029 g), stirred in a sealed tube under inert atmosphere for 18 hours, and concentrated; and the concentrate flash chromatographed on silica gel with 65% ethyl acetate-hexane.

Example 174

A suspension of EXAMPLE 174A (0.073 g) in 6N aqueous HCl (3 mL) was stirred in air for 38 hours at 90° C., cooled to 25° C., and lyophilized. The residue was triturated with diethyl ether, and filtered. NMR (500 MHz, DMSO-$d_6$/100° C.) δ ppm 8.92 (s, 1H), 7.98 (d, 1H), 7.94 (d, 2H), 7.66-7.55 (m, 1H), 7.5-7.42 (m, 2H), 4.87-4.75 (m, 2H), 4.08-3.82 (m, 5H), 3.69 (t, 2H), 2.38-2.28 (m, 1H), 2.27-2.17 (m, 1H).

Example 175 ethyl 6-fluoro-7-(3-((4-hydroxybenzyl)amino)pyrrolidin-1-yl)-4-oxo-1,4-dihydro-1,8-naphthyridine-3-carboxylate, trifluoroacetic acid salt

Example 175A

A solution of EXAMPLE 118B (120 mg) and 4-hydroxybenzaldehyde (43 mg) in methanol (1.5 mL) and dichloromethane (0.5 mL) at 25° C. was treated with acetic acid (148 μL) and sodium triacetoxyborohydride (112 mg), stirred for 12 hours, diluted with dichloromethane, washed with saturated sodium bicarbonate and brine, dried ($Na_2SO_4$), filtered, and concentrated. The concentrate was purified by reverse phase high performance liquid chromatography (HPLC) on a C8 column with 10-95% acetonitrile in water containing 0.1% trifluoroacetic acid.

Example 175

A solution of EXAMPLE 175A (60 mg) in ethanol (2 mL) at 25° C. was treated with 2M LiOH (250 μL), stirred for 20 minutes, neutralized with 1N HCl, and concentrated. The concentrate was dissolved in dimethylsulfoxide (1.5 mL) and purified by reverse phase high performance liquid chromatography (HPLC) on a C8 column with 10-95% acetonitrile in water containing 0.1% trifluoroacetic acid. NMR (300 MHz, DMSO-$d_6$) δ ppm 9.03 (s, 2H), 8.28 (d, 1H), 7.85 (d, 1H), 7.35 (d, 2H), 6.83 (d, 2H), 4.27-4.13 (m, 4H), 4.07-3.86 (m, 5H), 2.44-2.22 (m, 2H), 1.26 (t, 3H).

Example 176

6-fluoro-7-(3-((3-fluoro-4-methoxybenzyl)amino)pyrrolidin-1-yl)-4-oxo-1,4-dihydro-1,8-naphthyridine-3-carboxylic acid, citric acid salt This compound was prepared according to the procedure described in EXAMPLE 118 substituting 3-fluoro-4-methoxybenzaldehyde for 3-(methylthio)propanal in EXAMPLE 118C.

NMR (500 MHz, DMSO-d$_6$/CF$_3$COOD) δ ppm 8.30 (s, 1H), 7.74 (d, 1H), 7.20 (dd, 1H), 7.10 (d, 1H), 6.95, (m, 1H), 4.06-3.98 (m, 2H), 3.90-3.75 (m, 4H), 3.64 (m, 2H), 3.64 (s, 3H), 2.60-2.46 (m, 4H), 2.25-2.10 (m, 2H).

Example 177

7-((1S,4S)-2,5-diazabicyclo(2.2.1)hept-2-yl)-6-fluoro-1-(4-methoxybenzyl)-4-oxo-1,4-dihydro-1,8-naphthyridine-3-carboxylic acid Example 177A A solution of EXAMPLE 7A (1.68 g) in tetrahydrofuran (15 mL) at 0° C. was treated with 4-methoxybenzylamine (685.9 µL), stirred for 15 min, stirred for 3 hours at 25° C., treated with a solution of 1M tetrabutylammonium fluoride in tetrahydrofuran (5 mL), stirred for 2 days, and concentrated; and the concentrate chromatographed on silica gel with 0-4% methanol in dichloromethane.

Example 177B

A solution of EXAMPLE 177A (270 mg) in acetonitrile (6.9 mL) at 25° C. was treated with triethylamine (288 µL) and tert-butyl (1S,4S)-(−)-2,5-diazabicyclo(2.2.1)heptane-2-carboxylate (206 mg), stirred for 24 hours at 50° C., cooled to 25° C., treated with 1N NaOH (2.8 mL), stirred for 48 hours, diluted with water, acidified to pH 3.5 with 1N HCl, and filtered.

Example 177

A solution of EXAMPLE 177B (283.6 mg) in 4N HCl/dioxane (6 mL) t 25° C. was stirred for 2 hours, treated with diethyl ether, centrifuged, and decanted. The solid was triturated with diethyl ether and dichloromethane. NMR (300 MHz, DMSO-d$_6$) δ ppm 15.30 (bs, 1H), 9.60 (bs, 1H), 9.15 (s, 1H), 8.94 (bs, 1H), 8.12 (d, 1H), 7.30 (d, 2H), 6.91 (d, 2H), 5.64 (dd, 2H), 5.16 (d, 1H), 4.50 (s, 1H), 4.03 (m, 1H), 3.91 (m, 1H), 3.72 (s, 3H), 3.31 (m, 1H) (partially obscured by water peak), 3.13 (bs, 1H), 2.09 (dd, 2H).

Example 178

6-fluoro-4-oxo-7-(3-((quinolin-2-ylmethyl)amino)pyrrolidin-1-yl)-1,4-dihydro-1,8-naphthyridine-3-carboxylic acid, hemicitric acid salt This compound was prepared according to the procedure described in EXAMPLE 118 substituting quinoline-2-carbaldehyde for 3-(methylthio)propanal in EXAMPLE 118C. NMR (500 MHz, DMSO-d$_6$/CF$_3$COOD) δ ppm 8.55 (s, 1H), 8.51 (d, 1H), 8.12 (d, 1H), 8.05-7.99 (m, 2H), 7.86-7.83, (m, 1H), 7.69-7.66 (m, 2H), 4.82-4.73 (m, 2H), 4.31-3.90 (m, 5H), 2.85-2.71 (m, 2H), 2.45-2.51 (m, 2H).

Example 179

7-((1S,4S)-2,5-diazabicyclo(2.2.1)hept-2-yl)-1-(4-(dihydroxyboryl)benzyl)-6-fluoro-4-oxo-1,4-dihydro-1,8-naphthyridine-3-carboxylic acid Example 179A A solution of EXAMPLE 7A (172 mg) in acetonitrile (4 mL) at 25° C. was treated with 4-(4,4,5,5-tetramethyl-(1,3,2) dioxaborolan-2-yl)-benzylamine (137 mg) and N,N-diisopropylethylamine (450 µL), heated in a microwave reactor for 10 min at 50° C., and 20 min at 190° C., cooled, treated with tert-butyl (1S,4S)-(−)-2,5-diaza-bicyclo(2.2.1)heptane-2-carboxylate (119 mg), heated in a microwave reactor for 30 min at 100° C., cooled, treated with aqueous lithium hydroxide (2M, 1.2 mL), heated in a microwave reactor for 75 min at 100° C., and stirred for 9 days at 25° C., treated with water, acidified to pH 1 with aqueous HCl, and filtered.

Example 179

A solution of EXAMPLE 179A (162 mg) in dioxane (2 mL) at 25° C. was treated with HCl in dioxane (4M, 2.0 mL), stirred for 2 hours, treated with diethyl ether, and decanted. The residual solid was triturated with ethyl acetate and dichloromethane, dried, and recrystallized from methanol. NMR (300 MHz, DMSO-d$_6$) δ ppm 15.28 (s, 1H), 9.40 (s, 1H), 9.19 (s, 1H), 8.68 (s, 1H), 8.14 (d, 1H), 8.02 (s, 2H), 7.74 (d, 2H), 7.25 (d, 2H), 5.72 (m, 2H), 5.06 (s, 1H), 4.48 (s, 1H), 3.92 (m, 2H), 2.96 (m, 2H), 2.13 (m, 1H), 1.95 (m, 1H).

Example 180

N-(3-(aminomethyl)benzyl)-6-fluoro-7-pyrrolidin-1-yl-1,8-naphthyridin-4-amine

Example 180A

A solution of EXAMPLE 51C (13 g) in quinoline (120 mL) at 25° C. was treated with copper (I) oxide (6.6 g), stirred for 20 hours at 185° C., cooled to 25° C., and filtered; and the filtrate was concentrated.

Example 180B

A mixture of EXAMPLE 180A (11.5 g) and trifluoroacetic acid (100 mL) was stirred for 1.5 hours at 25° C., filtered, and the filtrate concentrated. The concentrate was triturated with diethyl ether and dichloromethane.

Example 180C

EXAMPLE 180B (3.6 g) in phosphorus oxychloride (60 mL) was heated at 100° C. for 1 hour, cooled to 25° C., and added to ice cold water (700 mL) and ammonium hydroxide (230 mL) over 30 minutes with vigorous stirring. The quenched reaction mixture (pH=6-7) was extracted with dichloromethane (2×400 mL). The extract was washed with water and brine, dried (Na$_2$SO$_4$), filtered, and concentrated.

Example 180

A solution of EXAMPLE 180C (45 mg) and 3-aminomethyl-benzylamine (49 mg) in N,N-dimethylacetamide (0.5 mL) was heated at 120° C. for 4 hours, cooled, and filtered; and the solid triturated with 1:1 diethyl ether/ethyl acetate and dried.

NMR (300 MHz, DMSO-d$_6$) δ ppm 8.34 (d, 1H), 8.13 (d, 1H), 7.99 (m, 1H, (—NH— proton)), 7.44 (s, 1H), 7.40-7.30 (m, 3H), 6.20, (d, 1H), 4.52 (d, 2H), 3.95 (s, 2H), 3.72-3.65 (m, 4H), 1.97-1.91 (m, 4H).

Example 181

6-acetyl-7-(3-aminopyrrolidin-1-yl)-4-oxo-1,4-dihydro-1,8-naphthyridine-3-carboxylic acid

Example 181A

A mixture of EXAMPLE 143D (0.193 g), triethylamine (4 mL), triphenylphosphine (0.0075 g) and palladium acetate (0.005 g) at 25° C. was treated with trimethylsilylacetylene (0.250 mL), stirred in a sealed tube under inert atmosphere for 3.5 hours at 80° C., and 18 hours at 25° C., treated with triethylamine (4 mL), triphenylphosphine (0.0075 g), palladium acetate (0.005 g) and trimethylsilylacetylene (0.250 mL), heated in a sealed tube under inert atmosphere for 7 hours at 80° C., and concentrated; and the concentrate flash chromatographed on silica gel with 33% ethyl acetate-hexane.

Example 181B

A solution of EXAMPLE 181A (0.116 g) in 2:1 tetrahydrofuran/methanol (10.5 mL) at 25° C. was treated with 2N NaOH (0.320 mL), heated for 1.5 hours at 55° C., cooled, and concentrated. A suspension of the concentrate in water acidified with dilute HCl, and extracted with chloroform; and the extract was dried (MgSO$_4$), filtered, and concentrated.

Example 181

A solution of EXAMPLE 181B (0.095 g) in trifluoroacetic acid (3 mL) at 25° C. was treated with concentrated sulfuric acid (three drops), stirred for 18 hours, and concentrated; and the concentrate purified by reverse phase high performance liquid chromatography (HPLC) on a C8 column with 0-95% acetonitrile in water containing 1.0% trifluoroacetic acid gradient. NMR (500 MHz, DMSO-d$_6$) δ 8.61 (s, 1H), 8.54 (s, 1H), 3.9-4.0 (m, 1H), 3.75-3.6 (m, 2H), 3.6-3.4 (m, 2H), 2.67 (s, 3H), 2.4-2.25 (m, 1H), 2.15-2.0 (m, 1H).

Example 182

6-fluoro-4-oxo-7-(3-((piperidin-4-ylmethyl)amino) pyrrolidin-1-yl)-1,4-dihydro-1,8-naphthyridine-3-carboxylic acid, trifluoroacetic acid salt This compound was prepared as described in EXAMPLE 122 substituting 1-piperidin-4-ylmethanamine for 4-(aminomethyl)benzylamine in EXAMPLE 122C.
NMR (300 MHz, DMSO-d$_6$) δ ppm 13.33 (s, 1H), 8.96 (m, 2H), 8.51 (d, 1H), 8.05 (m, 1H), 4.15-3.93 (m, 4H), 3.87-3.77 (m, 1H), 3.67-3.47 (m, 2H), 3.13-2.87 (m, 3H), 2.44-2.20 (m, 2H), 2.08-1.84 (m, 4H), 1.54-1.33 (m, 2H).

Example 183 ethyl 7-(3-aminopyrrolidin-1-yl)-6-fluoro-4-oxo-1-(3-phenylprop-2-ynyl)-1,4-dihydro-1,8-naphthyridine-3-carboxylate A solution of EXAMPLE 174A (0.209 g) in trifluoroacetic acid (3 ml) was stirred for 0.75 hour at 25° C., and concentrated. A solution of the concentrate in methanol (1 mL) was treated with diethyl ether, sonicated and filtered. NMR (500 MHz, CD$_3$OD/CDCl$_3$) δ ppm 8.93 (s, 1H), 7.62 (d, 1H), 7.47 (s, 1H), 7.40-7.32 (m, 3H), 5.33-5.18 (m, 2H), 4.38-4.35 (m, 2H), 4.19-4.04 (m, 3H), 3.88-3.84 (m, 2H), 2.44-2.30 (m, 2H), 1.39 (t, 3H).

Example 184

7-(3-aminopyrrolidin-1-yl)-6-fluoro-1-(4-methoxybenzyl)-4-oxo-1,4-dihydro-1,8-naphthyridine-3-carboxylic acid

Example 184A

A solution of EXAMPLE 7A (1.68 g) in tetrahydrofuran (15 mL) at 0° C. was treated with 4-methoxybenzylamine (685.9 μL), stirred for 15 minutes, then at 25° C. for 3 hours, treated with 1M tetrabutylammonium fluoride in tetrahydrofuran (5 mL), stirred at 25° C. for 2 days, and concentrated; and the concentrate was chromatographed on silica gel with 0-4% methanol in dichloromethane.

Example 184B

A solution of EXAMPLE 184A (270 mg) in acetonitrile (6.9 mL) at 25° C. was treated with triethylamine (288 μL) and tert-butyl pyrrolidin-3-ylcarbamate (192.5 mg), stirred for 24 hours, treated with 1N NaOH (2.8 mL), stirred for 48 hours at 25° C., treated with water, acidified to pH 3.5 with 1N HCl, and filtered.

Example 184

A solution of EXAMPLE 184B (362.6 mg) in 4N HCl/dioxane (6 mL) at 25° C. was stirred for 2 hours, treated with diethyl ether, centrifuged, and decanted; and the solid was triturated with diethyl ether and dichloromethane. NMR (300 MHz, DMSO-d$_6$) δ ppm 9.11 (s, 1H), 8.45 (bs, 3H), 8.36 (bs, 1H), 8.05 (d, 1H), 7.35 (m, 2H), 6.92 (m, 2H), 5.63 (m, 2H), 4.01 (m, 5H), 3.72 (s, 3H), 2.31 (m, 1H), 2.17 (m, 1H).

Example 185

4-(2,4-dimethoxybenzyl)-1-oxo-6-piperazin-1-yl-4,7,8,9-tetrahydro-1H-cyclopenta(c)-1,8-naphthyridine-2-carboxylic acid Example 149B (0.050 g) at 25° C. was treated with trifluoroacetic acid (5 mL), stirred for 5 minutes, treated with diethyl ether (200 mL), and filtered.
NMR (300 MHz, DMSO-d$_6$) δ ppm 15.65 (bs, 1H), 8.91 (s, 1H), 8.87 (bs, 2H), 7.05 (d, 1H), 6.60 (d, 1H), 6.48-6.46 (dd, 1H), 5.55 (s, 2H), 4.08 (bs, 4H), 3.84 (m, 4H), 3.77 (s, 3H), 3.74 (s, 3H), 3.41 (t, 2H), 2.96 (t, 2H), 2.08 (m, 2H).

Example 186

7-((1S,4S)-2,5-diazabicyclo(2.2.1)hept-2-yl)-6-fluoro-4-oxo-1-(pyridin-4-ylmethyl)-1,4-dihydro-1,8-naphthyridine-3-carboxylic acid A mixture of EXAMPLE 7A (168.3 mg), 4-(aminoethyl)-pyridine (51.0 μL) and N,N-diisopropylethylamine (450 μL) in acetonitrile (4.0 mL) was heated in a microwave reactor for 10 minutes at 50° C., and 20 minutes at 190° C., cooled, treated with tert-butyl-(1S,4S)-(−)-2,5-diaza-bicyclo (2.2.1)heptane-2-carboxylate (119 mg), heated in a microwave reactor for 30 minutes at 100° C., cooled, treated with 2M lithium hydroxide (1.25 mL), heated in a microwave reactor for 20 minutes at 100° C., and 18 hours at 25° C., diluted with water, acidified to pH 3 with 1M HCl and extracted with ethyl acetate. The extracts were washed with brine, dried (Na$_2$SO$_4$), filtered, and concentrated. A solution of the concentrate in dioxane (5.0 mL) at 25° C. was treated with 1M HCl/dioxane (3.0 mL), stirred for 18 hours, and concentrated. The concentrate was triturated with diethyl ether, ethyl acetate and dichloromethane. NMR (300 MHz, DMSO-d$_6$) δ ppm 9.25 (s, 1H), 8.63 (d, 2H), 8.15 (d, 1H), 7.53-7.47 (m, 2H), 5.84-5.80 (m, 2H), 3.93-2.87 (m, 4H), 2.13-2.05 (m, 2H), 1.94-1.87 (m, 2H).

Example 187

7-(3-aminopyrrolidin-1-yl)-4-oxo-6-prop-1-ynyl-1,4-dihydro-1,8-naphthyridine-3-carboxylic acid Example 187A A mixture of EXAMPLE 143D (0.253 g) and tributyl(1-propynyl)tin (0.2 mL) in anhydrous toluene (5 mL) at 25° C. was treated with tetrakis(triphenylphosphine)palladium(0) (0.011 g), stirred in a sealed tube under inert atmosphere for 18 hours at 75° C., and concentrated; and the concentrate flash chromatographed on silica gel with 50% ethyl acetate/hexanes.

Example 187B

EXAMPLE 187A (0.0493 g) in 2:1 tetrahydrofuran/methanol (6 mL) at 25° C. was treated with 2N NaOH (0.1 mL), heated for six hours at 55° C., and concentrated. A suspension of the concentrate was treated with aqueous citric acid, and extracted with chloroform. The extract was dried (MgSO$_4$), filtered, and concentrated.

Example 187

A solution of EXAMPLE 187B (0.0464 g) in trifluoroacetic acid (4 mL) at 25° C. was treated with concentrated sulfuric acid (four drops), stirred for three hours, and concentrated; and. the concentrate was purified by reverse phase high performance liquid chromatography (HPLC) on a C8 column with 0-95% acetonitrile in water containing 1.0% trifluoroacetic acid gradient. NMR (500 MHz, DMSO-d$_6$, 100° C.) δ ppm 8.46 (s, 1H), 8.21 (s, 1H), 4.2-3.9 (m, 5H), 2.38-2.28 (m, 1H), 2.17-2.05 (m, 1H), 2.08 (s, 3H).

Example 188

7-((1S,4S)-2,5-diazabicyclo(2.2.1)hept-2-yl)-1-(3,4-dimethoxybenzyl)-6-fluoro-4-oxo-1,4-dihydro-1,8-naphthyridine-3-carboxylic acid A solution of EXAMPLE 7A (336.1 mg) and triethylamine (0.696 mL) in acetonitrile (3.3 mL) at 25° C. was treated with veratrylamine (0.159 mL), stirred for 2 hours at 25° C., 4 hours at 40° C., and 4 days at 85° C., cooled, treated with potassium carbonate (50 mg) and acetonitrile (7 ml), heated for 2 days at 100° C., cooled to 25° C., treated with tert-butyl (1S,4S)-(−)-2,5-diazabicyclo(2.2.1)heptane-2-carboxylate (237.9 mg), heated for 24 hours at 50° C., cooled, treated with 1N NaOH (4 mL) and methanol (2 ml), heated for 8 hours at 40° C., cooled, treated with water, acidified to pH 3.5 with 1N HCl, and filtered. A solution of the solid in 4N HCl/dioxane (6.25 mL) was stirred for 2 hours at 25° C., treated with diethyl ether, centrifuged, and decanted; and the solid was triturated with diethyl ether and dichloromethane. NMR (300 MHz, DMSO-d$_6$) δ ppm 9.70 (bs, 1H), 9.11 (bs, 1H), 9.09 (s, 1H), 8.13 (d, 1H), 7.02 (d, 1H), 6.91 (m, 1H), 6.81 (m, 1H), 5.63 (dd, 2H), 5.16 (bs, 1H), 4.50 (br, 1H), 3.89 (m, 5H), 3.25 (br, 1H), 3.15 (br, 1H), 2.09 (dd, 2H).

Example 189

6-fluoro-7-(3-(((1R)-2-hydroxy-1-phenylethyl)amino)pyrrolidin-1-yl)-4-oxo-1,4-dihydro-1,8-naphthyridine-3-carboxylic acid, trifluoroacetic acid salt This compound was prepared as described in EXAMPLE 122 substituting (L)-(−)-2-phenylglycinol for 4-(aminomethyl)benzylamine in EXAMPLE 122C. NMR (300 MHz, DMSO-d$_6$) δ ppm 13.33 (s, 1H), 9.50-9.21 (bs, 2H), 8.52 (s, 1H), 8.07-7.97 (d, 1H), 7.62-7.42 (m, 5H), 4.56-4.44 (m, 1H), 4.15-3.73 (m, 7H), 2.32-2.21 (m, 2H).

Example 190

7-(3-((4-(aminosulfonyl)benzyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting p-aminomethyl benzenesulfonamide hydrochloride for N-(4-aminobutyl)guanidine in EXAMPLE 98C. NMR (300 MHz, CD$_3$OD) δ ppm 8.53 (s, 1H), 8.01 (d, 3H), 7.73 (d, 2H), 4.48 (s, 2H), 4.29-4.05 (m, 5H), 2.65-2.53 (m, 1H), 2.45-2.32 (m, 1H).

Example 191

6-fluoro-7-(3-((3-methoxybenzyl)amino)pyrrolidin-1-yl)-4-oxo-1,4-dihydro-1,8-naphthyridine-3-carboxylic acid, citric acid salt This compound was prepared according to the procedure described in EXAMPLE 118 substituting 3-methoxybenzaldehyde for 3-(methylthio)propanal in EXAMPLE 118C. NMR (500 MHz, DMSO-d$_6$/CF$_3$COOD) δ ppm 8.58 (s, 1H), 8.03 (d, 1H), 7.39 (t, 1H), 7.20 (bs, 1H), 7.14, (d, 1H), 7.03 (dd, 1H), 4.34-4.26 (m, 2H), 4.17-4.05 (m, 4H), 3.95-3.85 (m, 1H), 3.82 (s, 3H), 2.85-2.71 (m 4H), 2.50-2.40 (m, 2H).

Example 192

1-(2,4-dimethoxybenzyl)-6-fluoro-7-(3-((2-(1H-imidazol-5-yl)ethyl)amino)pyrrolidin-1-yl)-4-oxo-1,4-dihydro-1,8-naphthyridine-3-carboxylic acid, trifluoroacetic acid salt This compound was prepared as described in EXAMPLE 98D substituting 2-(1H-imidazol-5-yl)ethanamine for N-(4-aminobutyl)guanidine in EXAMPLE 98C. NMR (300 MHz, CD$_3$OD) δ ppm 8.85 (d, 1H), 8.70 (s, 1H), 7.92 (d, 1H), 7.47 (d, 1H), 7.30 (d, 1H), 6.60-6.50 (m, 2H), 5.45 (s, 2H), 4.30-3.90 (m, 5H), 3.81 (s, 3H), 3.77 (s, 3H), 3.55 (t, 2H), 3.25 (t, 2H), 2.65-2.50 (m, 1H), 2.45-2.35 (m, 1H).

Example 193

1-(2,4-dimethoxybenzyl)-6-fluoro-7-(3-((3-(1H-imidazol-1-yl)propyl)amino)pyrrolidin-1-yl)-4-oxo-1,4-dihydro-1,8-naphthyridine-3-carboxylic acid, trifluoroacetic acid salt This compound was prepared as described in EXAMPLE 98D substituting 3-(1H-imidazol-5-yl)propan-1-amine for N-(4-aminobutyl)guanidine in EXAMPLE 98C. NMR (300 MHz, CD$_3$OD) δ ppm 9.0 (s, 1H), 8.72 (s, 1H), 7.94 (d, 1H), 7.65 (d, 2H), 7.30 (d, 1H), 6.60-6.50 (m, 2H), 5.45 (s, 2H), 4.45 (t, 2H), 4.27-3.91 (m, 5H), 3.81 (s, 3H), 3.79 (s, 3H), 3.25 (t, 2H), 2.64-2.47 (m, 1H), 2.45-2.30 (m, 3H).

Example 194

7-(3-(2-carbamoyl-ethylamino)-pyrrolidin-1-yl)-6-fluoro-4-oxo-1,4-dihydro-1,8-naphthyridine-3-carboxylic acid This compound was prepared as described in EXAMPLE 98 substituting β-alaninamide HCl for N-(4-aminobutyl)guanidine in EXAMPLE 98C. NMR (300 MHz, CD$_3$OD) δ ppm 8.50 (s, 1H), 7.91 (d, 1H), 4.25-3.89 (m, 5H), 3.45 (t, 2H), 2.81 (t, 2H), 2.60-2.45 (m, 1H), 2.40-2.30 (m, 1H).

Example 195

6-fluoro-4-oxo-7-(3-((2-pyrrolidin-1-yl-ethyl)amino)pyrrolidin-1-yl)-1,4-dihydro-1,8-naphthyridine-3-carboxylic acid, trifluoroacetic acid salt This compound was prepared as described in EXAMPLE 98 substituting 2-pyrrolidin-1-ylethanamine for N-(4-aminobutyl)guanidine in EXAMPLE 98C. NMR (300 MHz, CD$_3$OD) δ ppm 8.53 (s, 1H), 7.93 (d, 1H), 4.21-3.88 (m, 5H), 3.63 (broad s, 4H), 3.53-3.41 (m, 4H), 2.63-2.47 (m, 1H), 2.42-2.31 (m, 1H), 2.17-2.07 (m, 4H).

Example 196

7-(3-aminopyrrolidin-1-yl)-6-fluoro-3-(((3-phenylpropyl)amino)methyl)-1,8-naphthyridin-4(1H),-one, trifluoracetic acid salt Example 196A A solution of EXAMPLE 266B (7.6 g) in dichloromethane (150 mL) at −78° C. was treated with diisobutylaluminum hydride (22 mL, 1M in dichloromethane) dropwise over 1 hour, stirred for 40 minutes, treated with 5% sodium potassium tartrate (75 mL) and dichloromethane (200 mL), stirred at 25° C. for 2 hours, and partitioned. The dichloromethane extracts were washed with aqueous sodium chloride, dried (Na$_2$SO$_4$), filtered, and concentrated. The concentrate was triturated with diethyl ether (500 mL), filtered, and dried; and the solid was flash chromatographed on silica gel with 0.5% methanol/chloroform.

Example 196B

A solution of EXAMPLE 196A (20 mg) in 1:2 dichloromethane/methanol (2.5 mL) at 25° C. was treated with 3-phenylpropan-1-amine, (8 mg), 36 mg of MP-BH$_3$CN (macroporous polystyrene-bound cyanoborohydride, Argonaut Technologies, 2.32 mmol/g), and acetic acid (7 µL), heated at 45° C. for 14 hours, filtered, and concentrated.

Example 196

A solution of EXAMPLE 196B in 10:1 trifluoroacetic acid/sulfuric acid (1 mL) was heated at 50° C. for 17 hours, cooled, and concentrated; and the concentrate was purified by reverse phase high performance liquid chromatography (HPLC) on a C8 column with 10-100% acetonitrile in water containing 0.1% trifluoroacetic acid. NMR (500 MHz, DMSO-d$_6$) δ ppm 12.10 (d, 1H), 8.51 (bs, 2H), 8.17 (bs, 3H), 7.97 (d, 1H), 7.88 (d, 1H), 7.29, (t, 2H), 7.20 (d, 2H), 7.12 (t, 1H), 3.99-3.90 (m, 6H), 3.85-3.77 (m, 3H), 2.64 (t, 2H), 2.35-2.27 (m, 1H), 2.12-2.05 (m, 1H), 1.96-1.90 (m, 2H).

Example 197

6-fluoro-7-(3-(((1S)-2-hydroxy-1-phenylethyl)amino)pyrrolidin-1-yl)-4-oxo-1,4-dihydro-1,8-naphthyridine-3-carboxylic acid, trifluoroacetic acid salt This compound was prepared as described in EXAMPLE 98 substituting (R)-(−)-2-phenylglycinol for N-(4-aminobutyl)guanidine in EXAMPLE 98C. NMR (300 MHz, CD$_3$OD) δ ppm 8.54 (s, 1H), 7.95 (d, 1H), 7.62-7.47 (m, 5H), 4.57-4.47 (m, 1H), 4.27-3.75 (m, 7H), 2.58-2.39 (m, 1H), 2.37-2.21 (m, 1H).

Example 198

7-(3-(benzyl (2-(dimethylamino)ethyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 122 substituting N-benzyl-N',N'-dimethylethane-1,2-diamine for 4-(aminomethyl)benzylamine in EXAMPLE 122C. NMR (300 MHz, CD$_3$OD) δ ppm 8.51 (s, 1H), 7.86 (d, 1H), 7.45-7.24 (m, 5H), 5.12 (s, 2H), 4.18-3.85 (m, 5H), 3.46 (bs, 4H), 2.87 (s, 6H), 2.42-2.31 (m, 1H), 2.23-2.02 (m, 1H).

Example 199

7-((3R,4S)-3-(benzylamino)-4-hydroxypyrrolidin-1-yl)-6-fluoro-4-oxo-1,4-dihydro-1,8-naphthyridine-3-carboxylic acid Example 199A 7-(3-Amino-4-hydroxy-pyrrolidin-1-yl)-1-(2-cyanoethyl)-6-fluoro-4-oxo-1,4-dihydro-(1,8)naphthyridine-3-carboxylic acid ethyl ester A solution of cis-3-amino-4-hydroxypyrrolidine (0.81 g), N,N-diisopropylethylamine (3.4 mL), and EXAMPLE 7C (1.60 g) in acetonitrile (50 mL) was stirred for 18 hours at 25° C., treated with dichloromethane (50 mL), washed with saturated ammonium chloride (3×20 mL), and brine (20 mL), dried (MgSO$_4$), filtered, and concentrated; and the concentrate recrystallized from methanol.

Example 199B 7-(3-Benzylamino-4-hydroxy-pyrrolidin-1-yl)-1-(2-cyano-ethyl)-6-fluoro-4-oxo-1,4-dihydro-(1,8)naphthyridine-3-carboxylic acid ethyl ester A solution of EXAMPLE 199A (0.12 g) and benzaldehyde (0.063 mL) in methanol (10 mL) and acetic acid (2 drops) was stirred for 30 minutes at 25° C., treated with sodium triacetoxyborohydride (0.196 g), stirred for 18 hours, and concentrated; and the concentrate chromatographed on silica gel with 5% methanol/dichloromethane.

Example 199

7-((3R,4S)-3-(benzylamino)-4-hydroxypyrrolidin-1-yl)-6-fluoro-4-oxo-1,4-dihydro-1,8-naphthyridine-3-carboxylic acid A solution of EXAMPLE 199B (0.1 g) in ethanol (1 mL) at 25° C. was treated with 1N NaOH (1 mL), stirred for 18 hours at 50° C., cooled, neutralized with 10% HCl, and filtered. NMR (300 MHz, DMSO-$d_5$) δ ppm 3.4-4.1 (m, 5H), 4.38 (bs, 1H), 7.3-7.45 (m, 5H), 7.96 (d, 1H), 8.47 (s, 1H).

Example 200

7-(3-aminopyrrolidin-1-yl)-3-(((3-(diethylamino)propyl)amino)methyl)-6-fluoro-1,8-naphthyridin-4(1H),-one, trifluoroacetic acid salt This compound was prepared according to the procedure described in EXAMPLE 196 substituting 1-(3-aminopropyl)-2-pyrrolidinone N,N-diethyl-1,3-propanediamine for 3-phenylpropan-1-amine in EXAMPLE 196B. NMR (500 MHz, DMSO-$d_6$) δ ppm 12.15 (d, 1H), 9.50 (bs, 1H), 8.68 (bs, 2H), 8.20 (bs, 3H), 7.98 (d, 1H), 7.88 (d, 1H), 3.99-3.90 (m, 5H), 3.85-3.77 (m, 2H), 3.12 (m, 6H), 3.02-2.95 (m, 2H), 2.35-2.27 (m 1H), 2.12-2.05 (m, 1H), 2.03-1.97 (m, 2H), 1.20 (t, 6H).

Example 201

6-fluoro-4-oxo-7-(3-((3-pyridin-4-ylbenzyl)amino)pyrrolidin-1-yl)-1,4-dihydro-1,8-naphthyridine-3-carboxylic acid

Example 201A

A solution of EXAMPLE 15A (5.0 g) and tert-butyl pyrrolidin-3-ylcarbamate (5.7 g) in acetonitrile (150 mL) at 25° C. was treated with triethylamine (10 mL), heated for 12 hours at reflux, cooled, treated with dichloromethane (200 mL), and washed with water, 10% citric acid and brine. The organic phase was dried (MgSO$_4$), filtered, and concentrated.

Example 201B

A solution of EXAMPLE 201A (7.1 g) in dichloromethane (200 mL) at 25° C. was treated with trifluoroacetic acid (20 mL), stirred for 1 hour, and concentrated; and the concentrate crystallized from diethyl ether.

Example 201C

A solution of EXAMPLE 201B (1.0 g), 3-bromobenzaldehyde (0.42 g), sodium cyanoborohydride (0.103 g) in methanol (20 mL) and dichloromethane (10 mL) at 25° C. was treated with acetic acid (0.613 g), stirred for 1 hour, treated with water (50 mL) and dichloromethane (100 mL), and partitioned. The organic layer was washed with 10% NaHCO$_3$, water and brine, dried (MgSO$_4$), filtered, and concentrated; and the concentrate chromatographed on silica gel with 3% methanol/dichloromethane.

Example 201D

A solution of EXAMPLE 201C (0.5 g), palladium (II) acetate (0.021 g), 2-(di-t-butylphosphino)biphenyl (0.055 g), triethylamine (0.28 g) and 4-tributylstannylpyridine (0.405 g) in N,N-dimethylformamide (60 mL) was heated in a sealed tube under an inert atmosphere for 1 hour at 100° C., filtered and treated with dichloromethane (100 mL), washed with water and brine, dried (MgSO$_4$), filtered, and concentrated; and the concentrate purified by reverse phase high performance liquid chromatography (HPLC) on a C18 column with 5%-80% acetonitrile in water containing 0.1% trifluoroacetic acid.

Example 201E

A refluxing solution of EXAMPLE 201D (0.262 g) in methanol (20 mL) at 25° C. was treated with 1M LiOH (10 ml), heated for 4 hours at reflux, cooled, treated with aqueous ammonium chloride, and filtered.

Example 201

Example 201E (0.14 g) was refluxed in trifluoroacetic acid (10 mL) and concentrated sulfuric acid (5 drops) for 6 hours, cooled, treated with ditheyl ether (200 mL), and filtered.

NMR (300 MHz, DMSO-$d_6$) δ ppm 13.26 (d, 1H), 9.18 (bs, 2H), 8.88 (d, 2H), 8.52 (d, 1H), 8.13 (t, 3H), 8.06 (s, 1H), 8.02 (t, 2H), 7.77-7.66 (tt, 2H), 4.41 (m, 2H), 4.08 (m, 2H), 3.87 (m, 1H), 2.41 (m, 2H).

Example 202

1-(4-aminobutyl)-7-((1S,4S)-2,5-diazabicyclo(2.2.1)hept-2-yl)-6-fluoro-4-oxo-1,4-dihydro-1,8-naphthyridine-3-carboxylic acid A mixture of EXAMPLE 7A (168.3 mg), tert-butyl 4-aminobutylcarbamate (95.5 µL), and diisopropylethylamine (450 µL) in acetonitrile (4.0 mL) was heated in a microwave reactor for 10 minutes at 50° C., and 20 minutes at 190° C., cooled, treated with tert-butyl-(1S,4S)-(−)-2,5-diaza-bicyclo(2.2.1)heptane-2-carboxylate (119 mg), heated in a microwave reactor for 30 minutes at 100° C., cooled, treated with 2M lithium hydroxide (1.25 mL), heated in a microwave reactor for 20 minutes at 100° C., and 18 hours at 25° C., treated with water, acidified to pH 3 with 1M HCl, and extracted with ethyl acetate. The extract was washed with brine, dried (Na$_2$SO$_4$), filtered, and concentrated. A solution of the concentrate in dioxane (5.0 mL) at 25° C. was treated with 1M HCl/dioxane (3.0 mL), stirred for three hours, and concentrated. The concentrate was triturated in diethyl ether, ethyl acetate, and dichloromethane. NMR (300 MHz, DMSO-$d_6$) δ ppm 9.00 (s, 1H), 8.15 (d, 1H), 7.96-7.78 (m, 3H), 5.22-5.16 (m, 1H), 4.60-4.41 (m, 3H), 4.22-4.13 (m, 1H), 3.96-3.85 (m, 1H), 2.88-2.73 (m, 3H), 2.25-2.17 (m, 1H), 2.07-1.99 (m, 1H), 1.94-1.79 (m, 2H), 1.72-1.49 (m, 3H).

Example 203

6-fluoro-7-(3-((2-methoxyethyl)amino)pyrrolidin-1-yl)-4-oxo-1,4-dihydro-1,8-naphthyridine-3-carboxylic acid, trifluoroacetic acid salt This compound was prepared as described in EXAMPLE 98 substituting 2-methoxyethanamine for N-(4-aminobutyl)guanidine in EXAMPLE 98C. NMR (300 MHz, CD$_3$OD) δ ppm 8.45 (s, 1H), 7.86 (d, 1H), 4.25-3.86 (m, 5H), 3.72 (t, 2H), 3.44 (s, 3H), 3.38 (t, 2H), 2.60-2.45 (m, 1H), 2.39-2.26 (m, 1H).

Example 204

7-(3-aminopyrrolidin-1-yl)-6-fluoro-5-methyl-4-oxo-1-(2,2,2-trifluoroethyl)-1,4-dihydro-1,8-naphthyridine-3-carboxylic acid Example 204A A solution of EXAMPLE 1C (179 mg) in acetonitrile (4 mL) at 25° C. was treated with 2,2,2-trifluoroethanamine (76 mg) and N,N-diisopropylethylamine (450 µL), heated in a microwave reactor for 10 min at 50° C., and 1 hour at 210° C., cooled, treated with tert-butyl pyrrolidin-3-ylcarbamate (112 mg), heated in a microwave reactor for 30 min at 100° C., cooled, treated with aqueous lithium hydroxide (1M, 2.8 mL) and a small amount of methanol, stirred for 18 hours at 25° C., treated with water, acidified to pH 1 with aqueous HCl, and filtered.

Example 204

A solution of EXAMPLE 204A (130 mg) in dioxane (2 mL) at 25° C. was treated with HCl in dioxane (4M, 2 mL), stirred for 2 hours, treated with diethyl ether, and the supernatent was removed. The residual solid was triturated with ethyl acetate and dichloromethane. NMR (500 MHz, DMSO-$d_6$) δ ppm 8.77 (s, 1H), 5.24 (m, 2H), 3.75 (m, 5H), 2.49 (d, 3H), 2.11 (m, 1H), 1.93 (m, 1H).

Example 205

7-azetidin-1-yl-4-oxo-6-prop-1-ynyl-1,4-dihydro-1,8-naphthyridine-3-carboxylic acid Example 205A A mixture of EXAMPLE 143B (3 g) and azetidine hydrochloride (1.4 g) in acetonitrile (100 mL) at 0° C. was treated dropwise with N,N-diisopropylethylamine (5 mL), stirred for 26 hours at 55° C., and concentrated. The concentrate was suspended in dilute citric acid, and filtered.

Example 205B

A mixture of EXAMPLE 205A (3.05 g) and 1,3-dichloro-5,5-dimethylimidazolidine-2,4-dione (1.6 g) in tetrahydrofuran (125 mL) was stirred for one hour at 25° C., and concentrated. The residue was suspended in dilute sodium bisulfite solution, and filtered.

Example 205C

A suspension of EXAMPLE 205B (0.200 g) and tributyl (1-propynyl)tin (0.200 mL) in anhydrous toluene (5 mL) at 25° C. was treated with tetrakis(triphenylphosphine)palladium(0) (0.011 g), stirred in a sealed tube under an inert atmosphere for nine hours at 75° C., and 18 hours at 25° C., and concentrated; and the concentrate was flash chromatographed on silica gel with 50% ethyl acetate/hexane Example 205D A solution of EXAMPLE 205C (0.0664 g) in 2/1 tetrahydrofuran/methanol (6 mL) at 25° C. was treated with 2N NaOH (0.180 mL), stirred for ninety minutes at 55° C., and concentrated. A suspension of the concentrate in dilute citric acid was centrifuged, and decanted. The pellet was suspended in water and lyophilized.

Example 205

A solution of EXAMPLE 205D (0.0614 g) in trifluoroacetic acid (3 mL) at 25° C. was treated with concentrated sulfuric acid (three drops), stirred for seventy minutes, concentrated, and treated with ice. The resulting solid was triturated with water and filtered. NMR (500 MHz, DMSO-$d_6$/CF$_3$COOD, 90° C.) δ ppm 8.75 (s, 1H), 8.17 (s, 1H), 4.62 (bs, 4H), 2.42-2.48 (m, 2H), 2.06 (s, 3H).

Example 206

7-((3R,4R)-3-amino-4-hydroxypyrrolidin-1-yl)-6-fluoro-4-oxo-1,4-dihydro-1,8-naphthyridine-3-carboxylic acid Example 206A A solution of 3-pyrroline (0.89 g) in dichloromethane (100 mL) at 0° C. was treated with di-tert-butyl dicarbonate (3.24 g), stirred for 15 minutes at 0° C., then 3 hours at 25° C., cooled to 0° C., treated with m-chlorobenzoic acid (60% pure, 4.1 g), stirred for 18 hours at 25° C., and filtered. The filtrate was treated with 10% sodium carbonate (40 mL) and saturated sodium thiosulfate (30 mL), and partitioned. The aqueous layer was extracted with dichloromethane (2×40 mL). The combined organic extracts were dried (MgSO$_4$), filtered and concentrated. The crude product was flash chromatographed on silica gel with 1:4 to 1:2 of ethyl acetate/hexanes.

Example 206B

A solution of lithium azide (5 mL, 20% weight in water) in water (20 mL) at 25° C. was treated with EXAMPLE 206A (1.8 g) in acetone (20 mL), heated at reflux for 18 hours, cooled, and concentrated. The remaining aqueous solution was extracted with dichloromethane (2×40 mL). The organic extracts were dried (MgSO$_4$), filtered and concentrated. NMR (CDCl$_3$) δ ppm 4.25 (m, 1H), 3.93 (bs, 1H), 3.77-3.55 (m, 2H), 3.50-3.30 (m, 2H), 1.47 (s, 9H).

Example 206C

A solution of EXAMPLE 206B (0.85 g) in dichloromethane (10 mL) at 25° C. was treated with 2N HCl in diethyl ether (10 mL), stirred for 18 hours, and concentrated. A solution of the concentrate in acetonitrile (20 mL) at 25° C. was treated with triethylamine (3 mL) and EXAMPLE 51A (1.19 g), stirred for 18 hours, concentrated, and the residue triturated with methanol.

Example 206D

A suspension of EXAMPLE 206C (0.266 g) and triphenyl phosphine (0.162 g) in tetrahydrofuran (30 mL) and water (1 mL) was heated for 18 hours at 50° C., concentrated; and the concentrate was purified by reverse phase high performance liquid chromatography (HPLC) on a C8 column with 10-95% acetonitrile in water containing 0.1% trifluoroacetic acid. NMR (DMSO-$d_6$) δ ppm 8.71 (s, 1H), 8.17 (bs, 3H), 7.90 (d, 1H), 7.15 (d, 1H), 6.61 (d, 1H), 6.48 (dd, 1H), 5.82 (bs 1H), 5.40 (s, 2H), 4.36 (m, 1H), 4.21 (q, 2H), 4.04 (m, 2H), 3.85 (m, 1H), 3.81 (s, 3H), 3.74 (s, 3H), 3.67 (m, 2H), 1.27 (t, 3H).

Example 206

7-((3R,4R)-3-amino-4-hydroxypyrrolidin-1-yl)-6-fluoro-4-oxo-1,4-dihydro-1,8-naphthyridine-3-carboxylic acid A solution of EXAMPLE 206D (0.064 g) in tetrahydrofuran/water (2 mL/1 mL) at 25° C. was treated with lithium hydroxide monohydrate (0.033 g), stirred for 18 hours, acidified with 2N HCl, and extracted with dichloromethane (2×10 mL). The extract was dried (MgSO$_4$), filtered, and concentrated. A solution of the concentrate in trifluoroacetic acid (2 mL) was heated for 0.5 hour at 70° C., cooled, and concentrated; and the concentrate was purified with reverse phase high performance liquid chromatography (HPLC) on a C8 column with 10-95% acetonitrile in water containing 0.1% trifluoroacetic acid. NMR (DMSO-d$_6$) δ ppm 15.4 (s, 1H), 8.54 (s, 1H), 8.06 (d, 1H), 5.86 (d, 1H), 4.38 (m, 1H), 4.08 (m, 2H), 3.88 (m, 1H), 3.72 (m, 2H).

Example 207

N-(2-((6-fluoro-7-pyrrolidin-1-yl-1,8-naphthyridin-4-yl)amino)ethyl)guanidine

Example 207A

A solution of EXAMPLE 180C (68 mg) in ethylenediamine (0.6 mL) was heated for 4.5 hours at 110° C. and concentrated. The concentrate was flash chromatographed on silica gel with 96:3:1 dichloromethane/methanol/ammonium hydroxide.

Example 207

A solution of EXAMPLE 207A (20 mg) and triethylamine (9 mg) in ethanol (0.6 mL) at 25° C. was treated with 2-ethyl-2-thiopseudourea hydrobromide (15 mg), stirred for 18 hours, and filtered; and the solid was triturated with cold (0° C.) methanol and dried. NMR (300 MHz, DMSO-d$_6$/CF$_3$COOD) δ ppm 8.40 (d, 1H), 8.20 (d, 1H), 6.71 (d, 1H), 3.85-3.72 (m, 4H), 3.65-3.59, (m, 2H), 3.53-3.45 (m, 2H), 2.05-1.95 (m, 4H).

Example 208

7-((1S,4S)-2,5-diazabicyclo(2.2.1)hept-2-yl)-6-fluoro-1-(2-(methylthio)benzyl)-4-oxo-1,4-dihydro-1,8-naphthyridine-3-carboxylic acid Example 208A A solution of EXAMPLE 7A (167 mg) in acetonitrile (4 mL) at 25° C. was treated with 1-(2-(methylthio)phenyl)methanamine (77 mg) and N,N-diisopropylethylamine (450 µL), heated in a microwave reactor for 10 min at 50° C., and 20 min at 190° C., cooled, treated with tert-butyl (1S,4S)-(−)-2,5-diaza-bicyclo(2.2.1)heptane-2-carboxylate (119 mg), heated in a microwave reactor for 30 min at 100° C., cooled, treated with aqueous lithium hydroxide (2M, 1.2 mL), heated in a microwave reactor for 15 min at 100° C., and stirred for 3 days at 25° C., treated with water, acidified to pH 1 with aqueous HCl, and filtered.

Example 208

A solution of EXAMPLE 208A (155 mg) in dioxane (2 mL) at 25° C. was treated with HCl in dioxane (4M, 2.5 mL), stirred for 2 hours, treated with diethyl ether, and decanted. The residual solid was triturated with ethyl acetate and dichloromethane and dried. NMR (300 MHz, DMSO-d$_6$) δ ppm 15.23 (s, 1H), 9.46 (s, 1H), 9.01 (s, 1H), 8.79 (s, 1H), 8.17 (d, 1H), 7.37 (m, 2H), 7.12 (dt, 1H), 6.87 (d, 1H), 5.76 (d, 1H), 5.65 (d, 1H), 4.89 (bs, 1H), 4.45 (s, 1H), 3.88 (m, 2H), 3.00 (m, 2H), 2.54 (m, 3H), 2.10 (d, 1H), 1.93 (d, 1H).

Example 209

1-(1,3-benzodioxol-5-ylmethyl)-7-((1S,4S)-2,5-diazabicyclo(2.2.1)hept-2-yl)-6-fluoro-4-oxo-1,4-dihydro-1,8-naphthyridine-3-carboxylic acid A solution of EXAMPLE 7A (336.1 mg) and triethylamine (0.696 mL) in acetonitrile (3.3 mL) was treated with 1,3-benzodioxol-5-ylmethylamine (0.131 mL), stirred for 2 hours at 25° C., 4 hours at 40° C., and 4 days at 85° C., cooled, treated with potassium cabonate (50 mg) and acetonitrile (7 ml), stirred for 2 days at 100° C., cooled to 25° C., treated with tert-butyl (1S,4S)-(−)-2,5-diazabicyclo(2.2.1)heptane-2-carboxylate (237.9 mg), stirred for 24 hours at 50° C., cooled, treated with 1N NaOH (4 mL) and methanol (2 ml), stirred for 8 hours at 40° C., cooled, treated with water, acidified to pH 3.5 with 1N HCl, and filtered. A solution of the solid in 4N HCl/dioxane (6.25 mL) was stirred for 2 hours at 25° C., treated with diethyl ether, centrifuged, and decanted; and the solid was triturated with diethyl ether, dichloromethane, and methanol. NMR (300 MHz, DMSO-d$_6$) δ ppm 15.28 (bs, 1H), 9.46 (bs, 1H), 9.13 (s, 1H), 8.77 (bs, 1H), 8.12 (d, 1H), 6.93 (m, 1H), 6.86 (m, 2H), 6.00 (s, 2H), 5.61 (dd, 2H), 5.17 (bs, 1H), 4.50 (bs, 1H), 3.94 (m, 2H), 3.27 (m, 1H) (partially obscured by water peak), 3.11 (m, 1H), 2.08 (dd, 2H).

Example 210

7-(3-aminopyrrolidin-1-yl)-6-fluoro-1-(2-(3-methoxyphenyl)ethyl)-5-methyl-4-oxo-1,4-dihydro-1,8-naphthyridine-3-carboxylic acid Example 210A A solution of EXAMPLE 1C (178 mg) in acetonitrile (4 mL) at 25° C. was treated with 2-(3-methoxyphenyl)ethanamine (100 mg) and N,N-diisopropylethylamine (450 µL), stirred in a microwave reactor for 10 min at 50° C., and 1 hour at 200° C., cooled, treated with tert-butyl pyrrolidin-3-ylcarbamate (112 mg), heated in a microwave reactor for 30 min at 100° C., cooled, treated with aqueous lithium hydroxide (1M, 2.8 mL) and a small amount of methanol, stirred for 18 hours at 25° C., treated with water, acidified to pH 1 with aqueous HCl, and filtered.

Example 210

A solution of EXAMPLE 210A (130 mg) in dioxane (2 mL) at 25° C. was treated with HCl in dioxane (4M, 2.5 mL), stirred for 2 hours, treated with diethyl ether, and the supernatent was removed. The residual solid was triturated with ethyl acetate and dichloromethane. NMR (500 MHz, DMSO-d$_6$) δ ppm 8.55 (s, 1H), 7.95 (m, 2H), 6.93 (t, 1H), 6.62 (s, 1H), 6.54 (m, 2H), 4.40 (m, 2H), 3.74 (m, 5H), 3.48 (s, 3H), 2.85 (t, 2H), 2.48 (s, 3H), 2.10 (m, 1H), 1.91 (m, 1H).

Example 211

6-fluoro-7-[(3aS,6aS)-hexahydropyrrolo[3,4-b]pyrrol-5(1H)-yl]-4-oxo-1,4-dihydro-1,8-naphthyridine-3-carboxylic acid Example 211A EXAMPLE 211A was prepared according to the procedure described in EXAMPLE 98D substituting EXAMPLE 103B for EXAMPLE 98C.

Example 211

EXAMPLE 211B was prepared according to the procedure described in EXAMPLE 98E substituting EXAMPLE 211A for EXAMPLE 98D. NMR (300 MHz, CD$_3$OD) δ ppm 8.55 (s, 1H), 8.01 (d, 1H), 4.48-4.32 (m, 2H), 4.12-4.01 (m, 2H), 3.92-3.84 (m, 1H), 3.58-3.31 (m, 3H), 2.45-2.32 (m, 1H), 2.18-2.06 (m, 1H).

Example 212

7-(3-((cyclopropylmethyl)amino)pyrrolidin-1-yl)-6-fluoro-4-oxo-1,4-dihydro-1,8-naphthyridine-3-carboxylic acid, citric acid salt This compound was prepared according to the procedure described in EXAMPLE 118 substituting cyclopropanecarboxaldehyde for 3-(methylthio)propanal in EXAMPLE 118C. NMR (500 MHz, DMSO-d$_6$/CF$_3$COOD) δ ppm 8.47 (s, 1H), 7.83 (d, 1H), 4.01-3.71 (m, 5H), 2.86-2.78 (m, 2H), 2.72-2.57 (m, 4H), 2.34-2.26 (m, 1H), 2.24-2.16 (m 1H), 1.03-0.93 (m, 1H), 0.56-0.51 (m, 2H), 0.31-0.27 (m, 2H).

Example 213

7-((1S,4S)-2,5-diazabicyclo(2.2.1)hept-2-yl)-1-(2,4-dimethoxybenzyl)-5-ethyl-6-fluoro-4-oxo-1,4-dihydro-1,8-naphthyridine-3-carboxylic acid Example 213A A solution of EXAMPLE 1D2 (380 mg) in acetonitrile (30 mL) at 25° C. was treated with tert-butyl (1S,4S)-2,5-diazabicyclo(2.2.1)heptane-2-carboxylate (336 mg) and triethylamine (3 mL), stirred for 6 hours at 80° C., treated with water, acidified with 10% aqueous citric acid, and filtered.

Example 213B

A suspension of EXAMPLE 213A (388 mg) in ethanol (10 mL) at 25° C. was treated with 1N LiOH (3 mL), heated for 1 hour at 80° C., acidified with 10% aqueous citric acid, treated with water, and dried.

Example 213

A solution of Example 213B (250 mg) in dichloromethane (6 mL) at 25° C. was treated with trifluoroacetic acid (3 mL), stirred for 3 hours, and concentrated. NMR (300 MHz, DMSO-d$_6$) δ ppm 15.73 (s, 1H) 9.21 (s, 1H) 8.95 (s, 1H) 8.55 (s, 1H) 7.11 (d, 1H) 6.60 (d, 1H) 6.50 (m, 1H) 5.53 (m, 2H) 5.13 (s, 1H) 4.52 (s, 1H) 3.90 (s, 2H) 3.77 (t, 3H) 3.75 (t, 3H) 3.29 (m, 2H) 2.71 (m, 2H) 2.17 (d, 1H) 1.98 (d, 1H) 1.19 (t, 3H).

Example 214

1-(5-aminopentyl)-7-((1S,4S)-2,5-diazabicyclo(2.2.1)hept-2-yl)-6-fluoro-4-oxo-1,4-dihydro-1,8-naphthyridine-3-carboxylic acid Example 214A A solution of EXAMPLE 7A (0.170 g) in acetonitrile (4 mL) at 25° C. was treated with tert-butyl 5-aminopentylcarbamate (0.104 mL) and diisopropylethylamine (0.45 mL), microwaved for ten minutes at 50° C., and twenty minutes at 190° C., cooled, treated with tert-butyl (1S,4S-)-(–)-2,5-diazabicyclo(2.2.1)heptane-2-carboxylate (0.115 g), microwaved for thirty minutes at 100° C., cooled, and concentrated; and the concentrate was flash chromatographed on silica gel with 65% ethyl acetate/hexane.

Example 214B

A solution of EXAMPLE 214A (0.142 g) in 2/1 tetrahydrofuran/methanol (6 mL) at 25° C. was treated with 2N NaOH (0.23 mL), stirred for one hour at 55° C., and concentrated. The residue was treated with water, adjusted to pH 6 with glacial acetic acid, and filtered.

Example 214

Example 214B (0.118 g) at 25° C. was treated with 1N HCl in acetic acid (3 mL), stirred for fifteen minutes, and lyophilized. The residue was suspended in diethyl ether, and filtered. NMR (500 MHz, DMSO-d$_6$/CF$_3$COOD) δ ppm 8.88 (s, 1H), 8.04 (d, 1H), 5.12 (s, 1H), 4.52 (s, 1H), 4.43 (t, 2H), 4.1-4.4 (m, 1H), 3.95-3.83 (m, 1H), 3.47-3.35 (m, 2H), 2.75 (t, 2H), 2.23-2.13 (m, 1H), 2.07-1.97 (m, 1H), 1.87-1.91 (m, 2H), 1.63-1.49 (m, 2H), 1.42-1.27 (m, 2H).

Example 215

7-((1S,4S)-2,5-diazabicyclo(2.2.1)hept-2-yl)-6-fluoro-1-(4-(methylthio)benzyl)-4-oxo-1,4-dihydro-1,8-naphthyridine-3-carboxylic acid Example 215A A solution of EXAMPLE 7A (168 mg) in acetonitrile (4 mL) at 25° C. was treated with 1-(4-(methylthio)phenyl)methanamine (79 mg) and N,N-diisopropylethylamine (450 μL), stirred in a microwave reactor for 10 min at 50° C., and 20 min at 190° C., cooled, treated with tert-butyl (1S,4S)-(–)-2,5-diaza-bicyclo(2.2.1)heptane-2-carboxylate (116 mg), stirred in a microwave reactor for 30 min at 100° C., cooled, treated with aqueous lithium hydroxide (2M, 1.2 mL), stirred in a microwave reactor for 15 min at 100° C., and stirred for 3 days at 25° C., treated with water, acidified to pH 3 with aqueous HCl, and filtered Example 215

A solution of EXAMPLE 215A (169 mg) in dioxane (2 mL) at 25° C. was treated with HCl in dioxane (4M, 2.5 mL), stirred for 2 hours, treated with diethyl ether, and the supernatent was removed. The residual solid was triturated with ethyl acetate and dichloromethane. NMR (300 MHz, DMSO-d$_6$) δ ppm 9.66 (bs, 1H); 9.18 (s, 1H); 8.99 (bs, 1H); 8.12 (d, 1H); 7.26 (m, 4H); 5.67 (m, 2H); 5.12 (s, 1H); 4.49 (s, 1H); 4.03 (m, 1H); 3.88 (m, 1H); 3.11 (m, 2H); 2.44 (s, 3H); 2.15 (m, 1H); 1.98 (m, 1H).

Example 216

7-(3-aminopyrrolidin-1-yl)-6-fluoro-4-oxo-1-(3-phenylpropyl)-1,4-dihydro-1,8-naphthyridine-3-carboxylic acid

Example 216A

Example 7A (0.17 g) in acetonitrile (4 mL) at 25° C. was treated with 3-phenylpropan-1-amine (0.071 mL) and N,N-diisopropylethylamine (0.5 mL), microwaved for ten minutes at 50° C., and twenty minutes at 190° C., cooled, treated with tert-butyl pyrrolidin-3-ylcarbamate (0.112 g), microwaved for thirty minutes at 100° C., cooled and concentrated.

Example 216B

A solution of EXAMPLE 216A (0.27 g) in 2/1 tetrahydrofuran/methanol (12 mL) at 25° C. was treated with 2N NaOH (1 mL), stirred for 3.5 hours at 55° C., and concentrated. The residue was diluted with water, acidified with dilute citric acid, and filtered.

Exampled 216

Example 216B (0.236 g) at 25° C. was treated with 1N HCl in acetic acid (5 mL), stirred for forty five minutes, triturated with diethyl ether, sonicated, and filtered. NMR (500 MHz, DMSO-d$_6$) δ ppm 8.89 (s, 1H), 8.6-8.4 (s, 3H), 7.99 (d, 1H), 7.3-7.13 (m, 5H), 4.52-4.4 (m, 2H), 4.05-3.6 (m, 5H), 2.67 (t, 2H), 2.35-2.21 (m, 1H), 2.2-2.05 (m, 3H).

Example 217

7-((1S,4S)-2,5-diazabicyclo(2.2.1)hept-2-yl)-1-(4-(dimethylamino)benzyl)-6-fluoro-4-oxo-1,4-dihydro-1,8-naphthyridine-3-carboxylic acid A solution of EXAMPLE 7A (336.1 mg) in acetonitrile (10 mL) at 25° C. was treated with 4-(dimethylamino)benzylamine dihydrochloride (234.3 mg) and potassium carbonate (367.2 mg), stirred for 2 hours at 25° C., and 16 hours at 50° C., cooled, treated with potassium carbonate (367.2 mg), stirred for 2 days at 85° C., cooled to 25° C., treated with tert-butyl (1S,4S)-(−)-2,5-diazabicyclo(2.2.1)heptane-2-carboxylate (237.9 mg), stirred 3 days at 50° C., cooled, treated with 1N NaOH (4 mL) and methanol (2 ml), stirred for 16 hours at 40° C., cooled to 25° C., treated with water, acidified to pH 8 with 1N HCl, and filtered. A solution of the solid (150 mg) in 4N HCl/dioxane (3 mL) was stirred for 2 hours at 25° C., treated with diethyl ether, and centrifuged; and the solid was triturated with diethyl ether, dichloromethane, and methanol. NMR (300 MHz, DMSO-d$_6$) delta ppm 9.77 (bs, 1H), 9.15 (bs, 1H), 9.12 (s, 1H), 8.12 (d, 1H), 7.31 (m, 2H), 7.03 (bs, 2H), 5.65 (m, 2H), 5.15 (bs, 1H), 4.49 (bs, 1H), 3.96 (m, 4H), 2.94 (s, 6H), 2.08 (dd, 2H).

Example 218

7-(3-aminopyrrolidin-1-yl)-3-(((3,4-difluorobenzyl)amino)methyl)-6-fluoro-1,8-naphthyridin-4(1H),-one, trifluoroacetic acid salt This compound was prepared according to the procedure described in EXAMPLE 196 substituting 3,4-difluorobenzylamine for 3-phenylpropan-1-amine in EXAMPLE 196B. NMR (500 MHz, DMSO-d$_6$) δ ppm 12.10 (d, 1H), 8.98 (bs, 2H), 8.15 (bs, 3H), 7.92 (d, 1H), 7.88 (d, 1H), 7.66-7.61 (m, 1H), 7.54-7.49 (m, 1H), 7.40-7.35 (m, 1H), 4.17 (m, 2H), 4.00-3.85 (m, 5H), 3.85-3.72 (m, 2H), 2.35-2.27 (m 1H), 2.12-2.05 (m, 1H).

Example 219

7-(3-((3,5-difluorobenzyl)amino)pyrrolidin-1-yl)-6-fluoro-4-oxo-1,4-dihydro-1,8-naphthyridine-3-carboxylic acid, hemicitric acid salt This compound was prepared according to the procedure described in EXAMPLE 118 substituting 3,5-difluorobenzaldehyde for 3-(methylthio)propanal in EXAMPLE 118C. NMR (300 MHz, DMSO-d$_6$/CF$_3$COOD) δ ppm 8.49 (s, 1H), 7.91 (d, 1H), 7.23-7.29 (m, 2H), 7.11-7.18 (m, 1H), 4.34-4.24 (m, 2H), 4.08-3.75 (m, 5H), 2.77-2.60 (m, 2H), 2.40-2.30 (m, 2H).

Example 220 ethyl 7-(3-aminopyrrolidin-1-yl)-6-fluoro-1-(2-(2-fluorophenyl)ethyl)-5-methyl-4-oxo-1,4-dihydro-1,8-naphthyridine-3-carboxylate A solution of EXAMPLE 1C (357.4 mg) in acetonitrile (10.2 mL) at 25° C. was treated with 2-(2-fluorophenyl)ethanamine (0.14 mL), stirred for 2 hours at 25° C., and 16 hours at 50° C., cooled, treated with potassium carbonate (374.5 mg), stirred for 2 days at 85° C., cooled to 25° C., treated with tert-butyl pyrrolidin-3-ylcarbamate (284.6 mg), stirred for 2 days at 25° C., and concentrated. A suspension of the concentrate in tetrahydrofuran (8 mL) and 4N HCl/dioxane (14 mL) was stirred for 2 hours at 25° C., treated with diethyl ether, and centrifuged; and the solid triturated with diethyl ether. The resulting solid was suspended in methanol and dichloromethane. The supernate was concentrated and the concentrate purified by reverse phase high performance liquid chromatography (HPLC) on a C8 column with 0% to 100% acetonitrile in water containing 0.1% trifluoroacetic acid. NMR (300 MHz, DMSO-d$_6$) δ ppm 8.26 (bs, 1H), 8.16 (m, 3H), 7.30 (m, 2H), 7.13 (m, 2H), 4.47 (m, 2H), 4.14 (q, 2H), 3.99 (m, 2H), 3.86 (m, 3H), 3.10 (dd, 2H), 2.64 (d, 3H), 2.32 (m, 1H), 2.11 (m, 1H), 1.21 (t, 3H).

Example 221

6-(benzyloxy)-7-((1S,4S)-2,5-diazabicyclo(2.2.1)hept-2-yl)-1-(2,4-dimethoxybenzyl)-4-oxo-1,4-dihydro-1,8-naphthyridine-3-carboxylic acid

Example 221A

A solution of EXAMPLE 158A (0.275 g) in tetrahydrofuran (15 mL) at 25° C. was treated with lithium hydroxide monohydrate (0.2 g) in water (15 mL), stirred for 18 hours, and concentrated.

Example 221

A mixture of benzyl alcohol (0.720 g) and 60% oily sodium hydride (0.205 g) in N,N-dimethylformamide (5 mL) was stirred at 25° C. for 10 min, treated with EXAMPLE 221A (0.160 g), stirred for 3 hours at 95° C., cooled, and concentrated. The concentrate was treated with 1:4 methanol/dichloromethane, acidified to a pH of about 1, and concentrated; and the residue was purified on a reverse phase high performance liquid chromatography (HPLC) on a C8 column with 10-95% acetonitrile in water containing 0.1% trifluoroacetic acid. NMR (DMSO-$d_6$) δ ppm pp, 8.67 (s, 1H), 7.79 (s, 1H), 7.53-7.33 (m, 7H), 6.58 (s, 1H), 6.53 (bs, 1H), 5.45 (m, 4H), 5.15 (m, 2H), 4.48 (bs, 1H), 4.05 (m, 3H), 3.84 (s, 3H), 3.74 (s, 3H), 2.28 (m, 1H), 2.03 (m, 1H).

Example 222

6-fluoro-4-oxo-7-(3-((thien-2-ylmethyl)amino)pyrrolidin-1-yl)-1,4-dihydro-1,8-naphthyridine-3-carboxylic acid, hemicitric acid salt This compound was prepared according to the procedure described in EXAMPLE 118 substituting 2-thiophenecarboxaldehyde for 3-(methylthio)propanal in EXAMPLE 118C. NMR (300 MHz, DMSO-$d_6$/$CF_3COOD$) δ ppm 8.49 (s, 1H), 7.95 (d, 1H), 7.56 (d, 1H), 7.29 (d, 1H), 7.05 (dd, 1H), 4.56-4.45 (m, 2H), 4.05-3.75 (m, 5H), 2.77-2.60 (m, 2H), 2.45-2.25 (m, 2H).

Example 223

7-((1S,4S)-2,5-diazabicyclo(2.2.1)hept-2-yl)-6-fluoro-4-oxo-1-propa-1,2-dienyl-1,4-dihydro-1,8-naphthyridine-3-carboxylic acid

Example 223A

A mixture of EXAMPLE 167A (0.5 g) and tert-butyl (1S,4S-)-(-)-2,5-diazabicyclo(2.2.1)heptane-2-carboxylate (0.34 g) in acetonitrile (15 mL) at 25° C. was treated with N,N-diisopropylethylamine (0.310 mL), stirred for two hours at 55° C., and concentrated. The residue was suspended in dilute HCl, and filtered.

Example 223B

A solution of EXAMPLE 223A (0.181 g) in 2/1 tetrahydrofuran/methanol (12 mL) at 25° C. was treated with 2N NaOH (0.58 mL), stirred for three hours at 55° C., cooled, concentrated, treated with water, acidified with 10% aqueous HCl, and centrifuged. The pellet was washed with water, and lyophilized. The resulting solid was purified by reverse phase high performance liquid chromatography (HPLC) on a C8 column with 20-95% acetonitrile in water containing 1.0% trifluoroacetic acid.

Example 223

EXAMPLE 223B (0.06 g) at 25° C. was treated with 1N HCl in acetic acid (2.5 mL), stirred for fifteen minutes, and lyophilized. The residue was suspended in diethyl ether, and filtered. NMR (500 MHz, DMSO-$d_6$) δ ppm 10-9.8 (s, 1H), 9.45-9.25 (s, 1H), 8.66 (s, 1H), 8.2-8.0 (m, 2H), 6.0 (d, 1H), 5.28 (s, 1H), 4.52 (s, 1H), 4.14 (s, 1H), 3.92 (m, 1H), 2.22-2.09 (m, 1H), 2.09-1.93 (m, 1H).

Example 224

7-(3-(bis(2-hydroxyethyl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 122 substituting diethanolamine for 4-(aminomethyl)benzylamine in EXAMPLE 122C. NMR (300 MHz, DMSO-$d_6$) δ ppm 13.30 (s, 1H), 9.59 (bs, 1H), 8.53 (s, 1H), 8.05 (d, 1H), 4.36-4.17 (m, 2H), 4.07-3.93 (m, 3H), 3.85-3.77 (m, 4H), 3.68-3.55 (m, 4H), 2.49-2.41 (m, 1H), 2.35-2.23 (m, 1H).

Example 225

6-fluoro-7-(3-(((3-methylthien-2-yl)methyl)amino)pyrrolidin-1-yl)-4-oxo-1,4-dihydro-1,8-naphthyridine-3-carboxylic acid, hemicitric acid salt This compound was prepared according to the procedure described in EXAMPLE 118 substituting 3-methyl-2-thiophenecarboxaldehyde for 3-(methylthio)propanal in EXAMPLE 118C. NMR (500 MHz, DMSO-$d_6$/$CF_3COOD$) δ ppm 8.49 (s, 1H), 7.94 (d, 1H), 7.45 (d, 1H), 6.89 (d, 1H), 4.45-4.37 (m, 2H), 4.07-3.77 (m, 5H), 2.77-2.63 (m, 2H), 2.42-2.27 (m, 2H), 2.25 (s, 3H).

Example 226

6-fluoro-7-(3-(((5-methylthien-2-yl)methyl)amino)pyrrolidin-1-yl)-4-oxo-1,4-dihydro-1,8-naphthyridine-3-carboxylic acid, hemicitric acid salt This compound was prepared according to the procedure described in EXAMPLE 118 substituting 5-methylthiophene-2-carbaldehyde for 3-(methylthio)propanal in EXAMPLE 118C. NMR (300 MHz, DMSO-$d_6$/$CF_3COOD$) δ ppm 8.58 (s, 1H), 8.03 (d, 1H), 7.14 (d, 1H), 6.79 (dd, 1H), 4.54-4.43 (m, 2H), 4.15-3.80 (m, 5H), 2.87-2.70 (m, 2H), 2.48 (s, 3H), 2.45-2.35 (m, 2H).

Example 227

7-(3-((4-(acetylamino)benzyl)amino)pyrrolidin-1-yl)-6-fluoro-4-oxo-1,4-dihydro-1,8-naphthyridine-3-carboxylic acid, citric acid salt This compound was prepared according to the procedure described in EXAMPLE 118 substituting N-(4-formylphenyl)acetamide for 3-(methylthio)propanal in EXAMPLE 118C. NMR (300 MHz, DMSO-$d_6$/$CF_3COOD$) δ ppm 8.49 (s, 1H), 7.95 (d, 1H), 7.61 (d, 2H), 7.40 (d, 2H), 4.23-4.12 (m, 2H), 4.05-3.70 (m, 5H), 2.77-2.60 (m, 4H), 2.40-2.29 (m, 2H), 1.99 (s, 3H).

Example 228

7-((3R,4S)-3-amino-4-hydroxypyrrolidin-1-yl)-6-fluoro-4-oxo-1,4-dihydro-1,8-naphthyridine-3-carboxylic acid

Example 228A 7-(3-Amino-4-hydroxy-pyrrolidin-1-yl)-1-(2-cyanoethyl)-6-fluoro-4-oxo-1,4-dihydro-(1,8)naphthyridine-3-carboxylic acid ethyl ester A mixture of cis-3-amino-4-hydroxypyrrolidine (0.81 g), N,N-diisopropylethylamine (3.4 mL), and EXAMPLE 7C (1.60 g) in acetonitrile (50 mL) was stirred at 25° C. for 18 hours, treated with dichloromethane (50 mL), washed with saturated ammonium chloride (3×20 mL), brine (20 mL), dried (MgSO$_4$), filtered, and concentrated. The residue was recrystallized from methanol to give the desired product.

Example 228

7-((3R,4S)-3-amino-4-hydroxypyrrolidin-1-yl)-6-fluoro-4-oxo-1,4-dihydro-1,8-naphthyridine-3-carboxylic acid A solution of EXAMPLE 228A (0.1 g) in ethanol (1 mL) at 25° C. was treated with 1N NaOH (1 mL), stirred for 18 hours at 50° C., cooled to 25° C., neutralized using 10% HCl, and filtered. NMR (300 MHz, DMSO-d$_6$) δ ppm 3.7-4.5 (m, 6H), 8.0 (d, 1H), 8.42 (bs, 1H), 8.49 (d, 2H), 13.41 (m, 1H).

Example 229

7-((1S,4S)-2,5-diazabicyclo(2.2.1)hept-2-yl)-1-(((1S,2R,5S)-6,6-dimethylbicyclo(3.1.1)hept-2-yl)methyl)-6-fluoro-4-oxo-1,4-dihydro-1,8-naphthyridine-3-carboxylic acid A mixture of EXAMPLE 7A (168.3 mg), (−)-cis-myrtanylamine (84.0 μL), and N,N-diisopropylethylamine (450 μL) in acetonitrile (4.0 mL) was heated in a microwave reactor for 10 minutes at 50° C., and 20 minutes at 190° C., cooled, treated with tert-butyl-(1S,4S)-(−)-2,5-diaza-bicyclo(2.2.1)heptane-2-carboxylate (119 mg), stirred in a microwave reactor for 30 minutes at 100° C., cooled, treated with 2M lithium hydroxide (1.25 mL), heated in a microwave reactor for 20 minutes at 100° C., and 18 hours at 25° C., diluted with water, acidified to pH 3 with 1M HCl, and filtered. A solution of the solid in dioxane (5.0 mL) at 25° C. was treated with 1M HCl/dioxane (3.0 mL), stirred for 18 hours, and concentrated. The concentrate was triturated diethyl ether, ethyl acetate, and dichloromethane. NMR (300 MHz, DMSO-d$_6$) δ ppm 8.85 (s, 1H), 8.13 (d, 1H), 5.17-5.09 (m, 1H), 4.72-4.60 (m, 1H), 4.56-4.50 (m, 1H), 4.33-4.22 (m, 1H), 4.08-3.85 (m, 2H), 3.46-3.34 (m, 2H), 2.66-2.52 (m, 1H), 2.39-2.27 (m, 1H), 2.25-2.16 (m, 1H), 2.06-1.53 (m, 7H), 1.21 (s, 3H), 1.17 (s, 3H).

Example 230 ethyl 7-(3-aminopyrrolidin-1-yl)-6-fluoro-1-(2-(4-hydroxyphenyl)ethyl)-5-methyl-4-oxo-1,4-dihydro-1,8-naphthyridine-3-carboxylate Example 230A A solution of EXAMPLE 1C (180 mg) in acetonitrile (4 mL) at 25° C. was treated with 4-(2-aminoethyl)phenol (76 mg) and N,N-diisopropylethylamine (450 μL), stirred in a microwave reactor for 10 min at 50° C., and 1 hour at 210° C., cooled, treated with tert-butyl pyrrolidin-3-ylcarbamate (112 mg), stirred in a microwave reactor for 30 min at 100° C., and concentrated.

Example 230

A solution of EXAMPLE 230A (130 mg) in dioxane (2 mL) at 25° C. was treated with HCl in dioxane (4M, 2 mL), stirred for 2 hours, diluted with diethyl ether, and the supernatent was removed. The residual solid was triturated with ethyl acetate and dichloromethane and purified by reverse phase high performance liquid chromatography (HPLC) on a C8 column with 0-100% acetonitrile in water containing 0.1% trifluoroacetic acid. NMR (500 MHz, DMSO-d$_6$) δ ppm 8.37 (s, 1H), 6.83 (d, 2H), 6.55 (d, 2H), 4.35 (m, 3H), 4.08 (q, 2H), 3.80 (m, 6H), 2.81 (t, 3H), 2.50 (d, 3H), 2.20 (m, 1H), 2.03 (m, 1H).

Example 231 ethyl 6-fluoro-7-(3-((1H-imidazol-2-ylmethyl)amino)pyrrolidin-1-yl)-4-oxo-1,4-dihydro-1,8-naphthyridine-3-carboxylate, trifluoroacetic acid salt This compound was prepared as described in EXAMPLE 175 substituting imidazole-2-carboxaldehyde for 4-hydroxybenzaldehyde in EXAMPLE 175A. NMR (300 MHz, DMSO-d$_6$) δ ppm 8.26 (s, 1H), 7.85 (d, 1H), 7.64 (d, 1H), 7.54 (d, 1H), 4.42 (s, 2H), 4.25-4.12 (q, 2H), 4.03-3.84 (m, 5H), 2.35-2.24 (m, 1H), 2.21-2.09 (m, 1H), 1.26 (t, 3H).

Example 232

7-((1S,4S)-2,5-diazabicyclo(2.2.1)hept-2-yl)-6-fluoro-4-oxo-1-(pyridin-3-ylmethyl)-1,4-dihydro-1,8-naphthyridine-3-carboxylic acid A solution of EXAMPLE 7A (336.1 mg) in acetonitrile (10 mL) at 25° C. was treated with 3-(aminomethyl)pyridine (107 μL), stirred for 2 hours at 25° C., and 16 hours at 50° C., cooled, treated with potassium carbonate (367.2 mg), stirred for 2 days at 85° C., cooled, treated with tert-butyl (1S,4S)-(−)-2,5-diazabicyclo(2.2.1)heptane-2-carboxylate (237.9 mg), stirred for 3 days at 50° C., treated with 1N NaOH (4 mL) and methanol (2 ml), stirred for 16 hours at 40° C., cooled, treated with water, acidified to pH 5.0 with 1N HCl, and filtered. A solution of the solid (150 mg) in 4N HCl/dioxane (3 mL) was stirred for 2 hours at 25° C., treated with diethyl ether and centrifuged, and triturated with diethyl ether and dichloromethane. NMR (300 MHz, DMSO-d$_6$) δ ppm 9.49 (bs, 1H), 9.28 (s, 1H), 8.80 (bs, 1H), 8.78 (d, 1 H), 8.63 (dd, 1H), 8.14 (d, 1H), 7.98 (m, 1H), 7.59 (dd, 1H), 5.79 (dd, 2H), 5.08 (bs, 1H), 4.47 (bs, 1H), 3.88 (m, 2H) (partially obscured by water peak), 3.55 (m, 2H) (partially obscured by water peak), 3.20 (m, 1H), 2.05 (dd, 2H).

Example 233

7-(3-((amino(imino)methyl)amino)pyrrolidin-1-yl)-6-fluoro-4-oxo-1,4-dihydro-1,8-naphthyridine-3-carboxylic acid, trifluoroacetic acid salt Example 233A EXAMPLE 233A was prepared according to the procedure described in EXAMPLE 113C substituting EXAMPLE 118B for EXAMPLE 113B.

Example 233

EXAMPLE 233B was prepared according to the procedure described in EXAMPLE 122D substituting EXAMPLE 233A for EXAMPLE 122C. NMR (300 MHz, CD$_3$OD) δ ppm 8.48 (s, 1H), 7.92 (d, 1H), 4.21-3.88 (m, 5H), 2.48-2.37 (m, 1H), 2.35-2.28 (m, 1H).

Example 234

7-(3-(((2,6-dioxo-1,2,3,6-tetrahydropyrimidin-4-yl)
methyl)amino)pyrrolidin-1-yl)-6-fluoro-4-oxo-1,4-
dihydro-1,8-naphthyridine-3-carboxylic acid

Example 234A

A suspension of EXAMPLE 118B (350 mg) in methanol (4 mL) and dichloromethane (4 mL) at 25° C. was treated with 2,6-dioxo-1,2,3,6-tetrahydro-pyrimidine-4-carbaldehyde mono hydrate (136 mg), sodium cyanoborohydride (36 mg) and acetic acid (0.205 mL), stirred for 18 hours, treated with additional amount of 2,6-dioxo-1,2,3,6-tetrahydro-pyrimidine-4-carbaldehyde mono hydrate (113 mg), stirred at 25° C. for 72 hours, treated with water and trifluoroacetic acid, and concentrated. The concentrate was treated with acetonitrile (5 mL), and filtered.

Example 234

A solution of EXAMPLE 234A (80 mg) in ethanol (5 mL) at 25° C. was treated with a solution of 1N LiOH (2 mL), stirred for 5 hours at 70° C., cooled, and concentrated; and the concentrate was purified by reverse phase high performance liquid chromatograph (HPLC) on a C18 column with 0-50% acetonitrile in water containing 0.1% trifluoroacetic acid. NMR (300 MHz, DMSO-$d_6$) δ ppm 15.44 (s, 1H) 13.29 (s, 1H) 11.17 (s, 1H) 10.97 (bs, 1H) 8.51 (s, 1H) 8.15 (bs, 1H) 8.03 (d, 1H) 5.70 (s, 1H) 3.96 (m, 7H) 2.27 (m, 2H)

Example 235

6-fluoro-4-oxo-7-(3-((pyridin-3-ylmethyl)amino)
pyrrolidin-1-yl)-1,4-dihydro-1,8-naphthyridine-3-
carboxylic acid, trifluoroacetic acid salt

Example 235A

The compound was prepared according to the procedure described in EXAMPLE 118 substituting 3-pridinecarboxaldehyde for 3-(methylthio)propanal.

Example 235

A suspension of EXAMPLE 235A (55 mg) in ethanol (1.75 mL) at 75° C. was treated with 1M LiOH (1 mL), stirred for 4 hours, concentrated, and purified by reverse phase high performance liquid chromatography (HPLC) on a C8 column with 0-100% acetonitrile in water containing 0.1% trifluoroacetic acid. NMR (300 MHz, DMSO-$d_6$/$CF_3COOD$) δ ppm 9.13 (s, 1H), 9.05 (d, 1H), 8.76 (d, 1H), 8.56 (s, 1H), 8.21 (dd, 1H), 8.06 (d, 1H), 4.65-4.55 (m, 2H), 4.20-3.87 (m, 5H), 2.52-2.37 (m, 2H).

Example 236

6-fluoro-7-(3-((2-furylmethyl)amino)pyrrolidin-1-
yl)-4-oxo-1,4-dihydro-1,8-naphthyridine-3-carboxylic acid, citric acid salt This compound was prepared according to the procedure described in EXAMPLE 118 substituting furfural for 3-(methylthio)propanal in EXAMPLE 118C. NMR (300 MHz, DMSO-$d_6$/$CF_3COOD$) δ ppm 8.49 (s, 1H), 7.95 (d, 1H), 7.56 (d, 1H), 7.29 (d, 1H), 7.07-7.04 (dd, 1H), 4.56-4.45 (m, 2H), 4.05-3.75 (m, 5H), 2.77-2.60 (m, 2H), 2.45-2.25 (m, 2H).

Example 237

6-(aminomethyl)-7-(3-aminopyrrolidin-1-yl)-4-oxo-
1,4-dihydro-1,8-naphthyridine-3-carboxylic acid

Example 237A

A solution of EXAMPLE 143D (0.75 g) and $Zn(CN)_2$ (0.329 g) in acetonitrile (60 mL, degassed, anhydrous) at 25° C. was treated with tris(dibenzylideneacetone)-dipalladium (0) (0.064 g) and 2-(di-t-butylphosphino)biphenyl (0.084 g), heated under an atmosphere of $N_2$ for 4 hours at reflux, and filtered. The filtrate was treated with dichloromethane (100 mL), washed with water and brine, dried ($MgSO_4$), filtered, and concentrated; and the concentrate was crystallized from dichloromethane/diethyl ether/hexanes.

Example 237B

A solution of EXAMPLE 237A (0.77 g), raney nickel (15.0 g), and di-tert-butyl dicarbonate (0.70 g) in dichloromethane (20 mL) and ethanol (20 mL) was heated at 50° C. in a pressurized (59 psi) atmosphere of $H_2$ for 10 hours, cooled, centrifuged, decanted, and concentrated. A solution of the concentrate in methanol (20 mL) was treated with 1M LiOH (5 ml) at 25° C., stirred for 4 hours at reflux, cooled, acidified with 10% citric acid, and filtered.

Example 237

Example 237B (0.30 g) was refluxed in trifluoroacetic acid (10 mL) and concentrated sulfuric acid (5 drops) for 6 hours, cooled, treated with diethyl ether (200 mL), and filtered.

NMR (300 MHz, DMSO-$d_6$) δ ppm 15.62 (s, 1H), 8.61 (s, 1H), 8.49 (s, 1H), 4.39 (d, 2H), 4.00-3.95 (m, 3H), 3.88-3.78 (m, 3H), 2.39-2.33 (m, 1H), 2.20-2.17 (m, 1H).

Example 238

N-(6-fluoro-7-pyrrolidin-1-yl-1,8-naphthyridin-4-
yl)-N,N',N'-trimethylethane-1,2-diamine A solution of EXAMPLE 180C (40 mg) in N,N,N'-trimethylethane-1,2-diamine (0.4 mL) was heated at 115° C. for 16 hours and concentrated. The concentrate was flash chromatographed on silica gel with chloroform. NMR (300 MHz, DMSO-$d_6$) δ ppm 8.40 (d, 1H), 8.08 (d, 1H), 6.68 (d, 1H), 3.75-3.65 (m, 4H), 3.25 (t, 2H), 2.89 (s, 3H), 2.54 (t, 2H), 2.17 (s, 6H), 1.97-1.91, (m, 4H).

Example 239

7-((1S,4S)-2,5-diazabicyclo(2.2.1)hept-2-yl)-6-
fluoro-4-oxo-1-(piperidin-4-ylmethyl)-1,4-dihydro-
1,8-naphthyridine-3-carboxylic acid

Example 239A

A solution of EXAMPLE 7A (170 mg) in acetonitrile (4 mL) at 25° C. was treated with tert-butyl 4-aminomethyl-piperidine-1-carboxylate (108 mg) and N,N-diisopropylethylamine (450 μL), heated in a microwave reactor for 10 min at 50° C., and 20 min at 190° C., cooled, treated with tert-butyl (1S,4S)-(−)-2,5-diaza-bicyclo(2.2.1)heptane-2-carboxylate (116 mg), heated in a microwave reactor for 30 min at 100° C., cooled, treated with aqueous lithium hydroxide (2M, 1.2 mL), heated in a microwave reactor for 15 min at 100° C., and 18 hours at 25° C., treated with water, acidified to pH 3 with aqueous HCl, and filtered.

Example 239

A slurry of EXAMPLE 239A (162 mg) in dioxane (2 mL) at 25° C. was treated with HCl in dioxane (4M, 2.5 mL), stirred for 2 hours, diluted with diethyl ether, and decanted. The residual solid was triturated with ethyl acetate and dichloromethane and dried. NMR (500 MHz, DMSO-$d_6$) δ ppm 8.94 (s, 1H); 8.09 (d, 1H); 5.14 (s, 1H); 4.52 (s, 1H); 4.39 (m, 2H); 4.03 (m, 1H); 3.90 (m, 1H); 3.41 (m, 2H); 3.25 (m, 2H); 2.78 (m, 2H); 2.18 (m, 2H); 2.01 (d, 1H); 1.67 (m, 2H); 1.46 (m, 2H).

Example 240 ethyl 7-((1S,4S)-2,5-diazabicyclo(2.2.1)hept-2-yl)-6-fluoro-4-oxo-1-(3-phenylprop-2-ynyl)-1,4-dihydro-1,8-naphthyridine-3-carboxylate Example 240A A solution of EXAMPLE 223A (0.156 g) in N,N-dimethylformamide (2 mL) at 25° C. was treated with iodobenzene (0.060 mL), triphenylphosphine (0.0146 g), copper (I) iodide (0.0078 g), triethylamine (0.1 mL) and palladium acetate (0.005 g), stirred in a sealed tube under inert atmosphere for one hour, and concentrated. The residue was partitioned with diethyl ether and water. The organic extract was concentrated.

Example 240

A solution of EXAMPLE 240A (0.186 g) in trifluoroacetic acid (3 ml) was stirred at 25° C. for thirty minutes, and concentrated. A suspension of the residue in methanol (1 mL) and diethyl ether (25 mL) was filtered. NMR (500 MHz, CDCl$_3$) δ ppm 8.93 (s, 1H), 8.0-7.85 (d, 1H), 7.43-7.32 (m, 5H), 5.4-5.27 (m, 2H), 5.27 (s, 1H) 4.4-4.25 (m, 2H), 4.22-4.11 (m, 1H), 4.05-3.98 (m, 1H), 3.64-3.57 (m, 1H), 3.55-3.42 (m, 1H), 2.4-2.28 (m, 1H), 2.26-2.14 (m, 1H), 1.38 (t, 3H).

Example 241

7-((1S,4S)-2,5-diazabicyclo(2.2.1)hept-2-yl)-6-fluoro-1-((5-methylpyrazin-2-yl)methyl)-4-oxo-1,4-dihydro-1,8-naphthyridine-3-carboxylic acid Example 241A A solution of EXAMPLE 7A (170 mg) in acetonitrile (4 mL) at 25° C. was treated with (5-methylpyrazin-2-yl)methylamine (63 mg) and N,N-diisopropylethylamine (450 µL), heated in a microwave reactor for 10 min at 50° C., and 20 min at 190° C., cooled, treated with tert-butyl (1S,4S)-2,5-diazabicyclo(2.2.1)heptane-2-carboxylate (116 mg), heated in a microwave reactor for 30 min at 100° C., cooled, treated with aqueous lithium hydroxide (2M, 1.2 mL), heated in a microwave reactor for 15 min at 100° C., and 18 hours at 25° C., treated with water, acidified to pH 1 with dilute HCl, and filtered.

Example 241

A solution of EXAMPLE 241A (160 mg) in dioxane (2 mL) at 25° C. was treated with HCl in dioxane (4M, 2.5 mL), stirred for 2 hours, treated with diethyl ether, and the supernatent was removed. The residual solid was triturated with ethyl acetate and methylene chloride and dried. NMR (300 MHz, DMSO-$d_6$) δ ppm 15.25 (s, 1H); 9.54 (bs, 1H); 9.19 (s, 1H); 8.77 (s, 2H); 8.42 (s, 1H); 8.10 (d, 1H); 5.84 (m, 2H); 5.07 (s, 1H); 4.47 (s, 1H); 3.90 (m, 2H); 3.01 (m, 2H); 2.46 (s, 3H); 2.13 (d, 1H); 1.97 (d, 1H).

Example 242 ethyl 7-(3-aminopyrrolidin-1-yl)-6-fluoro-5-methyl-4-oxo-1-(2-pyridin-4-ylethyl)-1,4-dihydro-1,8-naphthyridine-3-carboxylate A solution of EXAMPLE 1C (391 mg) in acetonitrile (11.2 mL) at 25° C. was treated with 2-pyridin-4-ylethanamine (0.14 mL), stirred for 2 hours at 25° C., and 16 hours at 50° C., cooled, treated with potassium carbonate (411.3 mg), stirred for 2 days at 85° C., cooled to 25° C., treated with tert-butyl pyrrolidin-3-ylcarbamate (312.5 mg), stirred for 2 days at 25° C., and concentrated. A solution of the concentrate in tetrahydrofuran (8 mL) at 25° C. was treated with 4N HCl/dioxane (15 mL), stirred for 2 hours, treated with diethyl ether and centrifuged. A suspension of the solid in methanol and dichloromethane was decanted, and the supernate was concentrated; and the concentrate purified by reverse phase high performance liquid chromatography (HPLC) on a C8 column with 0% to 100% acetonitrile in water containing 0.1% trifluoroacetic acid.
NMR (300 MHz, DMSO-$d_6$) δ ppm 8.67 (d, 2H), 8.41 (s, 1H), 8.20 (bs, 3H), 7.59 (d, 2H), 4.55 (dd, 2H), 4.16 (q, 2H), 3.91 (m, 5H), 3.24 (dd, 2H), 2.66 (d, 3H), 2.31 (m, 1H), 2.12 (m, 1H), 1.24 (t, 3H).

Example 243

7-(3-((2,6-difluorobenzyl)amino)pyrrolidin-1-yl)-6-fluoro-4-oxo-1,4-dihydro-1,8-naphthyridine-3-carboxylic acid, citric acid salt This compound was prepared according to the procedure described in EXAMPLE 118 substituting 2,6-difluorobenzaldehyde for 3-(methylthio)propanal in EXAMPLE 118C. NMR (500 MHz, DMSO-$d_6$/CF$_3$COOD) δ ppm 8.49 (s, 1H), 7.93 (d, 1H), 7.49 (m, 1H), 7.09 (t, 2H), 4.34-4.27 (m, 2H), 4.10-3.95 (m, 4H), 3.87-3.77 (m, 1H), 2.77-2.62 (m, 4H), 2.47-2.27 (m, 2H).

Example 244

7-((3R,4R)-3-(benzylamino)-4-hydroxypyrrolidin-1-yl)-6-fluoro-4-oxo-1,4-dihydro-1,8-naphthyridine-3-carboxylic acid Example 244A 7-(3-Benzylamino-4-hydroxy-pyrrolidin-1-yl)-1-(2,4-dimethoxy-benzyl)-6-fluoro-4-oxo-1,4-dihydro-(1,8)naphthyridine-3-carboxylic acid ethyl ester A solution of EXAMPLE 206D (0.103 g) in tetrahydrofuran (3 mL) and methanol (1 mL) at 25° C. was treated with benzaldehyde (0.023 g), stirred for 30 min, treated with sodium cyanoboronhydride (0.05 g), stirred for 3 hours at 25° C., treated with HCl in diethyl ether (2.0N, 0.5 mL), and concentrated; and the concentrate purified on a reverse phase high performance liquid chromatography (HPLC) on a C8 column with 10-95% acetonitrile in water containing 0.1% trifluoroacetic acid.

Example 244B 7-(3-Benzylamino-4-hydroxy-pyrrolidin-1-yl)-1-(2, 4-dimethoxy-benzyl)-6-fluoro-4-oxo-1,4-dihydro-(1, 8)naphthyridine-3-carboxylic acid A solution of EXAMPLE 244A (0.049 g) in tetrahydrofuran (3 mL) at 25° C. was treated with a solution of lithium hydroxide monohydrate (0.048 g) in water (3 mL), stirred for 18 hours, concentrated, acidified with HCl (2N in diethyl ether), and filtered.

Example 244

7-(3-Benzylamino-4-hydroxy-pyrrolidin-1-yl)-6-fluoro-4-oxo-1,4-dihydro-(1,8)naphthyridine-3-carboxylic acid A solution of EXAMPLE 244B (0.027 g) in trifluoroacetic acid (2 mL) was heated at 75° C. for 18 hours, and concentrated with a toluene azeotrope; and the residue was purified on a reverse phase HPLC on a C8 column with 10-95% acetonitrile in water containing 0.1% trifluoroacetic acid to provide an oily compound. A solution of the oily compound in 1:1 of methanol/dichloromethane was treated with 2N HCl in diethyl ether (0.5 mL), and concentrated. NMR (DMSO-$d_6$) δ ppm 13.34 (m, 1H), 9.72 (bs, 2H), 8.51 (d, 1H), 8.05 (d, 1H), 7.63 (m, 2H), 7.44 (m, 3H), 4.74 (bs, 1H), 4.40-4.00 (m, 5H), 3.70 (m, 2H).

Example 245

6-fluoro-4-oxo-7-(3-((3-(2-oxopyrrolidin-1-yl)propyl)amino)pyrrolidin-1-yl)-1,4-dihydro-1,8-naphthyridine-3-carboxylic acid, trifluoroacetic acid salt This compound was prepared as described in EXAMPLE 98 substituting 1-(3-aminopropyl)pyrrolidin-2-one for N-(4-aminobutyl)guanidine in EXAMPLE 98C. NMR (300 MHz, CH$_3$OD) δ ppm 8.51 (s, 1H), 7.91 (d, 1H), 4.21-3.89 (m, 5H), 3.52 (t, 2H), 3.48-3.38 (m, 2H), 3.23-3.11 (m, 2H), 2.58-2.28 (m, 4H), 2.16-1.94 (m, 4H).

Example 246

7-((1S,4S)-2,5-diazabicyclo(2.2.1)hept-2-yl)-1-(3,5-dimethoxybenzyl)-6-fluoro-4-oxo-1,4-dihydro-1,8-naphthyridine-3-carboxylic acid

Example 246A

A solution of EXAMPLE 7A (170 mg) in acetonitrile (4 mL) at 25° C. was treated with 3,5-dimethoxybenzylamine (85 mg) and N,N-diisopropylethylamine (450 μL), stirred in a microwave reactor for 10 min at 50° C., and 20 min at 190° C., cooled, treated with tert-butyl (1S,4S)-(−)-2,5-diaza-bicyclo(2.2.1)heptane-2-carboxylate (116 mg), stirred in a microwave reactor for 30 min at 100° C., cooled, treated with aqueous lithium hydroxide (4M, 0.6 mL), stirred in a microwave reactor for 15 min at 100° C., and stirred for 24 hours at 25° C., treated with water, acidified to pH 3 with aqueous HCl, and filtered.

Example 246

A solution of EXAMPLE 246A (150 mg) in dioxane (3 mL) at 25° C. was treated with HCl in dioxane (4M, 1.5 mL), stirred for 3 hours, concentrated, triturated with diethyl ether, ethyl acetate and dichloromethane and dried. NMR (300 MHz, DMSO-$d_6$) δ ppm 9.37 (bs, 1H); 9.14 (s, 1H); 8.64 (bs, 1H); 8.14 (d, 1H); 6.43 (m, 3H); 5.63 (m, 2H); 5.12 (s, 1H); 4.48 (s, 1H); 3.89 (m, 2H); 3.70 (s, 6H); 3.05 (m, 2H); 2.15 (d, 1H); 1.96 (d, 1H).

Example 247

7-(3-aminopyrrolidin-1-yl)-6-fluoro-3-((1,2,3,4-tetrahydronaphthalen-1-ylamino)methyl)-1,8-naphthyridin-4(1H),-one, trifluoroacetic acid salt This compound was prepared according to the procedure described in EXAMPLE 196 substituting 1,2,3,4-tetrahydronaphthalen-1-amine for 3-phenylpropan-1-amine in EXAMPLE 196B. NMR (500 MHz, DMSO-$d_6$) δ ppm 12.16 (d, 1H), 8.84 (bs, 2H), 8.11 (bs, 3H), 8.00 (d, 1H), 7.92 (d, 1H), 7.53 (d, 1H), 7.34-7.26 (m, 2H), 7.21 (d, 1H), 4.48 (m, 1H), 4.10-4.04 (m, 2H), 3.99-3.77 (m, 5H), 2.87-2.72 (m 2H), 2.35-2.26 (m, 1H), 2.21-2.15 (m, 1H), 2.11-2.05 (m, 2H), 2.01-1.93 (m, 1H), 1.80-1.70 (m, 1H).

Example 248 ethyl 7-(3-aminopyrrolidin-1-yl)-1-(2-(4-(aminosulfonyl)phenyl)ethyl)-6-fluoro-5-methyl-4-oxo-1,4-dihydro-1,8-naphthyridine-3-carboxylate A solution of EXAMPLE 1C (182 mg) in acetonitrile (4 mL) at 25° C. was treated with 4-(2-aminoethyl)benzenesulfonamide (100 mg) and N,N-diisopropylethylamine (450 μL), heated in a microwave reactor for 10 min at 50° C., and 1 hour at 200° C., cooled, treated with 3-(tert-butoxycarbonylamino)-pyrrolidine (112 mg), heated in a microwave reactor for 30 min at 100° C., cooled, and concentrated. A solution of the concentrate in dioxane (2 mL) was treated with HCl in dioxane (4M, 2.0 mL), stirred at 25° C. for 2 hours, treated with diethyl ether, and decanted. The residual solid was triturated with ethyl acetate and dichloromethane, dried, and purified by reverse phase high performance liquid chromatography (HPLC) on a C8 column with 0-100% acetonitrile in water containing 0.1% trifluoroacetic acid. NMR (500 MHz, DMSO-$d_6$) δ ppm 8.49 (s, 1H); 7.64 (d, 2H); 7.27 (d, 2H); 4.41 (m, 2H); 4.07 (q, 2H); 3.78 (m, 7H); 3.01 (t, 3H); 2.50 (d, 3H); 2.19 (m, 1H); 2.01 (m, 1H).

Example 249

1-(3-(aminomethyl)benzyl)-7-azetidin-1-yl-6-fluoro-4-oxo-1,4-dihydro-1,8-naphthyridine-3-carboxylic acid A solution of EXAMPLE 7A (168.1 mg) in acetonitrile (5 mL) was treated with tert-butyl 3-(aminomethyl)benzylcarbamate (124.1 mg), stirred for 2 hours at 25° C., and 16 hours at 50° C., cooled, treated with potassium carbonate (285.6 mg), heated for 2 days at 85° C., cooled, treated with azetidine hydrolchloride (112.3 mg), stirred for 2 days at 25° C., treated with 1N NaOH (2 mL) and methanol (2 ml), stirred for 16 hours at 25° C., treated with water, acidified to pH 3.5 with 1N HCl and filtered. A solution of the solid (39 mg) in a mixture of dichloromethane (2 mL) and trifluoroacetic acid (0.5 mL) was stirred at 25° C. for 2 hours, treated with diethyl ether and filtered. NMR (300 MHz, DMSO-$d_6$) δ ppm 15.48 (s, 1H), 9.10 (s, 1H), 8.06 (bs, 3H), 7.97 (d, 1H), 7.37 (m, 4H), 5.67 (s, 2H), 4.30 (bs, 4H), 3.98 (m, 2H), 2.41 (m, 2H) (partially obscured by DMSO peak).

Example 250

7-((1S,4S)-2,5-diazabicyclo(2.2.1)hept-2-yl)-6-fluoro-4-oxo-1-(3,4,5-trimethoxybenzyl)-1,4-dihydro-1,8-naphthyridine-3-carboxylic acid

Example 250A

A solution of EXAMPLE 7A (168 mg) in acetonitrile (4 mL) at 25° C. was treated with 3,4,5-trimethoxybenzylamine (97 mg) and N,N-diisopropylethylamine (450 µL), stirred in a microwave reactor for 10 min at 50° C., and 20 min at 190° C., cooled, treated with tert-butyl (1S,4S)-(−)-2,5-diaza-bicyclo(2.2.1)heptane-2-carboxylate (115 mg), heated in a microwave reactor for 30 min at 100° C., cooled, treated with aqueous lithium hydroxide (4M, 0.6 mL), heated in a microwave reactor for 15 min at 100° C., treated with water, acidified to pH 3 with aqueous HCl, and extracted with ethyl acetate. The organic phase was washed with water and concentrated.

Example 250

A solution of EXAMPLE 250A (290 mg) in dioxane (5 mL) at 25° C. was treated with HCl in dioxane (4M, 2.5 mL), stirred for 3 hours, concentrated, triturated with diethyl ether, ethyl acetate, and dichloromethane, and dried. NMR (300 MHz, DMSO-$d_6$) δ ppm 15.28 (s, 1H); 9.35 (bs, 1H); 9.12 (s, 1H); 8.77 (bs, 1H); 8.15 (d, 1H); 6.63 (s, 2H); 5.62 (m, 2H); 5.14 (s, 1H); 4.50 (s, 1H); 3.93 (m, 2H); 3.72 (s, 6H); 3.62 (s, 3H); 3.08 (m, 2H); 2.15 (d, 1H); 1.96 (d, 1H).

Example 251

7-((1S,4S)-2,5-diazabicyclo(2.2.1)hept-2-yl)-1-(2,3-dimethoxybenzyl)-6-fluoro-4-oxo-1,4-dihydro-1,8-naphthyridine-3-carboxylic acid

Example 251A

A solution of EXAMPLE 7A (175 mg) in acetonitrile (4 mL) at 25° C. was treated with 2,3-dimethoxybenzylamine (85 mg) and N,N-diisopropylethylamine (450 µL), heated in a microwave reactor for 10 min at 50° C., and 20 min at 195° C., cooled, treated with tert-butyl (1S,4S)-(−)-2,5-diaza-bicyclo(2.2.1)heptane-2-carboxylate (119 mg), heated in a microwave reactor for 20 min at 195° C., cooled, treated with water, acidified to pH 3 with aqueous HCl, and extracted with ethyl acetate. The extract was washed with water, and concentrated. A solution of the concentrate in ethanol (4 mL) at 25° C. was treated with LiOH (0.1M, 5 mL), stirred for 18 hours, treated with water, acidified to pH 1 with aqueous HCl, and filtered.

Example 251

A solution of EXAMPLE 251A (110 mg) in dioxane (5 mL) at 25° C. was treated with HCl in dioxane (4M, 1.5 mL), stirred for 3 hours, concentrated, and triturated with diethyl ether, ethyl acetate, and dichloromethane. NMR (300 MHz, DMSO-$d_6$) δ ppm 9.65 (bs, 1H); 9.05 (s, 1H); 8.90 (bs, 1H); 8.12 (d, 1H); 7.03 (m, 2H); 6.72 (m, 1H); 5.71 (m, 2H); 5.09 (s, 1H); 4.49 (s, 1H); 3.96 (m, 2H); 3.79 (s, 3H); 3.68 (s, 3H); 3.08 (m, 2H); 2.14 (d, 1H); 1.97 (d, 1H).

Example 252

7-(3-((2,4-difluorobenzyl)amino)pyrrolidin-1-yl)-6-fluoro-4-oxo-1,4-dihydro-1,8-naphthyridine-3-carboxylic acid, citric acid salt This compound was prepared according to the procedure described in EXAMPLE 118 substituting 2,4-difluorobenzaldehyde for 3-(methylthio)propanal in EXAMPLE 118C. NMR (500 MHz, DMSO-$d_6$/CF$_3$COOD) δ ppm 8.48 (s, 1H), 7.95 (d, 1H), 7.68-7.73 (m, 1H), 7.24-7.20 (m, 1H), 7.14-7.10 (m, 1H), 4.33-4.25 (m, 2H), 4.08-3.92 (m, 4H), 3.85-3.77 (m, 1H), 2.77-2.62 (m, 4H), 2.44-2.25 (m, 2H).

Example 253

7-((1S,4S)-2,5-diazabicyclo(2.2.1)hept-2-yl)-6-fluoro-4-oxo-1-(pyridin-2-ylmethyl)-1,4-dihydro-1,8-naphthyridine-3-carboxylic acid A solution of EXAMPLE 7A (336.1 mg) in acetonitrile (10 mL) was treated with 2-(aminomethyl)pyridine (0.108 mL), stirred for 2 hours at 25° C., and 16 hours at 50° C., cooled, treated with potassium carbonate (367.2 mg), heated for 2 days at 85° C., cooled to 25° C., treated with tert-butyl (1S,4S)-(−)-2,5-diazabicyclo(2.2.1)heptane-2-carboxylate (237.9 mg), heated for 3 days at 50° C., treated with 1N NaOH (4 mL) and methanol (2 ml), heated for 16 hours at 40° C., cooled to 25° C., treated with water, acidified to pH 5.0 with 1N HCl, and filtered. A solution of the solid (150 mg) in 4N HCl/dioxane (3 mL) was stirred at 25° C. for 2 hours, treated with diethyl ether, centrifuged and decanted. The solid was triturated with diethyl ether and dichloromethane. NMR (300 MHz, DMSO-$d_6$) δ ppm 9.78 (bs, 1H), 9.18 (s, 1H), 9.02 (br, 1H), 8.53 (m, 1H), 8.11 (d, 1H), 7.94 (m, 1H), 7.61 (d, 1H), 7.42 (m, 1H), 5.86 (dd, 2H), 4.99 (bs, 1H), 4.43 (bs, 1H), 3.90 (m, 4H) (obscured by water peak), 2.01 (dd, 2H).

Example 254 ethyl 7-(3-aminopyrrolidin-1-yl)-6-fluoro-5-methyl-4-oxo-1-(2-pyridin-2-ylethyl)-1,4-dihydro-1,8-naphthyridine-3-carboxylate A solution of EXAMPLE 1C (375.9 mg) in acetonitrile (10.7 mL) was treated with 2-pyridin-2-ylethanamine (0.13 mL), stirred for 2 hours at 25° C., and at 50° C. for 16 hours, cooled, treated with potassium carbonate (392.9 mg), heated for 2 days at 85° C., cooled to 25° C., treated with tert-butyl pyrrolidin-3-ylcarbamate (299.5 mg), stirred for 2 days at 25° C., and concentrated. A solution of the concentrate in tetrahydrofuran (8 mL) and 4N HCl/dioxane (15 mL) at 25° C. was stirred for 2 hours, treated with diethyl ether, centrifuged, and triturated with diethyl ether. The resulting solid was suspended in methanol and dichloromethane. The supernate was concentrated and the concentrate purified by reverse phase high performance liquid chromatography (HPLC) on a C8 column with 0% to 100% acetonitrile in water containing 0.1% trifluoroacetic acid. NMR (300 MHz, DMSO-$d_6$) δ ppm 8.61 (dd, 1H), 8.27 (s, 1H), 8.10 (bs, 3H), 7.92 (m, 1H), 7.42

(m, 2H), 4.66 (dd, 2H), 4.14 (q, 2H), 3.91 (m, 5H), 3.32 (dd, 2H), 2.66 (d, 3H), 2.31 (m, 1H), 2.10 (m, 1H), 1.23 (t, 3H).

Example 255

7-(3-aminopyrrolidin-1-yl)-6-fluoro-4-oxo-1-(piperidin-3-ylmethyl)-1,4-dihydro-1,8-naphthyridine-3-carboxylic acid A mixture of EXAMPLE 7A (168.3 mg), tert-butyl 3-(aminomethyl)piperidine-1-carboxylate (107 mg), and N,N-diisopropylethylamine (450 µL) in acetonitrile (4.0 mL) was heated in a microwave reactor for 10 minutes at 50° C., and 20 minutes at 190° C.; cooled, treated with tert-butyl pyrrolidin-3-ylcarbamate (112 mg), heated in a microwave reactor for 30 minutes at 100° C., cooled and concentrated. A solution of the concentrate in a mixture of tetrahydrofuran (2 mL) and methanol (1 mL) was treated with sodium hydroxide (2M, 800 µL), stirred for 4 hours at 50° C., cooled, concentrated, treated with water, acidified to pH 6 with 1M HCl, and filtered. The solid was treated with trifluoroacetic acid (2 mL), stirred for 2 hours at 25° C., and concentrated. The concentrate was purified by reverse phase high performance liquid chromatography (HPLC) on a C8 column with 10-100% acetonitrile in water containing 0.1% trifluoroacetic acid. NMR (300 MHz, DMSO-$d_6$) δ ppm 8.94 (s, 1H), 8.80-8.67 (m, 1H), 8.44-8.16 (m, 4H), 8.10 (d, 1H), 4.46-4.34 (m, 2H), 4.08-3.82 (m, 4H), 3.28-3.10 (m, 2H), 2.86-2.67 (m, 2H), 2.44-2.26 (m, 2H), 2.19-2.06 (m, 1H), 1.87-1.20 (m, 4H).

Example 256 ethyl 6-fluoro-4-oxo-7-(3-((1-phenylethyl)amino) pyrrolidin-1-yl)-1,4-dihydro-1,8-naphthyridine-3-carboxylate, trifluoroacetic acid salt This compound was prepared as described in EXAMPLE 175 substituting 1-phenylethanone for 4-hydroxybenzaldehyde in EXAMPLE 175A. NMR (300 MHz, DMSO-$d_6$) δ ppm 9.03 (bs, 2H), 8.26 (s, 1H), 7.85 (d, 1H), 7.60-7.41 (m, 5H), 4.63-4.53 (q, 1H), 4.21 (q, 2H), 4.03-3.77 (m, 5H), 2.33-2.21 (m, 1H), 2.16-2.05 (m, 1H), 1.59 (d, 3H), 1.26 (t, 3H).

Example 257 ethyl 7-((1S,4S)-2,5-diazabicyclo(2.2.1)hept-2-yl)-1-(2,4-dimethoxybenzyl)-6-fluoro-4-oxo-1,4-dihydro-1,8-naphthyridine-3-carboxylate A solution of EXAMPLE 158A (0.055 g) in ethanol (1.5 mL) at 25° C. was treated with HCl (2N in diethyl ether, 2 mL), stirred for 18 hours, and concentrated. NMR (DMSO-$d_6$) δ ppm 8.95 (s, 1H), 7.99 (d, 1H), 7.11 (d, 1H), 6.59 (d, 1H), 6.47 (dd, 1H), 5.52 (dd, 2H), 5.27 (bs, 1H), 4.60 (bs, 1H), 4.38 (q, 2H), 4.09 (m, 2H), 3.84 (s, 3H), 3.78 (s, 3H), 3.39 (m, 2H), 2.36 (d, 1H), 2.16 (d, 1H), 1.39 (t, 3H).

Example 258

7-(3-aminopyrrolidin-1-yl)-3-(((1,2-diphenylethyl) amino)methyl)-6-fluoro-1,8-naphthyridin-4(1H),-one, trifluoroacetic acid salt This compound was prepared according to the procedure described in EXAMPLE 196 substituting 1,2-diphenylethylamine for 3-phenylpropan-1-amine in EXAMPLE 196B. NMR (500 MHz, DMSO-$d_6$) δ ppm 12.08 (d, 1H), 9.15 (bs, 2H), 8.17 (bs, 3H), 7.87 (d, 1H), 7.83 (d, 1H), 7.42-7.34 (m, 4H), 7.19-7.12 (m, 4H), 6.99 (d, 2H), 4.53 (m, 1H), 3.97-3.80 (m, 7H), 3.54-3.50 (m, 1H), 3.21-3.16 (m 1H), 2.35-2.26 (m, 1H), 2.11-2.05 (m, 1H).

Example 259

$N^2$-[1-(6-carboxy-3-fluoro-5-oxo-5,8-dihydro-1,8-naphthyridin-2-yl)pyrrolidin-3-yl]-$N^5$-[imino(nitroamino)methyl]-L-ornithine This compound was prepared as described in EXAMPLE 98 substituting NG-nitro-L-arginine-methyl ester hydrochloride for N-(4-aminobutyl)guanidine in EXAMPLE 98C. NMR (300 MHz, DMSO-$d_6$) δ ppm 13.31 (s, 1H), 13.24 (s, 1H), 9.32 (bs, 2H), 8.51 (s, 1H), 8.01 (d, 1H), 4.08-3.71 (m, 5H), 3.24-3.08 (m, 3H), 2.33-2.06 (m, 2H), 1.84-1.69 (m, 2H), 1.66-147 (m, 2H).

Example 260

7-(3-((1-benzylpiperidin-4-yl)amino)pyrrolidin-1-yl)-6-fluoro-4-oxo-1,4-dihydro-1,8-naphthyridine-3-carboxylic acid, trifluoroacetic acid salt This compound was prepared as described in EXAMPLE 98 substituting 1-benzylpiperidin-4-amine for N-(4-aminobutyl)guanidine in EXAMPLE 98C. NMR (300 MHz, CD$_3$OD) δ ppm 8.54 (s, 1H), 7.97 (d, 1H), 7.53 (s, 5H), 4.38 (s, 2H), 4.27-3.89 (m, 5H), 3.73-3.59 (m, 3H), 3.25-3.09 (t, 2H), 2.61-2.41 (m, 3H), 2.37-2.23 (m, 1H), 2.12-1.95 (m, 2H).

Example 261

7-((1S,4S)-2,5-diazabicyclo(2.2.1)hept-2-yl)-6-fluoro-1-(2-methoxybenzyl)-4-oxo-1,4-dihydro-1,8-naphthyridine-3-carboxylic acid Example 261A A solution of EXAMPLE 7A (1.68 g) in acetonitrile (15 mL) at 0° C. was treated with 2-methoxybenzylamine (685.2 µL), stirred for 15 min at 0° C., and 3 hours at 25° C., treated with potassium carbonate (1.86 g), heated for 18 hours at 85° C., cooled, and treated with water. The product oiled out then became a sticky solid upon stirring. The aqueous layer was decanted and the solid dissolved in hot acetonitrile. The solution was cooled to 25° C., diluted with water, and filtered.

Example 261B

A solution of EXAMPLE 261A (250 mg) in acetonitrile (6.4 mL) at 25° C. was treated with triethylamine (178 µL) and tert-butyl (1S,4S)-(−)-2,5-diazabicyclo(2.2.1)heptane-2-carboxylate (152.5 mg), heated for 24 hours at 50° C., cooled, and partitioned between water and dichloromethane. The organic extracts were dried (MgSO$_4$), filtered, and concentrated.

Example 261C

A solution of EXAMPLE 261B (343 mg) in a mixture of 1N NaOH (2.5 mL) and methanol (6.2 ml) at 25° C. was stirred for 18 hours, treated with water and methanol, acidified to pH 3 with 1N HCl, and filtered.

Example 261

A solution of EXAMPLE 261C (100 mg) in 4N HCl/dioxane (5 mL) was stirred for 2 hours at 25° C., centrifuged, and triturated with diethyl ether and dichloromethane. NMR (300 MHz, DMSO-$d_6$) δ ppm 15.27 (bs, 1H), 9.50 (bs, 1H), 9.06 (s, 1H), 8.85 (bs, 1H), 8.11 (d, 1H), 7.32 (m, 1H), 7.17 (m, 1H), 7.05 (m, 1H), 6.92 (m, 1H), 5.64 (dd, 2H), 5.09 (bs, 1H), 4.49 (bs, 1H), 3.91 (bs, 2H), 3.79 (m, 3H), 3.25 (bs, 1H), 3.11 (bs, 1H), 2.06 (dd, 2H).

Example 262

7-(3-aminopyrrolidin-1-yl)-1-(4-carboxybenzyl)-6-fluoro-4-oxo-1,4-dihydro-1,8-naphthyridine-3-carboxylic acid A mixture of EXAMPLE 7A (168.3 mg), 4-(aminomethyl)benzoic acid hydrochloride (101 mg), and N,N-diisopropylethylamine (450 μL) in acetonitrile (4.0 mL) was heated in a microwave reactor for 10 minutes at 50° C., and 20 minutes at 190° C., cooled, treated with tert-butyl pyrrolidin-3-ylcarbamate (112 mg), heated in a microwave reactor for 30 minutes at 100° C., cooled, and concentrated. A solution of the concentrate in a mixture of tetrahydrofuran (2 mL) and methanol (1 mL) was treated with 2M sodium hydroxide (800 μL), stirred for 4 hours at 50° C., concentrated, treated with water, acidified to pH 3 with 1M HCl, and filtered. A mixture of the solid and trifluoroacetic acid (2 mL) was stirred at 25° C. for 2 hours, and concentrated; and the concentrate was purified by reverse phase high performance liquid chromatography (HPLC) on a C8 column with 10-100% acetonitrile in water containing 0.1% trifluoroacetic acid. NMR (300 MHz, DMSO-$d_6$) δ ppm 9.21 (s, 1H), 8.07 (d, 1H), 7.90 (d, 2H), 7.40 (d, 2H), 5.76 (s, 2H), 3.98-3.60 (m, 5H), 2.33-1.94 (m, 2H).

Example 263

6-fluoro-7-(3-fluoropyrrolidin-1-yl)-4-oxo-1,4-dihydro-1,8-naphthyridine-3-carboxylic acid

Example 263A

A mixture of EXAMPLE 51A (4 g) and pyrrolidin-3-ol (0.997 mL) in acetonitrile (95 mL) at 25° C. was treated with N,N-diisopropylethylamine (3.31 mL), heated for 18 hours at 50° C., cooled, and filtered.

Example 263B

A solution of EXAMPLE 263A (1.56 g) in dichloromethane (33 mL) at 25° C. was treated with methanesulfonyl chloride (0.269 mL) and N,N-diisopropylethylamine (1.15 mL), stirred for 2 hours, washed with 0.1 M hydrochloric acid, dried (MgSO$_4$), filtered, and concentrated; and the concentrate crystallized from diethyl ether.

Example 263C

A solution of EXAMPLE 263B (0.250 g) in acetonitrile (4.5 mL) at 25° C. was treated with tetrabutylammonium fluoride (1M, 1.36 mL), stirred for 30 minutes at 90° C., cooled, and concentrated. The residue was taken up in 0.01M sodium hydroxide, sonicated and filtered.

Example 263D

A solution of EXAMPLE 263C (0.150 g) in 1:1 ethanol/1M sodium hydroxide (12 mL) was heated at 60° C. for 4 hours, cooled to 25° C., poured into 0.1 M hydrochloric acid and filtered.

Example 263

6-Fluoro-7-(3-fluoro-pyrrolidin-1-yl)-4-oxo-1,4-dihydro-(1,8)naphthyridine-3-carboxylic acid EXAMPLE 263D (0.15 g) at 25° C. was treated with trifluoroacetic acid (7 mL), stirred for 18 hours, concentrated, treated with 1:1 dimethylsulfoxide/methanol, and filtered; and the crude product was purified by HPLC on a C8 column with 10-100% acetonitrile in water containing 0.1% trifluoroacetic acid. NMR (300 MHz, DMSO-$d_6$) δ ppm 2.21 (m, 2H), 3.92 (m, 4H), 5.48 (m, 1H), 8.01 (d, 1H), 8.48 (s, 1H), 15.46 (bs, 1H).

Example 264

1-benzyl-7-((1S,4S)-2,5-diazabicyclo(2.2.1)hept-2-yl)-6-fluoro-4-oxo-1,4-dihydro-1,8-naphthyridine-3-carboxylic acid A solution of EXAMPLE 7A (168.1 mg) in acetonitrile (5 mL) was treated with benzylamine (0.057 mL), stirred for 2 hours at 25° C., and 16 hours at 50° C., cooled, treated with potassium carbonate (183.6 mg), heated for 2 days at 85° C., cooled to 25° C., treated with tert-butyl (1S,4S)-(−)-2,5-diazabicyclo(2.2.1)heptane-2-carboxylate (237.9 mg), heated for 3 days at 50° C., treated with 1N NaOH (2 mL) and methanol (2 ml), heated for 16 hours at 40° C., cooled to 25° C., treated with water, acidified to pH 3.5 with 1N HCl, and filtered. A solution of the solid (150 mg) in a mixture of dichloromethane (4 mL) and trifluoroacetic acid (1 mL) was stirred for 2 hours at 25° C., treated with diethyl ether and filtered. NMR (500 MHz, DMSO-$d_6$/CF$_3$COOD, 60° C.) δ ppm 9.09 (s, 1H), 8.09 (d, 1H), 7.33 (m, 2H), 7.28 (m, 3H), 5.71 (dd, 2H), 5.08 (s, 1H), 4.49 (s, 1H), 3.88 (d, 2H), 3.23 (m, 1H), 3.08 (m, 1H), 2.06 (dd, 2H).

Example 265

7-(3-((2-ethylbutyl)amino)pyrrolidin-1-yl)-6-fluoro-4-oxo-1,4-dihydro-1,8-naphthyridine-3-carboxylic acid, citric acid salt This compound was prepared according to the procedure described in EXAMPLE 118 substituting 2-ethylbutanal for 3-(methylthio)propanal in EXAMPLE 118C. NMR (500 MHz, DMSO-$d_6$/CF$_3$COOD) δ ppm 8.49 (s, 1H), 7.95 (d, 1H), 4.10-3.92 (m, 4H), 3.80-3.74 (m, 1H), 2.94-2.86 (m, 2H), 2.77-2.63 (m, 4H), 2.38-2.32 (m, 1H), 2.28-2.22 (m, 1H), 1.60-1.55 (m, 1H), 1.41-1.29 (m, 4H), 0.83 (t, 6H).

Example 266

7-(3-aminopyrrolidin-1-yl)-3-benzoyl-1-(2,4-dimethoxybenzyl)-6-fluoro-1,8-naphthyridin-4(1H),-one, trifluoroacetic acid salt

Example 266A

A solution of EXAMPLE 36A (6.2 g) in tetrahydrofuran (175 mL) at 25° C. was treated with 1M LiOH (60 mL), stirred for 18 hours, concentrated, treated with 10% citric acid and extracted with dichloromethane. The extracts were washed with 10% citric acid, water and brine, dried (Na$_2$SO$_4$), filtered, and concentrated.

Example 266B

A solution of EXAMPLE 266A (500 mg) in chloroform (18 mL) at 25° C. was treated with N,O-dimethylhydroxylamine hydrochloride (228 mg), N,N-diisopropylethylamine (0.82 mL), 4-(N,N-dimethylamino)-pyridine (7 mg) and 2-(1H-benzotriazol-1-yl)-1,1,3-tetrauronium tetrafluoroborate (940 mg), stirred for 20 hours and concentrated. The concentrate was crystallized from diethyl ether, filtered and dried.

Example 266C

A solution of Example 266B (100 mg) in dichloromethane (5 mL) at 0° C. was treated with 1M phenylmagnesium bromide in tetrahydrofuran (0.9 mL), stirred for 1 hour, treated with saturated ammonium chloride, and extracted with dichloromethane. The extract was washed with brine and dried ($Na_2SO_4$), filtered, and concentrated; and the concentrate was flash chromatographed on silica gel with 0.5% methanol/chloroform.

Example 266

A solution of EXAMPLE 266C (10 mg) in trifluoroacetic acid (0.075 mL) and dichloromethane (0.15 mL) at 25° C. was stirred for 2 hours and concentrated; and the concentrate was triturated with diethyl ether, filtered, and dried. NMR (300 MHz, DMSO-$d_6$) δ ppm 8.41 (s, 1H), 8.06 (bs, 3H), 7.88 (d, 1H), 7.74-7.69 (m, 2H), 7.65-7.55 (m, 1H), 7.50-7.41 (m, 2H), 7.16 (d, 1H), 6.60 (d, 1H), 6.49 (dd, 1H), 5.43 (s, 2H), 4.05-3.70 (m, 5H), 3.79 (s, 3H), 3.75 (s, 3H), 2.40-2.25, (m, 1H), 2.18-2.03 (m, 1H).

Example 267

7-(3-((2-carboxy-2-(1H-imidazol-4-yl)ethyl)amino) pyrrolidin-1-yl)-6-fluoro-4-oxo-1,4-dihydro-1,8-naphthyridine-3-carboxylic acid, trifluoroacetic acid salt This compound was prepared as described in EXAMPLE 122 but substituting 3-amino-2-(1H-imidazol-4-yl)propanoic acid dihydrochloride for 4-(aminomethyl)benzylamine in EXAMPLE 122C. NMR (300 MHz, DMSO-$d_6$) δ ppm 13.25 (bs, 2H), 9.35 (bs, 2H), 8.98 (s, 1H), 8.53 (d 1H), 8.05 (d, 1H), 7.47 (d, 1H), 4.12-3.78 (m, 6H), 3.12 (d, 2H), 2.35-2.27 (m, 1H), 2.13-2.05 (m 1H).

Example 268

7-(3-aminopyrrolidin-1-yl)-3-((2,4-diflurobenzyl) amino)methyl)-6-fluoro-1,8-naphthyridin-4(1H)-one This compound was prepared as described in EXAMPLE 196 substituting 2,4-difluorobenzylamine for 3-phenylpropan-1-amine in EXAMPLE 196B. NMR (500 MHz, DMSO-$d_6$) δ ppm 12.11 (d, 1H), 8.98 (bs, 2H), 8.13 (bs, 3H), 7.98 (d, 1H), 7.88 (d, 1H), 7.69-7.64 (m, 1H), 7.37-7.33 (m, 1H), 7.21-7.17 (m, 1H), 4.19 (bs, 2H), 4.01 (bs, 2H), 3.98-3.78 (m, 5H), 2.35-2.27 (m, 1H), 2.13-2.05 (m 1H).

Example 269

1-(2,4-dimethoxybenzyl)-6-fluoro-4-oxo-7-(3-((3-(2-oxopyrrolidin-1-yl)propyl)amino)pyrrolidin-1-yl)-1, 4-dihydro-1,8-naphthyridine-3-carboxylic acid, trifluoroacetic acid salt This example was prepared as described in EXAMPLE 98 but substituting 1-(3-aminopropyl)pyrrolidin-2-one for N-(4-aminobutyl)guanidine in EXAMPLE 98C. NMR (300 MHz, CDCl$_3$) δ ppm 8.65 (s, 1H), 7.95 (d, 1H), 7.25 (d, 1H), 6.55-6.45 (m, 2H), 5.35 (s, 2H), 4.41-3.86 (m, 5H), 3.82 (s, 3H), 3.79 (s, 3H), 3.61-3.39 (m, 4H), 3.19-3.07 (m, 2H), 2.63-2.34 (m, 3H), 2.14-2.03 (m, 5H).

Example 270 ethyl 7-(3-aminopyrrolidin-1-yl)-1-(2-(2,5-dimethoxyphenyl)ethyl)-6-fluoro-5-methyl-4-oxo-1, 4-dihydro-1,8-naphthyridine-3-carboxylate A solution of EXAMPLE 1C (347.3 mg) in acetonitrile (9.9 mL) was treated with 2,5-dimethoxyphenethylamine (0.17 mL), stirred for 2 hours at 25° C. and 16 hours at 50° C. and cooled, treated with potassium carbonate (363.5 mg), heated for 2 days at 85° C. and cooled, treated with tert-butyl pyrrolidin-3-ylcarbamate (277.1 mg), stirred for 2 days at 25° C., and concentrated. A solution of the concentrate in tetrahydrofuran (8 mL) and 4N HCl/dioxane (16 mL) at 25° C. was stirred for 2 hours, treated with diethyl ether, centrifuged, and triturated with diethyl ether. The solid was extracted with methanol and dichloromethane, and the supernate was concentrated. The concentrate was purified by reverse phase high performance liquid chromatography (HPLC) on a C8 column with 0%-100% acetonitrile in water containing 0.1% trifluoroacetic acid. NMR (300 MHz, DMSO-$d_6$) δ ppm 8.12 (s, 1H), 8.10 (bs, 3H), 6.78 (m, 3H), 4.44 (dd, 2H), 4.13 (q, 2H), 4.00 (m, 2H), 3.87 (m, 3H), 3.65 (s, 3H), 3.59 (s, 3H), 3.00 (dd, 2H), 2.66 (d, 3H), 2.33 (m, 1H), 2.12 (m, 1H), 1.21 (t, 3H).

Example 271

7-(3-aminopyrrolidin-1-yl)-6-fluoro-4-oxo-1-(piperidin-4-ylmethyl)-1,4-dihydro-1,8-naphthyridine-3-carboxylic acid A mixture of EXAMPLE 7A (168.3 mg), tert-butyl piperidin-4-ylmethylcarbamate (107 mg), and N,N-diisopropylethylamine (450 μL) in acetonitrile (4.0 mL) was heated in a microwave reactor for 10 minutes at 50° C. and 20 minutes at 190° C. and cooled, treated with tert-butyl pyrrolidin-3-ylcarbamate (112 mg), stirred for 30 minutes at 100° C. and cooled, and concentrated. A solution of the concentrate in tetrahydrofuran (2 mL) and methanol (1 mL) was treated with 2M sodium hydroxide (800 μL), stirred for 4 hours at 50° C., and concentrated. The concentrate was treated with water, acidified to pH 6 with 1M HCl, and filtered. A solution of the solid in trifluoroacetic acid (2 mL) at 25° C. was stirred for 2 hours and concentrated; and the concentrate was purified by reverse phase (HPLC) on a C8 column with 10-100% acetonitrile in water containing 0.1% trifluoroacetic acid. NMR (300 MHz, DMSO-$d_6$) δ ppm 8.97 (s, 1H), 8.64-8.49 (m, 1H), 8.37-8.13 (m, 3H), 8.10 (d, 1H), 4.47-4.35 (m, 2H), 4.13-3.79 (m, 4H), 2.90-2.67 (m, 3H), 2.40-2.03 (m, 4H), 1.77-1.32 (m, 5H).

Example 272

7-(3-aminopyrrolidin-1-yl)-1-(((2R)-6,6-dimethylbicyclo(3.1.1)hept-2-yl)methyl)-6-fluoro-4-oxo-1,4-dihydro-1,8-naphthyridine-3-carboxylic acid A mixture of EXAMPLE 7A (168.3 mg), (−)-cis-myrtanylamine (84 μL), and N,N-diisopropylethylamine (450 μL) in acetonitrile (4 mL) was stirred in a microwave reactor for 10 minutes at 50° C. and 20 minutes at 190° C. and cooled, treated with tert-butyl pyrrolidin-3-ylcarbamate (112 mg), stirred for 30 minutes at 100° C. and cooled, and concentrated. A solution of the concentrate in tetrahydrofuran (2 mL) and methanol (1 mL) was treated with 2M sodium hydroxide (800 μL,), stirred for 4 hours at 50° C. and cooled, and concentrated. The concentrate was treated with water, acidified to pH 1 with 1M HCl, and filtered. A solution of the solid in trifluoroacetic acid (2 mL) at 25° C. stirred for 2 hours and concentrated; and the concentrate was purified by reverse phase (HPLC) on a C8 column with 10-100% acetonitrile in water containing 0.1% trifluoroacetic acid. NMR (300 MHz, DMSO-$d_6$) δ ppm 8.84 (d, 1H), 8.15-8.01 (m, 4H), 4.71-4.55 (m, 1H), 4.36-4.21 (m, 1H), 4.07-3.81 (m, 4H), 2.69-2.54 (m, 1H), 2.41-1.54 (m, 11H), 1.21 (s, 3H), 1.18 (s, 3H).

The forgoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound having formula (I)

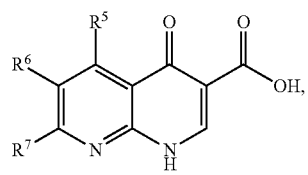

in which
  $R^5$ is alkyl, aryl, heteroaryl, halo, —OH, —$CF_3$, —$CH_2CF_3$, —$CF_2CF_3$, —$NH_2$, —$NHR^{11}$, —$NR^{11}R^{12}$, —NHC(O)$R^{11}$, —$NR^{11}$C(O)$R^{12}$, —NHS(O)$_2R^{11}$, —$NR^{11}$S(O)$_2R^{12}$, or —$OR^{11}$;
  $R^6$ is hydrogen, halogen, alkyl, —$N_3$, —CN, —$CH_2NH_2$, —$NO_2$, —C(O)H, —C(O)$R^{35}$—C≡CH—, —C≡C-(alkyl), —C≡C-(aryl), —C≡C—$CCl_3$, —C≡C—$CF_3$, —CH=$CH_2$, or —$OR^{11}$;
  $R^7$ is azetidinyl, pyrrolidinyl, piperidinyl, or piperazinyl;
  $R^{11}$ is alkyl, —($C_1$-$C_4$-alkylene)-alkenyl, —($C_1$-$C_4$-alkylene)-alkynyl, or alkyl substituted with one aryl substituent;
  $R^{12}$ is alkyl, —$NH_2$, —$NHR^{6a}$, or alkyl substituted with one substituent selected from the group consisting of cycloalkenyl, aryl, heteroaryl, heterocyclyl, —$NH_2$, —N($R^{15}$)($R^{16}$), —NHC(=NH)$NH_2$, —OC(O)C $F_3$, —OH, —O-(alkyl), —S-(alkyl), and —C(O)$NH_2$;
  $R^{6A}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidonyl, uracilyl, imidazolidinyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)-$NH_2$, —O-(alkyl)-$NR^{70}R^{71}$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2$NH(alkyl), —$SO_2$N(alkyl)$_2$, and phenyl substituted with alkyl;

$R^{15}$ and $R^{16}$ are independently alkyl or alkyl substituted with one substituent selected from the group consisting of —$NH_2$, —NH(alkyl), and —N(alkyl)$_2$;
  $R^{30}$ is alkyl or alkyl substituted with one substituent selected from the group consisting of halo and —O(alkyl);
  $R^{35}$ and $R^{36}$ are independently alkyl, alkenyl, alkyl substituted with four or five hydroxyl substituents, or alkyl substituted with one, two, or three substituents independently selected from the group consisting of —NH(=NH)$NH_2$, —OH, —$NH_2$, —NH(alkyl), —N(alkyl)$_2$, —NH($CH_2$(phenyl)), —S(alkyl), $R^{40}$, cycloalkyl, —$CO_2H$, =O, —NH(C=NH)$NHNO_2$, and cycloalkyl substituted with —$CH_2NH_2$;
  $R^{40}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2C$ $F_3$, -(alkyl)$NH_2$, —O-(alkyl)-$NR^{70}R^{71}$, —O(alkyl), —S(alkyl), —S(O)(alkyl), —$SO_2$(alkyl), —C(O)H, —C(O)(alkyl), —C(O)OH, —C(O)O(alkyl), —$NH_2$, —NH(alkyl), —N(alkyl)$_2$, —C(O)$NH_2$, —C(O)NH(alkyl), -(alkyl)-phenyl, —C(O)N(alkyl)$_2$, —OC(O)(alkyl), —OC(O)O(alkyl), —OC(O)$NH_2$, —OC(O)NH(alkyl), —OC(O)N(alkyl)$_2$, —NHC(O)H, —NHC(O)(alkyl), —NHC(O)O(alkyl), —NHC(O)$NH_2$, —NHC(O)NH(alkyl), —NHC(O)N(alkyl)$_2$, —$SO_2NH_2$, —$SO_2$NH(alkyl), —$SO_2$N(alkyl)$_2$, alkyl substituted with one phenyl substituent, and phenyl substituted with one, two, or three independently selected alkyl substituents;
  $R^{70}$ and $R^{71}$ are independently hydrogen, alkyl, alkenyl, alkyl substituted with four or five hydroxyl substituents, or alkyl substituted with one, two, or three substituents independently selected from the group consisting of —NH(=NH)$NH_2$, —OH, —$NH_2$, —NH(alkyl), —N(alkyl)$_2$, —NH($CH_2$(phenyl)), —S(alkyl), $R^{80}$, cycloalkyl, —$CO_2H$, =O, —NH(C=NH)$NHNO_2$, and cycloalkyl substituted with —$CH_2NH_2$; and
  $R^{80}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —$NO_2$, =O, —$CF_3$, —$CH_2CF_3$, —$CF_2CF_3$, —$OCF_3$, —$OCH_2CF_3$, —$OCF_2CF_3$, -(alkyl)-$NH_2$, —O-(alkyl)-$NH_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents;

in which each foregoing aryl, heteroaryl, heterocyclyl, and bicyclic heterocyclyl is unsubstituted or substituted with one, two, three, four, or five substituents independently selected from the group consisting of (a) one, two, three, four, or five independently selected $R^{5a}$ substituents, (b) alkyl substituted with one, two, three, four, or five independently selected $R^{20a}$ substituents, (c) —NH(alkyl), in which the alkyl part of the —NH(alkyl) is substituted with one, two, three, four, or five independently selected $R^{20a}$ substituents; and (d) —N($R^{35}$)-(alkyl), in which the alkyl part of the —N($R^{35}$)-(alkyl), is substituted with one, two, three, four or five independently selected $R^{20a}$ substituents;

in which $R^{5a}$ is alkyl, alkenyl, alkynyl, cycloalkyl, halo, —CN, —OH, —SH, —NH$_2$, —NO$_2$, =O, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)R$^{35}$, —SO$_2$R$^{35}$, —B(OH)$_2$, —C(O)H, —C(O)R$^{35}$, —C(O)OH, —C(O)OR$^{35}$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)R$^{35}$, —OC(O)NH$_2$, —OC(O)NH(R$^{35}$), —OC(O)N(R$^{35}$)(R$^{36}$), —NHC(O)H, —NHC(O)R$^{35}$, —NHC(O)OR$^{35}$, —NHC(O)NH$_2$, —NHC(NH)NH$_2$), —NHC(O)NH(R$^{35}$), —NHC(O)N(R$^{35}$)(R$^{36}$), —SO$_2$NH$_2$, —SO$_2$NH(R$^{35}$), —SO$_2$N(R$^{35}$)(R$^{36}$), or $R^{81}$;

$R^{20A}$ is cycloalkyl, halo, —CN, —OH, —SH, =O, —OR$^{30}$, —SR$^{30}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), —C(O)N(R$^{35}$)(R$^{36}$), —OC(O)R$^{35}$, —OC(O)NH$_2$, —NHC(NH)NH$_2$, —NHC(NH)NHNO$_2$, —OC(O)NH(R$^{35}$), —OC(O)N(R$^{35}$)(R$^{36}$), —SO$_2$NH$_2$, —SO$_2$NH(R$^{35}$), —SO$_2$N(R$^{35}$)(R$^{36}$), or —CH=CH$_2$;

$R^{81}$ is phenyl, naphthyl, furyl, thienyl, pyrrolyl, oxazolyl, thiazolyl, imidazolyl, pyrazolyl, isoxazolyl, isothiazolyl, 1,2,3-oxadiazolyl, 1,2,3-thiadiazolyl, 1,3,4-thiadiazolyl, 1,2,3-triazolyl, pyridyl, quinolinyl, pyrazinyl, pyrimidinyl, cyclohexyl, pyrrolidinyl, pyrrolidinyl substituted with =O, uracilyl, imidazolidinyl, cyclohexyl, piperidinyl, piperazinyl, morpholinyl, thiomorpholinyl, or methyl optionally substituted with one, two or three substituents independently selected from the group consisting of alkyl, alkenyl, alkynyl, cycloalkyl, halo, —CN, —OH, —SH, —NO$_2$, =O, —CF$_3$, —CH$_2$CF$_3$, —CF$_2$CF$_3$, —OCF$_3$, —OCH$_2$CF$_3$, —OCF$_2$CF$_3$, -(alkyl)-NH$_2$, —O-(alkyl)-NH$_2$, —O-(alkyl)-NH(alkyl), —O-(alkyl)-N(alkyl)$_2$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), -(alkyl)-phenyl, —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, alkyl substituted with one phenyl substituent, and phenyl substituted with one, two, or three independently selected alkyl substituents; and each foregoing cycloalkyl and bicyclic cycloalkyl is unsubstituted or substituted with one or two substituents independently selected from the group consisting of alkyl, alkenyl, alkynyl, cycloalkyl, halo, —CN, —OH, =O, —CF$_3$, —OR$^{30}$, —C(O)R$^{35}$, —C(O)OH, —C(O)OR$^{35}$, —NH$_2$, —NH(R$^{35}$), —N(R$^{35}$)(R$^{36}$), —C(O)NH$_2$, —C(O)NH(R$^{35}$), and —C(O)N(R$^{35}$)(R$^{36}$).

2. A composition for the treatment of bacterial infections in a fish or a mammal, the composition comprising a therapeutically effective amount of a compound of claim 1.

3. A method of treatment of bacterial infection in a fish or a mammal, the method comprising administering to the fish or the mammal a therapeutically effective amount of a compound of claim 1.

4. A composition for inhibiting bacterial protein synthesis in a fish or a mammal, the composition comprising a therapeutically effective amount of a compound of claim 1.

5. A composition for inhibiting bacterial growth in a fish or a mammal, the composition comprising a therapeutically effective amount of a compound of claim 1.

6. A composition for treatment of antibacterial-resistant bacterial infection in a fish or a mammal, the composition comprising a therapeutically effective amount of compound of claim 1.

7. A method for inhibiting bacterial protein synthesis in a fish or a mammal, the method comprising administering to the fish or the mammal a therapeutically effective amount of a compound of claim 1.

8. A method for inhibiting bacterial growth in a fish or a mammal, the method comprising administering to the fish or the mammal a therapeutically effective amount of a compound of claim 1.

9. A composition for the treatment of antibacterial-resistant bacterial infection in a fish or a mammal, the composition comprising a therapeutically effective amount of compound of claim 1.

10. A compound which is 7-((3R)-3-aminopyrrolidin-1-yl)-6-fluoro-5-methyl-4-oxo-1,4-dihydro-1,8-naphthyridine-3-carboxylic acid, 7-(3-aminopyrrolidin-1-yl)-6-fluoro-5-methyl-4-oxo-1,4-dihydro-1,8-naphthyridine-3-carboxylic acid, 7-(3-aminopyrrolidin-1-yl)-5-ethyl-6-fluoro-4-oxo-1,4-dihydro-1,8-naphthyridine-3-carboxylic acid, 7-((3S)-3-aminopyrrolidin-1-yl)-6-fluoro-5-methyl-4-oxo-1,4-dihydro-1,8-naphthyridine-3-carboxylic acid, 7-azetidin-1-yl-6-fluoro-5-methyl-4-oxo-1,4-dihydro-1,8-naphthyridine-3-carboxylic acid, 7-(3-aminopyrrolidin-1-yl)-6-fluoro-5-iodo-4-oxo-1,4-dihydro-1,8-naphthyridine-3-carboxylic acid, 7-azetidin-1-yl-4-oxo-5-(trifluoromethyl)-1,4-dihydro-1,8-naphthyridine-3-carboxylic acid, 7-azetidin-1-yl-5-methyl-4-oxo-1,4-dihydro-1,8-naphthyridine-3-carboxylic acid, 7-(3-aminopyrrolidin-1-yl)-6-fluoro-5-methyl-4-oxo-1,4-dihydro-1,8-naphthyridine-3-carboxamide, 7-(3-aminopyrrolidin-1-yl)-4-oxo-5-(trifluoromethyl)-1,4-dihydro-1,8-naphthyridine-3-carboxylic acid, 4-oxo-7-pyrrolidin-1-yl-5-(trifluoromethyl)-1,4-dihydro-1,8-naphthyridine-3-carboxylic acid, 5-methyl-4-oxo-7-(3-pyridin-3-ylpyrrolidin-1-yl)-1,4-dihydro-1,8-naphthyridine-3-carboxylic acid, 6-fluoro-5-methyl-4-oxo-7-pyrrolidin-1-yl-1,4-dihydro-1,8-naphthyridine-3-carboxylic acid, 6-chloro-5-methyl-7-(3-(methylamino)pyrrolidin-1-yl)-4-oxo-1,4-dihydro-1,8-naphthyridine-3-carboxylic acid, 7-(3-aminopyrrolidin-1-yl)-6-chloro-5-methyl-4-oxo-1,4-dihydro-1,8-naphthyridine-3-carboxylic acid, 6-bromo-5-methyl-7-(3-(methylamino)pyrrolidin-1-yl)-4-oxo-1,4-dihydro-1,8-naphthyridine-3-carboxylic acid, 7-(3-aminopyrrolidin-1-yl)-5,6-dimethyl-4-oxo-1,4-dihydro-1,8-naphthyridine-3-carboxylic acid, 7-(3-(aminomethyl)pyrrolidin-1-yl)-6-bromo-5-methyl-4-oxo-1,4-dihydro-1,8-naphthyridine-3-carboxylic acid, 7-(3-aminopyrrolidin-1-yl)-6-bromo-5-methyl-4-oxo-1,4-dihydro-1,8-naphthyridine-3-carboxylic acid, 7-(3-aminopyrrolidin-1-yl)-6-bromo-5-methyl-4-oxo-1,4-dihydro-1,8-naphthyridine-3-carboxylic acid, 7-azetidin-1-yl-4-oxo-5-(trifluoromethyl)-1,4-dihydro-1,8-naphthyridine-3-carboxylic acid, 5-methyl-7-(3-(methylamino)pyrrolidin-1-yl)-4-oxo-1,4-dihydro-1,8-naphthyridine-3-carboxylic acid, 6-chloro-7-(3-(dimethylamino)pyrrolidin-1-yl)-5-methyl-4-oxo-1,4-dihydro-1,8-naphthyridine-3-carboxylic acid, 7-(3-(aminomethyl)pyrrolidin-1-yl)-5-methyl-4-oxo-1,4-dihydro-1,8-naphthyridine-3-carboxylic acid, 7-(3-((4-aminobenzyl)amino)pyrrolidin-1-yl)-6-fluoro-4-oxo-1,4-dihydro-1,8-naphthyridine-3-carboxylic acid, or a therapeutically acceptable salt thereof.

11. The compound 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

12. A composition for the treatment of bacterial infections in a fish or a mammal, the composition comprising a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

13. A method of treatment of bacterial infection in a fish or a mammal, the method comprising administering to the fish or the mammal a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

14. A composition for inhibiting bacterial protein synthesis, the composition comprising a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

15. A composition for inhibiting bacterial growth in a fish or a mammal, the composition comprising a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

16. A composition for treatment of antibacterial-resistant bacterial infection in a fish or a mammal, the composition comprising a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

17. A method for inhibiting bacterial protein synthesis in a fish or a mammal, the method comprising administering to the fish or the mammal a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

18. A method for inhibiting bacterial growth in a fish or a mammal, the method comprising administering to the fish or the mammal a therapeutically acceptable amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

19. A composition for the treatment of antibacterial-resistant bacterial infection in a fish or a mammal, the composition comprising a therapeutically effective amount of 7-((3R)-3-aminopyrrolidin-1-yl)-6-fluoro-5-methyl-oxo-1,4-dihydro-1,8-naphthyridine-3-carboxylic acid, or a therapeutically acceptable salt thereof.

* * * * *